US011001900B2

(12) United States Patent
Apte et al.

(10) Patent No.: US 11,001,900 B2
(45) Date of Patent: May 11, 2021

(54) METHOD AND SYSTEM FOR CHARACTERIZATION FOR FEMALE REPRODUCTIVE SYSTEM-RELATED CONDITIONS ASSOCIATED WITH MICROORGANISMS

(71) Applicant: PSOMAGEN, INC., Rockville, MD (US)

(72) Inventors: Zachary Apte, San Francisco, CA (US); Elisabeth Bik, San Francisco, CA (US); Sara W. Bird, San Francisco, CA (US); Luis E. Leon, Santiago (CL); Pamela A. Nieto, Santiago (CL); Victor Alegria-Mera, Santiago (CL); Cristian Bravo, Santiago (CL); Juan P. Cardenas, Santiago (CL); Paulo Covarrubias, Santiago (CL); Sarah L. Gupta, San Francisco, CA (US); Kira Harman, San Francisco, CA (US); Juan Jimenez, Santiago (CL); Felipe Melis-Arcos, Santiago (CL); Camila F. Navas, Santiago (CL); Harold Nunez, Santiago (CL); Eduardo Olivares, Santiago (CL); Nicolas Ordenes-Aenishanslins, Santiago (CL); Francisco J. Ossandon, San Francisco, CA (US); Ignacio Varas, Santiago (CL); Patricia Vera-Wolf, Santiago (CL); Donna Marie B. Hongo, San Francisco, CA (US); Laurens Kraal, San Francisco, CA (US); Nathaniel A. Walton, San Francisco, CA (US); Amanda Morton, San Francisco, CA (US); Juan P. Bustamante, Santiago (CL); Kwasi Addae, San Francisco, CA (US); Graham Gass, San Francisco, CA (US); Katia Soto-Liebe, Santiago (CL); Juan A. Ugalde, Santiago (CL); Eduardo H. Morales, Santiago (CL); Daniel Almonacid, San Francisco, CA (US); Jessica Richman, San Francisco, CA (US)

(73) Assignee: PSOMAGEN, INC., Rockville, MD (US)

(*) Notice: Subject to any disclaimer, the term of this patent is extended or adjusted under 35 U.S.C. 154(b) by 0 days.

(21) Appl. No.: 16/115,542

(22) Filed: Aug. 28, 2018

(65) Prior Publication Data
US 2019/0078142 A1 Mar. 14, 2019

Related U.S. Application Data

(63) Continuation-in-part of application No. 15/198,818, filed on Jun. 30, 2016, now Pat. No. 10,415,105.

(Continued)

(51) Int. Cl.
*C12Q 1/689* (2018.01)
*C12Q 1/04* (2006.01)
(Continued)

(52) U.S. Cl.
CPC .............. *C12Q 1/689* (2013.01); *C12Q 1/04* (2013.01); *C12Q 1/6883* (2013.01); *C12Q 1/705* (2013.01); *C12Q 1/708* (2013.01); *G16B 5/00* (2019.02); *G16B 20/00* (2019.02); *G16B 30/00* (2019.02); *G16B 40/00* (2019.02); *G16H 10/40* (2018.01); *G16H 50/20* (2018.01); *G16H 50/30* (2018.01); *C12Q 2600/106* (2013.01); *C12Q 2600/112* (2013.01); *C12Q 2600/16* (2013.01);
(Continued)

(58) Field of Classification Search
None
See application file for complete search history.

(56) References Cited

U.S. PATENT DOCUMENTS 5,891,630 A 4/1999 Eggers et al.
8,478,544 B2 7/2013 Colwell et al.
(Continued)

FOREIGN PATENT DOCUMENTS

WO 2014144092 9/2014
WO 2015-013214 A2 1/2015
(Continued)

OTHER PUBLICATIONS

Boon, Mathilde E. "The cellient system for paraffin histology can be combined with HPV testing and morphotyping the vaginal microbiome thanks to BoonFixing." Obstetrics and gynecology international 2013 (2013).*

(Continued)

*Primary Examiner* — G Steven Vanni
(74) *Attorney, Agent, or Firm* — Morgan, Lewis & Bockius LLP

(57) ABSTRACT

Embodiments of a method and/or system for characterizing one or more female reproductive system-related conditions can include determining a microorganism dataset associated with a set of subjects; and/or performing a characterization process associated with the one or more female reproductive system-related conditions, based on the microorganism dataset, where performing the characterization process can additionally or alternatively include performing a female reproductive system-related characterization process for the one or more female reproductive system-related conditions, and/or determining one or more therapies.

23 Claims, 36 Drawing Sheets
Specification includes a Sequence Listing.

Related U.S. Application Data

(60) Provisional application No. 62/653,402, filed on Apr. 5, 2018, provisional application No. 62/585,131, filed on Nov. 13, 2017, provisional application No. 62/551,155, filed on Aug. 28, 2017, provisional application No. 62/186,793, filed on Jun. 30, 2015.

(51) Int. Cl.

| | | |
|---|---|---|
| *C12Q 1/70* | (2006.01) | |
| *G16B 5/00* | (2019.01) | |
| *G16B 20/00* | (2019.01) | |
| *G16B 30/00* | (2019.01) | |
| *G16B 40/00* | (2019.01) | |
| *C12Q 1/6883* | (2018.01) | |
| *G16H 10/40* | (2018.01) | |
| *G16H 50/30* | (2018.01) | |
| *G16H 50/20* | (2018.01) | |
| *G16B 40/20* | (2019.01) | |
| *G16B 40/30* | (2019.01) | |
| *G16B 50/30* | (2019.01) | |

(52) U.S. Cl.
CPC .............. *G16B 40/20* (2019.02); *G16B 40/30* (2019.02); *G16B 50/30* (2019.02)

(56) References Cited

U.S. PATENT DOCUMENTS

| | | | |
|---|---|---|---|
| 9,663,831 | B2 | 5/2017 | Apte et al. |
| 9,703,929 | B2 | 7/2017 | Apte et al. |
| 9,710,606 | B2 | 7/2017 | Apte et al. |
| 2002/0146745 | A1 | 10/2002 | Natan et al. |
| 2005/0255552 | A1 | 11/2005 | Flynn et al. |
| 2010/0129816 | A1 | 5/2010 | Savelkoul et al. |
| 2010/0172874 | A1 | 7/2010 | Turnbaugh et al. |
| 2012/0045771 | A1 | 2/2012 | Beier et al. |
| 2012/0149584 | A1 | 6/2012 | Olle et al. |
| 2013/0045874 | A1 | 2/2013 | Ehrlich |
| 2013/0184164 | A1 | 7/2013 | Moon et al. |
| 2014/0093478 | A1 | 4/2014 | Turnbaugh et al. |
| 2014/0136120 | A1 | 5/2014 | Colwell et al. |
| 2014/0199281 | A1 | 7/2014 | Henn et al. |
| 2016/0362738 | A1 | 12/2016 | Apte et al. |
| 2017/0002432 | A1 | 1/2017 | Apte et al. |

FOREIGN PATENT DOCUMENTS

| | | |
|---|---|---|
| WO | 2015067936 | 5/2015 |
| WO | 2017-004379 A1 | 1/2017 |

OTHER PUBLICATIONS

U.S. Appl. No. 15/198,818, "Non-Final Office Action", dated Sep. 20, 2018, 12 pages.

U.S. Appl. No. 15/198,818, "Restriction Requirement", dated Mar. 22, 2018, 6 pages.

Cole et al., "The Ribosomal Database Project: Improved Alignments and New Tools for rRNA Analysis", Nucleic Acids Research, vol. 37, Jan. 2009, pp. D141-D145.

Darmanis et al., "ProteinSeq: High-Performance Proteomic Analyses by Proximity Ligation and Next Generation Sequencing", PLoS One, vol. 6, No. 9, e25583, Sep. 2011, pp. 1-10.

Mahmood et al., "Western Blot: Technique, Theory, and Trouble Shooting", North American Journal of Medical Sciences, vol. 4, No. 9, Sep. 2012, pp. 429-434.

Prediger, "Improving Immuno-PCR by Optimizing Antibody-Oligo Conjugation", IDT DECODED Newsletter, Available on the Internet: <https://www.idtdna.com/pages/education/decoded/article/improving-immuno-pcr-by-optimizing-antibody-oligo-conjugation>, Mar. 11, 2015, 7 pages.

International Search Report and Written Opinion dated Mar. 6, 2019 issued in corresponding PCT/US2018/048412.

\* cited by examiner

Collecting your sample

Remember to wash your hands thoroughly before and after sampling.

❶ 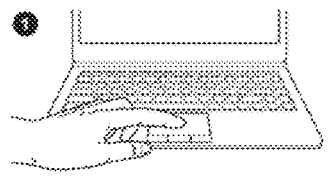

Register
- Sign in to Website
- Confirm your 9-digit kit ID and your SmartJane tube serial number.
- Log the date of your sample and click "confirm."

❷ 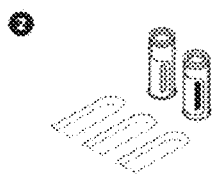

Get ready
- Remove the lids from the SmartJane™ and PCR water tubes, but keep them nearby.
- Stand the tubes upright in the tray.
- Remove 1 swab from the swab package.

❸ 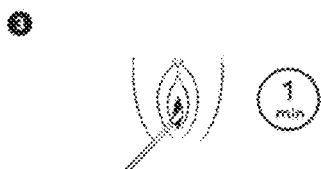

Swab
- Wet the swab in the sterile PCR water.
- Squat slightly and insert as far into the vagina as possible while still comfortable.
- Swab the interior for 1 minute.

❹ 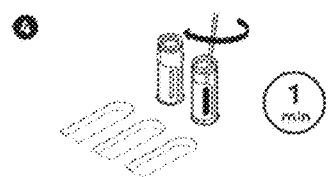

Stir
- Insert the swab into the SmartJane tube.
- Stir the swab for 1 minute.
- Remove the swab fully from the tube and discard the swab.

❺ 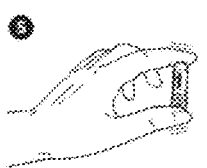

Shake
- Tightly replace the lid
- Shake the tube for 1 minute.

❻ 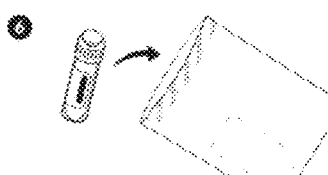

Send
- Place the sealed tube in the return bag
- Seal the bag and place it in the mailer.
- Seal the mailer and drop it in any mailbox.
- You may now dispose of the packaging.

FIG. 3

Production Primers

Forward Primer

```
              P5                    Index                  Nextera         Stagger        16S
AATGATACGGCGACCACCGAGATCTACAC XXXXXXX TCGTCGGCAGCGTCAGATGTGTATAAGAGACAG XXXX GTGTGCCAGCMGCCGCGGTAA
```

Reverse Primer

```
              P5                  Index                Nextera            Stagger        16S
CAAGCAGAAGACGGCATACGAGAT XXXXXXX GTCTCGTGGGCTCGGAGATGTGTATAAGAGACAG XXXX CCGGACTACHVGGGTWTCTAAT
```

---

2-step PCR Primers

Forward Primer                                                                                                    or HPV

```
                                                Index              Nextera
PCR #2: Forward Index Primer
AATGATACGGCGACCACCGAGATCTACAC XXXXXXX TCGTCGGCAGCGTC                               Stagger        16S
              P5                              TCGTCGGCAGCGTCAGATGTGTATAAGAGACAG XXXX GTGTGCCAGCMGCCGCGGTAA
                                              PCR #1: 16S-NNNN-F-Primer
```

Reverse Primer                                                                                                    or HPV

```
                                              Index              Nextera
PCR #2: Reverse Index Primer
CAAGCAGAAGACGGCATACGAGAT XXXXXXX GTCTCGTGGGCTCGG                                 Stagger        16S
              P7                            GTCTCGTGGGCTCGGAGATGTGTATAAGAGACAG XXXX CCGGACTACHVGGGTWTCTAAT
                                            PCR #1: 16S-NNNN-R-Primer
```

FIG. 11

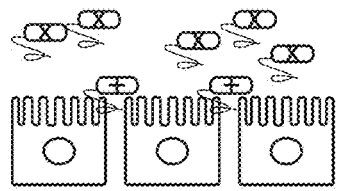
block pathogen entry
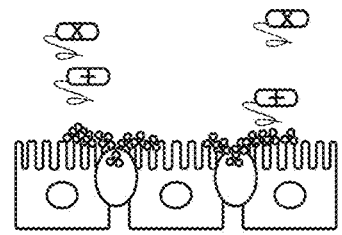
form mucous barrier
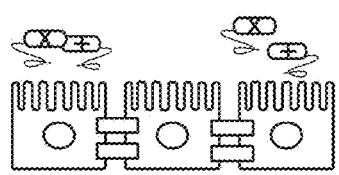
enhance apical tight junctions
produce antimicrobial factors
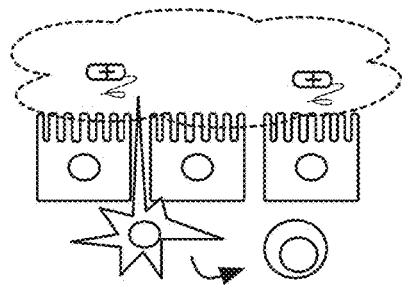
stimulate anti-inflammatory cytokines
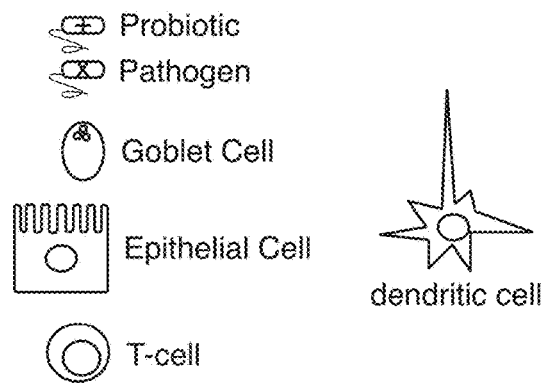
FIG. 20

SmartJane™ Sample Report

Report ID R94872664
Report Type Final

Patient
Name: Jane Doe
DOB: February 21, 1984
Age: 34
Gender: Female
Patient ID: 430AB9N4321KD

Order
Report Date: April 27, 2018
Provider: Steve Doe
Provider NPI: 1394214521
Order Date: April 5, 2018

Sample
Type: Swab
Source: Vaginal
Collected: April 10, 2018
Received: April 13, 2018

About this test

Detecting a microorganism by this test does not imply diagnosis of a disease state. Similarly, a lack of detection does not exclude the presence of a disease-causing microorganism or diagnosis of a disease state. The SmartJane test is not intended to replace routine exams with your doctor, including regular Pap smears.

Results and interpretation of this test

Your SmartJane screening test results indicate your sample is negative for high-risk HPV and negative for low-risk HPV. However, please continue to comply with your doctor's advice regarding routine exams.

Your sample tested positive for 1 of 4 STIs on the SmartJane test: Mycoplasma genitalium. Your sample tested negative for Chlamydia, Gonorrhea, and Syphilis. Please see your doctor as soon as possible.

Human Papillomavirus (HPV)

High-risk HPV ● Negative

High-risk types of the human papillomavirus (HPV) are types of HPV that have been associated with cervical cancer.

Your sample tested negative for all 14 high-risk HPV types on the SmartJane test.

| High-risk HPV type | 16 | 18 | 31 | 33 | 35 | 39 | 45 | 51 | 52 | 56 | 58 | 59 | 66 | 68 |
|---|---|---|---|---|---|---|---|---|---|---|---|---|---|---|
| High-risk HPV results | O | O | O | O | O | O | O | O | O | O | O | O | O | O |

Low-risk HPV ● Negative

Low-risk types of HPV have not been associated with cervical cancer, but may cause genital warts.

Your sample tested negative for all 5 low-risk HPV types on the SmartJane test.

| Low-risk HPV type | 6 | 11 | 42 | 43 | 44 |
|---|---|---|---|---|---|
| Low-risk HPV results | O | O | O | O | O |

Sexually Transmitted Infections (STIs)

| | |
|---|---|
| *Chlamydia trachomatis* (Chlamydia) | ● Negative |
| *Mycoplasma genitalium* | ● Positive |
| *Neisseria gonorrhoeae* (Gonorrhea) | ● Negative |
| *Treponema pallidum* (Syphilis) | ● Negative |

FIG. 26A

SmartJane™ Sample Report

Patient: Jane Doe
DOB: February 21, 1984

Health Conditions of the Vaginal Microbiome

In the following pages you will find information about how your vaginal microbiome is involved in 10 different health conditions. When organisms in your microbiome are outside of the healthy range, the condition is more likely, based on scientific literature. Some organisms have a more significant impact on the condition than others. Where possible, all the results for each condition are summarized in the "Significance Index" where the impact of each organism is weighted. Below you find the Significance Index for 7 health conditions in 3 categories.

Significance Index

The Significance Index provides information about your results, summarizing all the microbial associations found with a given health condition into a single value. The Significance Index is calculated using healthy ranges that have been determined for each microorganism using a cohort of self-reported healthy individuals. Results include microorganisms selected from scientific literature that are both associated with and inversely associated with a health condition.

Low significance 0 20 40 60 80 100 High significance

The Significance Index is expressed as a numerical value from 0 to 100. A lower Significance Index indicates that your microbiome has a lower number of microorganisms outside the healthy range, while a higher Significance Index indicates that your microbiome has an increased number of microorganisms outside the healthy range.

The Significance Index does not predict the likelihood of developing a specific disease, nor does it imply protection against a specific disease. Detection of a microorganism by this test does not imply a diagnosis. Similarly, a lack of detection does not exclude the presence of a disease-causing microorganism or a diagnosis of disease. Please consult your healthcare provider to interpret the results provided in this report.

STI Associated Conditions

| Condition | Significance Index |
|---|---|
| Pelvic Inflammatory Disease | 33 |
| Infertility | 33 |

Vaginal Dysbiosis Associated Conditions

| Condition | Significance Index |
|---|---|
| Bacterial Vaginosis | 14 |
| Aerobic Vaginitis | 0 |

FIG. 26B

SmartJane™ Sample Report

Patient: Jane Doe
DOB: February 21, 1984

HPV Associated Conditions

The presence of certain strains of human papillomavirus (HPV) in your vagina may cause distinctive lesions or pathologies, from genital warts to the development of cervical cancer. HPV infection is common and often resolves on its own without further complication. However, if you have a positive result, please consult with a medical professional for follow up. Other vaginal microorganisms may also affect how your body responds to HPV infection.

Human Papillomavirus Infection

| Association | Organism | Result | Out of Range |
|---|---|---|---|
|  | High-risk HPV (1-6) | ● Negative |  |
|  | Low-risk HPV (2,4-6) | ● Negative |  |
| Associated | *Gardnerella* (7) | ● Normal |  |
|  | *Gardnerella vaginalis* (8) | ● Normal |  |
|  | *Sneathia* (9) | ● Normal |  |
| Inversely associated | *Fusobacterium nucleatum* (10) | ● Low | ⚠ Condition more likely |
|  | *Lactobacillus iners* (9) | ● Low | ⚠ Condition more likely |

Cervical Cancer

| Association | Organism | Result | Out of Range |
|---|---|---|---|
|  | High-risk HPV (11-19) | ● Negative |  |

Squamous Intraepithelial Lesions (High- and Low-grade)

| Association | Organism | Result | Out of Range |
|---|---|---|---|
|  | High-risk HPV (19,20-23) | ● Negative |  |

Genital Warts

| Association | Organism | Result | Out of Range |
|---|---|---|---|
|  | Low-risk HPV (5,24-29) | ● Negative |  |

FIG. 26C

SmartJane™ Sample Report

Patient: Jane Doe
DOB: February 21, 1984

STI Associated Conditions

The presence of certain microorganisms may cause active sexually transmitted infections (STIs), and may also be related to cervical inflammation (cervicitis), pelvic inflammation (pelvic inflammatory disease), and infertility. A positive result in your sample is not a diagnosis; similarly, a negative result does not rule out the possibility of disease. Please consult with a medical professional for follow up.

Sexually Transmitted Infection

| Association | Organism | Result | Out of Range |
|---|---|---|---|
| Associated | *Chlamydia trachomatis* [30-32] | Negative | |
| | *Mycoplasma genitalium* [33] | Positive | ⚠ Condition more likely |
| | *Neisseria gonorrhoeae* [34,35] | Negative | |
| | *Treponema pallidum* [36] | Negative | |

Cervicitis

| Association | Organism | Result | Out of Range |
|---|---|---|---|
| Associated | High-risk HPV [37] | Negative | |
| | *Chlamydia trachomatis* [38] | Negative | |
| | *Mycoplasma genitalium* [37] | Positive | ⚠ Condition more likely |
| Inversely associated | *Lactobacillus* [39] | Low | ⚠ Condition more likely |

Pelvic Inflammatory Disease

Significance Index 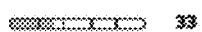 33

| Association | Organism | Result | Out of Range |
|---|---|---|---|
| Associated | *Chlamydia trachomatis* [40-42] | Negative | |
| | *Mycoplasma genitalium* [46,47] | Positive | ⚠ Condition more likely |
| | *Neisseria gonorrhoeae* [40,42-45] | Negative | |

Infertility

Significance Index 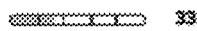 33

| Association | Organism | Result | Out of Range |
|---|---|---|---|
| Associated | *Chlamydia trachomatis* [40] | Negative | |
| | *Mycoplasma genitalium* [41] | Positive | ⚠ Condition more likely |
| | *Neisseria gonorrhoeae* [40] | Negative | |

FIG. 26D

SmartJane™ Sample Report                           Patient  Jane Doe
                                                   DOB  February 21, 1984

Vaginal Dysbiosis Associated Conditions

Vaginal dysbiosis is a term that describes an imbalance in the aerobic and anaerobic microorganisms normally present in your vagina. Vaginal dysbiosis may or may not have active clinical symptoms. Please consult with a medical professional for follow up regarding these results.

Bacterial Vaginosis                            Significance Index ━━━━━▶

| Association | Organism | Result | Out of Range |
|---|---|---|---|
| Associated | *Aerococcus* (48,49) | ● Normal | |
| | *Aerococcus christensenii* (50) | ● Normal | |
| | *Atopobium* (48,51) | ● Normal | |
| | *Atopobium vaginae* (49,50,53) | ● Normal | |
| | *Dialister microaerophilus* (50,53) | ● Normal | |
| | *Gardnerella* (48) | ● Normal | |
| | *Gardnerella vaginalis* (49-51,54) | ● Normal | |
| | *Gemella* (48,53) | ● Normal | |
| | *Megasphaera* (49-50) | ● Normal | |
| | *Mobiluncus curtisii* (55,56) | ● Normal | |
| | *Papillibacter* (49) | ● Normal | |
| | *Parvimonas* (48) | ● Normal | |
| | *Peptoniphilus* (48) | ● Normal | |
| | *Peptostreptococcus* (48,54) | ● Normal | |
| | *Porphyromonas* (48) | ● Normal | |
| | *Prevotella* (48-50,53,54) | ● Normal | |
| | *Prevotella amnii* (50,57) | ● Normal | |
| | *Prevotella timonensis* (50,53) | ● Normal | |
| | *Sneathia* (48,50) | ● Normal | |

FIG. 26E

SmartJane™ Sample Report

Patient: Jane Doe
DOB: February 21, 1984

Vaginal Imbalance (continued)

Bacterial Vaginosis (continued) — Significance Index

| Association | Organism | Result | Out of Range |
|---|---|---|---|
| Inversely associated | Lactobacillus | Low | ⚠ Condition more likely |
| | Lactobacillus iners | Low | ⚠ Condition more likely |
| | Lactobacillus jensenii | Low | ⚠ Condition more likely |

Aerobic Vaginitis — Significance Index

| Association | Organism | Result | Out of Range |
|---|---|---|---|
| Associated | Gardnerella vaginalis | Normal | |
| | Staphylococcus aureus | Normal | |
| | Streptococcus agalactiae | Normal | |

FIG. 26F

METHOD AND SYSTEM FOR CHARACTERIZATION FOR FEMALE REPRODUCTIVE SYSTEM-RELATED CONDITIONS ASSOCIATED WITH MICROORGANISMS

CROSS-REFERENCE TO RELATED APPLICATIONS

This application is a continuation-in-part of U.S. application Ser. No. 15/198,818 filed 30 Jun. 2016, which claims the benefit of U.S. Provisional Application Ser. No. 62/186,793 filed 30 Jun. 2015, which are each incorporated in its entirety herein by this reference.

This application additionally claims the benefit of U.S. Provisional Application Ser. No. 62/551,155 filed 28 Aug. 2017, U.S. Provisional Application Ser. No. 62/585,131 filed 13 Nov. 2017, and U.S. Provisional Application Ser. No. 62/653,402 filed 5 Apr. 2018, which are each incorporated in its entirety herein by this reference.

REFERENCE TO A "SEQUENCE LISTING" SUBMITTED AS ASCII TEXT FILES VIA EFS-WEB

The Sequence Listing written in file SEQ_101215-P36US-0035346.TXT created on Nov. 28, 2018, 54,128 bytes, machine format IBM-PC, MS-Windows operating system, in accordance with 37 C.F.R. §§ 1.821- to 1.825, is hereby incorporated by reference in its entirety for all purposes.

TECHNICAL FIELD

The disclosure generally relates to genomics and microbiology.

BACKGROUND

A microbiome can include an ecological community of commensal, symbiotic, and pathogenic microorganisms that are associated with an organism. Characterization of the human microbiome is a complex process. The human microbiome includes over 10 times more microbial cells than human cells, but characterization of the human microbiome is still in nascent stages such as due to limitations in sample processing techniques, genetic analysis techniques, and resources for processing large amounts of data. Present knowledge has clearly established the role of microbiome associations with multiple health conditions, and has become an increasingly appreciated mediator of host genetic and environmental factors on human disease development. The microbiome is suspected to play at least a partial role in a number of health/disease-related states. Further, the microbiome may mediate effects of environmental factors on human, plant, and/or animal health. Given the profound implications of the microbiome in affecting a user's health, efforts related to the characterization of the microbiome, the generation of insights from the characterization, and the generation of therapeutics configured to rectify states of dysbiosis should be pursued. Conventional approaches for analyzing the microbiomes of humans and/or providing therapeutic measures based on gained insights have, however, left many questions unanswered.

Cervical cancer is one of the major causes of cancer-related deaths in women, with an annual worldwide mortality of 250,000. Human papillomavirus (HPV) DNA can be detected in almost all (>99%) cervical cancer specimens, and HPV is therefore considered the predominant causative agent for cervical cancer.

A woman's health is critical for her general well-being and reproductive success, and is in part determined by microbiome composition, the presence of pathogens associated with sexually transmitted infections (STI), and the presence of human papillomavirus (HPV) types that can cause genital warts or cervical cancer. For example, the composition of a woman's vaginal microbiome can play an important role in women's health and reproductive success.

As such, there is a need in the field of microbiology for a new and useful method and/or system for characterizing, monitoring, diagnosing, and/or intervening in one or more health conditions associated with women's health (e.g., female reproductive system-related conditions; etc.), such as for individualized and/or population-wide use.

BRIEF DESCRIPTION OF THE FIGURES

FIG. 3 includes a flowchart representation of variations of an embodiment of a method;

FIG. 11 includes specific examples of primers (Production Primers, Forward Primer=SEQ ID NO: 79; Production Primers, Reverse Primer=SEQ ID NO: 80; 2-step PCR Primers, Forward Primer, PCR #2 Forward Index Primer=SEQ ID NO: 81; 2-step PCR Primers, Forward Primer, PCR #1 16S-NNNN-F-Primer=SEQ ID NO: 82; 2-step PCR Primers, Reverse Primer, PCR #2 Reverse Index Primer=SEQ ID NO: 83; 2-step PCR Primers, Reverse Primer, PCR #1 16S-NNNN-R-Primer=SEQ ID NO: 84);

FIG. 20 includes variations of mechanisms by which probiotic-based therapies operate in an embodiment of a method;

FIG. 26A-26F include specific examples of notifications based on one or more female reproductive system-related characterizations.

DESCRIPTION OF THE EMBODIMENTS

The following description of the embodiments is not intended to limit the embodiments, but rather to enable any person skilled in the art to make and use.

1. Overview

Figure 1A:
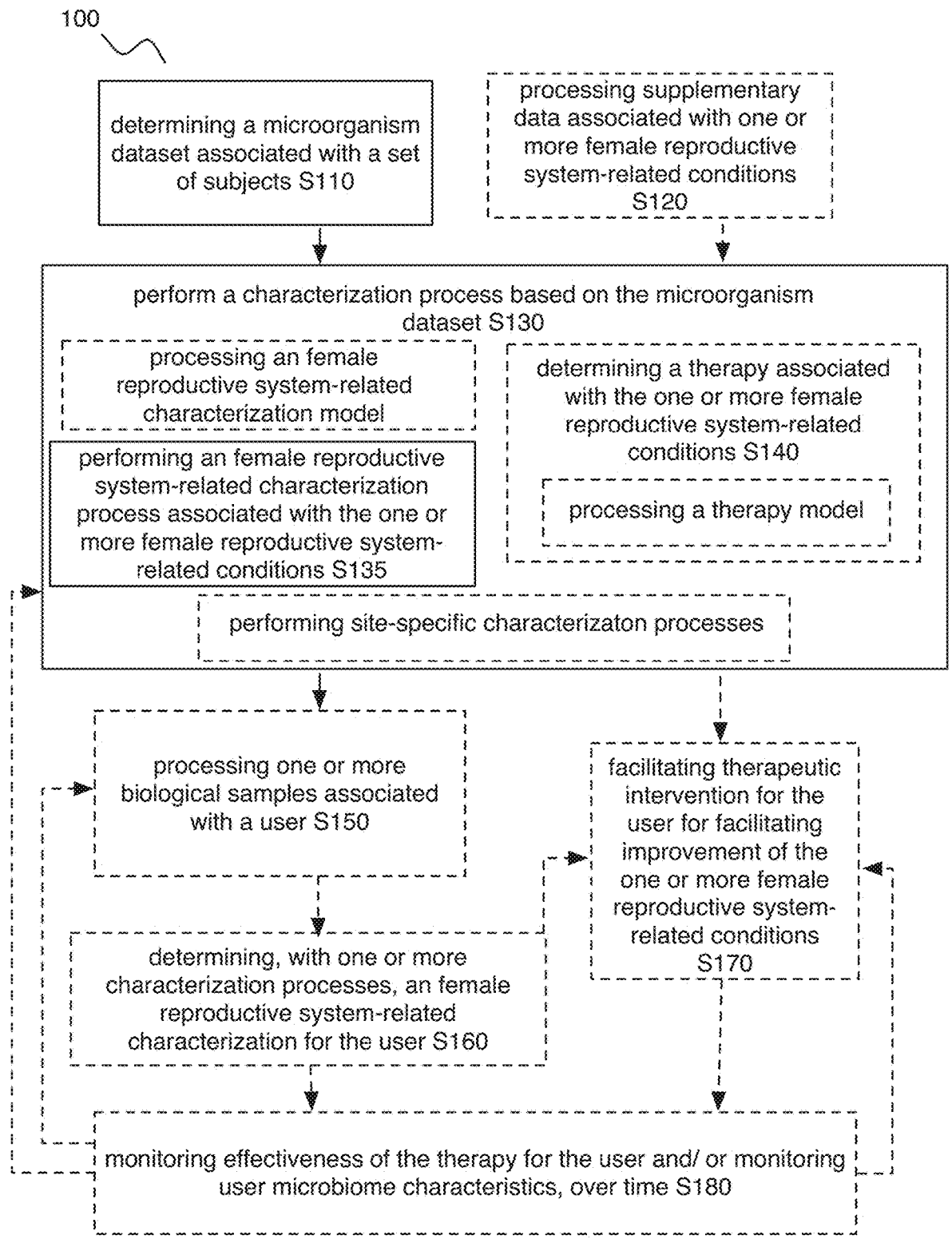
FIG. 1A-1C includes flowchart representations of variations of an embodiment of a method.
Figure 1B:
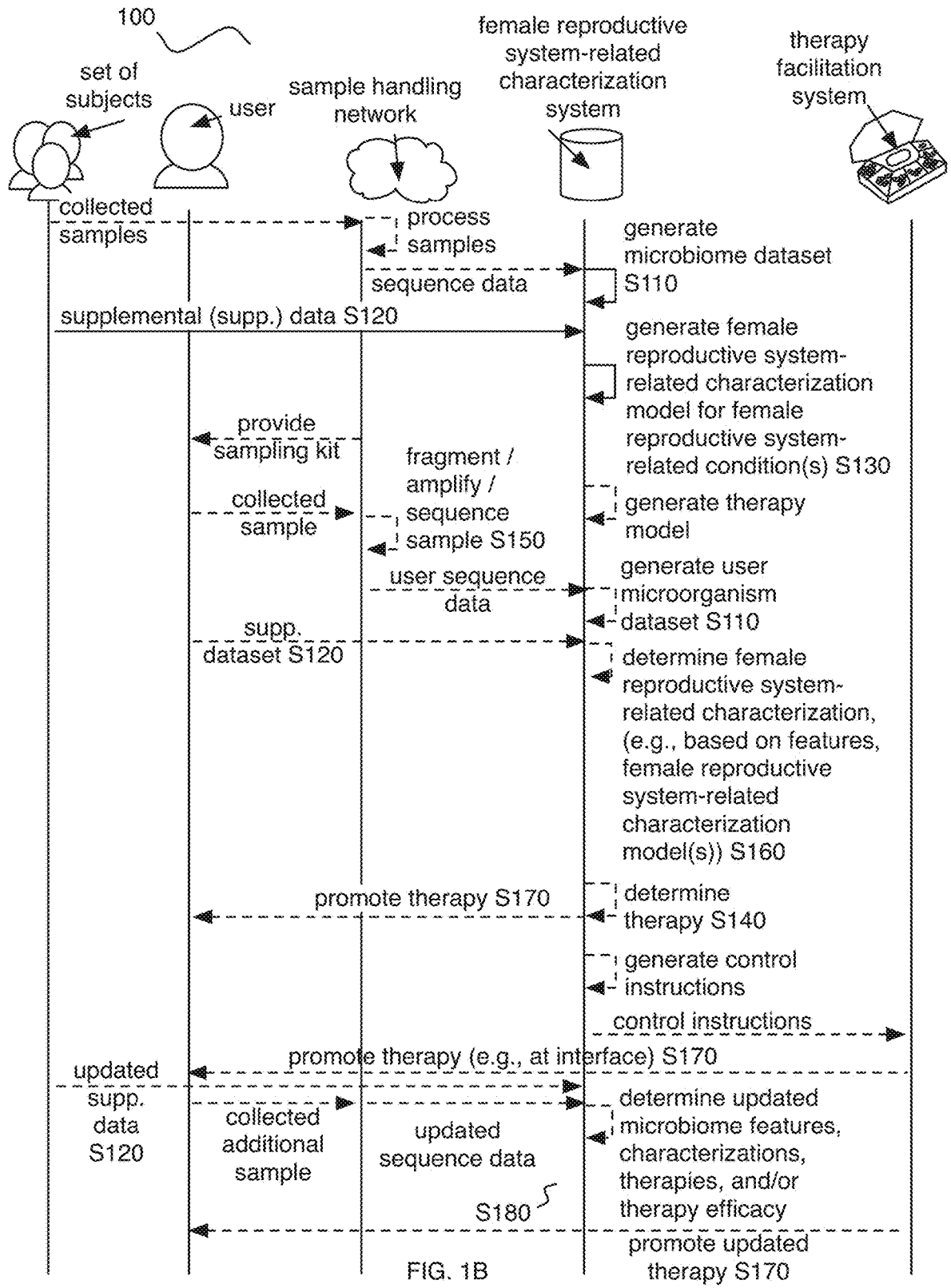
Figure 1C:
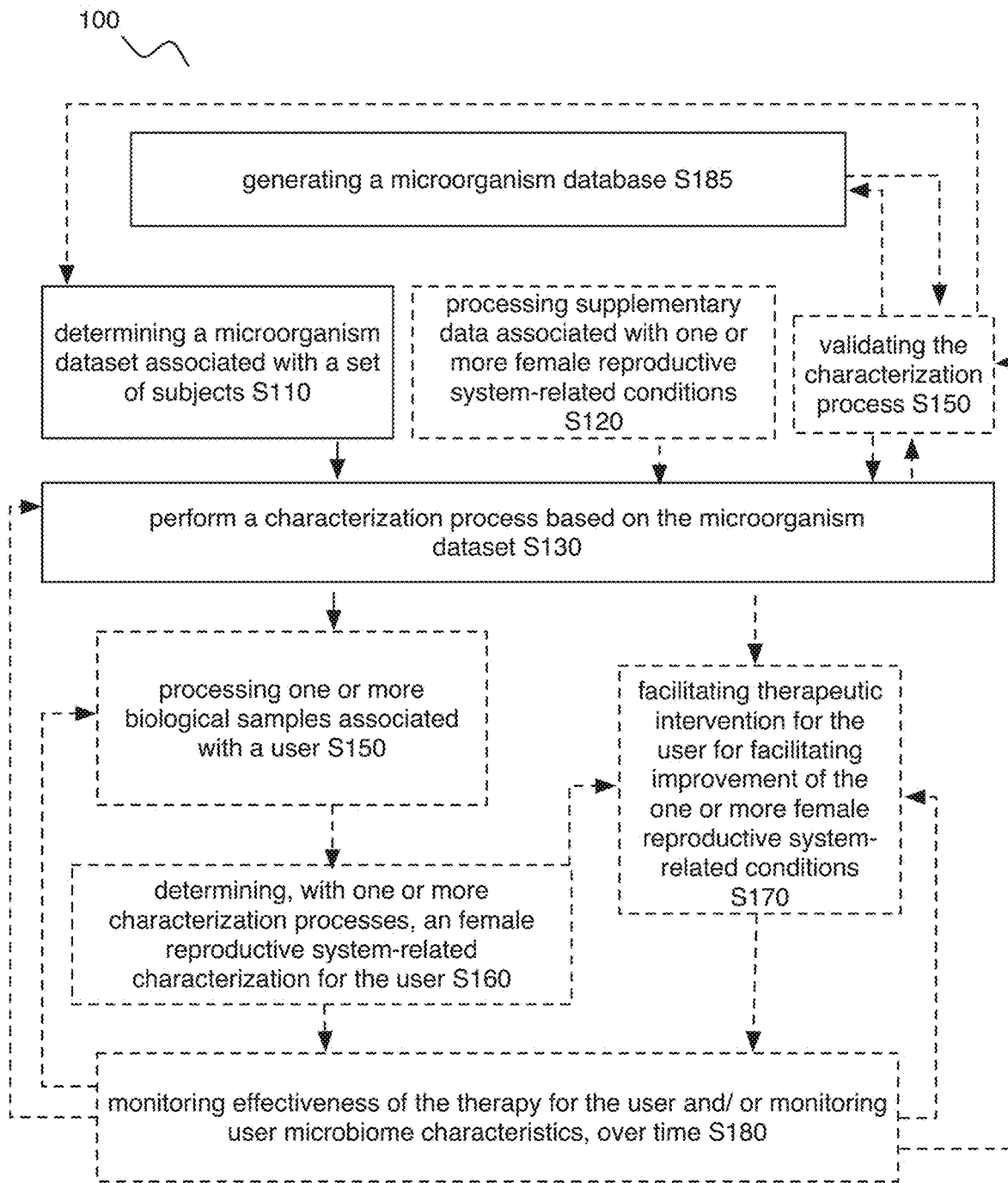

As shown in FIG. 1A-1C, embodiments of a method 100 (e.g., for characterizing one or more female reproductive system-related conditions, etc.) can include: determining a microorganism dataset (e.g., microorganism sequence dataset, microbiome composition diversity dataset such as based upon a microorganism sequence dataset, microbiome functional diversity dataset such as based upon a microorganism sequence dataset, etc.) associated with a set of users (e.g., determining the microorganism dataset based on samples from a set of subjects) S110; and/or performing a characterization process (e.g., pre-processing, feature determination, feature processing, female reproductive system-related characterization model processing, etc.) associated with the one or more female reproductive system-related conditions, based on the microorganism dataset (e.g., based on microbiome composition features and/or microbiome functional features derived from the microorganism dataset and associated with the one or more female reproductive system-related conditions; etc.) S130, where performing the characterization process can additionally or alternatively include performing a female reproductive system-related characterization process for the one or more female reproductive system-related conditions S135, and/or determining one or more therapies (e.g., determining therapies for preventing, ameliorating, reducing the risk of, and/or otherwise improving the one or more female reproductive system-related conditions, etc.) S140.

Embodiments of the method 100 can additionally or alternatively include one or more of: processing supplementary data associated with (e.g., informative of; describing; indicative of; correlated with, etc.) one or more female reproductive system-related conditions S120; processing one or more biological samples associated with a user (e.g., subject, human, animal, patient; etc.) S150; determining, with one or more characterization processes, a female reproductive system-related characterization for the user for one or more female reproductive system-related conditions, based on a user microorganism dataset (e.g., user microorganism sequence dataset; user microbiome composition dataset; user microbiome function dataset; user microbiome features derived from the user microorganism dataset, where the user microbiome features can correspond to feature values for the microbiome features determined from one or more characterization processes; etc.) associated with a biological sample of the user S160; facilitating therapeutic intervention for the one or more female reproductive system-related conditions for the user (e.g., based upon the female reproductive system-related characterization and/or a therapy model; etc.) S170; monitoring effectiveness of one or more therapies and/or monitoring other suitable components (e.g., microbiome characteristics, etc.) for the user (e.g., based upon processing a series of biological samples from the user), over time (e.g., such as to assess user microbiome characteristics such as user microbiome composition features and/or functional features associated with the therapy, for the user over time, etc.) S180; processing a microorganism database S185; validating S190; and/or any other suitable processes.

In a specific example, the method 100 (e.g., for characterizing at least one female reproductive system-related condition associated with microorganisms, etc.) can include determining a microorganism sequence dataset associated with a set of subjects (e.g., including subjects with the female reproductive system-related condition; including subjects without the female reproductive system-related conditions, where samples and/or data associated with such subjects can act as a control; etc.), based on microorganism nucleic acids from samples associated with the set of subjects, where the samples include at least one sample associated with one or more female reproductive system-related conditions; collecting, for the set of subjects, supplementary data associated with one or more female reproductive system-related conditions; determining a set of microbiome features including at least one of a set of microbiome composition features and a set of microbiome functional features, based on the microorganism sequence dataset; generating a female reproductive system-related characterization model based on the supplementary data and the set of microbiome features, where the female reproductive system-related characterization model is associated with the one or more female reproductive system-related conditions; determining a female reproductive system-related characterization for a user for the one or more female reproductive system-related conditions based on the female reproductive system-related characterization model; and facilitating therapeutic intervention for a user for the one or more female reproductive system relation conditions (e.g., providing a therapy to the user for facilitating improvement of the one or more female reproductive system-related conditions, etc.) based on the female reproductive system-related characterization.

In a specific example, the method 100 (e.g., for characterizing at least one female reproductive system-related condition associated with microorganisms, etc.) can include collecting a sample from a user (e.g., via sample kit provision and collection, etc.), where the sample includes microorganism nucleic acids corresponding to the microorganisms associated with one or more female reproductive system-related conditions; determining a microorganism dataset associated with the user based on the microorganism nucleic acids of the sample (e.g., based on sample preparation and/or sequencing with the sample, etc.); determining user microbiome features (e.g., including at least one of user microbiome composition features and user microbiome functional features, etc.) based on the microorganism dataset, where the user microbiome features are associated with the one or more female reproductive system-related conditions; determining a female reproductive system-related characterization for the user for the one or more female reproductive system-related conditions based on the user microbiome features; and/or facilitating therapeutic intervention in relation to a therapy for the user for facilitating improvement of the one or more female reproductive system-related conditions (e.g., promoting the therapy to the user; etc.), based on the female reproductive system-related characterization.

In a specific example, the at least one female reproductive system-related condition can include an HPV infection and at least one of bacterial vaginosis, cervicitis, pelvic inflammatory disease, idiopathic infertility, aerobic vaginitis, and infertility; the set of microbiome composition features can include a first subset of microbiome composition features associated with a set of bacterial targets, and a second subset of microbiome features associated with a set of HPV targets; the set of bacterial targets can include at least one of *Aerococcus* (genus), *Aerococcus christensenii* (species), *Atopobium* (genus), *Atopobium vaginae* (species), *Chlamydia trachomatis* (species), *Dialister micraerophilus* (species), *Fusobacterium* (genus), *Fusobacterium nucleatum* (species), *Gardnerella* (genus), *Gardnerella vaginalis* (species), *Gemella* (genus), *Lactobacillus* (genus), *Lactobacillus iners* (species), *Lactobacillus jensenii* (species), *Megasphaera* (genus), *Mobiluncus* (genus), *Mobiluncus curtisii* (species), *Mobiluncus mulieris* (species), *Mycoplasma genitalium* (species), *Neisseria gonorrhoeae* (species), *Papillibacter* (genus), *Parvimonas* (genus), *Peptoniphilus* (genus), *Peptostreptococcus* (genus), *Porphyromonas* (genus), *Prevotella* (genus), *Prevotella amnii* (species), *Prevotella timonensis* (species), *Sneathia* (genus), *Staphylococcus aureus* (species), *Streptococcus agalactiae* (species), and *Treponema pallidum* (species); the set of HPV targets can include at least one of HPV types 6, 11, 42, 43, 44, 16, 18, 31, 33, 35, 39, 45, 51, 52, 56, 58, 59, 66, and 68.

Embodiments of the method 100 and/or system 200 can function to characterize (e.g., assess, evaluate, diagnose, describe, etc.) one or more female reproductive system-related conditions (e.g., characterizing the female reproductive system-related conditions themselves, such as determining microbiome features correlated with and/or otherwise associated with the female reproductive system-related conditions; characterizing one or more female reproductive system-related conditions for one or more users, such as determining propensity metrics for the one or more female reproductive system-related conditions for the one or more users; etc.) and/or one or more users for one or more female reproductive system-related conditions.

Embodiments of the method 100 and/or system 200 can additionally or alternatively function to enable, provide, facilitate analyses for, include, and/or be associated with a women's health assay that can combine one or more of: self-sampling, sequencing-based HPV detection and genotyping, microbiome analysis (e.g., vaginal microbiome analysis, etc.), and/or STI-associated pathogen detection. In a specific example, embodiments can enable, provide, facilitate analyses for, include, and/or be associated with an assay including genotyping and detection of 14 hrHPV types, 5 low-risk HPV types (lrHPV), and/or the relative abundance of 32 bacterial taxa of clinical importance, including one or more of *Lactobacillus, Sneathia, Gardnerella*, and/or 4 pathogens involved in STI (e.g., *Chlamydia trachomatis, Mycoplasma genitalium, Neisseria gonorrhoeae,* and *Treponema pallidum*, which can cause chlamydia, genital tract infections, gonorrhea, and syphilis, respectively, etc.) such as with high sensitivity, specificity, and reproducibility. In a specific example, embodiments can enable, provide, facilitate analyses for, include, and/or be associated with a women's health assay that can not only detect whether HPV is present in a sample, but can also identifies the presence of one or more specific types of HPV by using sequencing analysis, such as including the most prevalent hrHPV types in cervical cancer lesions (e.g., 16 and 18) but can additionally or alternatively detect additional hrHPV types (e.g., 12 or more additionally types), such as through applying broad-range primers. Such HPV coverage can account for changing prevalences of hrHPV types that may shift in the setting of newly introduced HPV vaccines. In a specific example, the women's health assay can additionally or alternatively detect and report the relative abundance of commensal and pathogenic bacteria (and/or any suitable microorganisms associated with women's health, etc.) in samples (e.g., vaginal samples).

Additionally or alternatively, embodiments of the method 100 and/or system 200 can function to identify microbiome features and/or other suitable data associated with (e.g., positive correlated with, negatively correlated with, etc.) one or more female reproductive system-related conditions, such as for use as biomarkers (e.g., for diagnostic processes, for treatment processes, etc.). In examples, female reproductive system-related characterization can be associated with at least one or more of microbiome composition (e.g., microbiome composition diversity, etc.), microbiome function (e.g., microbiome functional diversity, etc.), and/or other suitable microbiome-related aspects. In an example, microorganism features (e.g., describing composition, function, and/or diversity of recognizable patterns, such as in relation to relative abundance of microorganisms that are present in a user's microbiome, such as for subjects exhibiting one or more female reproductive system-related conditions; etc.) and/or microorganism datasets (e.g., from which microbiome features can be derived, etc.) can be used for characterizations (e.g., diagnoses, risk assessments, etc.), therapeutic intervention facilitation, monitoring, and/or other suitable purposes, such as by using bioinformatics pipelines, analytical techniques, and/or other suitable approaches described herein. Additionally or alternatively, embodiments of the method 100 and/or system 200 can function to perform cross-condition analyses for a plurality of female reproductive system-related conditions (e.g., performing characterization processes for a plurality of female reproductive system-related conditions, such as determining correlation, covariance, comorbidity, and/or other suitable relationships between different female reproductive system-related conditions, etc.), such as in the context of characterizing (e.g., diagnosing; providing information related to; etc.) and/or treating a user.

Additionally or alternatively, embodiments can function to facilitate therapeutic intervention (e.g., therapy selection; therapy promotion and/or provision; therapy monitoring; therapy evaluation; etc.) for one or more female reproductive system-related conditions, such as through promotion of associated therapies (e.g., in relation to specific body sites such as a gut site, skin site, nose site, mouth site, genital site, other suitable body sites, other collection sites; therapies determined by therapy models; etc.). Additionally or alternatively, embodiments can function to generate models (e.g., female reproductive system-related characterization models such as for phenotypic prediction; therapy models such as for therapy determination; machine learning models such as for feature processing; etc.), such as models that can be used to characterize and/or diagnose users based on their microbiome (e.g., user microbiome features; as a clinical diagnostic; as a companion diagnostic, etc.), and/or that can be used to select and/or provide therapies for subjects in relation to one or more female reproductive system-related conditions. Additionally or alternatively, embodiments can perform any suitable functionality described herein.

As such, data from populations of users (e.g., populations of subjects associated with one or more female reproductive system-related conditions; positively or negatively correlated with one or more female reproductive system-related conditions; etc.) can be used to characterize subsequent users, such as for indicating microorganism-related states of health and/or areas of improvement, and/or to facilitate therapeutic intervention (e.g., promoting one or more therapies; facilitating modulation of the composition and/or functional diversity of a user's microbiome toward one or more of a set of desired equilibrium states, such as states correlated with improved health states associated with one or more female reproductive system-related conditions; etc.), such as in relation to one or more female reproductive system-related conditions. Variations of the method 100 can further facilitate selection, monitoring (e.g., efficacy monitoring, etc.) and/or adjusting of therapies provided to a user, such as through collection and analysis (e.g., with female reproductive system-related characterization models) of additional samples from a user over time (e.g., throughout the course of a therapy regimen, through the extent of a user's experiences with female reproductive system-related conditions; etc.), across body sites (e.g., across sample collection sites of a user, such as collection sites corresponding to a particular body site type such as a gut site, mouth site, nose site, skin site, genital site; etc.), in addition or alternative to processing supplementary data over time, such as for one or more female reproductive system-related conditions. However, data from populations, subgroups, individuals, and/or other suitable entities can be used by any suitable portions of embodiments of the method 100 and/or system 200 for any suitable purpose.

Embodiments of the method 100 and/or system 200 can preferably determine and/or promote (e.g., provide; present; notify regarding; etc.) characterizations and/or therapies for one or more female reproductive system-related conditions, and/or any suitable portions of embodiments of the method 100 and/or system 200 can be performed in relation to female reproductive system-related conditions. In specific examples, as shown in FIG. 26A-26F, notifications based on one or more characterizations can be provided to one or more users.

Female reproductive system-related conditions can include one or more of: HPV infection, cervical cancer, syphilis, squamous intraepithelial lesions (high- and low-grade), cervicitis, pelvic inflammatory disease, bacterial vaginosis, aerobic vaginitis, idiopathic infertility, chlamydia, endometriosis, genital herpes, genital warts, gonorrhea, painful periods, polycystic ovarian syndrome, urinary tract infection, STIs, women's health-related conditions, and/or any suitable conditions associated with the female reproductive system and/or women's health.

Additionally or alternatively, female reproductive system-related conditions can include one or more of: diseases, symptoms, causes (e.g., triggers; etc.), associated severity, behaviors (e.g., physical activity behavior; alcohol consumption; smoking behaviors; stress-related characteristics; other psychological characteristics; sickness; social behaviors; caffeine consumption; alcohol consumption; sleep habits; other habits; diet-related behaviors such as fiber intake, fruit intake, vegetable intake; meditation and/or other relaxation behaviors; lifestyle conditions associated with female reproductive system-related conditions; lifestyle conditions informative of, correlated with, indicative of, facilitative of, and/or otherwise associated with diagnosis and/or therapeutic intervention for female reproductive system-related conditions; behaviors affecting and/or otherwise associated with the female reproductive system and/or female reproductive system-related conditions; etc.), environmental factors, demographic-related characteristics (e.g., age, weight, race, gender, etc.), phenotypes (e.g., phenotypes measurable for a human, animal, plant, fungi body; phenotypes associated with female reproductive system and/or other related aspects, etc.), and/or any other suitable aspects associated with female reproductive system-related conditions. In an example, one or more female reproductive system-related conditions can interfere with normal physical, mental, social and/or emotional function.

Embodiments of the method 100 and/or system 200 can be implemented for a single user, such as in relation to applying one or more sample handling processes and/or characterization processes for processing one or more biological samples (e.g., collected across one or more collection sites, etc.) from the user, for female reproductive system-related characterization, facilitating therapeutic intervention, and/or for any other suitable purpose. Additionally or alternatively, embodiments can be implemented for a population of subjects (e.g., including the user, excluding the user), where the population of subjects can include subjects similar to and/or dissimilar to any other subjects for any suitable type of characteristics (e.g., in relation to female reproductive system-related conditions, demographic characteristics, behaviors, microbiome composition and/or function, etc.); implemented for a subgroup of users (e.g., sharing characteristics, such as characteristics affecting female reproductive system-related characterization and/or therapy determination; etc.); implemented for plants, animals, microorganisms, and/or any other suitable entities. Thus, information derived from a set of subjects (e.g., population of subjects, set of subjects, subgroup of users, etc.) can be used to provide additional insight for subsequent users. In a variation, an aggregate set of biological samples is preferably associated with and processed for a wide variety of subjects, such as including subjects of one or more of: different demographic characteristics (e.g., genders, ages, marital statuses, ethnicities, nationalities, socioeconomic statuses, sexual orientations, etc.), different female reproductive system-related conditions (e.g., health and disease states; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable characteristic (e.g., characteristics influencing, correlated with, and/or otherwise associated with microbiome composition and/or function, etc.). In examples, as the number of subjects increases, the predictive power of processes implemented in portions of embodiments of the method 100 and/or system 200 can increase, such as in relation to characterizing subsequent users (e.g., with varying characteristics, etc.) based upon their microbiomes (e.g., in relation to different collection sites for samples for the users, etc.). However, portions of embodiments of the method 100 and/or system 200 can be performed and/or configured in any suitable manner for any suitable entity or entities.

In variations, portions of embodiments of the method 100 can be repeatedly performed in any suitable order and/or any suitable components of embodiments of the system 200 can be repeatedly applied, such as to improve any suitable portions of embodiments of the method 100 and/or any suitable components of embodiments of the system 200. In an example, portions of embodiments of the method 100 can be repeatedly performed to enable refining of one or more microorganism databases (e.g., improving taxonomic databases through identifying new markers associated with different taxa and/or conditions, such as by collecting and analyzing additional samples, such as samples collected from subjects over time, the course of one or more female reproductive system-related conditions, and/or therapeutic interventions; etc.); refining of the characterization process (e.g., through updating reference abundances used to compare against user relative abundances of targets for identifying clinically relevant results; through generation and updating of characterization models; through increasing the number of conditions that can be characterized using a single biological sample; etc.); the therapy process (e.g., through monitoring and modulating microbiome composition with therapies over time such as through iteratively performing characterization processes over time, such as where the therapies can be selected based on characterization results possessing sensitivity, specificity, precision, and negative predictive value; etc.), and/or other suitable processes.

Data described herein (e.g., microbiome features, microorganism datasets, models, female reproductive system-related characterizations, supplementary data, notifications, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with female reproductive system-related characterizations, such as where the female reproductive system-related characterization describes the female reproductive system-related conditions and/or user microbiome status at a particular time; etc.); changes in temporal indicators (e.g., changes in female reproductive system-related characterizations over time, such as in response to receiving a therapy; latency between sample collection, sample analysis, provision of a female reproductive system-related characterization or therapy to a user, and/or other suitable portions of embodiments of the method 100; etc.); and/or any other suitable indicators related to time.

Additionally or alternatively, parameters, metrics, inputs, outputs, and/or other suitable data can be associated with value types including: scores (e.g., female reproductive system-related condition propensity scores; feature relevance scores; correlation scores, covariance scores, microbiome diversity scores, severity scores; etc.), individual values (e.g., individual female reproductive system-related condition scores, such as condition propensity scores, for different collection sites, etc.), aggregate values, (e.g., overall scores based on individual microorganism-related scores for different collection sites, etc.), binary values (e.g., presence or absence of a microbiome feature; presence or absence of a female reproductive system-related condition; etc.), relative values (e.g., relative taxonomic group abundance, relative microbiome function abundance, relative feature abundance, etc.), classifications (e.g., female reproductive system-related condition classifications and/or diagnoses for users; feature classifications; behavior classifications; demographic characteristic classifications; etc.), confidence levels (e.g., associated with microorganism sequence datasets; with microbiome diversity scores; with other female reproductive system-related characterizations; with other outputs; etc.), identifiers, values along a spectrum, and/or any other suitable types of values. Any suitable types of data described herein can be used as inputs (e.g., for different analytical techniques, models, and/or other suitable components described herein), generated as outputs (e.g., of different analytical techniques, models, etc.), and/or manipulated in any suitable manner for any suitable components associated with the method 100 and/or system 200.

One or more instances and/or portions of embodiments of the method 100 and/or processes described herein can be performed asynchronously (e.g., sequentially), concurrently (e.g., parallel data processing; concurrent cross-condition analysis; multiplex sample processing, such as multiplex amplification of microorganism nucleic acid fragments corresponding to target sequences associated with female reproductive system-related conditions; performing sample processing and analysis for substantially concurrently evaluating a panel of female reproductive system-related conditions; computationally determining microorganism datasets, microbiome features, and/or characterizing female reproductive system-related conditions in parallel for a plurality of users; such as concurrently on different threads for parallel computing to improve system processing ability; etc.), in temporal relation (e.g., substantially concurrently with, in response to, serially, prior to, subsequent to, etc.) to a trigger event (e.g., performance of a portion of the method 100), and/or in any other suitable order at any suitable time and frequency by and/or using one or more instances of the system 200, components, and/or entities described herein. In an example, the method 100 can include generating a microorganism dataset based on processing microorganism nucleic acids of one or more biological samples with a bridge amplification substrate of a next generation sequencing platform (and/or other suitable sequencing system) of a sample handling system, and determining microbiome features and microbiome functional diversity features at computing devices operable to communicate with the next generation sequencing platform. However, the method 100 and/or system 200 can be configured in any suitable manner.

2. Examples

Microbiome analysis can enable accurate and/or efficient characterization and/or therapy provision (e.g., according to portions of embodiments of the method 100, etc.) for female reproductive system-related conditions caused by, correlated with, and/or otherwise associated with microorganisms. Specific examples of the technology can overcome several challenges faced by conventional approaches in characterizing a female reproductive system-related conditions and/or facilitating therapeutic intervention. First, conventional approaches can require patients to visit one or more care providers to receive a characterization and/or a therapy recommendation for a female reproductive system-related condition (e.g., through diagnostic medical procedures such as in-clinic cervical cancer screening), which can amount to inefficiencies and/or health-risks associated with the amount of time elapsed before diagnosis and/or treatment, with inconsistency in healthcare quality, and/or with other aspects of care provider visitation. Second, conventional genetic sequencing and analysis technologies for human genome sequencing can be incompatible and/or inefficient when applied to the microbiome (e.g., where the human microbiome can include over 10 times more microbial cells than human cells; where viable analytical techniques and the means of leveraging the analytical techniques can differ; where optimal sample processing techniques can differ, such as for reducing amplification bias; where different approaches to female reproductive system-related characterizations can be employed; where the types of conditions and correlations can differ; where causes of the associated conditions and/or viable therapies for the associated conditions can differ; where sequence reference databases can differ; where the microbiome can vary across different body regions of the user such as at different collection sites; etc.). Third, the onset of sequencing technologies (e.g., next-generation sequencing, associated technologies, etc.) has given rise to technological issues (e.g., data processing and analysis issues for the plethora of generated sequence data; issues with processing a plurality of biological samples in a multiplex manner; information display issues; therapy prediction issues; therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, specific examples of the technology can include a women's health assay that combines self-sampling, sequencing-based HPV detection and genotyping, microbiome analysis (e.g., vaginal microbiome analysis, etc.), and STI-associated pathogen detection, which can enable comprehensive women's health screening (e.g., vaginal microbiome sequencing; etc.). In specific examples, offering women the opportunity to self-collect vaginal specimens poses lowers barriers for women to be screened, and thus can lead to increased participation rates. In specific examples, the women's health assay can complement regular screening programs, such as where portions of embodiments of the method 100 and/or components of embodiments of the system 200 can leverage results from the women's health assay to recommend physician examination, such as where characterizations can include positive results of one or more female reproductive system-related conditions, which can thereby positively impact rates of detection of cervical cancer and/or other suitable female reproductive system-related conditions, and potentially save lives. In specific examples, characterizations and/or other suitable data can be used to assist care providers in diagnosis, therapeutics, and/or otherwise providing healthcare.

Second, specific examples of the technology can transform entities (e.g., users, biological samples, therapy facilitation systems including medical devices, etc.) into different states or things. For example, the technology can transform a biological sample into components able to be sequenced and analyzed to generate microorganism dataset and/or microbiome features usable for characterizing users in relation to one or more female reproductive system-related conditions (e.g., such as through use of next-generation sequencing systems, multiplex amplification operations; etc.). In another example, the technology can identify, discourage and/or promote (e.g., present, recommend, provide, administer, etc.), therapies (e.g., personalized therapies based on a female reproductive system-related characterization; etc.) and/or otherwise facilitate therapeutic intervention (e.g., facilitating modification of a user's microbiome composition, microbiome functionality, etc.), which can prevent and/or ameliorate one or more female reproductive system-related conditions, such as thereby transforming the microbiome and/or health of the patient (e.g., improving a health state associated with a female reproductive system-related condition; etc.), such as applying one or more microbiome features (e.g., applying correlations, relationships, and/or other suitable associations between microbiome features and one or more female reproductive system-related conditions; etc.). In another example, the technology can transform microbiome composition and/or function at one or more different body sites of a user (e.g., one or more different collection sites; vagina; female reproductive system body sites; etc.), such as targeting and/or transforming microorganisms associated with a gut, nose, skin, mouth, and/or genitals (e.g., vagina; etc.) microbiome (e.g., by facilitating therapeutic intervention in relation to one or more site-specific therapies; etc.). In another example, the technology can control therapy facilitation systems (e.g., dietary systems; automated medication dispensers; behavior modification systems; diagnostic systems; disease therapy facilitation systems; etc.) to promote therapies (e.g., by generating control instructions for the therapy facilitation system to execute; etc.), thereby transforming the therapy facilitation system.

Second, specific examples of the technology can confer improvements in computer-related technology (e.g., improving computational efficiency in storing, retrieving, and/or processing microorganism-related data for female reproductive system-related conditions; computational processing associated with biological sample processing, etc.) such as by facilitating computer performance of functions not previously performable. For example, the technology can apply a set of analytical techniques in a non-generic manner to non-generic microorganism datasets and/or microbiome features (e.g., that are recently able to be generated and/or are viable due to advances in sample processing techniques and/or sequencing technology, etc.) for improving female reproductive system-related characterizations and/or facilitating therapeutic intervention for female reproductive system-related conditions.

Third, specific examples of the technology can confer improvements in processing speed, female reproductive system-related characterization, accuracy, microbiome-related therapy determination and promotion, and/or other suitable aspects in relation to female reproductive system-related conditions. For example, the technology can leverage non-generic microorganism datasets to determine, select, and/or otherwise process microbiome features of particular relevance to one or more female reproductive system-related conditions (e.g., processed microbiome features relevant to a female reproductive system-related condition; cross-condition microbiome features with relevance to a plurality of female reproductive system-related conditions, etc.), which can facilitate improvements in accuracy (e.g., by using the most relevant microbiome features; by leveraging tailored analytical techniques; etc.), processing speed (e.g., by selecting a subset of relevant microbiome features; by performing dimensionality reduction techniques; by leveraging tailored analytical techniques; etc.), and/or other computational improvements in relation to phenotypic prediction (e.g., indications of the female reproductive system-related conditions, etc.), other suitable characterizations, therapeutic intervention facilitation, and/or other suitable purposes. In a specific example, the technology can apply feature-selection rules (e.g., microbiome feature-selection rules for composition, function; for supplemental features extracted from supplemental datasets; etc.) to select an optimized subset of features (e.g., microbiome functional features relevant to one or more female reproductive system-related conditions; microbiome composition diversity features such as reference relative abundance features indicative of healthy, presence, absence, and/or other suitable ranges of taxonomic groups associated with female reproductive system-related conditions; user relative abundance features that can be compared to reference relative abundance features correlated with female reproductive system-related conditions and/or therapy responses; etc.) out of a vast potential pool of features (e.g., extractable from the plethora of microbiome data such as sequence data; identifiable by univariate statistical tests; etc.) for generating, applying, and/or otherwise facilitating characterization and/or therapies (e.g., through models, etc.). The potential size of microbiomes (e.g., human microbiomes, animal microbiomes, etc.) can translate into a plethora of data, giving rise to questions of how to process and analyze the vast array of data to generate actionable microbiome insights in relation to female reproductive system-related conditions. However, the feature-selection rules and/or other suitable computer-implementable rules can enable one or more of: shorter generation and execution times (e.g., for generating and/or applying models; for determining female reproductive system-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with female reproductive system-related conditions, such as while optimizing for improving specificity, reducing amplification bias, and/or other suitable parameters; etc.); model simplification facilitating efficient interpretation of results; reduction in overfitting; network effects associated with generating, storing, and applying female reproductive system-related characterizations for a plurality of users over time in relation to female reproductive system-related conditions (e.g., through collecting and processing an increasing amount of microbiome-related data associated with an increasing number of users to improve predictive power of the female reproductive system-related characterizations and/or therapy determinations; etc.); improvements in data storage and retrieval (e.g., storing and/or retrieving female reproductive system-related characterization models; storing specific models such as in association with different users and/or sets of users, with different female reproductive system-related conditions; storing microorganism datasets in association with user accounts; storing therapy monitoring data in association with one or more therapies and/or users receiving the therapies; storing features, female reproductive system-related characterizations, and/or other suitable data in association with a user, set of users, and/or other entities to improve delivery of personalized characterizations and/or treatments for the female reproductive system-related conditions, etc.), and/or other suitable improvements to technological areas.

Fourth, specific examples of the technology can amount to an inventive distribution of functionality across components including a sample handling system, a female reproductive system-related characterization system, and a plurality of users, where the sample handling system can handle substantially concurrent processing of biological samples (e.g., in a multiplex manner) from the plurality of users, which can be leveraged by the female reproductive system-related characterization system in generating personalized characterizations and/or therapies (e.g., customized to the user's microbiome such as in relation to the user's dietary behavior, probiotics-associated behavior, medical history, demographic characteristics, other behaviors, preferences, etc.) for female reproductive system-related conditions.

Fifth, specific examples of the technology can improve the technical fields of at least genomics, microbiology, microbiome-related computation, diagnostics, therapeutics, microbiome-related digital medicine, digital medicine generally, modeling, and/or other relevant fields. In an example, the technology can model and/or characterize different female reproductive system-related conditions, such as through computational identification of relevant microorganism features (e.g., which can act as biomarkers to be used in diagnoses, facilitating therapeutic intervention, etc.) for female reproductive system-related conditions. In another example, the technology can perform cross-condition analysis to identify and evaluate cross-condition microbiome features associated with (e.g., shared across, correlated across, etc.) a plurality of a female reproductive system-related conditions (e.g., diseases, phenotypes, etc.). Such identification and characterization of microbiome features can facilitate improved health care practices (e.g., at the population and individual level, such as by facilitating diagnosis and therapeutic intervention, etc.), by reducing risk and prevalence of comorbid and/or multi-morbid female reproductive system-related conditions (e.g., which can be associated with environmental factors, and thereby associated with the microbiome, etc.). In specific examples, the technology can apply unconventional processes (e.g., sample processing processes; computational analysis processes; etc.), such as to confer improvements in technical fields.

Sixth, the technology can leverage specialized computing devices (e.g., devices associated with the sample handling system, such as next-generation sequencing systems; female reproductive system-related characterization systems; therapy facilitation systems; etc.) in performing suitable portions associated with embodiments of the method 100 and/or system 200.

Specific examples of the technology can, however, provide any suitable improvements in the context of using non-generalized components and/or suitable components of embodiments of the system 200 for female reproductive system-related characterization, microbiome modulation, and/or for performing suitable portions of embodiments of the method 100.

Portions of the embodiments of the method 100 can enable, provide, facilitate analyses for, include, and/or be associated with a women's health assay that can combine one or more of: self-sampling, sequencing-based HPV detection and genotyping, microbiome analysis (e.g., vaginal microbiome analysis, etc.), and/or STI-associated pathogen detection.

In a specific example, de-identified cervicovaginal swab specimens of known STI pathogen status can be obtained (e.g., including samples reported to be positive for *C. trachomatis* and negative for *N. gonorrhoeae*, and including samples reported to be negative for *C. trachomatis* and positive for *N. gonorrhoeae*; etc.), where each sample can be tested in replicates for DNA extraction, 16S rRNA gene amplification, target identification, and/or other suitable processes (e.g., described herein).

Figure 6:
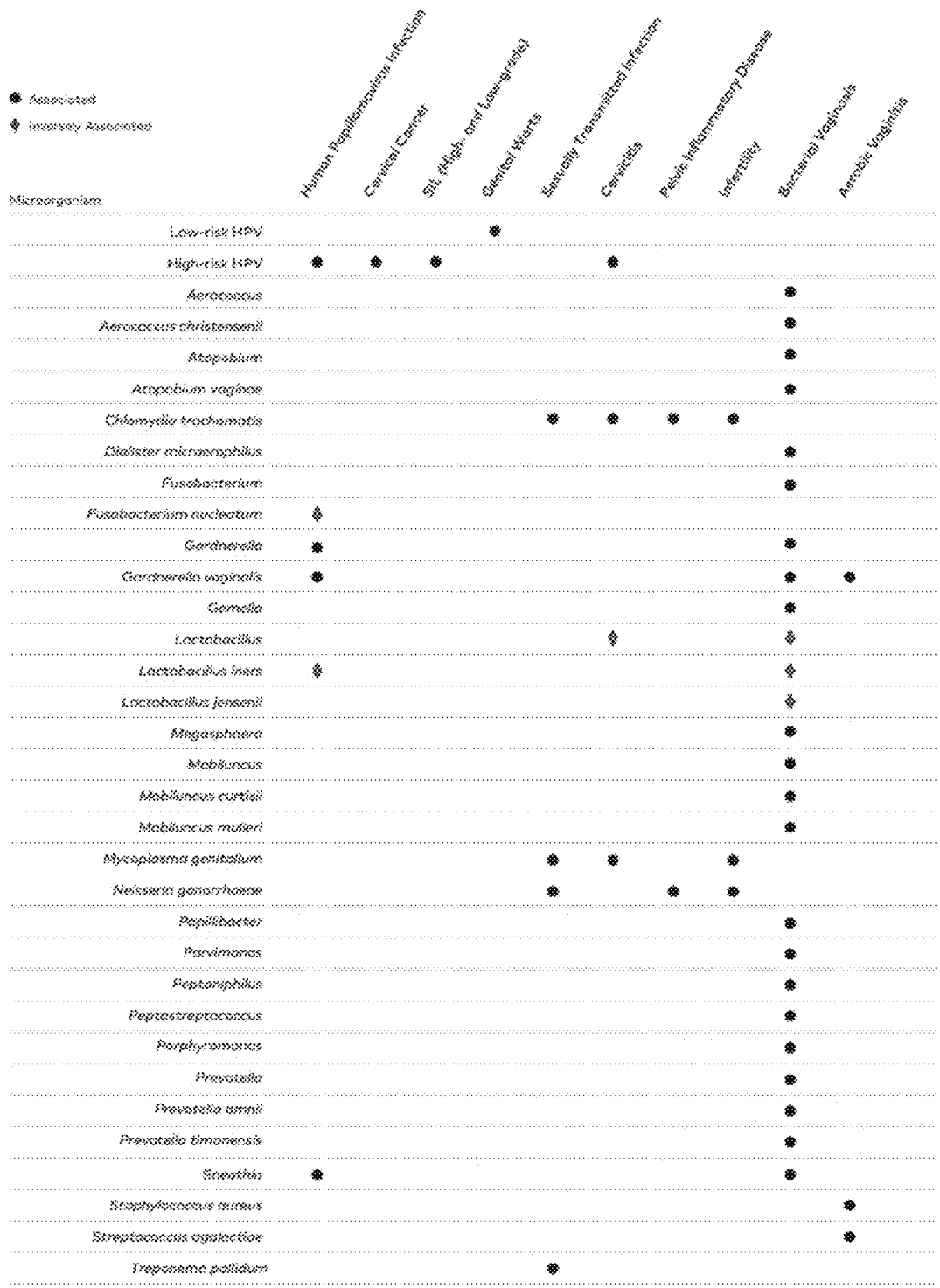
FIG. 6 includes a specific example of targets associated with at least one female reproductive system-related condition.
Figure 7A:
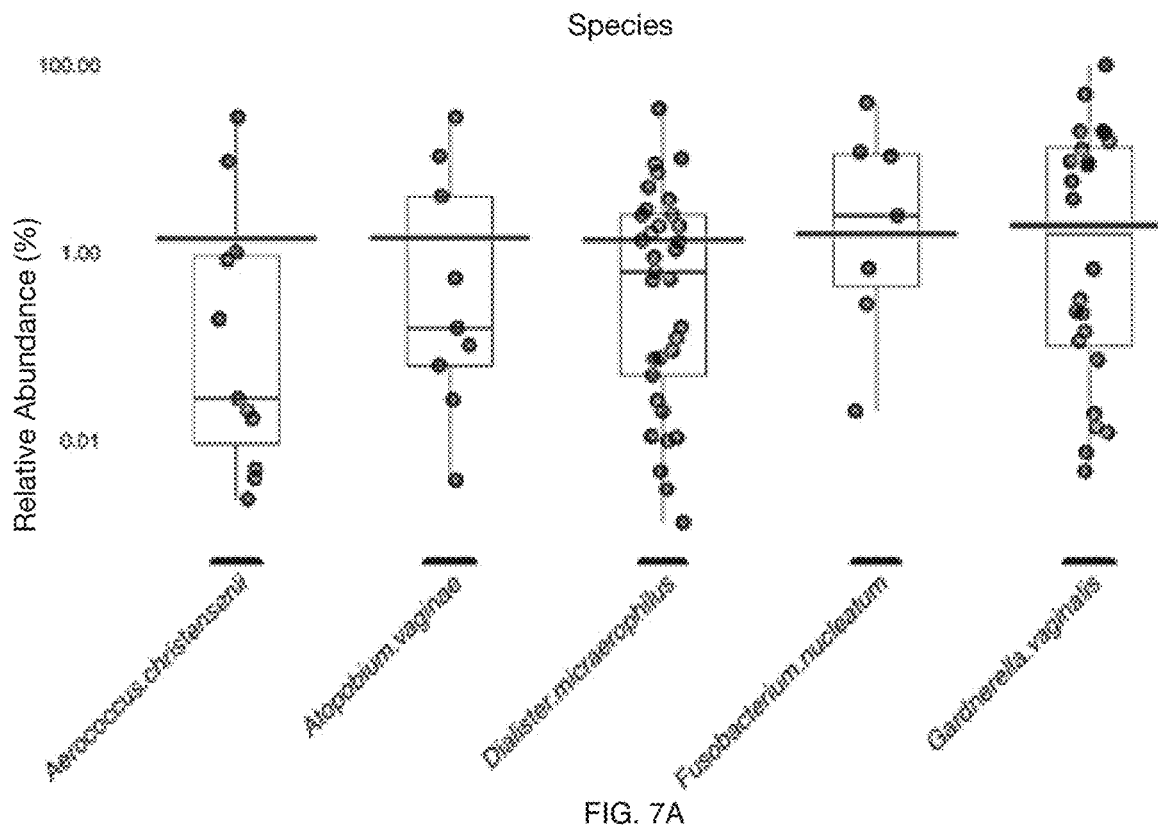
FIG. 7A-7D includes specific examples of healthy reference relative abundance ranges.
Figure 7B:
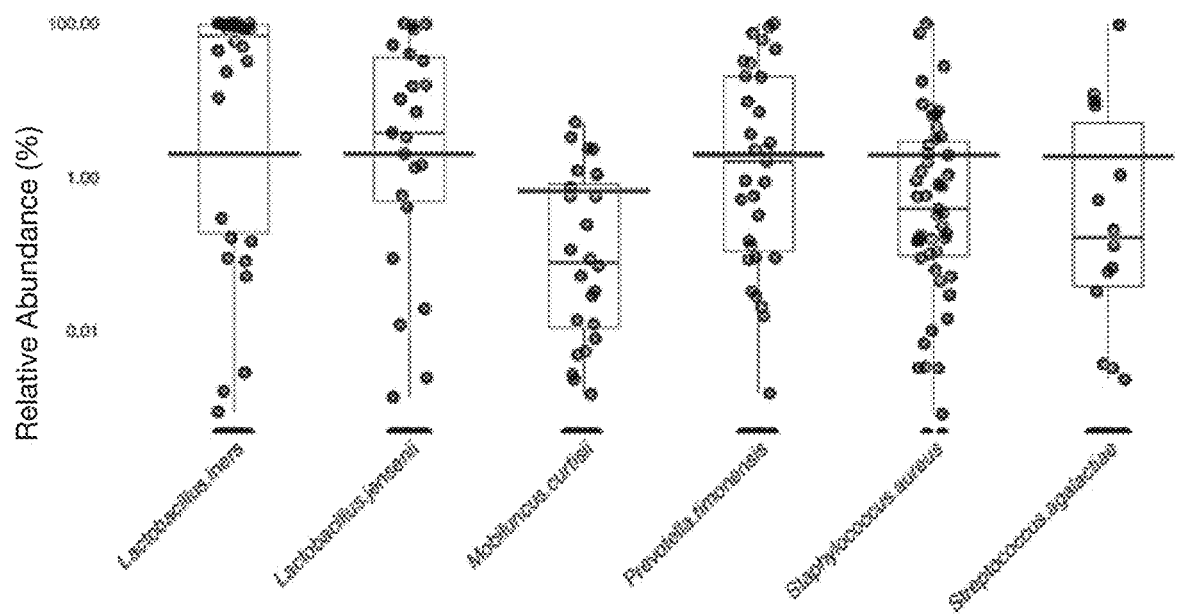
Figure 7C:
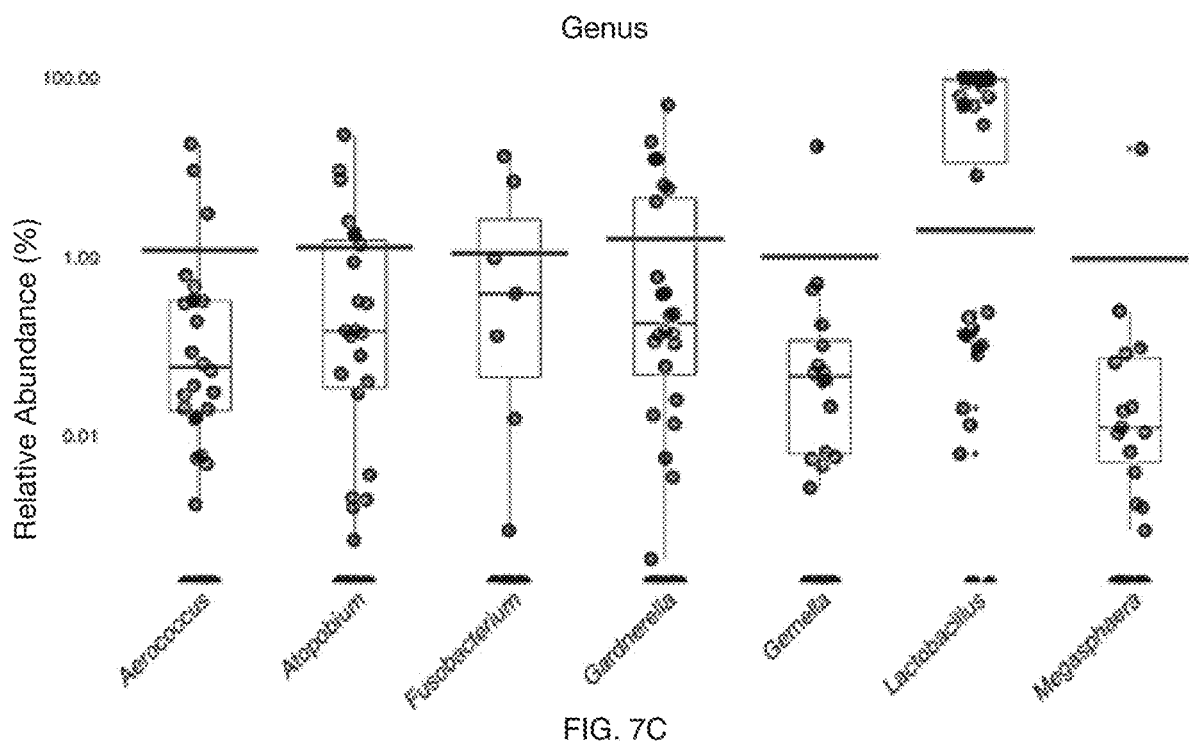
Figure 7D:
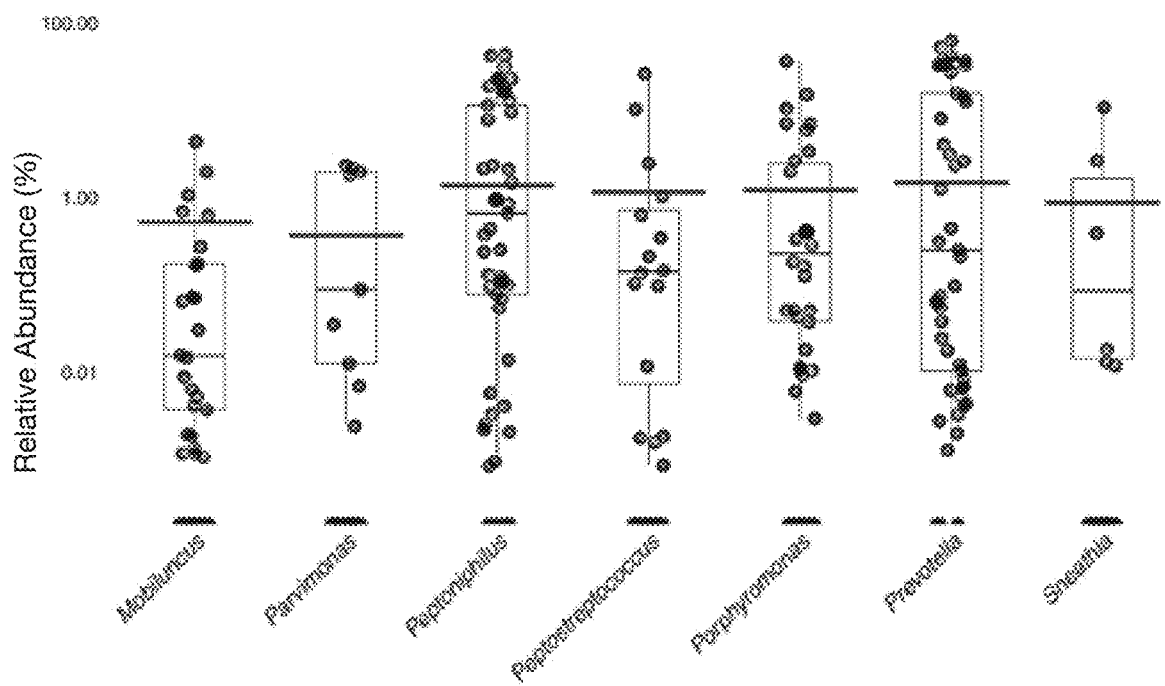
Figure 13:
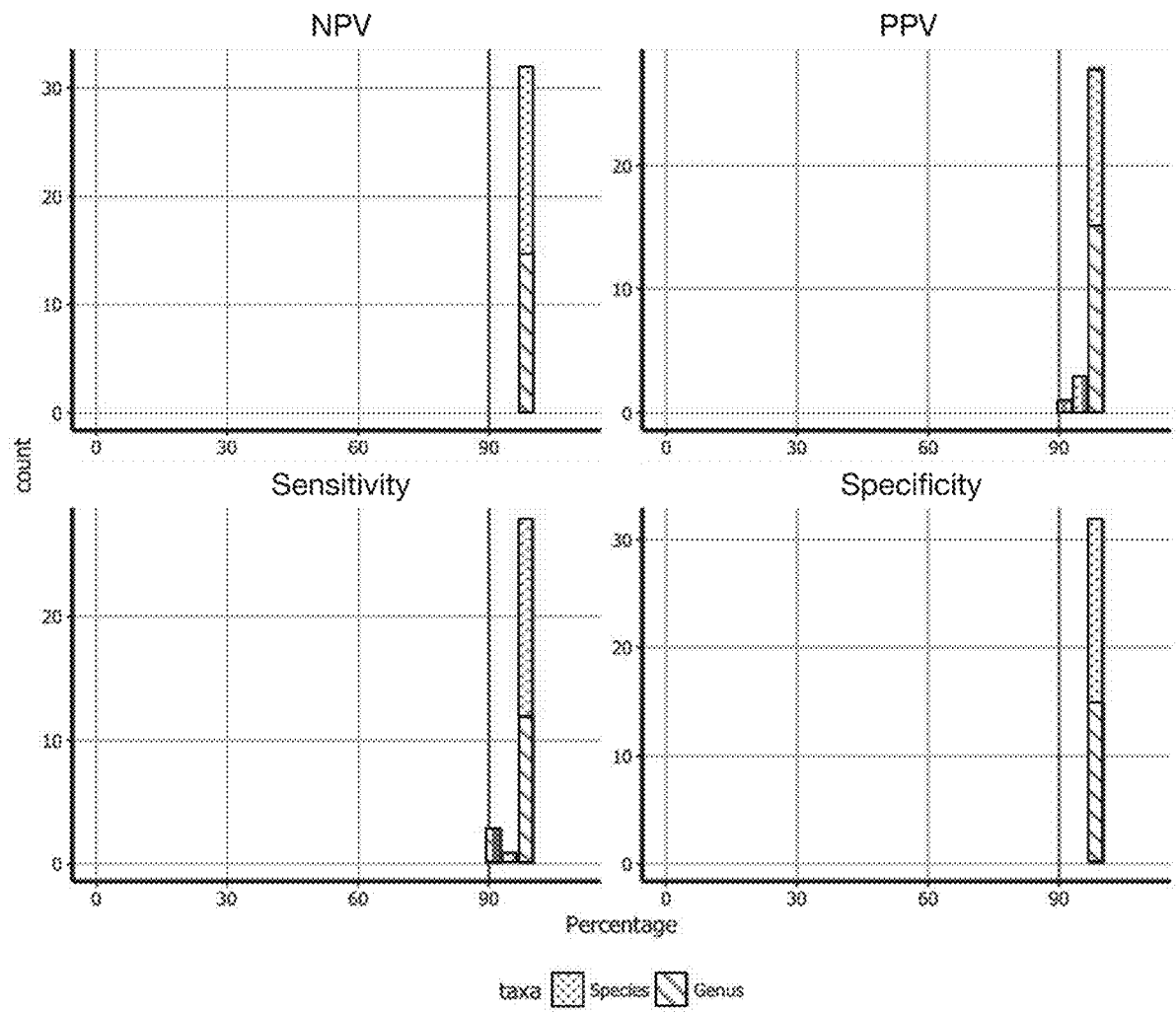
FIG. 13 includes specific examples of performance metrics for targets.

In variations, microorganism targets for a women's health assay (e.g., as shown in Table 1; as shown in FIG. 6; etc.) can be determined, such as through in silico analyses. In an example, third party sources (e.g., database, clinical literature, scientific literature, sources related to vaginal health, etc.) can be analyzed, such as where relevant associations between female reproductive system-related conditions and microorganism taxa (e.g., vaginal microbiota, etc.) can be filtered based on selecting associations with high statistical significance that were found in humans subjects (e.g., as opposed to laboratory animals and/or bioreactors, etc.), and/or performed on case/control, cohorts or randomized studied population. In silico analyses can additionally or alternatively include determining performance metrics for identification of each taxa (e.g., sensitivity, specificity, positive and negative predictive value, etc.), such as where sequences assigned to each taxon in a microorganism database (e.g., SILVA database, etc.) can be considered as real positives for that taxon; and assuming amplification with up to two mismatches with the primers used, sequences for each taxa can be identified that would produce an amplicon, and evaluation can be performed whether the amplicon is unique to the taxon of interest (ti) or also shared by sequences from different taxa (dt), where the number of true positives (TP), true negatives (TN), false positives (FP) and false negatives (FN) can be computed for different tolerance ratios for the quotient dt/ti, such as for assessing in silico performance metrics (e.g., as shown in FIG. 13; where specificity=TN/(TN+FP); sensitivity=TP/(TP+FN); positive predictive value (PPV)=TP/(TP+FP); and negative predictive value (NPV)=TN/(TN+FN); based on a cutoff of 90% (vertical line); etc.). In a specific example, out of a set of bacterial targets initially selected, 32 targets (and/or other suitable number of targets) can be selected for a women's health assay, such as based on threshold performance metrics (e.g., all four in silico performance metrics above 90%), such as targets described in Table 1.

In variations, HPV targets (e.g., high risk HPV (hrHPV) and/or low risk HPV (lrHPV) targets; etc.) can additionally or alternatively be included in a women's health assay (e.g., in addition to determined bacterial targets, etc.). In an example, HPV targets can be selected based on associations with cervical cancer lesions and/or genital warts (e.g., as shown in Table 1, etc.). Determining HPV targets for inclusion can be based one or more of: HPV reference genomes (e.g., obtained from relevant databases such as a PaVE database; etc.), sequence recognizability (E.g., using only revised and recognized sequences; 180 HPV genomes), in silico analyses (e.g., in silico PCR amplification using a set of 15 forward and 6 reverse primers, such as primers described herein, targeting the L1 gene and allowing up to 4 mismatches and/or any suitable number of mismatches between primers and target sequences, such as leading to L1 genes from 118 HPV genomes being able to be amplified in silico; etc.), associations with female reproductive system-related conditions (e.g., determining 19 HPV genomes, including 14 hrHPV types (16, 18, 31, 33, 35, 39, 45, 51, 52, 56, 58, 59, 66, 68) and 5 lrHPV types (6, 11, 42, 43, 44) based on associations; etc.); and/or other suitable criteria. In examples, to evaluate the performance metrics for identification of the HPV targets, sequences of the L1 segment of HPV genomes from databases (e.g., NCBI database; etc.) can be used; the search can be filtered to sequences with length in the range 1,500-10,000 bp (and/or other suitable lengths) and with correct assignment of the type of the HPV (e.g., 4177 sequences); the sequences can be amplified in silico using primers (e.g., described herein), which can generate an amplicon set (e.g., 161,398 amplicons, etc.); where the sequences can be mapped using any suitable mapping approaches (e.g., VSEARCH at 95% of identity against an HPV amplicon reference database including the amplicons produced by the reference genomes in PaVE for the 19 HPV types and/or other suitable types, etc.) for the determined HPV targets. In examples, performance metrics can be calculated in a manner analogous to calculation of performance metrics for 16S rRNA gene targets and/or other suitable targets. In a specific example, correct assignment of an amplicon (e.g., NCBI amplicon, etc.) against the reference can be counted as a true positive, and an incorrect assignment can be considered as a false negative, and where false negatives can be considered for the genomes (e.g., from NCBI, etc.) that the primers could not amplify. In a specific example, targets (e.g., 19 HPV types, etc.) can be obtained for targets with performance metrics for sensitivity, specificity, positive predictive value (PPV) and/or negative predictive values (NPV) above a threshold (e.g., 90%, etc.), such as shown in Table 6.

In variations, the method 100 can include sample processing specific for the women's health assay and/or other suitable components. In an example, the determining a microorganism dataset (e.g., performing sample processing for determining a microorganism dataset; etc.) can include performing first primer-based amplification for bacterial targets associated with the at least one female reproductive system-related condition; and performing second primer-based amplification for HPV targets associated with the at least one female reproductive system-related condition. In an example, the HPV targets can include at least one of HPV types 42, 39, 56, 35, 66, 33, and 42, and where performing the second primer-based amplification for the HPV targets includes performing the second primer-based amplification with at least one of a first HPV-associated primer and a second HPV-associated primer, where the first HPV-associated primer includes a first primer sequence including CGTCCTAAAGGGAATTGATC (SEQ ID NO: 78), and where the second HPV-associated primer includes a second primer sequence including GCACAAGGCCAT-AATAATGG (SEQ ID NO: 63). In examples, DNA is extracted from vaginal samples (and/or other suitable samples; samples collected from provided sampling kits; etc.), pools thereof, and/or sDNA dilutions, such as in tubes and/or other suitable containers including lysis/stabilization buffer. In examples, for 16S rRNA gene amplification, extracted DNA is used as input of a one-step PCR protocol to amplify the V4 variable region of the 16S rRNA gene, where the PCR can include universal primers 515F and 806R (and/or any suitable primers), both with sample-specific indices and Illumina tags and/or other suitable tags for facilitating sequencing; where PCR can be performed as described herein, and where following amplification, DNA can be pooled by taking the same volume from each reaction. In examples, for HPV target amplification, extracted DNA can be used as the input of a PCR protocol to amplify the HPV L1 gene; to each sample, sDNA with a randomized HPV type 16 sequence was added as an internal positive control; the first PCR mix includes a set of HPV specific primers (e.g., including HPV_RSMY09-LvJJ_Forward: 5' CGTCCTAAAGGGAATTGATC (SEQ ID NO: 78), and HPV_PGMY11-CvJJ_Reverse: 5' GCACAAGGCCAT-AATAATGG (SEQ ID NO: 63), as shown in Table 9, etc.), where the primers can include sequencing adaptor regions; where the PCR products from the first amplification round can be used as input for a second PCR step including sample-specific forward and reverse indices and Illumina tags (and/or other suitable tags for facilitating sequencing; etc.); where PCR products from the second step can be pooled for sequencing. In examples, libraries (e.g., The 16S rRNA gene and HPV PCR consolidated library pools, etc.) can be separately quantified (e.g., by qPCR using the KAPA Library Quant Kit (Bio-Rad iCycler qPCR Mix) and a BioRad MyiQ iCycler, etc.). In examples, sequencing of libraries can be performed with any suitable sequencing technologies (e.g., in a paired-end modality on the Illumina NextSeq 500 platform rendering 2×150 bp paired-end sequences, etc.).

In variations, the method 100 can include processing sequencing outputs (and/or other suitable processes for facilitating characterization processes; etc.). In examples, for bacterial targets (and/or other suitable targets), after sequencing, demultiplexing of reads according to sample-specific barcodes can be performed (e.g., using Illumina's BCL2FASTQ algorithm, etc.); reads can be filtered using an average Q-score >30; forward and reverse 16S rRNA gene reads can be appended together after removal of primers and any leading bases, and clustered (e.g., using Swarm algorithm; using a distance of one nucleotide and the "fastidious" and "usearch-abundance" flags; etc.); where the most abundant sequence per cluster can be considered the real biological sequence and can be assigned the count of all reads in the cluster; where the representative reads from all clusters can be subjected to chimera removal (e.g., using the VSEARCH algorithm, etc.); and where reads passing all above filters (filtered reads) can be aligned (e.g., using 100% identity over 100% of the length against the true positive 16S rRNA gene sequences identified in silico from SILVA for each of the targets identified for the women's health assay, such as 32 taxonomic groups described in Table 1, FIG. 6, etc.). In examples, the relative abundance of each taxon can be determined by dividing the count linked to that taxa by the total number of filtered reads.

In examples, for HPV targets (and/or other suitable targets), after sequencing, sequencing reads can be demultiplexed (e.g., using BCL2FASTQ, etc.); primers can be removed (e.g., using cutadapt, etc.); reads can be removed with a length less than 125 bp, and a mean quality score below 30 (e.g., using Trimmomatic; etc.); forward and reverse paired reads can be joined (e.g., using scripts; etc.) and converted to a fasta file and/or other suitable file; identical sequences can be merged and written to a file (e.g., in fasta format) and sorted by decreasing abundance (e.g., using VSEARCH, etc.); target sequences (e.g., in the fasta files, etc.) can be compared to database sequences (e.g., fasta-formatted query database sequences (19 HPV target sequences); using the global pairwise alignment option with VSEARCH; using 95 percent sequence identity; etc.) to obtain the counts for each HPV type within a different sample. In examples, the HPV portion of the women's health assay can be considered positive if the number of sequence reads assigned to the specific HPV types was above the threshold at the limit of detection, and greater than a previously defined cutoff, where, to set this cutoff, normalization steps can be employed. In a specific example, normalization steps can include in silico PCR amplification, where a different number of combinations of primers amplify different HPV targets (e.g. HPV16 is amplified using 66 different combinations, while HPV43 is amplified with 10 combinations), reflecting the sequence variability within the primer binding site among HPVs, which can mean that the spiked-in internal control and the target HPV have different amplification efficiencies; and to avoid this bias, the internal control (which has the primer sites for HPV16) is normalized for the amplification factor (number of primer combinations that generate an amplicon) of each HPV type; and the number of HPV-assigned reads can be divided by the total number of normalized reads assigned to the spike, and a sample was considered HPV-positive if that ratio was above 0.1 (e.g., which can correspond to approximately 500 target molecules, etc.).

In variations, the method 100 can include evaluating intra- and/or inter-run precision. In examples, intra-run technical repeatability can be assessed by including replicates (e.g., 9 replicates, etc.) of the same vaginal pool (e.g., including 96 vaginal samples derived from 11 individuals) into the same DNA extraction, 16S rRNA gene amplification, and sequencing run. In examples, the experiment can be repeated in a second sequencing run to yield another set of replicate samples (e.g., 9 replicates) analyzed within the same run. Additionally or alternatively, inter-run technical reproducibility can be evaluated by processing replicates of a set of vaginal samples on different days by different operators (e.g., 3 replicates of a set of 18 vaginal samples on 3 different days by 3 different operators; etc.), where samples included in the analysis can include those with least 10,000 reads (e.g., and where at least two of the three replicates were present, etc.). In examples, comparison of the results, both intra- and inter-run, can be performed using the raw counts of the assay targets (e.g., 32 bacterial species- and genus-level targets, etc.), and data can be and visualized (e.g., using Principal Coordinates Analysis (PCoA), etc.), such as based on a distance matrix calculated using the Bray-Curtis method.

Figure 12A:
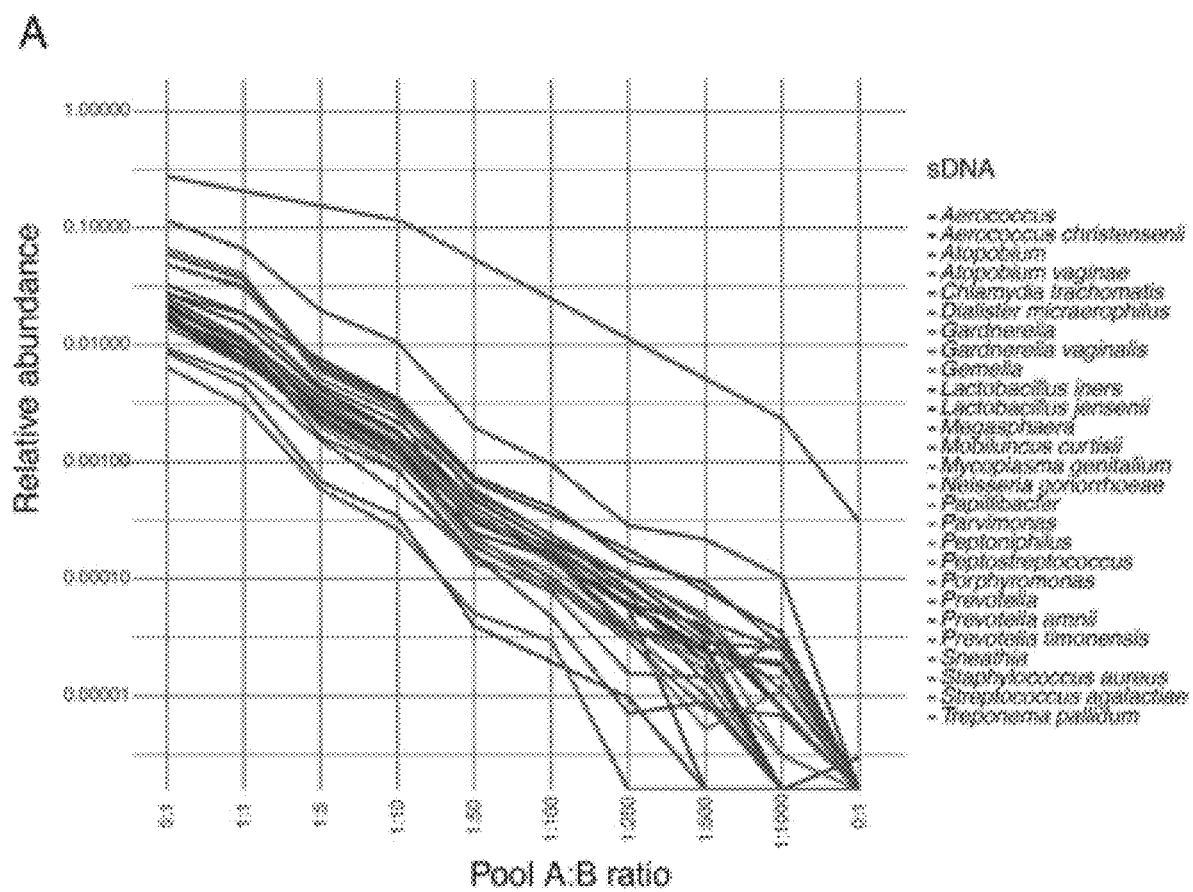
FIG. 12A-12B include specific examples of limits of detection of synthetic DNAs (sDNAs)
Figure 12B:
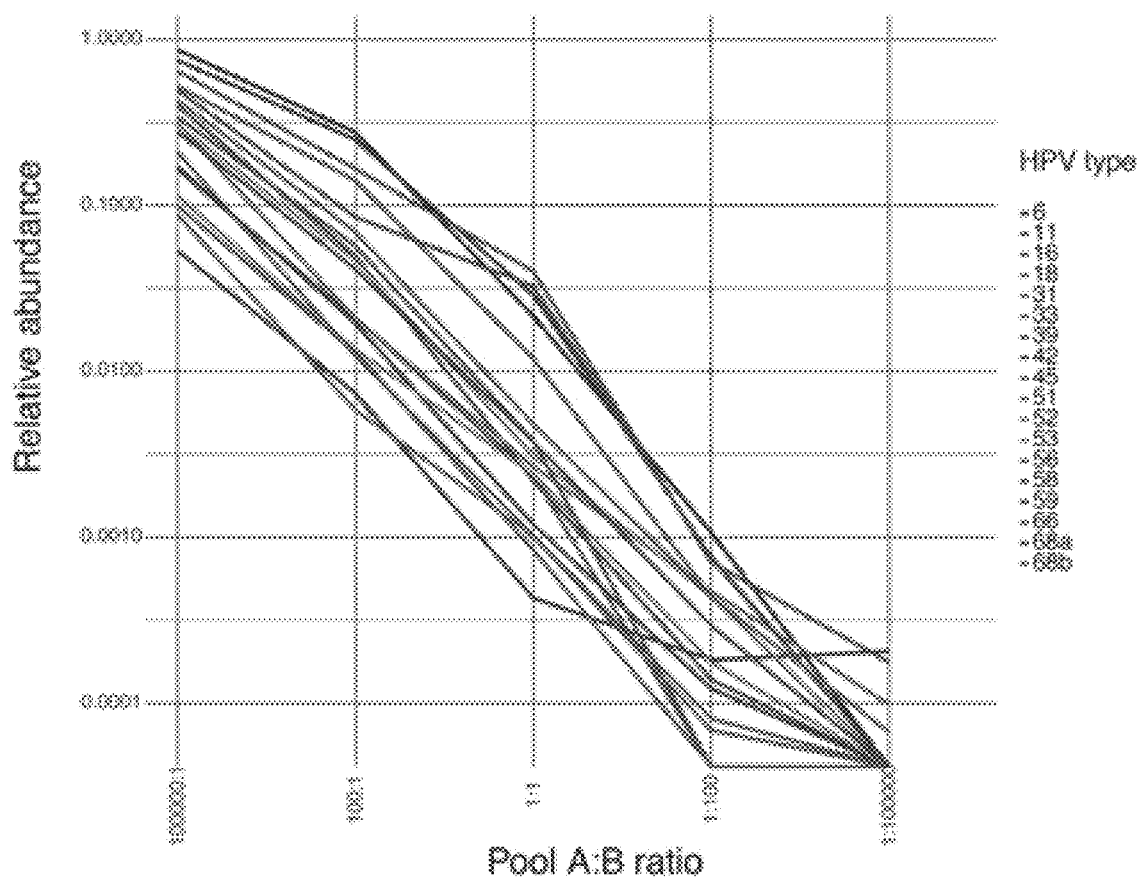

In variations, the method 100 can include determining limits of detection (LOD) for one or more targets (e.g., of the women's health assay; etc.). In examples, for each bacterial target, the LOD can be determined by combining different dilutions of pools of sDNAs, followed by DNA extraction, amplification of the V4 region of the 16S rRNA gene using broad range primers, and sequencing, where the LOB can be set as the average number of reads in blank wells (e.g., 77 blank wells; 18.57 reads) plus standard deviations (e.g., 1.65 standard deviations; 29.70 reads); where the results can be used to calculate the threshold of identification for each taxon as the LOB+1.65 standard deviations (48.27) plus the standard deviation of the taxon at LOD*1.65 (e.g., as shown in Table 10). In a specific example, for the 32 bacterial taxa targeted by a women's health assay, the threshold related to LODs can be in the range 49.0 to 65.2 reads (e.g., as shown in Table 10). In examples, to determine the LOD for HPV targets, different dilutions of pools of sDNAs were mixed as done for the bacterial targets; and the molecules were then amplified, sequenced, and analyzed by bioinformatics processes described herein (e.g., HPV bioinformatics pipeline. Etc.). In a specific example, for HPV targets for a women's health assay, the threshold related to LODs can be in the range 40.8 to 224.8 reads (e.g., as shown in Table 11). In a specific example, LODs for sDNAs representing bacterial and viral targets can be determined, such as shown in FIG. 12A-12B (e.g., where dilutions of two pools of sDNAs were mixed in different amounts, and microbial targets were amplified and sequenced; for each dilution and target, the relative abundance in samples with 10,000 reads or more are shown; where FIG. 12A includes LODs of bacterial targets; and FIG. 12B includes LOD of HPV targets; and for each dilution and HPV type, the relative abundance in samples with 10,000 reads or more are shown; etc.).

Figure 14:
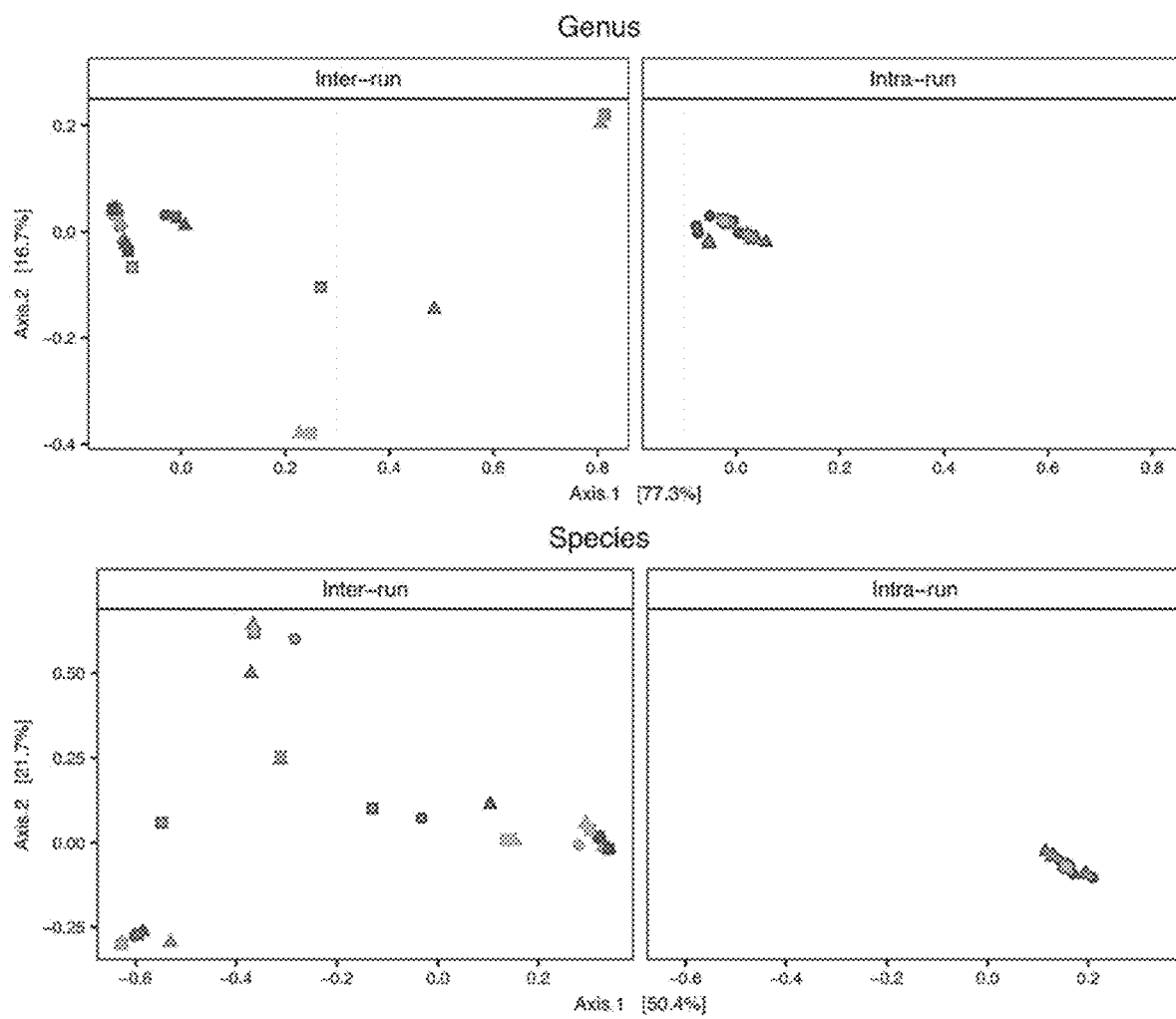
FIG. 14 includes specific examples of inter- and intra-run variability.

In variations, the method 100 can include evaluating intra- and/or inter-run variability (e.g., as shown in FIG. 14). In examples, intra-run technical variability can be evaluated in a combined set of replicates (e.g., 18 replicates, etc.) of the same vaginal pool. In a specific example, each of which yielded 10,000 reads or more. In examples, ordination plots of both genus and species level bacterial communities (e.g., as shown in FIG. 14) can show a tight clustering of intra-run technical replicates, indicating that within a single sequencing run, results generated by the laboratory process and the bioinformatics analysis were consistent.

In examples, for inter-run analysis, a total set of groups (e.g., 11 groups) of replicates (at least two samples) can be analyzed for passing the filtering criteria (over 10,000 reads). In a specific example, the PCoA visualization at genus and species level shows a dispersion of the different samples, but with a clustering according to the respective replicates (e.g., as shown in FIG. 14), which can suggest that there is limited within-sample variation when the same samples are processed on different days by different operators.

In variations, healthy microorganism abundance ranges can be determined for a women's health assay. In a specific example, for determination of the healthy ranges of the bacterial targets (e.g., 32 bacterial targets described in Table 1), a set of vaginal specimens, each from a different woman (e.g., average age 48.4±15.6 years) can be selected, such as based on completion of a voluntary health survey and/or no report of one or more female reproductive system-related conditions including one or more of: bacterial vaginosis, cervical cancer, genital herpes or warts, urinary tract infection, or infection with HPV, *C. trachomatis*, *T. pallidum*, yeast infection, and/or other suitable conditions, and/or based on reporting of no antibiotic usage in a time period (e.g., six months) prior to sampling.

However, portions of the embodiments of the method 100, such as for enabling, providing, facilitate analyses for, and/or otherwise being associated with a women's health assay, can be performed in any suitable manner.

3.1 Determining a Microorganism Dataset.

Embodiments of the method 100 can include Block S110, which can include determining a microorganism dataset (e.g., microorganism sequence dataset, microbiome composition diversity dataset such as based upon a microorganism sequence dataset, microbiome functional diversity dataset such as based upon a microorganism sequence dataset, etc.) associated with a set of users S110. Block S110 can function to process samples (e.g., biological samples; non-biological samples; an aggregate set of samples associated with a population of subjects, a subpopulation of subjects, a subgroup of subjects sharing a demographic characteristic and/or other suitable characteristics; a user sample; etc.), in order to determine compositional, functional, pharmacogenomics, and/or other suitable aspects associated with the corresponding microbiomes, such as in relation to one or more female reproductive system-related conditions.

Compositional and/or functional aspects can include one or more of aspects at the microorganism level (and/or other suitable granularity), including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and/or functional aspects can also be represented in terms of operational taxonomic units (OTUs). Compositional and/or functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to facilitate determination of microbiome features (e.g., generation of a microorganism sequence dataset usable for identifying microbiome features; etc.) for the characterization process of Block S130 and/or other suitable portions of embodiments of the method 100 (e.g., where Block S110 can lead to outputs of microbiome composition datasets, microbiome functional datasets, and/or other suitable microorganism datasets from which microbiome features can be extracted, etc.), where the features can be microorganism-based (e.g., presence of a genus of bacteria), genetic-based (e.g., based upon representation of specific genetic regions and/or sequences), functional-based (e.g., presence of a specific catalytic activity), and/or any other suitable microbiome features.

In a variation, Block S110 can include assessment and/or processing based upon phylogenetic markers (e.g., for generating microorganism datasets, etc.) derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with female reproductive system-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, markers can include any other suitable marker(s) associated with microbiome composition, microbiome functionality, and/or female reproductive system-related conditions.

Figure 21:
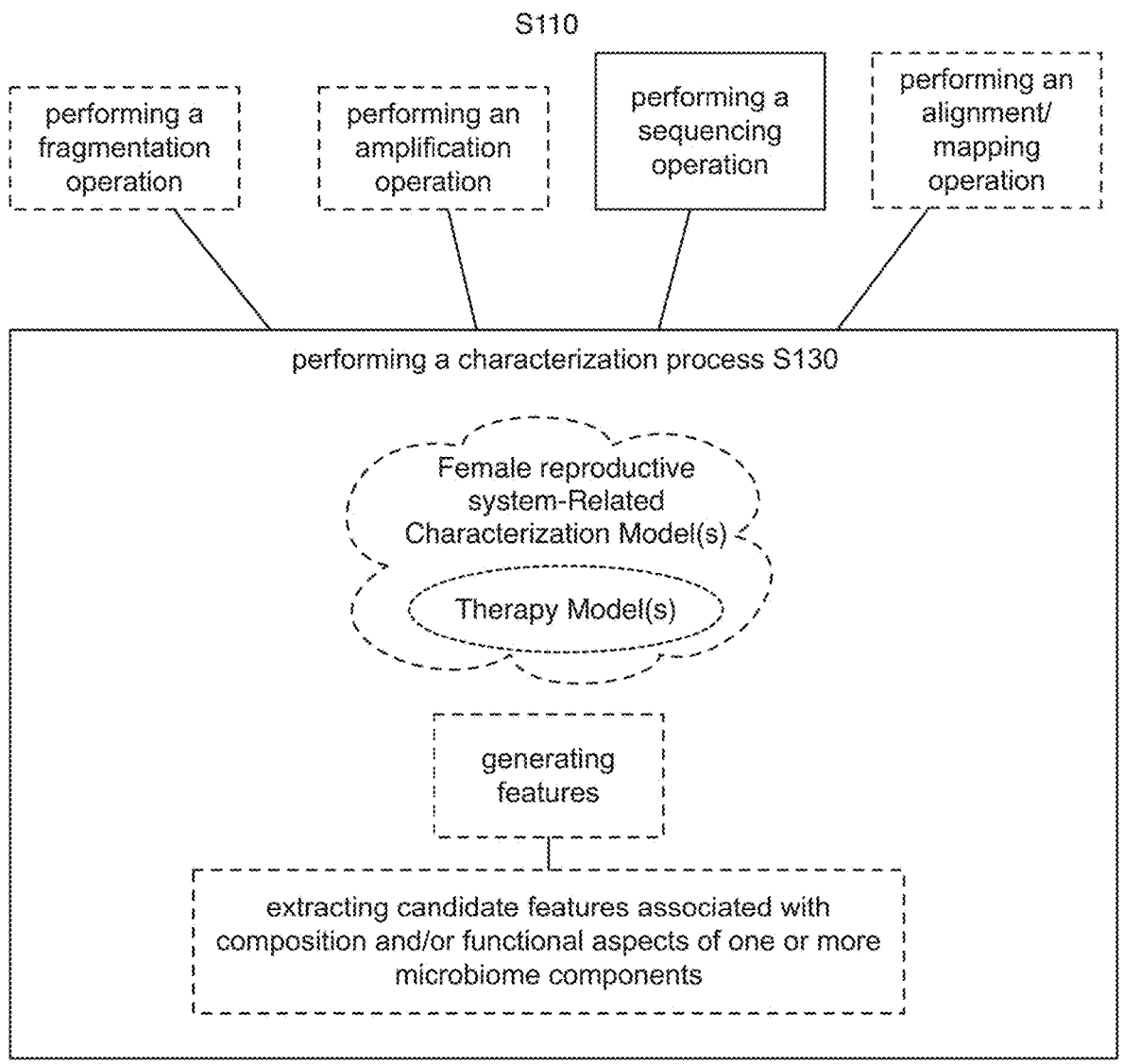
FIG. 21 includes variations of sample processing in an embodiment of a method.

Characterizing the microbiome composition and/or functional aspects for each of the aggregate set of biological samples thus preferably includes a combination of sample processing techniques (e.g., wet laboratory techniques; as shown in FIG. 21), including, but not limited to, amplicon sequencing (e.g., 16S, 18S, ITS), UMIs, 3 step PCR, CRISPR, use of primers, and/or computational techniques (e.g., utilizing tools of bioinformatics), to quantitatively and/or qualitatively characterize the microbiome and functional aspects associated with each biological sample from a subject or population of subjects.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block S110 can include: collecting biological samples from a set of users (e.g., biological samples collected by the user with a sampling kit including a sample container, etc.), where the biological samples include microorganism nucleic acids associated with the female reproductive system-related condition (e.g., microorganism nucleic acids including target sequences correlated with a female reproductive system-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S110 can involve chemical methods (e.g., using a detergent, using a solvent, using a surfactant, etc.). Additionally or alternatively, lysing or disrupting in Block S110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Additionally or alternatively include incorporated barcode sequences and/or UMIs specific to biological samples, to users, to female reproductive system-related conditions, to taxa, to target sequences, and/or to any other suitable components, which can facilitate a post-sequencing identification process (e.g., for mapping sequence reads to microbiome composition and/or microbiome function aspects; etc.). In a specific example, applying primers can include amplifying 16S genes (e.g., genes coding for 16S rRNA) with universal V4 primers (e.g., 515F: GTGCCAGCMGCCGCGGTAA (SEQ ID NO: 85) and 806R: GGACTACHVGGGTWTCTAAT (SEQ ID NO: 86)), other suitable primers associated with variable (e.g., semi-conserved hypervariable regions, etc.) regions (e.g., V1-V8 regions), and/or any other suitable portions of RNA genes. Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.). In another specific example, performing amplification can include normalization steps to balance libraries and detect all amplicons in a mixture independent of the amount of starting material, such as 3 step PCR, bead based normalization, and/or other suitable techniques.

In variations, sequencing of purified nucleic acids can include methods involving targeted amplicon sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, UMIs, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing can include Illumina sequencing (e.g., with a HiSeq platform, with a MiSeq platform, with a NextSeq platform, etc.) using a sequencing-by-synthesis technique. In another specific example, the method 100 can include: identifying one or more primer types compatible with one or more genetic targets associated with one or more female reproductive system-related conditions (e.g., a biomarker of the one or more female reproductive system-related conditions; positively correlated with; negatively correlated with; causative of; etc.); determining a microorganism dataset (e.g., microorganism sequence dataset; such as with a next-generation sequencing system; etc.) for one or more users (e.g., set of subjects) based on the one or more primer types (e.g., based on primers corresponding to the one or more primer types, and on the microorganism nucleic acids included in collected biological samples, etc.), such as through fragmenting the microorganism nucleic acids, and/or performing a singleplex amplification process and/or a multiplex amplification process for the fragmented microorganism nucleic acids based on the one or more identified primer types (e.g., primers corresponding to the primer types, etc.) compatible with the one or more genetic targets associated with the female reproductive system-related condition; and/or promoting (e.g., providing), based on a female reproductive system-related characterization derived from a microorganism dataset, a therapy for the user condition (e.g., for the female reproductive system-related condition; enabling selective modulation of a microbiome of the user in relation to at least one of a population size of a desired taxon and a desired microbiome function, etc.). In a specific example, where determining the microorganism dataset can include generating amplified microorganism nucleic acids through at least one of a singleplex amplification process and a multiplex amplification process for the microorganism nucleic acids; and determining, with a next-generation sequencing system, the microorganism dataset based on the amplified microorganism nucleic acids.

In examples, the biological samples can correspond to a one or more collection sites including at least one of a gut collection site (e.g., corresponding to a body site type of a gut site), a skin collection site (e.g., corresponding to a body site type of a skin site), a nose collection site (e.g., corresponding to a body site type of a nose site), a mouth collection site (e.g., corresponding to a body site type of a mouth site), and a genitals collection site (e.g., corresponding to a body site type of a genital site). In a specific example, determining a microorganism dataset (e.g., microorganism sequence dataset, etc.) can include identifying a first primer type compatible with a first genetic target associated with one or more female reproductive system-related conditions and a first collection site of the set of collection sites; identifying a second primer type compatible with a second genetic target associated with the one or more female reproductive system-related conditions and a second collection site of the set of collection sites; and generating the microorganism dataset for the set of subjects based on the microorganism nucleic acids, the first primers corresponding to the first primer type, and second primers corresponding to the second primer type.

In variations, primers (e.g., of a primer type corresponding to a primer sequence; etc.) used in Block S110 and/or other suitable portions of embodiments of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with female reproductive system-related conditions (e.g., primers compatible with genetic targets including microorganism sequence biomarkers for microorganisms correlated with female reproductive system-related conditions; etc.), microbiome composition features (e.g., identified primers compatible with a genetic target corresponding to microbiome composition features associated with a group of taxa correlated with a female reproductive system-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., female reproductive system-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block S110 and/or other suitable portions of embodiments of the method 100 can be selected through processes described in Block S110 (e.g., primer selection based on parameters used in generating the taxonomic database) and/or any other suitable portions of embodiments of the method 100. Additionally or alternatively, primers (and/or processes associated with primers) can include and/or be analogous to that described in U.S. application Ser. No. 14/919,614, filed 21 Oct. 2015, which is herein incorporated in its entirety by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and/or any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features associated with (e.g., derived from) compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases.

Any suitable processes described in Block S120 can be performed in a multiplex manner for any suitable number of biological samples. In an example, Block S120 can include barcoding a plurality of samples with forward and reverse indexes (e.g., unique combinations), sequencing the plurality of samples in a multiplex manner; and, after sequencing, demultiplexing the samples corresponding to different users (e.g., with a BCL2FASTQ algorithm, etc.). Additionally or alternatively, any number of instances of portions of Block S110 can be performed at any suitable time and frequency. However, processing biological samples, determining microorganism datasets, and/or other associated aspects can be performed in any suitable manner analogous to that described in U.S. application Ser. No. 16/047,840 filed 27 Jul. 2018, which is herein incorporated in its entirety by this reference.

However, processing biological samples, generating a microorganism dataset, and/or other associated aspects can be performed in any suitable manner.

3.1.A Determining a Microorganism Dataset Associated with One or More Female Reproductive System-Related Conditions Embodiments of the method 100 can include determining a microorganism dataset S110, which can additionally or alternatively include determining a microorganism dataset associated with one or more female reproductive system-related conditions S115.

Figure 8:
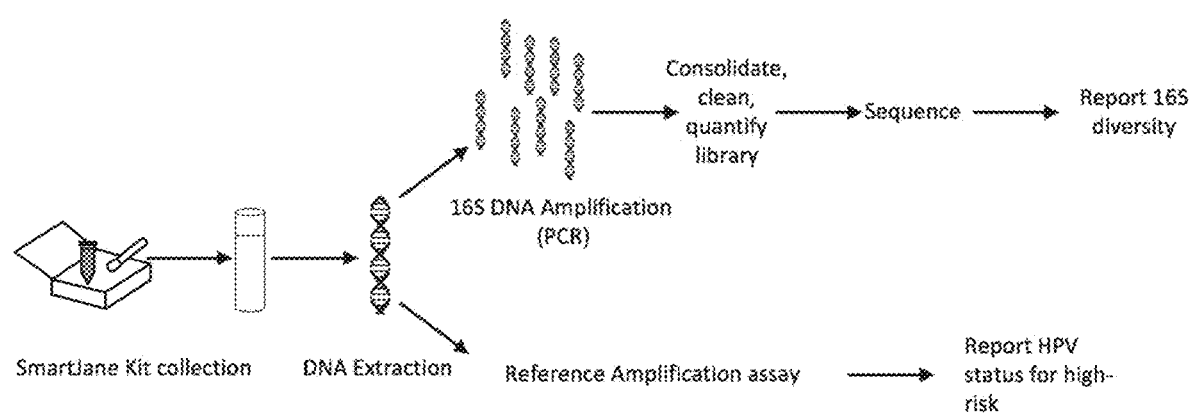
FIG. 8 includes a flowchart representation of amplification in a variation of an embodiment of a method.

In variations, determining a microorganism dataset can include determining a microorganism dataset associated with HPV. In a specific example, HPV detection (and/or other suitable analyses associated with female reproductive system-related characterization, etc.) can be performed as described in FIG. 8: following self-sampling by a user (e.g., at-home sample collection, etc.), with the sample collected in a tube and/or other suitable container, is brought into a laboratory and accessioned; for each sample, two separate sub-samples are generated and labeled, one for HPV genotyping (and/or another existing HPV detection technology, e.g. a digene test) and one for the 16S amplification; DNA in the samples is extracted using a clinical extraction pipeline (e.g., as shown in the FIG. 8); upon DNA extraction, approximately half the DNA (e.g., 50 ul) is removed to a new 96-well plate (and/or any suitable plate and/or container) by using an automated fluids controller (e.g., an automated liquid handler) and/or other suitable device; the remainder of the DNA is used for 16S V4 amplification, consolidation, size selection, quantitation, and sequencing (e.g., vaginal panel characterization pipeline); where such a specific example and/or other suitable variants can ensure the detection of high-risk HPV (e.g., HPV types 16, 18, 26, 31, 33, 35, 39, 45, 51, 52, 53, 56, 58, 59, 66, 68a, 68b, 70, 73, 82, etc.) in addition to 16S microbiome diversity, such as through processing the microorganism dataset to determine features for use in female reproductive system-related characterizations.

Figure 9:
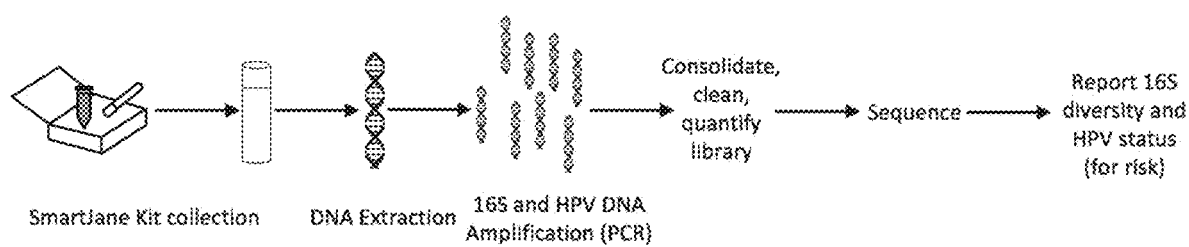
FIG. 9 includes a flowchart representation of amplification in a variation of an embodiment of a method.
Figure 10:
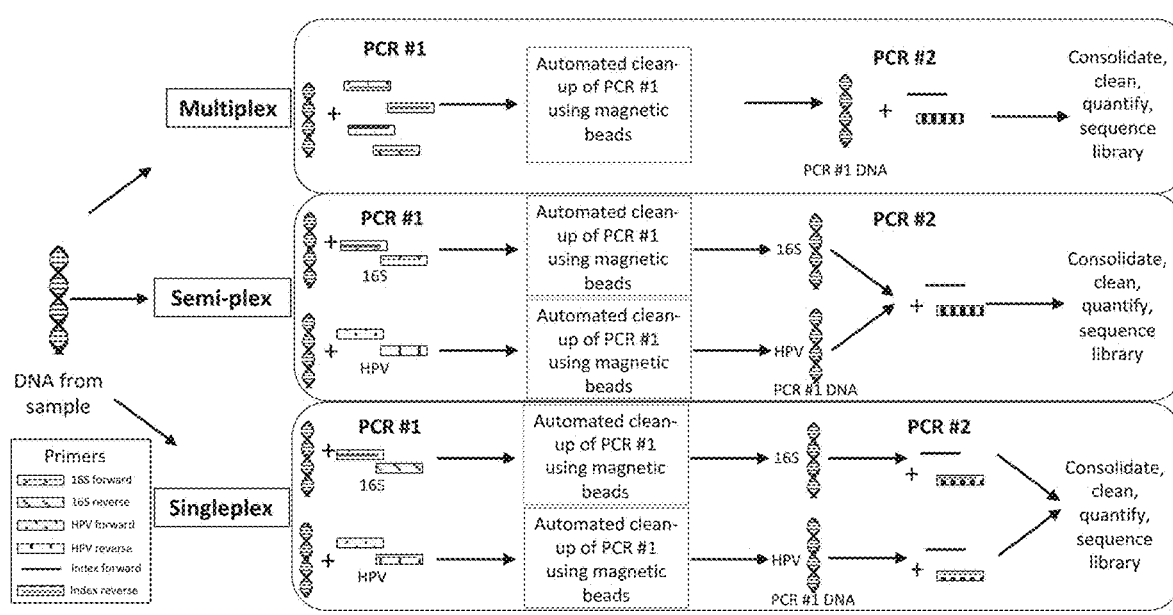
FIG. 10 includes a flowchart representation of amplification in variations of an embodiment of a method.

In a specific example, HPV detection (and/or other suitable analyses associated with female reproductive system-related characterization, etc.) can be performed described in FIG. 9: following self-sampling by a user (e.g., at-home sample collection, etc.), with the sample collected in a tube and/or other suitable container, is brought into a laboratory and accessioned; DNA in the samples is extracted using a clinical extraction pipeline (e.g., as shown in FIG. 9); samples are extracted into a 96-well plate (and/or any suitable plate and/or container) by using an automated fluids controller (e.g., automated liquid handler) and/or other suitable device, with each well representing a unique sample; upon extraction, the DNA is amplified in a 2-step PCR (e.g., as shown in FIG. 10) using primers specific for the 16S V4 region (e.g., as shown in FIG. 11) as well as primers targeting the L1 gene of HPV (e.g., as shown in FIG. 11); where the first PCR amplifies the 16S V4 region and the L1 gene of multiple HPV strains, while simultaneously adding Nextera adaptors; where the primers used for the second PCR bind to the Nextera adaptors from the first PCR and add indexing barcodes to distinguish each sample from one another, plus Illumina P5/P7 adaptors; where the 16S V4 primers used for each reaction includes a single forward and reverse primer with the same 16S priming site; however, the 16S primers differ from sample to sample based on the stagger sequences inserted between the Nextera adaptor and the 16S priming site, which can function to add diversity to the amplicon library; and where, for the HPV primers, a mix of forward and reverse primers are used that together can amplify a large set of clinically relevant HPV strains including at least both low-risk and high-risk.

In specific examples, such as for facilitating identification of bacterial targets (e.g., for a women's health assay), determining a microorganism dataset associated with one or more female reproductive system-related conditions (and/or other suitable portions of embodiments of the method 100) can additionally or alternatively include performing PCR on extracted DNA (e.g., DNA extracted following approaches described in relation to collected vaginal samples) using a suitable set of ssDNA oligonucleotide primers for amplifying a diverse array of 16S ribosomal RNA coding sequences; where the primers can include one or more adapters (e.g., for Illumina sequencing, etc.), one or more DNA barcodes for sample de-multiplexing, and/or other suitable components; PCR reactions can then be cleaned with magnetic beads, and libraries can be generated, quantitated, and/or loaded into one or more sequencing systems (e.g., an Illumina sequencer, etc.); data is de-multiplexed and analysed (e.g., using a bioinformatic pipeline, such as including portions of embodiments of the method 100; etc.); sequencing reads passing filters and assigned to previously selected bacterial targets (e.g., through a characterization process) can be used in determining one or more female reproductive system-related characterizations (e.g., for notification to the user, such as the user corresponding to the analyzed sample; etc.).

In specific examples, such as for facilitating identification of HPV targets (e.g., for a women's health assay), determining a microorganism dataset associated with one or more female reproductive system-related conditions (and/or other suitable portions of embodiments of the method 100) can additionally or alternatively include: performing PCR on extracted DNA (e.g., DNA extracted following approaches described in relation to collected vaginal samples) using a set of oligonucleotide primers associated with (e.g., targeting; designed against; complementary to; etc.) the L1 protein (and/or other suitable targets) of 21 different strains of HPV (and/or any suitable type and number of HPV strains); where the primers can include universal adapter sequences at the 5' end; one or more synthetic dsDNA spike molecules can additionally or alternatively be added to the PCR reaction (and/or added to any suitable components) at a known concentration (and/or any suitable concentration); where the synthetic dsDNA spike molecules (e.g., sequences thereof) can be amplified by the aforementioned primer set (and/or other suitable primers), and can include a known scrambled nucleotide sequence with a similar ATGC composition to the 21 HPV targets (and/or other suitable targets) (e.g., similar sequence to a sequence region of the HPV targets and/or other suitable targets, etc.); PCR reactions are cleaned with magnetic beads, and then subjected to a second PCR reaction with primers that anneal to the previously mentioned universal adapter sequence, where the PCR products (e.g., after the second PCR step) include all the necessary adapters for sequencing (e.g., Illumina sequencing, etc.), and one or more DNA barcodes for sample de-multiplexing; the second PCR reactions are then cleaned with magnetic beads, and libraries are generated, quantitated, and/or loaded into one or more sequencing systems (e.g., an Illumina sequencer, etc.); data is de-multiplexed, filtered and assigned using our bioinformatic pipeline (e.g., using a bioinformatic pipeline, such as including portions of embodiments of the method 100; etc.); where determining a female reproductive system-related characterization can include determining a ratio between the number of sequencing reads assigned to one of the 21 natural HPV strains (and/or other suitable targets) versus the synthetic spike (e.g., the synthetic dsDNA spike molecules); performing the one or more ratio determinations for any suitable number of targets and/or synthetic spikes; where the ratio(s) and/or sequencing reads can be used for the female reproductive system-related characterization, which can be used to notify one or more users (e.g., a user corresponding to the analyzed sample) regarding HPV strain status, such as depending on the magnitude of the calculated rati(os) for HPV/spike sequencing reads for each of the 21 detected strains (and/or other suitable targets). In a specific example, determining the microorganism dataset can include performing a first primer-based amplification for bacterial targets; performing a second primer-based amplification with a set of components including: a set of primers associated with the L1 protein of the HPV targets, and a set of synthetic dsDNA spike molecules of known concentration and comprising known scrambled nucleotide sequences with similar ATGC composition to at least one sequence region of the HPV targets; where the user microbiome features can include one or more ratios of sequencing reads between the HPV targets and the set of synthetic dsDNA spike molecules; and where determining the female reproductive system-related characterization can include determining the female reproductive system-related characterization for the user for the at least one female reproductive system-related condition based on the at least one ratio of sequencing reads between the HPV targets and the set of synthetic dsDNA spike molecules.

However, using synthetic spike molecules, barcodes, primers, and/or other suitable components for facilitating microorganism dataset and/or characterization determination can be performed in any suitable manner.

In variations, determining a microorganism dataset associated with one or more female reproductive system-related conditions (and/or any suitable portions of embodiments of the method 100) can include one or more PCR approaches (e.g., as shown in FIG. 10). In a variation, as shown in FIG. 10, a PCR approach can include 2-step PCR corresponding to a multiplex PCR, where a single forward and reverse primer specific for the 16S V4 region and the primers that can amplify the L1 gene of HPV are combined in the same PCR reaction; following this PCR, in a 96-well format and/or other suitable format, the samples can be cleaned by purification methods (e.g., magnetic beads; etc.) to remove PCR contaminants; and for the second step PCR, a constant volume can be used as a template for the second PCR, where this PCR can include a single forward and reverse primer for each sample with unique indexing barcodes using an automated fluids controller (e.g., an automated liquid handler).

In a variation, as shown in FIG. 10, a PCR approach can include 2-step PCR corresponding to a semi-plex PCR, where a single forward and reverse primer specific for the 16S V4 region or primers that can amplify the L1 gene of HPV are used in different PCR reactions; following the PCR, in a 96-well format and/or other suitable format, the samples are cleaned by purification methods (e.g., magnetic beads) and/or any other suitable manner to remove PCR contaminants; for the second step PCR, a constant volume from each of the first PCRs is combined and used as template for the second PCR, where this PCR can include a single forward and reverse primer for each sample with unique indexing barcodes, and can be performed using an automated fluids controller (e.g., an automated liquid handler).

In a variation, as shown in FIG. 10, a PCR approach can include a 2-step PCR corresponding to a singleplex PCR, where a single forward and reverse primer specific for the 16S V4 region or primers that can amplify the L1 gene of HPV are used in different PCR reactions; following the PCR, in a 96-well format and/or other suitable format, the samples can be cleaned by purification methods (e.g., magnetic beads) and/or any other suitable manner to remove PCR contaminants; for the second PCR, a constant volume from the first PCR is used as template for each of the second PCRs for both 16S V4 and HPV, which are kept separate, where this PCR can include a single forward and reverse primer with unique indexing barcodes for each sample or for each PCR (e.g. 16S V4 or HPV), and can be performed using an automated fluids controller (e.g. an automated liquid handler).

Additionally or alternatively, Block S120 can implement any other 2-step PCR methodology and/or other suitable PCR approach configured to facilitate processing.

In variations, following a 2nd PCR stage (e.g., in 2-step PCR), the samples can be normalized by bead-based purification, SYBR-based quantification, and/or other suitable approaches, such that the same quantity of DNA from each sample (from a total of up to five 96-well plates) can be consolidated. Additionally or alternatively, a constant volume from each sample can be removed (e.g., from a total of up to five 96-well plates) and transferred into a single tube to be consolidated, such as by using an automated fluids controller (e.g., an automated liquid handler). In examples, clean-up of the consolidated amplicon library can include a column-based clean-up method, such as the Zymo 'Select-a-size DNA Clean & Concentrator' to clean-up the PCR additives, as well as to remove any primer dimers. In examples, clean-up of the consolidated amplicon library can include use of magnetic beads to purify the consolidated library. In examples, additional or alternative purification approaches can include one or more of: purification by column, PCR product purification, and/or any other suitable approaches.

In a variation, the DNA library can be quantified using a quantifying assay (e.g., the Quant-iT dsDNA assay) and using an automated fluids controller (e.g., an automated liquid handler) and/or any other suitable approaches.

Determining a microorganism dataset (e.g., associated with one or more female reproductive system-related conditions; etc.) can include sequencing one or more generated DNA libraries (e.g., sequencing libraries; etc.) using next-generation sequencing technologies (e.g., NextSeq 500; such as to determine microorganism datasets for use in determining female reproductive system-related characterizations), using an automated fluids controller (e.g., an automated liquid handler) and/or any suitable sequencing technologies (e.g., described herein, etc.), and/or other suitable approaches.

Determining a microorganism dataset (e.g., associated with one or more female reproductive system-related conditions; etc.) can include, in relation to sequence reads (and/or any suitable outputs of sequencing technologies; etc.), one or more of: filtering, trimming, appending, clustering, labeling (e.g., as the actual genetic sequence; as an error; etc.), and/or other suitable processing of sequencing outputs.

In an example, the method 100 can include generating a set of processed sequence reads, which can include one or more of: amplifying the 16S gene; filtering the reads using an average Q-score >30; further filtering the reads using a same nucleotide repeat criteria of, for example, 9 identical nucleotides, trimming primers and leading bases from the reads; appending forward and reverse reads; clustering using a distance of 1 nucleotide (e.g., with the Swarm algorithm); labeling the most abundant read sequence per cluster as the actual genetic sequence; for each cluster, assigning the most abundant read sequence with a count corresponding to the number of reads in the cluster; and performing chimera removal on the most abundant read sequence per cluster (e.g., using a VSEARCH algorithm, etc.). However, sequencing can be performed in any suitable manner.

In an example, the method 100 can include generating a set of processed sequence reads based on amplification of the L1 gene of HPV viruses, where generating the set of processed sequence reads can include one or more of: filtering the reads based on a quality score above 30; trimming primers and leading and trailing bases of the reads; determining the count of HPV reads based on different approaches depending on the type of database used. In a specific example, the identification of the reads as L1 genes from HPV can be performed against a reference amplicon database, such as where further filtering can include removing reads that can contain a same nucleotide repeat of, for example, 9 identical nucleotides, concatenating forward and reverse reads; clustering using a distance of 1 nucleotide (e.g., with the Swarm algorithm); labeling the most abundant read sequence per cluster as the actual genetic sequence; for each cluster, assigning the most abundant read sequence with a count corresponding to the number of reads in the cluster; and performing chimera removal on the most abundant read sequence per cluster (e.g., using a VSEARCH algorithm, etc.). In a specific example, the processed sequence reads can be used in determining microbiome composition features (e.g., in Block S130). In a specific example, reads can be identified as L1 genes from HPV based on mapping against reference genomes, such as where further processing the reads can include mapping reads against the complete HPV genomes using reference alignment software (e.g., BOWTIE2, BWA, etc.). In examples, the aligned/mapped reads can be stored in "sam" and/or "bam" files types, and uniquely mapped reads can be obtained with any suitable software (e.g., Samtools).

In an example, the at least one female reproductive system-related condition can be associated with bacterial targets and HPV targets, and where determining the microorganism dataset can include: determining a first set of processed sequence reads associated with the bacterial targets based on filtering of a first set of sequence reads derived from the microorganism nucleic acids (e.g., from a sample); and determining a second set of processed sequence reads associated with the HPV targets based on filtering of a second set of sequence reads derived from the microorganism nucleic acids, where determining the user microbiome features can include determining the user microbiome features based on the first and the second set of processed sequence reads. In an example, determining the user microbiome features can include determining first alignment data based on alignment of the first set of processed sequence reads to 16S rRNA gene sequences associated with the bacterial targets; determining second alignment data based on alignment of the second set of processed sequence reads to HPV sequences associated with the HPV targets; and determining the user microbiome features based on the first and the second alignment data.

In variations, the method 100 can include providing sample kits for self-sampling. In a specific example, a vaginal self-collection kit can be provided to users, the kit including (e.g., as shown in FIG. 3) a sterile swab, a tube with sterile water, a tube with zirconia beads in a proprietary lysis and stabilization buffer that preserves the DNA for transport at ambient temperatures, sampling instructions, and/or other suitable components. Users can be instructed to wet the swab with the sterile water, insert the swab into the vagina as far as is comfortable, make circular movements around the swab's axis for 1 minute (and/or other suitable time period), and then stir the swab for 1 minute (and/or other suitable time period) into the tube with lysis buffer and beads; after shaking the tube for 1 minute (and/or other suitable time period) to homogenize, the tube can be shipped by users to a laboratory. In a specific example, cotton swabs are utilized to obtain samples from the vaginal mucosa; samples are resuspended in a proprietary buffer (and/or other suitable solutions and/or materials) that allows the storage of intact nucleic acids at room temperature for several weeks (and/or other suitable time period), such as where the buffer can include zirconia beads for cell disruption, and/or other suitable materials; resuspended samples are then subjected to mechanical shearing in a cell/tissue disrupter; sample supernatants are then mixed with DNA-binding magnetic beads in a buffer with a suitable ionic strength for DNA capture; and/or extracted DNA is resuspended in nuclease-free water.

However, sample processing associated with female reproductive system-related conditions and/or determining a microorganism dataset associated with female reproductive system-related conditions can be performed in any suitable manner.

3.2 Processing Supplementary Data.

Embodiments of the method 100 can additionally or alternatively include Block S120, which can include processing (e.g., receiving, collecting, transforming, determining supplementary features, ranking supplementary features, identifying correlations, etc.) supplementary data (e.g., one or more supplementary datasets, etc.) associated with (e.g., informative of; describing; indicative of; correlated with; etc.) one or more female reproductive system-related conditions, one or more users, and/or other suitable entities. Block S120 can function to process data for supplementing microorganism datasets, microbiome features (e.g., in relation to determining female reproductive system-related characterizations and/or facilitating therapeutic intervention, etc.), and/or can function to supplement any suitable portion of the method 100 and/or system 200 (e.g., processing supplementary data for facilitating one or more characterization processes, such as in Block S130; such as for facilitating training, validating, generating, determining, applying and/or otherwise processing female reproductive system-related characterization models, etc.). In an example, supplementary data can include at least one of survey-derived data, user data, site-specific data, and device data (and/or other suitable supplementary data), where an example of method 100 can include determining a set of supplementary features based on the at least one of the survey-derived data, the user data, the site-specific data, and the device data (and/or other suitable supplementary data); and generating one or more female reproductive system-related characterization models based on the supplementary features, microbiome features, and/or other suitable data.

Supplementary data can include any one or more of: survey-derived data (e.g., data from responses to one or more surveys surveying for one or more female reproductive system-related conditions, for any suitable types of data described herein; etc.); site-specific data (e.g., data informative of different collection sites, such as prior biological knowledge indicating correlations between microbiomes at specific collection sites and one or more female reproductive system-related conditions; etc.); female reproductive system-related condition data (e.g., data informative of different female reproductive system-related conditions, such as in relation to microbiome characteristics, therapies, users, etc.); device data (e.g., sensor data; contextual sensor data associated with female reproductive system; wearable device data; medical device data; user device data such as mobile phone application data; web application data; etc.); user data (e.g., user medical data current and historical medical data such as historical therapies, historical medical examination data; medical device-derived data; physiological data; data associated with medical tests; social media data; demographic data; family history data; behavior data describing behaviors; environmental factor data describing environmental factors; diet-related data such as data from food establishment check-ins, data from spectrophotometric analysis, user-inputted data, nutrition data associated with probiotic and/or prebiotic food items, types of food consumed, amount of food consumed, caloric data, diet regimen data, and/or other suitable diet-related data; etc.); prior biological knowledge (e.g., informative of female reproductive system-related conditions, microbiome characteristics, associations between microbiome characteristics and female reproductive system-related conditions, etc.); and/or any other suitable type of supplementary data.

In variations, processing supplementary data can include processing survey-derived data, where the survey-derived data can provide condition data (e.g., indicating presence, absence, and/or severity of one or more female reproductive system-related conditions; etc.), physiological data, demographic data, behavior data, environmental factor data (e.g., describing environmental factors, etc.), other types of supplementary data, and/or any other suitable data. Physiological data can include information related to physiological features (e.g., height, weight, body mass index, body fat percent, body hair level, medical history, etc.). Demographic data can include information related to demographic characteristics (e.g., gender, age, ethnicity, marital status, number of siblings, socioeconomic status, sexual orientation, etc.). Behavioral data can describe behaviors including one or more: health-associated states (e.g., health and disease states), dietary habits (e.g., alcohol consumption, caffeine consumption, omnivorous, vegetarian, vegan, sugar consumption, acid consumption, consumption of wheat, egg, soy, treenut, peanut, shellfish, food preferences, allergy characteristics, consumption and/or avoidance of other food items, etc.), behavioral tendencies (e.g., levels of physical activity, drug use, alcohol use, habit development, etc.), different levels of mobility (e.g., amount of exercise such as low, moderate, and/or extreme physical exercise activity; related to distance traveled within a given time period; indicated by mobility sensors such as motion and/or location sensors; etc.), different levels of sexual activity (e.g., related to numbers of partners and sexual orientation), and any other suitable behavioral data. Survey-derived data can include quantitative data, qualitative data, and/or other suitable types of survey-derived data, such as where qualitative data can be converted to quantitative data (e.g., using scales of severity, mapping of qualitative responses to quantified scores, etc.). Processing survey-derived data can include facilitating collection of survey-derived data, such as by providing one or more surveys to one or more users, subjects, and/or other suitable entities. Surveys can be provided in-person (e.g., in coordination with sample kit provision and/or reception of samples; etc.), electronically (e.g., during account setup; at an application executing at an electronic device of a subject, at a web application and/or website accessible through an internet connection; etc.), and/or in any other suitable manner.

Additionally or alternatively, processing supplementary data can include processing sensor data (e.g., sensors of female reproductive system-related devices, wearable computing devices, mobile devices; biometric sensors associated with the user, such as biometric sensors of a user smart phone; etc.). Sensor data can include any one or more of: physical activity- and/or physical action-related data (e.g., accelerometer data, gyroscope data, location sensor data such as GPS data, and/or other mobility sensor data from one or more devices such as a mobile device and/or wearable electronic device, etc.), sensor data describing environmental factors (e.g., temperature data, elevation data, climate data, light parameter data, pressure data, air quality data, etc.), biometric sensor data (e.g., blood pressure data; temperature data; pressure data associated with swelling; heart rate sensor data; fingerprint sensor data; optical sensor data such as facial images and/or video; data recorded through sensors of a mobile device; data recorded through a wearable or other peripheral device; etc.), and/or any other suitable data associated with sensors. Additionally or alternatively, sensor data can include data sampled at one or more: optical sensors (e.g., image sensors, light sensors, cameras, etc.), audio sensors (e.g., microphones, etc.), temperature sensors, volatile compound sensors, air quality sensors, weight sensors, humidity sensors, depth sensors, location sensors (GPS receivers; beacons; indoor positioning systems; compasses; etc.), motion sensors (e.g., accelerators, gyroscope, magnetometer, motion sensors integrated with a device worn by a user, etc.), biometric sensors (e.g., heart rate sensors such as for monitoring heart rate; fingerprint sensors; facial recognition sensors; bio-impedance sensors, etc.), pressure sensors, proximity sensors (e.g., for monitoring motion and/or other aspects of third-party objects; etc.), flow sensors, power sensors (e.g., Hall effect sensors), virtual reality-related sensors, augmented reality-related sensors, and/or or any other suitable types of sensors.

Additionally or alternatively, supplementary data can include medical record data and/or clinical data. As such, portions of the supplementary dataset can be derived from one or more electronic health records (EHRs). Additionally or alternatively, supplementary data can include any other suitable diagnostic information (e.g., clinical diagnosis information). Any suitable supplementary data (e.g., in the form of extracted supplementary features, etc.) can be combined with and/or used with microbiome features and/or other suitable data for performing portions of embodiments of the method 100 (e.g., performing characterization processes, etc.) and/or system 200. For example, supplementary data associated with (e.g., derived from, etc.) computed tomography (CT scan), ultrasound, biopsy, blood test, cancer screening exams, urine test (e.g., to detect infection;

etc.), diagnostic imaging, other suitable diagnostic procedures associated with female reproductive system-related conditions, survey-related information, and/or any other suitable test can be used to supplement (e.g., for any suitable portions of embodiments of the method 100 and/or system 200).

Additionally or alternatively, supplementary data can include therapy-related data including one or more of: therapy regimens, types of therapies, recommended therapies, therapies used by the user, therapy adherence, and/or other suitable data related to therapies. For example, supplementary data can include user adherence metrics (e.g., medication adherence, probiotic adherence, physical exercise adherence, dietary adherence, etc.) in relation one or more therapies (e.g., a recommended therapy, etc.). However, processing supplementary data can be performed in any suitable manner.

3.3 Performing a Characterization Process.

Embodiments of the method 100 can include Block S130, which can include, performing a characterization process (e.g., pre-processing; feature generation; feature processing; site-specific characterization, such as characterization specific to one or more particular body sites, such as for samples collected at collection sites corresponding to the body site, such as multi-site characterization for a plurality of body sites; cross-condition analysis for a plurality of female reproductive system-related conditions; model generation; etc.) associated with one or more female reproductive system-related conditions, such as based on a microorganism dataset (e.g., derived in Block S110, etc.) and/or other suitable data (e.g., supplementary dataset; etc.) S130. Block S130 can function to identify, determine, extract, and/or otherwise process features and/or feature combinations that can be used to determine female reproductive system-related characterizations for users or and sets of users, based upon their microbiome composition (e.g., microbiome composition diversity features, etc.), function (e.g., microbiome functional diversity features, etc.), and/or other suitable microbiome features (e.g., such as through the generation and application of a characterization model for determining female reproductive system-related characterizations, etc.).

As such, the characterization process can be used as a diagnostic tool that can characterize a subject (e.g., in terms of behavioral traits, in terms of medical conditions, in terms of demographic characteristics, etc.) based upon their microbiome composition and/or functional features, in relation to one or more of their health condition states (e.g., female reproductive system-related condition states), behavioral traits, medical conditions, demographic characteristics, and/or any other suitable traits. Such characterizations can be used to determine, recommend, and/or provide therapies (e.g., personalized therapies, such as determined by way of a therapy model, etc.), and/or otherwise facilitate therapeutic intervention. Additionally or alternatively, characterization processes can be based on microorganism databases (e.g., including associations between one or more microbiome features and one or more female reproductive system-related conditions; etc.).

Performing a characterization process S130 can include pre-processing microorganism datasets, microbiome features, and/or other suitable data for facilitation of downstream processing (e.g., determining female reproductive system-related characterizations, etc.). In an example, performing a characterization process can include, filtering a microorganism dataset (e.g., filtering a microorganism sequence dataset, such as prior to applying a set of analytical techniques to determine the microbiome features, etc.), by at least one of: a) removing first sample data corresponding to first sample outliers of a set of biological samples (e.g., associated with one or more female reproductive system-related conditions, etc.), such as where the first sample outliers are determined by at least one of principal component analysis, a dimensionality reduction technique, and a multivariate methodology; b) removing second sample data corresponding to second sample outliers of the set of biological samples, where the second sample outliers can determined based on corresponding data quality for the set of microbiome features (e.g., removing samples corresponding to a number of microbiome features with high quality data below a threshold condition, etc.); and c) removing one or more microbiome features from the set of microbiome features based on a sample number for the microbiome feature failing to satisfy a threshold sample number condition, where the sample number corresponds to a number of samples associated with high quality data for the microbiome feature. However, pre-processing can be performed with any suitable analytical techniques in any suitable manner.

In performing the characterization process, Block S130 can use computational methods (e.g., statistical methods, machine learning methods, artificial intelligence methods, bioinformatics methods, etc.) to characterize a subject as exhibiting features (e.g., where determining user microbiome features can include determining feature values for microbiome features identified by characterization processes as correlated with and/or otherwise associated with one or more female reproductive system-related conditions, etc.) associated with one or more female reproductive system-related conditions (e.g., features characteristic of a set of users with the one or more female reproductive system-related conditions, etc.).

Figure 19:
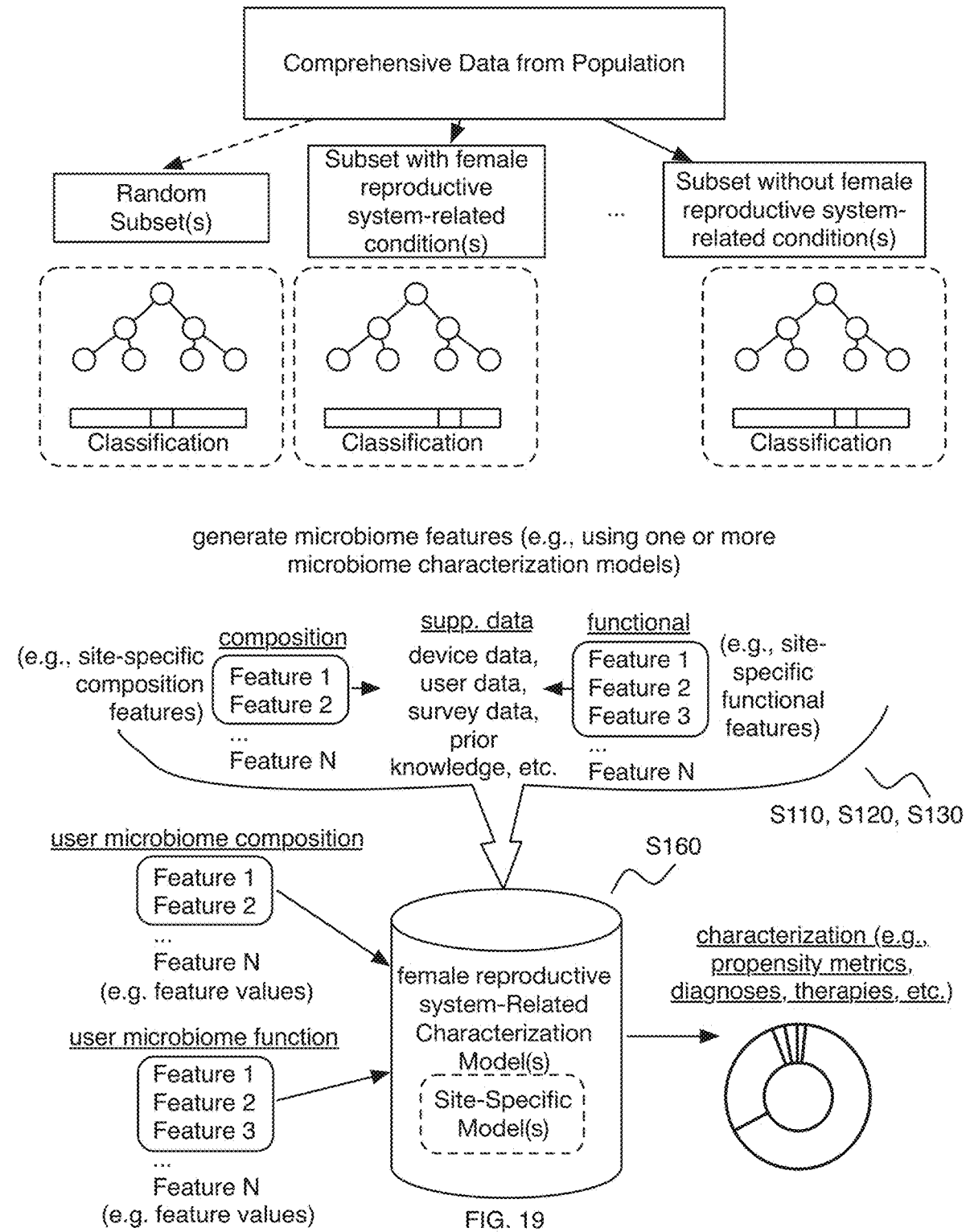
FIG. 19 includes a variation of a process for generation of a characterization model in an embodiment of a method.

As shown in FIG. 19, performing characterization processes can include determining one or more microbiome features associated with one or more female reproductive system-related conditions (e.g., identifying microbiome features with greatest relevance to one or more female reproductive system-related conditions; determining user microbiome features, such as presence, absence, and/or values of user microbiome features corresponding to the identified microbiome features associated with the one or more female reproductive system-related conditions, etc.), such as through applying one or more analytical techniques. In an example, determining microbiome features (e.g., microbiome composition features, microbiome functional features, etc.) can applying a set of analytical techniques including at least one of a univariate statistical test, a multivariate statistical test, a dimensionality reduction technique, and an artificial intelligence approach, such as based on a microorganism dataset (e.g., microorganism sequence dataset, etc.), and where the microbiome features can be configured to improve computing system-related functionality associated with the determining of the female reproductive system-related characterization for the user (e.g., in relation to accuracy, reducing error, processing speed, scaling, etc.). In an example, determining microbiome features (e.g., user microbiome features, etc.) can include applying a set of analytical techniques to determine at least one of presence of at least one of a microbiome composition diversity feature and a microbiome functional diversity feature, absence of the at least one of the microbiome composition diversity feature and the microbiome functional diversity feature, a relative abundance feature describing relative abundance of different taxonomic groups associated with the first female reproductive system-related condition, a ratio feature describing a ratio between at least two microbiome features associated with the different taxonomic groups, an interaction feature describing an interaction between the different taxonomic groups, and a phylogenetic distance feature describing phylogenetic distance between the different taxonomic groups, such as based on the microorganism dataset, and where the set of analytical techniques can include at least one of a univariate statistical test, a multivariate statistical test, a dimensionality reduction technique, and an artificial intelligence approach.

In variations, upon identification of represented groups of microorganisms of the microbiome associated with a biological sample, generating features associated with (e.g., derived from) compositional and functional aspects of the microbiome associated with a biological sample can be performed. In a variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features associated with (e.g., derived from) relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S130 can, however, include determination of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, determining microbiome features can be performed in any suitable manner.

In variations, performing a characterization process can include performing one or more multi-site analyses (e.g., with female reproductive system-related characterization models; generating a multi-site characterization, etc.) associated with a plurality of collection sites, such as performing female reproductive system-related characterizations based on a set of site-specific features including a first subset of site-specific features associated with a first body site, and a second subset of site-specific features associated with a second body site. However, multi-site analyses can be performed in any suitable manner.

In variations, performing a characterization process can include performing one or more cross-condition analyses (e.g., using female reproductive system-related characterization models, etc.) for a plurality of female reproductive system-related conditions. In an example, performing cross-condition analyses can include determining a set of cross-condition features (e.g., as part of determining microbiome features, etc.) associated with a plurality of female reproductive system-related conditions (e.g., a first female reproductive system-related condition and a second female reproductive system-related condition, etc.) based on one or more analytical techniques, where determining a female reproductive system-related characterization can include determining the female reproductive system-related characterization for a user for the plurality of female reproductive system-related conditions (e.g., first and the second female reproductive system-related conditions, etc.) based on one or more female reproductive system-related characterization models, and where the set of cross-condition features is configured to improve the computing system-related functionality associated with the determining of the female reproductive system-related characterization for the user for the plurality of female reproductive system-related conditions. Performing cross-condition analyses can include determining cross-condition correlation metrics (e.g., correlation and/or covariance between data corresponding to different female reproductive system-related conditions, etc.) and/or other suitable metrics associated with cross-condition analyses. However, performing cross-condition analyses can be performed in any suitable manner.

In a variation, characterization can be based upon features associated with (e.g., derived from) a statistical analysis (e.g., an analysis of probability distributions) of similarities and/or differences between a first group of subjects exhibiting a target state (e.g., a female reproductive system-related condition state) and a second group of subjects not exhibiting the target state (e.g., a "normal" state). In implementing this variation, one or more of a Kolmogorov-Smirnov (KS) test, a permutation test, a Cramér-von Mises test, any other statistical test (e.g., t-test, z-test, chi-squared test, test associated with distributions, etc.), and/or other suitable analytical techniques can be used. In particular, one or more such statistical hypothesis tests can be used to assess a set of features having varying degrees of abundance in a first group of subjects exhibiting a target state (e.g., a sick state) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in subjects with a female reproductive system-related condition vs. subjects without the female reproductive system-related condition; in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microorganism dataset, etc.) including any one or more of: a prediction analysis, multi hypothesis testing, a random forest test, principal component analysis, and/or other suitable analytical techniques.

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features associated with (e.g., derived from) the microbiome diversity dataset and/or the supplementary dataset. In variations, microbiome features can be associated with (e.g., include, correspond to, typify, etc.) at least one of: presence of a microbiome feature from the microbiome features (e.g., user microbiome features, etc.), absence of the microbiome features from the microbiome features, relative abundance of different taxonomic groups associated with the female reproductive system-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, a statistical inference method, and/or other suitable analytical techniques. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

In a variation, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing, such as to increase robustness of the model.

In a variation, Block S130 and/or other portions of embodiments of the method 100 can include applying computer-implemented rules (e.g., models, feature selection rules, etc.) to process population-level data, but can additionally or alternatively include applying computer-implemented rules to process microbiome-related data on a demographic characteristic-specific basis (e.g., subgroups sharing one or more demographic characteristics such as therapy regimens, dietary regimens, physical activity regimens, ethnicity, age, gender, weight, behaviors, etc.), condition-specific basis (e.g., subgroups exhibiting a specific female reproductive system-related condition, a combination of female reproductive system-related conditions, triggers for the female reproductive system-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S130 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more female reproductive system-related characterization models (e.g., female reproductive system-related condition models, therapy models, etc.) for one or more female reproductive system-related conditions (e.g., for outputting characterizations for users describing user microbiome characteristics in relation to female reproductive system-related conditions; therapy models for outputting therapy determinations for one or more female reproductive system-related conditions; etc.). The characterization models preferably leverage microbiome features as inputs, and preferably output female reproductive system-related characterizations and/or any suitable components thereof; but characterization models can use any suitable inputs to generate any suitable outputs. In an example, Block S130 can include transforming the supplementary data, the microbiome composition diversity features, and the microbiome functional diversity features, other microbiome features, outputs of female reproductive system-related characterization models, and/or other suitable data into one or more characterization models (e.g., training a female reproductive system-related characterization model based on the supplementary data and microbiome features; etc.) for one or more female reproductive system-related conditions. In another example, the method 100 can include: determining a population microorganism sequence dataset (e.g., including microorganism sequence outputs for different users of the population; etc.) for a population of users associated with one or more female reproductive system-related conditions, based on a set of samples from the population of users (e.g., and/or based on one or more primer types associated with the female reproductive system-related condition; etc.); collecting a supplementary dataset associated with diagnosis of the one or more female reproductive system-related conditions for the population of subjects; and generating the female reproductive system-related characterization model based on the population microorganism sequence dataset and the supplementary dataset. In an example, the method 100 can include determining a set of user microbiome features for the user based on a sample from the user, where the set of user microbiome features is associated with microbiome features associated with a set of subjects (e.g., microbiome features determined to be correlated with one or more female reproductive system-related conditions, based on processing biological samples corresponding to a set of subjects associated with the one or more female reproductive system-related conditions; a set microbiome composition features and the set of microbiome functional features; etc.); determining a female reproductive system-related characterization, including determining a therapy for the user for the one or more female reproductive system-related conditions based on a therapy model and the set of user microbiome features; providing the therapy (e.g., providing a recommendation for the therapy to the user at a computing device associated with the user, etc.) and/or otherwise facilitating therapeutic intervention.

Figure 24A:
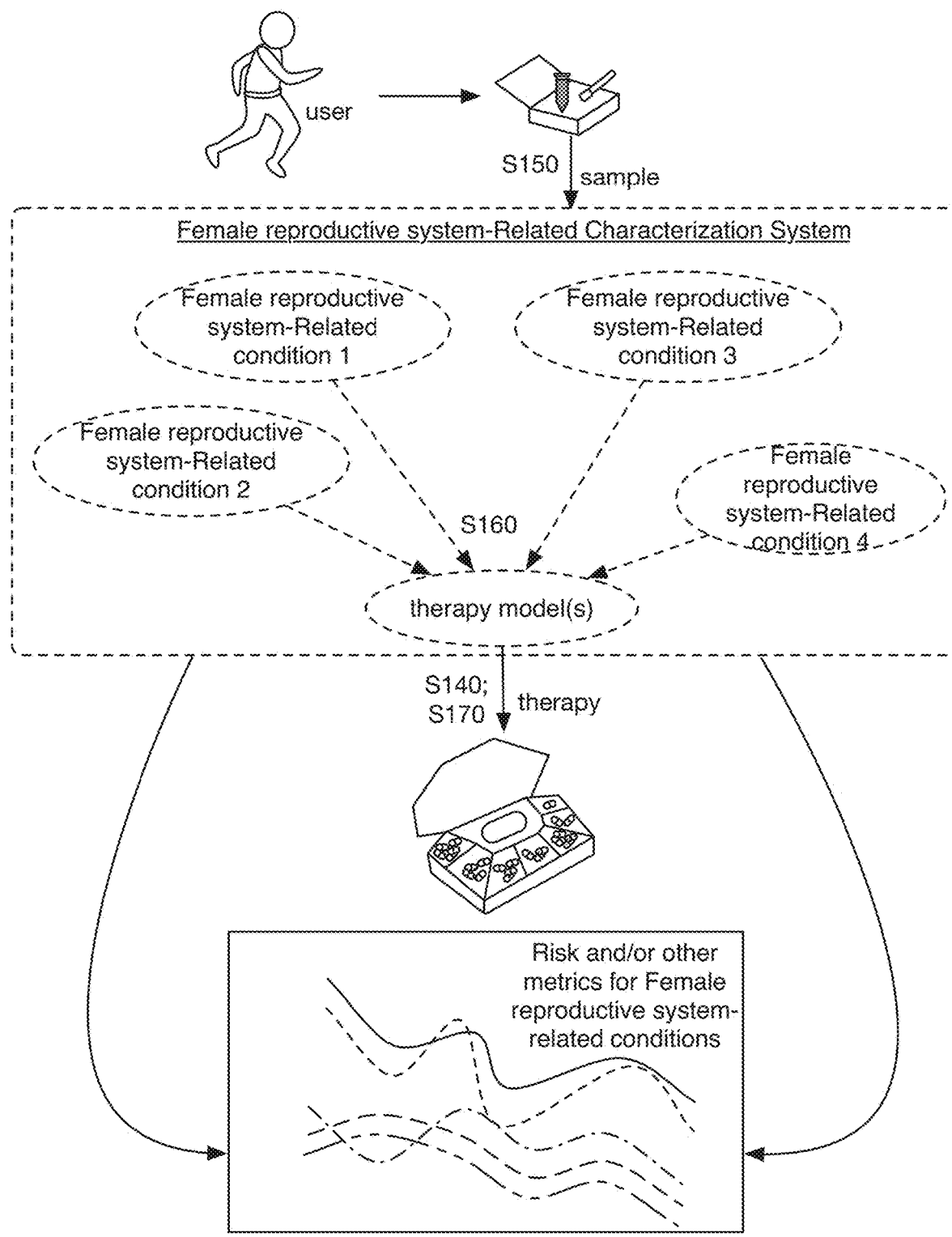
FIG. 24A-24B includes variations of performing characterization processes with models.
Figure 24B:
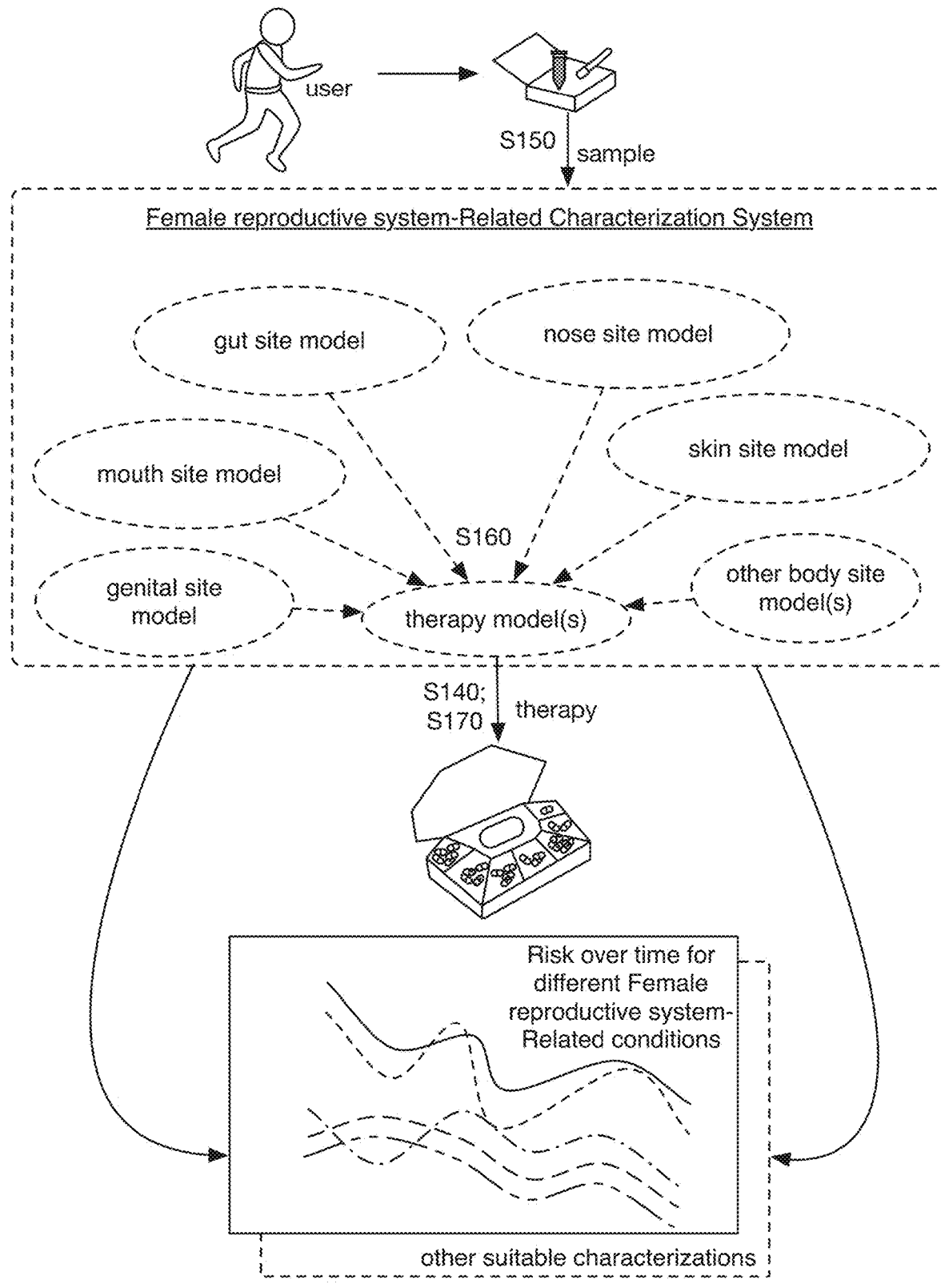

In another variation, as shown in FIG. 24A-24B, different female reproductive system-related characterization models and/or other suitable models (e.g., generated with different algorithms, with different sets of features, with different input and/or output types, applied in different manners such as in relation to time, frequency, component applying the model, etc.) can be generated for different female reproductive system-related conditions, different user demographic characteristics (e.g., based on age, gender, weight, height, ethnicity; etc.), different body sites (e.g., a gut site model, a nose site model, a skin site model, a mouth site model, a genitals site model, etc.), individual users, supplementary data (e.g., models incorporating prior knowledge of microbiome features, female reproductive system-related conditions, and/or other suitable components; features associated with biometric sensor data and/or survey response data vs. models independent of supplementary data, etc.), and/or other suitable criteria. In an specific example, the method 100 can include collecting first site-specific samples associated with a first body site (e.g., a gut site; samples collected by users at body collection sites corresponding to the first body site; one or more suitable body sites; etc.); determining a microorganism dataset based on the site-specific samples; determining first site-specific microbiome features (e.g., site-specific composition features; site-specific functional features; suitable microbiome features described herein in relation to female reproductive system-related conditions; features associated with the first body site; etc.) based on the microorganism dataset; determining a first site-specific female reproductive system-related characterization model (e.g., a gut site-specific female reproductive system-related characterization model; etc.) based on the first site-specific microbiome features; and determining a female reproductive system-related condition for a user for the female reproductive system-related condition based on the first site-specific female reproductive system-related characterization model (e.g., using the first site-specific female reproductive system-related characterization model to process user microbiome features, such as user site-specific microbiome features, derived based on a user sample collected at a body collection site of the user corresponding to the first body site; etc.). In a specific example, the method 100 can include collecting second site-specific samples associated with a second body site (e.g., at least one of a skin site, a genital site, a mouth site, and a nose site; one or more suitable body sites; etc.); determining second site-specific microbiome features (e.g. site-specific composition features; site-specific functional features; features associated with the second body site; etc.); generating a second site-specific female reproductive system-related characterization model (e.g., associated with the second body site; etc.) based on the second site-specific composition features; collecting a user sample from an additional user, the user sample associated with the second body site (e.g., collected by the additional user at a collection site corresponding to the second body site; etc.); and determining an additional female reproductive system-related characterization for the additional user for the female reproductive system-related condition based on the second site-specific female reproductive system-related characterization model (e.g., selecting the second site-specific female reproductive system-related characterization model, from a set of site-specific female reproductive system-related characterization models, to apply based on the association between the user sample and the body site, such as selecting a skin site-specific female reproductive system-related characterization model to apply based on a user sample being collected from a skin collection site of the user; etc.).

In variations, determining female reproductive system-related characterizations and/or any other suitable characterizations can include determining site-specific female reproductive system-related characterizations (e.g., site-specific analyses) including female reproductive system-related characterizations in relation to specific body sites (e.g., gut, healthy gut, skin, nose, mouth, genitals, other suitable body sites, other sample collection sites, etc.), such as through any one or more of: determining a female reproductive system-related characterization based on a female reproductive system-related characterization model derived based on site-specific data (e.g., defining correlations between a female reproductive system-related condition and microbiome features associated with one or more body sites); determining a female reproductive system-related characterization based on a user biological sample collected at one or more body sites, and/or any other suitable site-related processes. In examples, machine learning approaches (e.g., classifiers, deep learning algorithms, SVM, random forest), parameter optimization approaches (e.g., Bayesian Parameter Optimization), validation approaches (e.g., cross validation approaches), statistical tests (e.g., univariate statistical techniques, multivariate statistical techniques, correlation analysis such as canonical correlation analysis, etc.), dimension reduction techniques (e.g., PCA), and/or other suitable analytical techniques (e.g., described herein) can be applied in determining site-related (e.g., body site-related, etc.) characterizations (e.g., using a one or more approaches for one or more sample collection sites, such as for each type of sample collection site, etc.), other suitable characterizations, therapies, and/or any other suitable outputs. In a specific example, performing a characterization process (e.g., determining a female reproductive system-related characterization; determining microbiome features; based on a female reproductive system-related characterization model; etc.) can include applying at least one of: machine learning approaches, parameter optimization approaches, statistical tests, dimension reduction approaches, and/or other suitable approaches (e.g., where microbiome features such as a set of microbiome composition diversity features and/or a set of microbiome functional diversity features can be associated with microorganisms collected at least at one of a gut site, a skin site, a nose site, a mouth site, a genitals site, etc.). In another specific example, characterization processes performed for a plurality of sample collection sites can be used to generate individual characterizations that can be combined to determine an aggregate characterization (e.g., an aggregate microbiome score, such as for one or more conditions described herein, etc.). However, the method 100 can include determining any suitable site-related (e.g., site-specific) outputs, and/or performing any suitable portions of embodiments of the method 100 (e.g., collecting samples, processing samples, determining therapies) with site-specificity and/or other site-relatedness in any suitable manner.

Characterization of the subject(s) can additionally or alternatively implement use of a high false positive test and/or a high false negative test to further analyze sensitivity of the characterization process in supporting analyses generated according to embodiments of the method 100.

Figure 4:
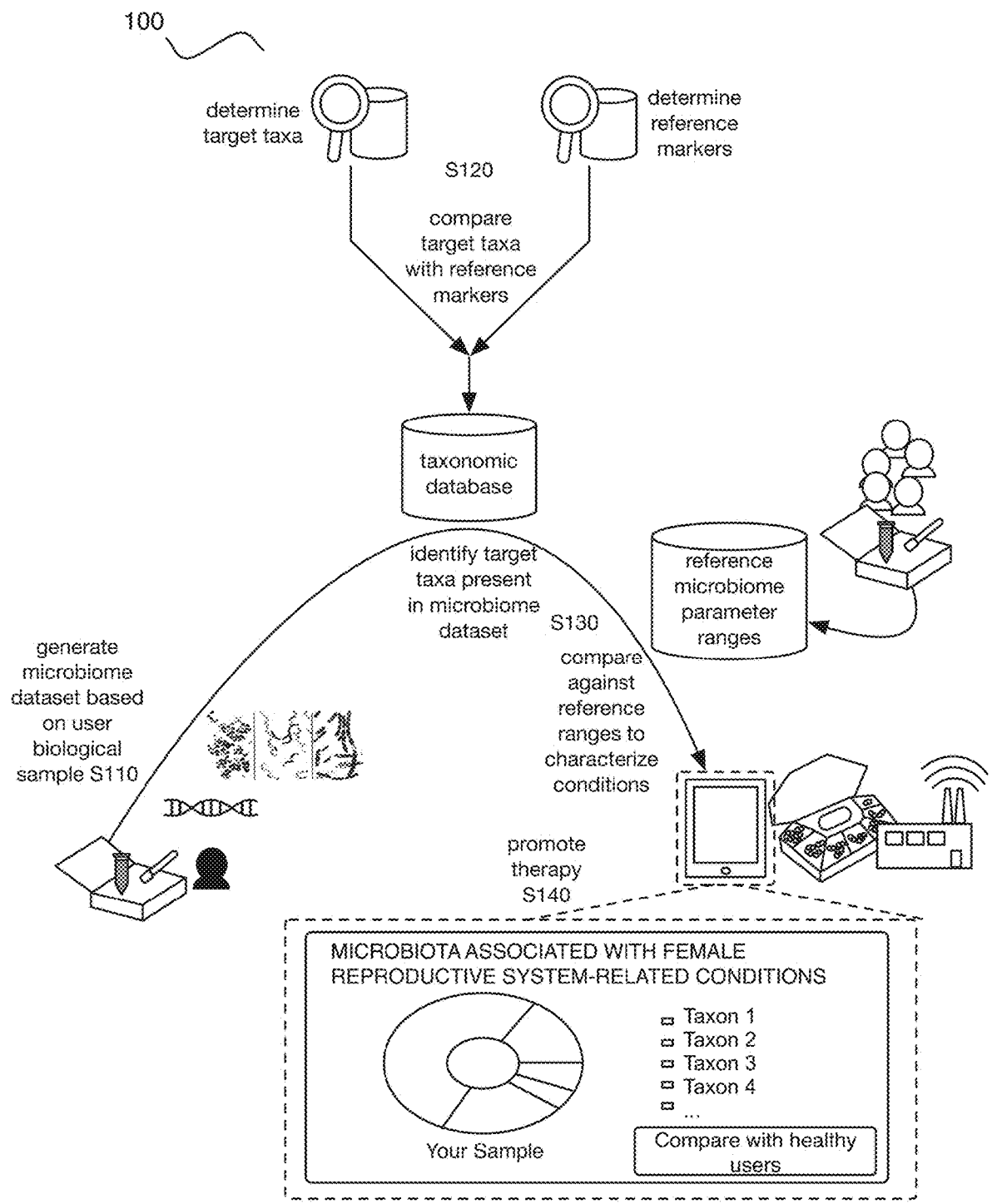
FIG. 4 includes a flowchart representation of variations of an embodiment of a method.
Figure 5:
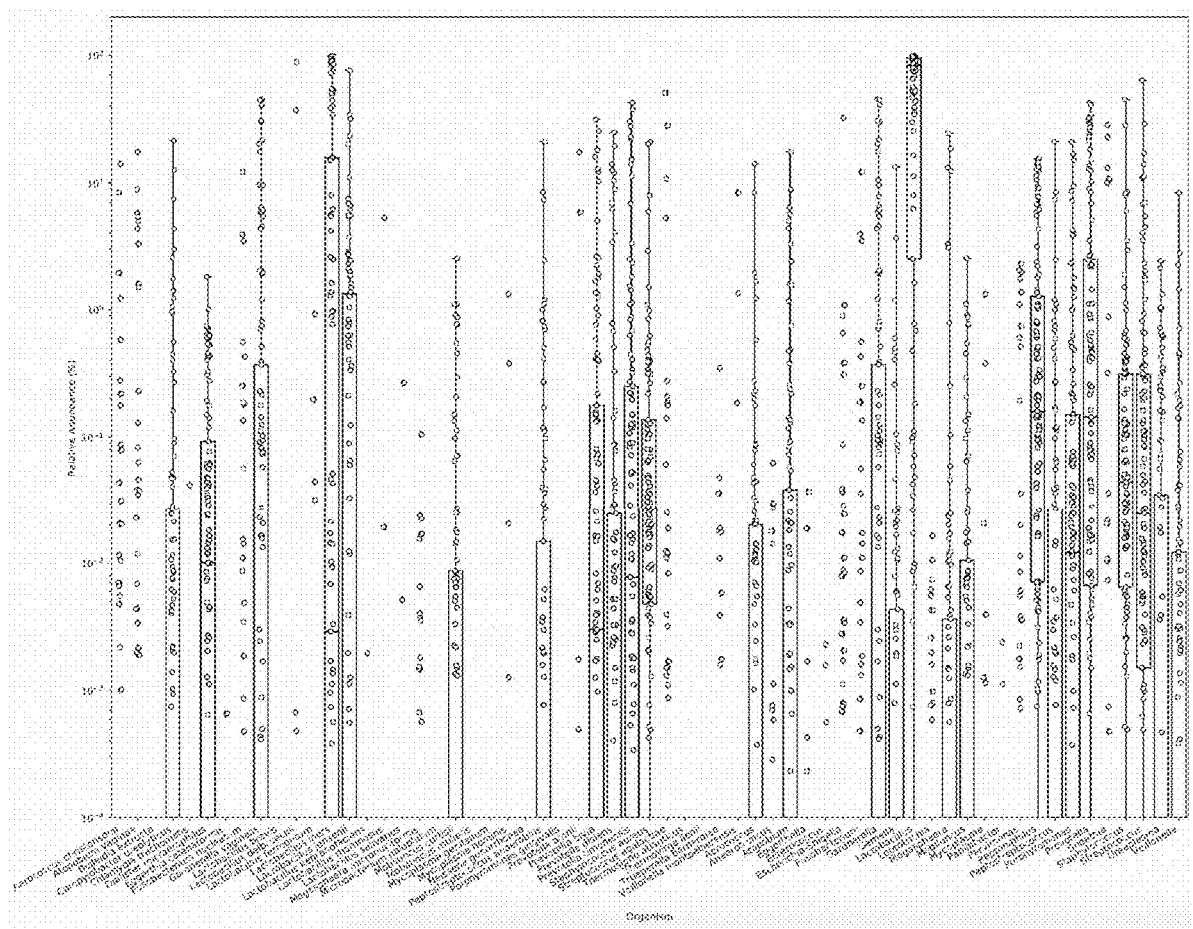
FIG. 5 includes a specific example of a chart representation of reference relative abundance ranges.

As shown in FIG. 4-5, performing a characterization process can include determining one or more reference microbiome parameter ranges (e.g., a healthy reference relative abundance range, where the range can be associated with a healthy microbiome and/or the absence of one or more conditions; a risk reference relative abundance range associated with the presence of and/or risk of one or more conditions; microorganism composition range for abundance of one or more taxa; phylogenetic diversity of the microorganisms present in the sample; microorganism functional diversity range for functional features associated with one or more taxa; etc.); determining a user microbiome parameter for a user; and/or generating a characterization for the user based on a comparison between the user microbiome parameter and the reference microbiome parameter range (e.g., characterizing a user as possessing an unhealthy microbiome composition in relation to bacterial targets of a women's health assay based on the user microbiome parameter indicating an abundance outside of the healthy reference ranges for different bacterial targets; etc.) and/or any other suitable operations. Microbiome parameter ranges can have any suitable lower- and upper-limits (e.g., a lower-limit above 0% for a relative abundance of *Lactobacillus*). Reference microbiome parameter ranges can include ranges representing any suitable confidence intervals (e.g., 99% confidence intervals across a population of users). In an example, reference relative abundance ranges can be calculated for any suitable taxa (e.g., from the target list of taxa for a women's health assay), such as based on dividing the count of reads corresponding to that taxa by the total number of reads (e.g., total number of clustered and filtered reads); however, reference relative abundance ranges can be calculated in any suitable manner.

In a variation, determining reference microbiome parameter ranges can be performed empirically. For example, Block S130 can include collecting biological samples and supplementary datasets from a population of users. The population of users can include users associated with any suitable state of microbiome composition, microbiome phylogenetic diversity, microbiome functional diversity, conditions, and/or other suitable characteristics, where the supplementary datasets (e.g., digitally administered surveys at an application executing on mobile devices associated with the users) can be informative of the characteristics. In a specific example, the method 100 can include: processing biological samples from a population of healthy users (e.g., users never diagnosed with STDs, vaginal-related symptoms, and/or other conditions, etc.); processing the biological samples (e.g., as in Block S120) to determine microorganism sequences; determining relative abundance of each taxa (e.g., from the target list of taxa) for each user; and generating healthy ranges for each of the taxa based on the relative abundances across the population of healthy users. However, empirically determining reference microbiome parameter ranges can be performed in any suitable manner. In a specific example, the supplementary data can indicate a lack of the at least one female reproductive system-related condition for a subset of subjects from a set of subjects; where determining the set of microbiome features can include determining healthy reference microbiome parameters ranges associated with the subset of subjects, based on the microorganism sequence dataset; and where generating the female reproductive system-related characterization model can include generating the female reproductive system-related characterization model (e.g., a model employing analytical techniques to compare reference microbiome parameter ranges to user microbiome features and/or parameters; etc.) includes based on the supplementary data and the healthy reference microbiome parameters ranges. In a variation, determining reference microbiome parameter ranges can be performed non-empirically, such as based on manually and/or automatically processing condition-related information sources.

In a specific example, performing characterization processes can include determining healthy reference microbiome parameters ranges (e.g., as shown in FIG. 7A-7D) for a set of targets for a women's health assay (e.g., 32 bacterial targets, etc.) based on analyses of a set of samples (e.g., a set of 50 vaginal samples, etc.), where the samples can be selected based on one or more of: self-reported healthy individuals, no usage of antibiotics six months prior, and/or no current urinary tract or vaginal infections, including the presence of STDs. In specific examples, as shown in FIG. 7A-7D (e.g., where each dot represents the relative abundance of a different bacterial target on genus level or species level within a different vaginal sample; boxes indicate the 25th-76th percentile, with the median indicated inside each box; horizontal line indicates the 99% confidence interval of each distribution; etc.), *Lactobacillus* can be the most abundant genus, with the widest abundance distribution; at the species level, a similar distribution of the relative abundances can be found, including a wide range and a high relative abundance for *Lactobacillus iners*.

However, determining reference microbiome parameter ranges can be performed in any suitable manner.

In variations, determining a user microbiome parameter for a user is preferably based on generated microorganism sequences derived from biological samples of the user (e.g., clustered and filtered reads; etc.). For example, determining a user microbiome parameter can include determining a relative abundance for different taxa (e.g., identified in the target list of taxa). In further examples, determining user microbiome parameters can include extracting microbiome composition features, microbiome phylogenetic diversity features, and/or microbiome functional features. In a specific example, the method 100 can include: determining reference microbiome parameter ranges from values of microbiome composition features, microbiome phylogenetic diversity features, and/or microbiome functional diversity features (e.g., derived from biological samples of healthy users, etc.); and comparing the user microbiome composition feature values, user microbiome phylogenetic diversity feature values, and/or user microbiome functional diversity feature values to the reference microbiome parameter ranges to determine characterizations for the user (e.g., for conditions positively and/or negatively associated with the reference microbiome parameter ranges).

In relation to Block S130, comparing one or more user microbiome parameters to one or more reference microbiome parameter ranges associated with one or more characteristics (e.g., taxa, conditions, etc.) can include characterizing the user as possessing the characteristic (e.g., a healthy microbiome, etc.) or not possessing the characteristic based on whether the user microbiome parameter values fall inside or outside the reference microbiome parameter ranges. For example, Block S130: can include deriving a healthy reference relative abundance range for *Neisseria gonorrhoeae*; and characterizing the user as at risk of pelvic inflammatory disease in response to the user having a relative abundance of *Neisseria gonorrhoeae* exceeding the healthy reference relative abundance range. However, comparing one or more user vaginal microbiome parameters can be performed in any suitable manner. In another example, Block S130 can include deriving a healthy reference relative abundance range for *Lactobacillus iners*, and characterizing the user as at risk of Bacterial Vaginosis in response to the user having a relative abundance of *Lactobacillus iners* reducing the healthy reference relative abundance range.

Additionally or alternatively for Block S130, performing the characterization process can be based on thresholds (e.g., determining risk of a condition based on relative abundances of a set of taxa in relation to a set of thresholds associated with the condition, etc.), weights (e.g., weighting relative abundance of a first taxa more heavily than relative abundance of a second taxa, such as when the first taxa has a greater correlation with the condition of interest, etc.), machine learning models (e.g., a classification model trained on microbiome features and corresponding labels for taxa stored in the taxonomic database; etc.), computer-implemented rules (e.g., feature-engineering rules for extracting microbiome features; model generation rules; user preference rules; microorganism sequence generation rules; sequence alignment rules; etc.), and/or any other suitable aspects. In a specific example, a significance index for each health condition is calculated as the overall statistical association obtained from scientific literature for all members of the microbiome detected that affect the condition; the identified correlations undergo a custom statistical meta-analysis and data transformations to calculate the overall association of the microbiome with the condition, based on the clinical results of the associated microbiome; and the significance index is expressed as a range from 0 to 100 representing the state of the microbiome associated with the health condition.

Additionally or alternatively, performing characterization processes can include applying any suitable combination of analytical techniques, such as analogous to that described in U.S. application Ser. No. 16/047,840 filed 27 Jul. 2018, which is herein incorporated in its entirety by this reference.

However, performing one or more characterization processes S130 can be performed in any suitable manner.

3.3.A Female Reproductive System-Related Characterization Process.

Performing a characterization process S130 can include performing a female reproductive system-related characterization process (e.g., determining a characterization for one or more female reproductive system-related conditions; determining and/or applying one or more female reproductive system-related characterization models; etc.) S135, such as for one or more users (e.g., for data corresponding to samples from a set of subjects for generating one or more female reproductive system-related characterization models, such as where one or more subjects are associated with the female reproductive system-related conditions, such as subjects diagnosed with the one or more female reproductive system-related conditions; for a single user for generating a female reproductive system-related characterization for the user, such as through using one or more female reproductive system-related characterization models, such as through applying the one or more female reproductive system-related characterization models to a user microbiome sequence dataset derived from sequencing a sample from the user; etc.) and/or for one or more female reproductive system-related conditions.

In variations, performing a female reproductive system-related characterization process can include determining microbiome features associated with one or more female reproductive system-related conditions. In an example, performing a female reproductive system-related characterization process can include applying one or more analytical techniques (e.g., statistical analyses) to identify the sets of microbiome features (e.g., microbiome composition features, microbiome composition diversity features, microbiome functional features, microbiome functional diversity features, etc.) that have the highest correlations (e.g., positive correlations, negative correlations, etc.) with one or more female reproductive system-related conditions (e.g., features associated with a single female reproductive system-related condition, cross-condition features associated with multiple female reproductive system-related conditions and/or other suitable female reproductive system-related conditions, etc.). In a specific example, determining a set of microbiome features (e.g., correlated with and/or otherwise associated with one or more female reproductive system-related conditions; for use in generating one or more female reproductive system-related characterization models; etc.) can include applying a set of analytical techniques to determine at least one of presence of at least one of a microbiome composition diversity feature and a microbiome functional diversity feature, absence of the at least one of the microbiome composition diversity feature and the microbiome functional diversity feature, a relative abundance feature describing relative abundance of different taxonomic groups associated with the female reproductive system-related condition, a ratio feature describing a ratio between at least two microbiome features associated with the different taxonomic groups, an interaction feature describing an interaction between the different taxonomic groups, and a phylogenetic distance feature describing phylogenetic distance between the different taxonomic groups, based on the microorganism sequence dataset, and/or where the set of analytical techniques can include at least one of a univariate statistical test, a multivariate statistical test, a dimensionality reduction technique, and an artificial intelligence approach.

In a specific example, performing a female reproductive system-related characterization process can facilitate therapeutic intervention for one or more female reproductive system-related conditions, such as through facilitating intervention associated with therapies having a positive effect on a state of one or more users in relation to the one or more female reproductive system-related conditions. In another specific example, performing a female reproductive system-related characterization process (e.g., determining features with highest correlations to one or more female reproductive system-related conditions, etc.) can be based upon a random forest predictor algorithm trained with a training dataset derived from a subset of the population of subjects (e.g., subjects having the one or more female reproductive system-related conditions; subjects not having the one or more female reproductive system-related conditions; etc.), and validated with a validation dataset derived from a subset of the population of subjects. However, determining microbiome features and/or other suitable aspects associated with one or more female reproductive system-related conditions can be performed in any suitable manner.

In variations, performing a female reproductive system-related characterization process can include performing a female reproductive system-related characterization process for any suitable female reproductive system-related conditions described herein. In a specific example, such a process can be based on a random forest predictor algorithm trained with a training dataset derived from a subset of the population of subjects, and validated with a validation dataset derived from a subset of the population of subjects.

Microbiome features (e.g., microbiome composition features; site-specific composition features associated with one or more body sites; microbiome functional features; site-specific functional features associated with one or more body sites; etc.) associated with one or more female reproductive system-related conditions (e.g., positively correlated with; negatively correlated with; useful for diagnosis; etc.) can include features (e.g., microbiome composition features, etc.) associated with any combination of one or more of the following taxa (e.g., features describing abundance of; features describing relative abundance of; features describing functional aspects associated with; features derived from; features describing presence and/or absence of; etc.), such as in relation to one or more body sites (e.g., where microbiome composition features can include site-specific composition features associated with the one or more body sites, such as where correlations between the composition features and the one or more female reproductive system-related conditions can be specific to the one or more body sites, such as specific to microbiome composition observed at the body site from samples collected at a body collection site corresponding to the body site; etc.): *Bacteroides* sp. AR20 (e.g., Gut site, etc.), *Bacteroides* sp. AR29 (e.g., Gut site, etc.), *Bacteroides* sp. D22 (e.g., Gut site, etc.), *Alistipes* sp. EBA6-25cl2 (e.g., Gut site, etc.), *Actinobacteria* (e.g., Gut site, etc.), *Alistipes* sp. EBA6-25cl2 (e.g., Gut site, etc.), *Bacteroidales* (e.g., Gut site, etc.), *Bacteroides* (e.g., Gut site, etc.), *Bacteroides* sp. AR20 (e.g., Gut site, etc.), *Bacteroides* sp. AR29 (e.g., Gut site, etc.), *Bacteroides* sp. D22 (e.g., Gut site, etc.), *Bacteroidetes* (e.g., Gut site, etc.), *Bacteroidia* (e.g., Gut site, etc.), *Barnesiella* (e.g., Gut site, etc.), *Barnesiella intestinihominis* (e.g., Gut site, etc.), *Betaproteobacteria* (e.g., Gut site, etc.), *Blautia luti* (e.g., Gut site, etc.), *Blautia* sp. Ser8 (e.g., Gut site, etc.), *Burkholderiales* (e.g., Gut site, etc.), *Clostridia* (e.g., Gut site, etc.), *Clostridiales* (e.g., Gut site, etc.), *Collinsella* (e.g., Gut site, etc.), *Coriobacteriales* (e.g., Gut site, etc.), *Dorea* (e.g., Gut site, etc.), *Dorea longicatena* (e.g., Gut site, etc.), *Eggerthella* (e.g., Gut site, etc.), *Eisenbergiella tayi* (e.g., Gut site, etc.), *Faecalibacterium prausnitzii* (e.g., Gut site, etc.), *Flavobacteriales* (e.g., Gut site, etc.), *Flavobacteriia* (e.g., Gut site, etc.), *Fusicatenibacter saccharivorans* (e.g., Gut site, etc.), *Lachnospira pectinoschiza* (e.g., Gut site, etc.), Lactobacillaceae (e.g., Gut site, etc.), *Megasphaera* (e.g., Gut site, etc.), *Odoribacter* (e.g., Gut site, etc.), Oscillospiraceae (e.g., Gut site, etc.), *Roseburia* (e.g., Gut site, etc.), *Roseburia* sp. 11SE39 (e.g., Gut site, etc.), Ruminococcaceae (e.g., Gut site, etc.), *Sarcina* (e.g., Gut site, etc.), *Subdoligranulum variabile* (e.g., Gut site, etc.), Sutterellaceae (e.g., Gut site, etc.), *Terrisporobacter* (e.g., Gut site, etc.), *Bifidobacterium* (e.g., Gut site, etc.), *Actinobacteria* (e.g., Gut site, etc.), *Alistipes* sp. EBA6-25cl2 (e.g., Gut site, etc.), *Alistipes* sp. HGB5 (e.g., Gut site, etc.), *Anaerostipes* sp. 5_1_63FAA (e.g., Gut site, etc.), *Bacteroides acidifaciens* (e.g., Gut site, etc.), *Bacteroides* sp. AR20 (e.g., Gut site, etc.), *Bacteroides* sp. AR29 (e.g., Gut site, etc.), *Bacteroides* sp. D22 (e.g., Gut site, etc.), *Bacteroides thetaiotaomicron* (e.g., Gut site, etc.), Bifidobacteriaceae (e.g., Gut site, etc.), *Bifidobacteriales* (e.g., Gut site, etc.), *Bifidobacterium* (e.g., Gut site, etc.), *Blautia luti* (e.g., Gut site, etc.), *Faecalibacterium prausnitzii* (e.g., Gut site, etc.), *Flavonifractor plautii* (e.g., Gut site, etc.), *Fusicatenibacter* (e.g., Gut site, etc.), *Fusicatenibacter saccharivorans* (e.g., Gut site, etc.), *Hespellia* (e.g., Gut site, etc.), *Lachnospira pectinoschiza* (e.g., Gut site, etc.), *Moryella* (e.g., Gut site, etc.), Oscillospiraceae (e.g., Gut site, etc.), *Roseburia* sp. 11SE39 (e.g., Gut site, etc.), *Subdoligranulum variabile* (e.g., Gut site, etc.), Bifidobacteriaceae (e.g., Gut site, etc.), *Bifidobacteriales* (e.g., Gut site, etc.), *Bifidobacterium* (e.g., Gut site, etc.), *Clostridia* (e.g., Gut site, etc.), *Clostridiales* (e.g., Gut site, etc.), *Negativicutes* (e.g., Gut site, etc.), *Selenomonadales* (e.g., Gut site, etc.), Veillonellaceae (e.g., Gut site, etc.), *Alistipes* sp. RMA9912 (e.g., Gut site, etc.), *Bacteroides caccae* (e.g., Gut site, etc.), *Bacteroides* sp. AR29 (e.g., Gut site, etc.), *Bacteroides* sp. D22 (e.g., Gut site, etc.), *Bacteroides vulgatus* (e.g., Gut site, etc.), *Bilophila* sp. 4_1_30 (e.g., Gut site, etc.), *Intestinimonas* (e.g., Gut site, etc.), Prevotellaceae (e.g., Gut site, etc.), *Actinobacteria* (e.g., Gut site, etc.), *Actinobacteria* (e.g., Genital site, etc.), *Alistipes putredinis* (e.g., Gut site, etc.), *Alistipes* sp. EBA6-25cl2 (e.g., Gut site, etc.), *Alistipes* sp. NML05A004 (e.g., Gut site, etc.), *Alphaproteobacteria* (e.g., Gut site, etc.), *Anaerostipes* sp. 5_1_63FAA (e.g., Gut site, etc.), *Bacilli* (e.g., mouth site, etc.), *Bacilli* (e.g., Genital site, etc.), Bacteroidaceae (e.g., Gut site, etc.), *Bacteroidales* (e.g., Gut site, etc.), *Bacteroides* (e.g., Gut site, etc.), *Bacteroides caccae* (e.g., Gut site, etc.), *Bacteroides* sp. AR20 (e.g., Gut site, etc.), *Bacteroides* sp. AR29 (e.g., Gut site, etc.), *Bacteroides* sp. D22 (e.g., Gut site, etc.), *Bacteroides* sp. SLC1-38 (e.g., Gut site, etc.), *Bacteroides thetaiotaomicron* (e.g., Gut site, etc.), *Bacteroidetes* (e.g., Gut site, etc.), *Bacteroidia* (e.g., Gut site, etc.), *Barnesiella intestinihominis* (e.g., Gut site, etc.), *Blautia luti* (e.g., Gut site, etc.), *Blautia* sp. Ser8 (e.g., Gut site, etc.), *Blautia* sp. YHC-4 (e.g., Gut site, etc.), *Blautia stercoris* (e.g., Gut site, etc.), *Blautia wexlerae* (e.g., Gut site, etc.), *Butyricimonas* (e.g., Gut site, etc.), *Clostridia* (e.g., Gut site, etc.), Clostridiaceae (e.g., Gut site, etc.), *Clostridiales* (e.g., Gut site, etc.), *Clostridium* (e.g., Gut site, etc.), *Collinsella* (e.g., Gut site, etc.), *Collinsella aerofaciens* (e.g., Gut site, etc.), *Collinsella aerofaciens* (e.g., Gut site, etc.), Coriobacteriaceae (e.g., Gut site, etc.), *Coriobacteriales* (e.g., Gut site, etc.), *Coriobacteriia* (e.g., Gut site, etc.), *Dielma* (e.g., Gut site, etc.), *Dielma* (e.g., Gut site, etc.), *Dorea formicigenerans* (e.g., Gut site, etc.), *Dorea longicatena* (e.g., Gut site, etc.), *Eggerthella* (e.g., Gut site, etc.), *Eggerthella* sp. HGA1 (e.g., Gut site, etc.), *Eisenbergiella* (e.g., Gut site, etc.), *Eisenbergiella tayi* (e.g., Gut site, etc.), *Faecalibacterium* (e.g., Gut site, etc.), *Faecalibacterium prausnitzii* (e.g., Gut site, etc.), *Firmicutes* (e.g., mouth site, etc.), Flavobacteriaceae (e.g., Gut site, etc.), *Flavobacteriales* (e.g., Gut site, etc.), *Flavobacteriia* (e.g., Gut site, etc.), *Flavonifractor plautii* (e.g., Gut site, etc.), *Fusicatenibacter* (e.g., Gut site, etc.), *Fusicatenibacter saccharivorans* (e.g., Gut site, etc.), *Hespellia* (e.g., Gut site, etc.), *Lachnospira pectinoschiza* (e.g., Gut site, etc.), Lactobacillaceae (e.g., Gut site, etc.), Lactobacillaceae (e.g., Genital site, etc.), Lactobacillales (e.g., Genital site, etc.), *Lactobacillus* (e.g., Gut site, etc.), *Lactobacillus* (e.g., Genital site, etc.), *Marvinbryantia* (e.g., Gut site, etc.), *Megasphaera* (e.g., Gut site, etc.), *Moryella* (e.g., Gut site, etc.), *Odoribacter* (e.g., Gut site, etc.), *Odoribacter splanchnicus* (e.g., Gut site, etc.), Oscillospiraceae (e.g., Gut site, etc.), *Parabacteroides* (e.g., Gut site, etc.), Porphyromonadaceae (e.g., mouth site, etc.), *Rhodospirillales* (e.g., Gut site, etc.), *Roseburia inulinivorans* (e.g., Gut site, etc.), *Roseburia* sp. 11SE39 (e.g., Gut site, etc.), Ruminococcaceae (e.g., Gut site, etc.), *Sarcina* (e.g., Gut site, etc.), *Selenomonadales* (e.g., Gut site, etc.), *Subdoligranulum* (e.g., Gut site, etc.), *Subdoligranulum variabile* (e.g., Gut site, etc.), *Terrisporobacter* (e.g., Gut site, etc.), *Terrisporobacter* (e.g., Gut site, etc.), Bacteroidaceae (e.g., Gut site, etc.), *Bacteroides* (e.g., Gut site, etc.), *Barnesiella intestinihominis* (e.g., Gut site, etc.), Clostridiaceae (e.g., Gut site, etc.), Coriobacteriaceae (e.g., Gut site, etc.), *Coriobacteriales* (e.g., Gut site, etc.), *Coriobacteriia* (e.g., Gut site, etc.), *Eggerthella* (e.g., Gut site, etc.), *Eggerthella* sp. HGA1 (e.g., Gut site, etc.), *Eisenbergiella* (e.g., Gut site, etc.), *Flavonifractor plautii* (e.g., Gut site, etc.), *Lachnospira pectinoschiza* (e.g., Gut site, etc.), Lactobacillaceae (e.g., Gut site, etc.), *Lactobacillus* (e.g., Gut site, etc.), *Moryella* (e.g., Gut site, etc.), *Roseburia* sp. 11SE39 (e.g., Gut site, etc.), *Sarcina* (e.g., Gut site, etc.), *Terrisporobacter* (e.g., Gut site, etc.), *Bacteroidales* (e.g., skin site, etc.), *Bacteroidia* (e.g., skin site, etc.), Acidaminococcaceae (e.g., Gut site, etc.), *Actinobacteria* (e.g., Gut site, etc.), *Actinobacteria* (e.g., Genital site, etc.), *Actinobacteria* (e.g., Gut site, etc.), *Actinomycetales* (e.g., Genital site, etc.), *Alistipes* sp. EBA6-25cl2 (e.g., Gut site, etc.), *Anaerococcus* (e.g., nose site, etc.), *Anaerostipes* sp. 5_1_63FAA (e.g., Gut site, etc.), *Bacilli* (e.g., mouth site, etc.), *Bacilli* (e.g., Genital site, etc.), Bacteroidaceae (e.g., Gut site, etc.), *Bacteroidales* (e.g., Gut site, etc.), *Bacteroides* (e.g., Gut site, etc.), *Bacteroides* sp. AR20 (e.g., Gut site, etc.), *Bacteroides* sp. AR29 (e.g., Gut site, etc.), *Bacteroides* sp. D22 (e.g., Gut site, etc.), *Bacteroides* sp. EBA5-17 (e.g., Gut site, etc.), *Bacteroides* sp. SLC1-38 (e.g., Gut site, etc.), *Bacteroides thetaiotaomicron* (e.g., Gut site, etc.), *Bacteroidetes* (e.g., Gut site, etc.), *Bacteroidia* (e.g., Gut site, etc.), *Barnesiella* (e.g., Gut site, etc.), *Barnesiella intestinihominis* (e.g., Gut site, etc.), *Betaproteobacteria* (e.g., Gut site, etc.), Bifidobacteriaceae (e.g., Gut site, etc.), *Bifidobacteriales* (e.g., Gut site, etc.), *Bifidobacterium* (e.g., Gut site, etc.), *Blautia luti* (e.g., Gut site, etc.), *Blautia* sp. YHC-4 (e.g., Gut site, etc.), *Burkholderiales* (e.g., Gut site, etc.), *Butyricimonas* (e.g., Gut site, etc.), *Butyricimonas* (e.g., Gut site, etc.), *Clostridia* (e.g., Gut site, etc.), Clostridiaceae (e.g., Gut site, etc.), *Clostridiales* (e.g., Gut site, etc.), *Collinsella* (e.g., Gut site, etc.), *Collinsella aerofaciens* (e.g., Gut site, etc.), Coriobacteriaceae (e.g., Gut site, etc.), *Coriobacteriales* (e.g., Gut site, etc.), *Coriobacteriia* (e.g., Gut site, etc.), Corynebacteriaceae (e.g., Gut site, etc.), Corynebacteriaceae (e.g., Genital site, etc.), *Corynebacteriales* (e.g., Gut site, etc.), *Corynebacteriales* (e.g., Genital site, etc.), *Corynebacterium* (e.g., Gut site, etc.), *Corynebacterium* (e.g., Genital site, etc.), *Dorea* (e.g., Gut site, etc.), *Dorea formicigenerans* (e.g., Gut site, etc.), *Dorea longicatena* (e.g., Gut site, etc.), *Eisenbergiella* (e.g., Gut site, etc.), *Eisenbergiella tayi* (e.g., Gut site, etc.), *Enterorhabdus* (e.g., Gut site, etc.), *Erysipelatoclostridium* (e.g., Gut site, etc.), Erysipelotrichaceae (e.g., Gut site, etc.), *Erysipelotrichales* (e.g., Gut site, etc.), *Erysipelotrichia* (e.g., Gut site, etc.), *Faecalibacterium prausnitzii* (e.g., Gut site, etc.), *Firmicutes* (e.g., Genital site, etc.), *Firmicutes* (e.g., Gut site, etc.), *Flavonifractor plautii* (e.g., Gut site, etc.), *Fusicatenibacter* (e.g., Gut site, etc.), *Fusicatenibacter saccharivorans* (e.g., Gut site, etc.), *Hespellia* (e.g., Gut site, etc.), *Lachnospira pectinoschiza* (e.g., Gut site, etc.), Lactobacillaceae (e.g., nose site, etc.), Lactobacillaceae (e.g., Gut site, etc.), Lactobacillaceae (e.g., Genital site, etc.), Lactobacillales (e.g., Genital site, etc.), *Lactobacillus* (e.g., nose site, etc.), *Lactobacillus* (e.g., Gut site, etc.), *Lactobacillus* (e.g., Genital site, etc.), *Marvinbryantia* (e.g., Gut site, etc.), *Moryella* (e.g., Gut site, etc.), *Negativicutes* (e.g., Gut site, etc.), *Odoribacter splanchnicus* (e.g., Gut site, etc.), *Oscillospira* (e.g., Gut site, etc.), Oscillospiraceae (e.g., Gut site, etc.), *Parabacteroides* (e.g., Gut site, etc.), *Phascolarctobacterium* (e.g., Gut site, etc.), Prevotellaceae (e.g., Gut site, etc.), *Proteobacteria* (e.g., Gut site, etc.), *Roseburia inulinivorans* (e.g., Gut site, etc.), *Roseburia* sp. 11SE39 (e.g., Gut site, etc.), *Sarcina* (e.g., Gut site, etc.), *Selenomonadales* (e.g., Gut site, etc.), *Subdoligranulum* (e.g., Gut site, etc.), *Subdoligranulum variabile* (e.g., Gut site, etc.), *Sutterella wadsworthensis* (e.g., Gut site, etc.), *Sutterella wadsworthensis* (e.g., Gut site, etc.), Sutterellaceae (e.g., Gut site, etc.), *Terrisporobacter* (e.g., Gut site, etc.), Veillonellaceae (e.g., Gut site, etc.), *Verrucomicrobiae* (e.g., Gut site, etc.), *Verrucomicrobiales* (e.g., Gut site, etc.), and/or other suitable taxa (e.g., described in Table 2)

Additionally or alternatively, microbiome features can include features associated with one or more of the targets described in Table 1.

Additionally or alternatively, microbiome features can include features associated with one or more of the following taxa: *Actinomyces* (genus), *Aerococcus* (genus), *Alloio-

*coccus* (genus), *Anaerococcus* (genus), *Anaeroglobus* (genus), *Anaerostipes* (genus), *Anaerotruncus* (genus), *Arcanobacterium* (genus), *Arthrospira* (genus), *Atopobium* (genus), *Bacteroides* (genus), *Bulleidia* (genus), *Campylobacter* (genus), *Catenibacterium* (genus), Coriobacteriaceae (family), *Corynebacterium* (genus), *Dialister* (genus), *Eggerthella* (genus), *Enterococcus* (genus), *Escherichia* (genus), *Finegoldia* (genus), *Fusobacterium* (genus), *Gardnerella* (genus), *Gemella* (genus), Lactobacillaceae (family), Lactobacillales (order), *Lactobacillus* (genus), *Leptotrichia* (genus), *Megasphaera* (genus), *Mobiluncus* (genus), *Moryella* (genus), *Mycoplasma* (genus), *Papillibacter* (genus), *Parvimonas* (genus), *Peptococcus* (genus), *Peptoniphilus* (genus), *Peptostreptococcus* (genus), Porphyromonadaceae (family), *Porphyromonas* (genus), *Prevotella* (genus), Prevotellaceae (family), *Pseudomonas* (genus), *Ruminococcus* (genus), *Segniliparus* (genus), *Shigella* (genus), *Sneathia* (genus), *Staphylococcus* (genus), *Streptococcus* (genus), *Treponema* (genus), *Ureaplasma* (genus), *Veillonella* (genus), Veillonellaceae (family), *Aerococcus christensenii* (species), *Aerococcus* spp. (genus), *Algoriphagus aquatilis* (species), *Anaerococcus* spp. (genus), *Anaerococcus tetradius* (species), *Anaerococcus vaginalis* (species), *Anoxybacillus pushchinoensis* (species), *Atopobium* spp. (genus), *Atopobium vaginae* (species), *Bacteroides fragilis* (species), *Bacteroides* spp. (genus), *Bifidobacterium animalis* subsp. *lactis* (species), *Bifidobacterium dentium* (species), *Bifidobacterium lactis* (species), *Bifidobacterium longum* subsp. *suis* (species), *Bulleidia extructa* (species), *Burkholderia fungorum* (species), *Burkholderia phenoliruptrix* (species), *Caldicellulosiruptor saccharolyticus* (species), *Campylobacter* spp. (genus), *Campylobacter ureolyticus* (species), *Candida albicans* (species), *Candida glabrata* (species), *Candida krusei* (species), *Candida lusitaniae* (species), *Candidatus Mycoplasma girerdii* (species), *Catenibacterium* spp. (genus), *Chlamydia trachomatis* (species), *Chondromyces robustus* (species), Clostridiales BVAB2 (species), Clostridiales BVAB3 (species), *Clostridium cavendishii* (species), *Clostridium viride* (species), *Cryobacterium psychrophilum* (species), *Dialister micraerophilus* (species), *Dickeya chrysanthemi* (species), *Eggerthia catenaformis* (species), *Erwinia chrysanthemi* (species), *Escherichia coli* (species), *Escherichia fergusonii* (species), *Exiguobacterium acetylicum* (species), *Fusobacterium nucleatum* (species), *Fusobacterium* spp. (genus), *Gardnerella* spp. (genus), *Gardnerella vaginalis* (species), *Gemella* sp. (genus), *Haemophilus ducreyi* (species), *Klebsiella granulomatis* (species), Lachnospiraceae BVAB1 (species), *Lactobacillus acidophilus* (species), *Lactobacillus brevis* (species), *Lactobacillus casei* (species), *Lactobacillus casei Shirota* (species), *Lactobacillus crispatus* (species), *Lactobacillus delbrueckii* (species), *Lactobacillus fermentum* (species), *Lactobacillus gasseri* (species), *Lactobacillus iners* (species), *Lactobacillus jensenii* (species), *Lactobacillus johnsonii* (species), *Lactobacillus kefiranofaciens* (species), *Lactobacillus paracasei* FJ861111.1 (species), *Lactobacillus pentosus* strain S-PT84 (species), *Lactobacillus plantarum* (species), *Lactobacillus reuteri* (species), *Lactobacillus reuteri* RC-14 (species), *Lactobacillus rhamnosus* (species), *Lactobacillus rhamnosus* (strain BMX54) (species), *Lactobacillus rhamnosus* BMX 54 (species), *Lactobacillus rhamnosus* GR-1 (species), *Lactobacillus salivarius* (species), *Lactobacillus vaginalis* (species), *Leptotrichia* spp. (genus), *Maribacter orientalis* (species), *Megasphaera genomosp* (species), *Megasphaera micronuciformis* (species), *Megasphaera* spp. (genus), *Microbacterium halophilum* (species), *Mobiluncus curtisii* (species), *Mobiluncus mulieris* (species), *Moorella glycerini* (species), *Mycoplasma genitalium* (species), *Mycoplasma hominis* (species), *Mycoplasma muris* (species), *Neisseria gonorrhoeae* (species), *Paeniclostridium sordellii* (species), *Papillibacter* spp. (genus), *Parastreptomyces abscessus* (species), *Parvimonas micra* (species), *Parvimonas* spp. (genus), *Pasteurella multocida* (species), *Pediococcus ethanolidurans* (species), *Peptoniphilus harei* (species), *Peptoniphilus indolicus* (species), *Peptoniphilus* spp. (genus), *Peptostreptococcus anaerobius* (species), *Peptostreptococcus massiliae* (species), *Peptostreptococcus* spp. (genus), *Porphyromonas gingivalis* (species), *Porphyromonas levii* (species), *Porphyromonas* sp. (genus), *Porphyromonas uenonis* (species), *Prevotella amnii* (species), *Prevotella bivia* (species), *Prevotella disiens* (species), *Prevotella intermedia* (species), *Prevotella oralis* (species), *Prevotella oris* (species), *Prevotella timonensis* (species), *Pseudomonas* spp. (genus), *Ralstonia pickettii* (species), *Ruminococcus* spp. (genus), *Sanguibacter keddieii* (species), *Sneathia amnii* (species), *Sneathia sanguinegens* (species), *Sneathia* spp. (genus), *Staphylococcus aureus* (species), *Staphylococcus mulans* (species), *Staphylococcus pasteuri* (species), *Staphylococcus simiae* (species), *Staphylococcus simulans* (species), *Staphylococcus* spp. (genus), *Staphylococcus warneri* (species), *Streptococcus agalactiae* (species), *Streptococcus anginosus* (species), *Streptococcus intermedius* (species), *Streptococcus pyogenes* (species), *Streptococcus viridans* (species), *Thermosipho atlanticus* (species), *Thermovirga lienii* (species), *Treponema pallidum* (species), *Trichomonas vaginalis* (species), *Trueperella bernardiae* (species), *Ureaplasma parvum* (species), *Ureaplasma urealyticum* (species), *Veillonella montpellierensis* (species), *Veillonella parvula* (species), *Virgibacillus proomii* (species), *Zobellia laminariae* (species), HPV 3 (virus variant), HPV 6 (virus variant), HPV 16 (virus variant), HPV 18 (virus variant), HPV 31 (virus variant), HPV 33 (virus variant), HPV 35 (virus variant), HPV 39 (virus variant), HPV 43 (virus variant), HPV 45 (virus variant), HPV 51 (virus variant), HPV 52 (virus variant) HPV 53 (virus variant), HPV 54 (virus variant), HPV 56 (virus variant), HPV 58 (virus variant), HPV 59 (virus variant), HPV 66 (virus variant), HPV 68 (virus variant), HPV (virus), HPV (multiple type) (virus), taxa described in Table 3, any combination of taxa and/or virus variant, and/or any other suitable taxa (e.g., where the taxa can be associated with marker-associated, etc.). In examples, markers associated with one or more of the plurality of taxa can include 16S rRNA genetic sequences associated with the plurality of taxa. The markers and/or the plurality of taxa can be associated (e.g., positively associated, negatively associated, etc.) with one or more: conditions, pathogens, commensal bacteria, probiotic bacteria, and/or any other marker-associated information, where such associations can be stored in microorganism databases, applied in characterization processes, and/or otherwise processed.

Additionally or alternatively, microbiome features associated with one or more female reproductive system-related conditions can include microbiome functional features (e.g., features describing functions associated with one or more microorganisms, such as microorganisms classified under taxa described herein; features describing functional diversity; features describing presence, absence, abundance, and/or relative abundance; etc.) corresponding to functions from and/or otherwise associated with (e.g., such as in relation to one or more body sites, where microbiome functional features can include site-specific functional features associated with the one or more body sites, such as where correlations between the functional features and the one or more female reproductive system-related conditions can be specific to the body site, such as specific to microbiome function corresponding to microorganisms observed at the body site from samples collected at a body collection site corresponding to the body site; etc.) one or more of: Clusters of Orthologous Groups (COG) databases (e.g., COG, COG2, etc.), Kyoto Encyclopedia of Genes and Genomes (KEGG) databases (e.g., KEGG2, KEGG3, KEGG4, etc.), and/or any other suitable database available (e.g., databases with microorganism function data, etc.). However, microbiome features can include any suitable microbiome functional features associated with any suitable microorganism function, human function, and/or other suitable functionality.

In variations, site-specific female reproductive system-related characterization models (e.g., for determining female reproductive system-related characterizations based on processing user site-specific microbiome features associated with one or more body sites also associated with the site-specific female reproductive system-related characterization model; etc.) and/or female reproductive system-related characterizations (e.g., associated with a body site, etc.) can be determined based on site-specific microbiome features (e.g., associated with one or more body sites; etc.) described herein (e.g., site-specific composition features; site-specific functional features; etc.). In examples, the method 100 can include determining user microbiome features (e.g., for a user for which a female reproductive system-related characterization and/or therapy can be determined and/or promoted; determining feature values for a user for microbiome features determined to be associated with, such as correlated with, the one or more female reproductive system-related conditions; etc.) including site-specific microbiome features associated with one or more body sites.

In variations, female reproductive system-related characterization models and/or female reproductive system-related characterizations can be determined based on microbiome features (e.g., associated with the one or more female reproductive system-related conditions; etc.) including microbiome composition features (e.g., site-specific composition features; etc.) and microbiome functional features (e.g., site-specific functional features, etc.). In an example, the method 100 can include determining site-specific composition features (e.g., associated with a gut site; composition features described herein; etc.) and site-specific functional features (e.g., associated with a gut site; functional features described herein; etc.); and generating a site-specific female reproductive system-related characterization model (e.g., associated with the gut site and/or vaginal site; for processing data derived from samples collected at gut collection sites; etc.) based on the site-specific composition features, the site-specific functional features, and/or other suitable data (e.g., supplementary data, etc.); and/or determining one or more female reproductive system-related characterizations for one or more users based on the site-specific female reproductive system-related characterization model and user microbiome features (e.g., derived from user samples collected at gut collection sites; etc.).

In specific examples, microbiome composition features (e.g., including site-specific composition features, etc.) described herein, microbiome functional features described herein, and/or other suitable microbiome features can be determined based on one or more microorganism datasets (e.g., microorganism sequence dataset, etc.) determined based on samples (e.g., sequencing of microorganism nucleic acids of the samples, etc.) from a set of subjects associated with the female reproductive system-related condition (e.g., a set of subjects including subjects with the female reproductive system-related condition; including subjects without the female reproductive system-related condition, where such samples and/or associated data can act as a control; a population of subjects; etc.).

In a variation, any suitable combination of microbiome features described herein can be used for an HPV characterization process (e.g., determining and/or applying HPV characterization model for performing diagnosis and/or suitable characterizations of an HPV condition; facilitating determination of and/or application of a therapy model and/or therapies for an HPV condition; etc.). In an example, a combination of microbiome feature can be predictive of the likelihood of HPV infection for an individual, based on his/her own microbiome sample, including presence, absence, relative abundance or any other microbiome features derived from sample analysis (e.g., site-specific sample analysis).

In variations, any suitable combination of microbiome features described herein can be used in prevention, treatment of, and/or suitable facilitation of therapeutic intervention for one or more female reproductive system-related conditions associated with microorganisms, such as for restoring vaginal microbiota to a healthy cohort (e.g., improving microbiome diversity), such as including modulation of the presence, absence or relative abundance of microorganisms in a human gut microbiome and/or other suitable microbiomes associated with suitable body sites (e.g., towards a target microbiome composition and/or functionality associated with users with a healthy microbiome, etc.). However, microbiome features associated with female reproductive system-related conditions can be applied in any suitable manner for prevention, treatment of, and/or suitable facilitation of therapeutic intervention for one or more female reproductive system-related conditions.

In an example, the method 100 can include determining a female reproductive system-related characterization for the user for a first female reproductive system-related condition and a second female reproductive system-related condition based on a first set of composition features (e.g., including at least one or more of the microbiome features described above in relation to the first variation; including any suitable combination of microbiome features; etc.), a first female reproductive system-related characterization model, a second set of composition features (e.g., including at least one or more of the microbiome features described above in relation to the second variation; including any suitable combination of microbiome features; etc.), and a second female reproductive system-related characterization model, where the first female reproductive system-related characterization model is associated with the first female reproductive system-related condition (e.g., where the first female reproductive system-related characterization model determines characterizations for the first female reproductive system-related condition, etc.), and where the second female reproductive system-related characterization model is associated with the second female reproductive system-related condition (e.g., where the second female reproductive system-related characterization model determines characterizations for the second female reproductive system-related condition, etc.). In the example, determining user microbiome features can include determining first user microbiome functional features associated with first functions from at least one of Cluster of Orthologous Groups (COG) database and Kyoto Encyclopedia of Genes and Genomes (KEGG) database, where the first user microbiome functional features are associated with the first female reproductive system-related condition; and determining second user microbiome functional features associated with second functions from at least one of the COG database and the KEGG database, where the second user microbiome functional features are associated with the second female reproductive system-related condition, where determining the female reproductive system-related characterization can include determining the female reproductive system-related characterization for the user for the first female reproductive system-related condition and the second female reproductive system-related condition based on the first set of composition features, the first user microbiome functional features, the first female reproductive system-related characterization model, the second set of composition features, the second user microbiome functional features, and the second female reproductive system-related characterization model. Additionally or alternatively, any combinations of microbiome features can be used with any suitable number and types of female reproductive system-related characterization models to determine female reproductive system-related characterization for one or more female reproductive system-related conditions, in any suitable manner.

In examples, the method 100 can include generating one or more female reproductive system-related characterization models based on any suitable combination of microbiome features described above and/or herein (e.g., based on a set of microbiome composition features including features associated with at least one of the taxa described herein; and/or based on microbiome functional features described herein, such as corresponding to functions from databases described herein; etc.). In an example, performing a characterization process for a user can include characterizing a user as having one or more female reproductive system-related conditions, such as based upon detection of, values corresponding to, and/or other aspects related to microbiome features described herein (e.g., microbiome features described above, etc.), and such as in a manner that is an additional (e.g., supplemental to, complementary to, etc.) or alternative to typical approaches of diagnosis, other characterizations (e.g., treatment-related characterizations, etc.), treatment, monitoring, and/or other suitable approaches associated with female reproductive system-related conditions. In variations, the microbiome features can be used for diagnostics, other characterizations, treatment, monitoring, and/or any other suitable purposes and/or approaches associated with female reproductive system-related conditions.

Any suitable taxa, associations, features, and/or other suitable data can be derivable in any suitable manner described in U.S. application Ser. No. 16/047,840 filed 27 Jul. 2018, which is herein incorporated in its entirety by this reference.

However, determining one or more female reproductive system-related characterizations can be performed in any suitable manner.

3.3.B Determining a Therapy.

Performing a characterization process S130 (e.g., performing a female reproductive system-related therapy) can include Block S140, which can include determining one or more therapies (e.g., therapies configured to modulate microbiome composition, function, diversity, and/or other suitable aspects, such as for improving one or more aspects associated with female reproductive system-related conditions, such as in users characterized based on one or more characterization processes; etc.). Block S140 can function to identify, select, rank, prioritize, predict, discourage, and/or otherwise determine therapies (e.g., facilitate therapy determination, etc.). For example, Block S140 can include determining one or more of probiotic-based therapies, bacteriophage-based therapies, small molecule-based therapies, and/or other suitable therapies, such as therapies that can shift a subject's microbiome composition, function, diversity, and/or other characteristics (e.g., microbiomes at any suitable sites, etc.) toward a desired state (e.g., equilibrium state, etc.) in promotion of a user's health, for modifying a state of one or more female reproductive system-related conditions, and/or for other suitable purposes.

Therapies (e.g., female reproductive system-related therapies, etc.) can include any one or more of: consumables (e.g., probiotic therapies, prebiotic therapies, medication such as antibiotics, allergy or cold medication, bacteriophage-based therapies, consumables for underlying conditions, small molecule therapies, etc.); device-related therapies (e.g., monitoring devices; sensor-based devices; medical devices; implantable medical devices; etc.); surgical operations; psychological-associated therapies (e.g., cognitive behavioral therapy, anxiety therapy, talking therapy, psychodynamic therapy, action-oriented therapy, rational emotive behavior therapy, interpersonal psychotherapy, relaxation training, deep breathing techniques, progressive muscle relaxation, meditation, etc.); behavior modification therapies (e.g., physical activity recommendations such as increased exercise; dietary recommendations such as reducing sugar intake, increased vegetable intake, increased fish intake, decreased caffeine consumption, decreased alcohol consumption, decreased carbohydrate intake; smoking recommendations such as decreasing tobacco intake; weight-related recommendations; sleep habit recommendations etc.); topical administration therapies (e.g., topical probiotic, prebiotic, and/or antibiotics; bacteriophage-based therapies); environmental factor modification therapies; modification of any other suitable aspects associated with one or more female reproductive system-related conditions; and/or any other suitable therapies (e.g., for improving a health state associated with one or more female reproductive system-related conditions, such as therapies for improving one or more female reproductive system-related conditions, therapies for reducing the risk of one or more female reproductive system-related conditions, etc.). In examples, types of therapies can include any one or more of: probiotic therapies, bacteriophage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health.

In variations, therapies can include site-specific therapies associated with one or more body sites, such as for facilitating modification of microbiome composition and/or function at one or more different body sites of a user (e.g., one or more different collection sites, etc.), such as targeting and/or transforming microorganisms associated with a gut site, nose site, skin site, mouth site, and/or genital site (e.g., vaginal site); such as by facilitating therapeutic intervention in relation to one or more therapies configured to specifically target one or more user body sites, such as microbiome at one or more of the user body sites; such as for facilitating improvement of one or more female reproductive system-related conditions (e.g., by modifying user microbiome composition and/or function at a particular user body site towards a target microbiome composition and/or function, such as microbiome composition and/or function at a particular body site and associated with a healthy microbiome status and/or lack of the one or more female reproductive system-related condition; etc.). Site-specific therapies can include any one or more of consumables (e.g., targeting a gut site microbiome and/or microbiomes associated with any suitable body sites; etc.); topical therapies (e.g., for modifying a skin microbiome, a nose microbiome, a mouth microbiome, a genitals microbiome, etc.); and/or any other suitable types of therapies. In an example, the method 100 can include collecting a sample associated with a first body site (e.g., including at least one of a gut site, a skin site, a genital site such as vaginal site, a mouth site, and a nose site, etc.) from a user; determining site-specific composition features associated with the first body site; determining a female reproductive system-related characterization for the user for the female reproductive system-related condition based on the site-specific composition features; and facilitating therapeutic intervention in relation to a first site-specific therapy for the user (e.g., providing the first site-specific therapy to the user; etc.) for facilitating improvement of the female reproductive system-related condition, based on the female reproductive system-related characterization, where the first site-specific therapy is associated with the first body site. In an example, the method 100 can include collecting a post-therapy sample from the user after the facilitation of the therapeutic intervention in relation to the first site-specific therapy (e.g., after the providing of the first site-specific therapy; etc.), where the post-therapy sample is associated with a second body site (e.g., including at least one of the gut site, the skin site, the genital site such as vaginal site, the mouth site, and the nose site; etc.); determining a post-therapy female reproductive system-related characterization for the user for the female reproductive system-related condition based on site-specific features associated with the second body site; and facilitating therapeutic intervention in relation to a second site-specific therapy for the user (e.g., providing a second site-specific therapy to the user; etc.) for facilitating improvement of the female reproductive system-related condition, based on the post-therapy female reproductive system-related characterization, where the second site-specific therapy is associated with the second body site.

In a variation, therapies can include one or more bacteriophage-based therapies (e.g., in the form of a consumable, in the form of a topical administration therapy, etc.), where one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Additionally or alternatively, bacteriophage-based therapies can be used to increase the relative abundances of bacterial populations not targeted by the bacteriophage(s) used. However, bacteriophage-based therapies can be used to modulate characteristics of microbiomes (e.g., microbiome composition, microbiome function, etc.) in any suitable manner, and/or can be used for any suitable purpose.

In variations, therapies can include one or more probiotic therapies and/or prebiotic therapies associated with any combination of at least one or more of (e.g., including any combination of one or more of, at any suitable amounts and/or concentrations, such as any suitable relative amounts and/or concentrations; etc.) any suitable taxa described herein (e.g., in relation to one or more microbiome composition features associated with one or more female reproductive system-related conditions, etc.), such as any suitable taxa described in Section 3.3.A and/or any other suitable microorganisms associated with any suitable taxonomic groups (e.g., microorganisms from taxa described herein, such as in relation to microbiome features; taxa associated with functional features described herein, etc.). For one or more probiotic therapies and/or other suitable therapies, microorganisms associated with a given taxonomic group, and/or any suitable combination of microorganisms can be provided at dosages of 0.1 million to 10 billion CFU, and/or at any suitable amount (e.g., as determined from a therapy model that predicts positive adjustment of a patient's microbiome in response to the therapy; different amounts for different taxa; same or similar amounts for different taxa; etc.). In an example, a subject can be instructed to ingest capsules including the probiotic formulation according to a regimen tailored to one or more of his/her: physiology (e.g., body mass index, weight, height), demographic characteristics (e.g., gender, age), severity of dysbiosis, sensitivity to medications, and any other suitable factor. In examples, probiotic therapies and/or prebiotic therapies can be used to modulate a user microbiome (e.g., in relation to composition, function, etc.) for facilitating improvement of one or more female reproductive system-related conditions. In examples, facilitating therapeutic intervention can include promoting (e.g., recommending, informing a user regarding, providing, administering, facilitating obtainment of, etc.) one or more probiotic therapies and/or prebiotic therapies to a user, such as for facilitating improvement of one or more female reproductive system-related conditions.

In a specific example of probiotic therapies, as shown in FIG. 20, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis. However, probiotic therapies and/or prebiotic therapies can be configured in any suitable manner.

In another specific example, therapies can include medical-device based therapies (e.g., associated with human behavior modification, associated with treatment of disease-related conditions, etc.).

In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different female reproductive system-related characterizations. In variations, support vector machines, as a supervised machine learning algorithm, can be used to generate the therapy provision model. However, any other suitable machine learning algorithm described above can facilitate generation of the therapy provision model.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographic characteristics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies and/or prebiotic therapies (e.g., associated with probiotic therapies determined by a therapy model applied by a therapy facilitation system, etc.) can include microorganisms that are culturable (e.g., able to be expanded to provide a scalable therapy) and/or non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic and/or prebiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent. However, probiotic therapies, prebiotic therapies and/or other suitable therapies can include any suitable combination of microorganisms associated with any suitable taxa described herein, and/or therapies can be configured in any suitable manner.

Block S140 can include executing, storing, retrieving, and/or otherwise processing one or more therapy models for determining one or more therapies. Processing one or more therapy models is preferably based on microbiome features. For example, generating a therapy model can based on microbiome features associated with one or more female reproductive system-related conditions, therapy-related aspects such as therapy efficacy in relation to microbiome characteristics, and/or other suitable data. Additionally or alternatively, processing therapy models can be based on any suitable data. In an example, processing a therapy model can include determining one or more therapies for a user based on one or more therapy models, user microbiome features (e.g., inputting user microbiome feature values into the one or more therapy models, etc.), supplementary data (e.g., prior knowledge associated with therapies such as in relation to microorganism-related metabolization; user medical history; user demographic data, such as describing demographic characteristics; etc.), and/or any other suitable data. However, processing therapy models can be based on any suitable data in any suitable manner.

Female reproductive system-related characterization models can include one or more therapy models. In an example, determining one or more female reproductive system-related characterizations (e.g., for one or more users, for one or more female reproductive system-related conditions, etc.), can include determining one or more therapies, such as based on one or more therapy models (e.g., applying one or more therapy models, etc.) and/or other suitable data (e.g., microbiome features such as user microbiome features, microorganism dataset such as user microorganism datasets, etc.). In a specific example, determining one or more female reproductive system-related characterizations can include determining a first female reproductive system-related characterization for a user (e.g., describing propensity for one or more female reproductive system-related conditions; etc.); and determining a second female reproductive system-related characterization for the user based on the first female reproductive system-related characterization (e.g., determining one or more therapies, such as for recommendation to a user, based on the propensity for one or more female reproductive system-related conditions; etc.). In a specific example, a female reproductive system-related characterization can include both propensity-related data (e.g., diagnostic data; associated microbiome composition, function, diversity, and/or other characteristics; etc.) and therapy-related data (e.g., recommended therapies; potential therapies; etc.). However, female reproductive system-related characterizations can include any suitable data (e.g., any combination of data described herein, etc.).

Processing therapy models can include processing a plurality of therapy models. For example, different therapy models can be processed for different therapies (e.g., different models for different individual therapies; different models for different combinations and/or categories of therapies, such as a first therapy model for determining consumable therapies and a second therapy model for determining psychological-associated therapies; etc.). In an example, different therapy models can be processed for different female reproductive system-related conditions, (e.g., different models for different individual female reproductive system-related conditions; different models for different combinations and/or categories of female reproductive system-related conditions, etc.). Additionally or alternatively, processing a plurality of therapy models can be performed for (e.g., based on; processing different therapy models for; etc.) any suitable types of data and/or entities. However, processing a plurality of therapy models can be performed in any suitable manner, and determining and/or applying one or more therapy models can be performed in any suitable manner.

3.4 Processing a User Biological Sample.

Embodiments of the method 100 can additionally or alternatively include Block S150, which can include processing one or more biological samples from a user (e.g., biological samples from different collection sites of the user, etc.). Block S150 can function to facilitate generation of a microorganism dataset for a user, such as for use in deriving inputs for the characterization process (e.g., for generating a female reproductive system-related characterization for the user, such as through applying one or more female reproductive system-related characterization models, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the user and/or an environment of the user in a non-invasive manner. In variations, non-invasive manners of sample reception can use any one or more of: a permeable substrate (e.g., a swab configured to wipe a region of a user's body, toilet paper, a sponge, etc.), a non-permeable substrate (e.g., a slide, tape, etc.) a container (e.g., vial, tube, bag, etc.) configured to receive a sample from a region of a user's body, and any other suitable sample-reception element. In a specific example, the biological sample can be collected from one or more of the user's nose, skin, genitals (e.g., vagina), mouth, and gut (e.g., through stool samples, etc.) in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the user without facilitation by another entity (e.g., a caretaker associated with a user, a health care professional, an automated or semi-automated sample collection apparatus, etc.), or can alternatively be taken from the body of the user with the assistance of another entity. In one example, where the biological sample is taken from the user without facilitation by another entity in the sample extraction process, a sample-provision kit can be provided to the user. In the example, the kit can include one or more swabs for sample acquisition, one or more containers configured to receive the swab(s) for storage, instructions for sample provision and setup of a user account, elements configured to associate the sample(s) with the user (e.g., barcode identifiers, tags, etc.), and a receptacle that allows the sample(s) from the user to be delivered to a sample processing operation (e.g., by a mail delivery system). In another example, where the biological sample is extracted from the user with the help of another entity, one or more samples can be collected in a clinical or research setting from the user (e.g., during a clinical appointment). The biological sample can, however, be received from the user in any other suitable manner.

Furthermore, processing and analyzing biological samples (e.g., to generate a user microorganism dataset; etc.) from the user is preferably performed in a manner similar to that of one of the embodiments, variations, and/or examples of sample reception described in relation to Block S110 above, and/or any other suitable portions of embodiments of the method 100 and/or system 200. As such, reception and processing of the biological sample in Block S150 can be performed for the user using similar processes as those for receiving and processing biological samples used to perform the characterization processes of the method 100, such as in order to provide consistency of process. However, biological sample reception and processing in Block S150 can additionally or alternatively be performed in any other suitable manner.

3.5 Determining a Female Reproductive System-Related Characterization.

Embodiments of the method 100 can additionally or alternatively include Block S160, which can include determining, with one or more characterization processes (e.g., one or more characterization processes described in relation to Block S130, etc.), a female reproductive system-related characterization for the user, such as based upon processing one or more microorganism dataset (e.g., user microorganism sequence dataset, microbiome composition dataset, microbiome functional diversity dataset; processing of the microorganism dataset to extract user microbiome features (e.g., extract feature values; etc.) that can be used to determine the one or more female reproductive system-related characterizations; etc.) derived from the biological sample of the user. Block S160 can function to characterize one or more female reproductive system-related conditions for a user, such as through extracting features from microbiome-derived data of the user, and using the features as inputs into an embodiment, variation, or example of the characterization process described in Block S130 above (e.g., using the user microbiome feature values as inputs into a microbiome-related condition characterization model, etc.). In an example, Block S160 can include generating a female reproductive system-related characterization for the user based on user microbiome features and a female reproductive system-related condition model (e.g., generated in Block S130). Female reproductive system-related characterizations can be for any number and/or combination of female reproductive system-related conditions (e.g., a combination of female reproductive system-related conditions, a single female reproductive system-related condition, and/or other suitable female reproductive system-related conditions; etc.), users, collection sites, and/or other suitable entities. Female reproductive system-related characterizations can include one or more of: diagnoses (e.g., presence or absence of a female reproductive system-related condition; etc.); risk (e.g., risk scores for developing and/or the presence of a female reproductive system-related condition; information regarding female reproductive system-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with female reproductive system-related conditions; etc.); therapy determinations; other suitable outputs associated with characterization processes; and/or any other suitable data.

In another variation, a female reproductive system-related characterization can include a microbiome diversity score (e.g., in relation to microbiome composition, function, etc.) associated with (e.g., correlated with; negatively correlated with; positively correlated with; etc.) a microbiome diversity score correlated with one or more female reproductive system-related conditions. In examples, the female reproductive system-related characterization can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide therapies; etc.) can be performed in any suitable manner.

Determining a female reproductive system-related characterization in Block S160 preferably includes determining features and/or combinations of features associated with the microbiome composition and/or functional features of the user (e.g., determining feature values associated with the user, the feature values corresponding to microbiome features determined in Block S130, etc.), inputting the features into the characterization process, and receiving an output that characterizes the user as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the user. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable female reproductive system-related characterizations.

In some variations, features extracted from the microorganism dataset of the user can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of embodiments of the method 100.

Determining a female reproductive system-related characterization preferably includes extracting and applying user microbiome features (e.g., user microbiome composition diversity features; user microbiome functional diversity features; extracting feature values; etc.) for the user (e.g., based on a user microorganism dataset), characterization models, and/or other suitable components, such as by employing processes described in Block S130, and/or by employing any suitable approaches described herein.

Figure 22:
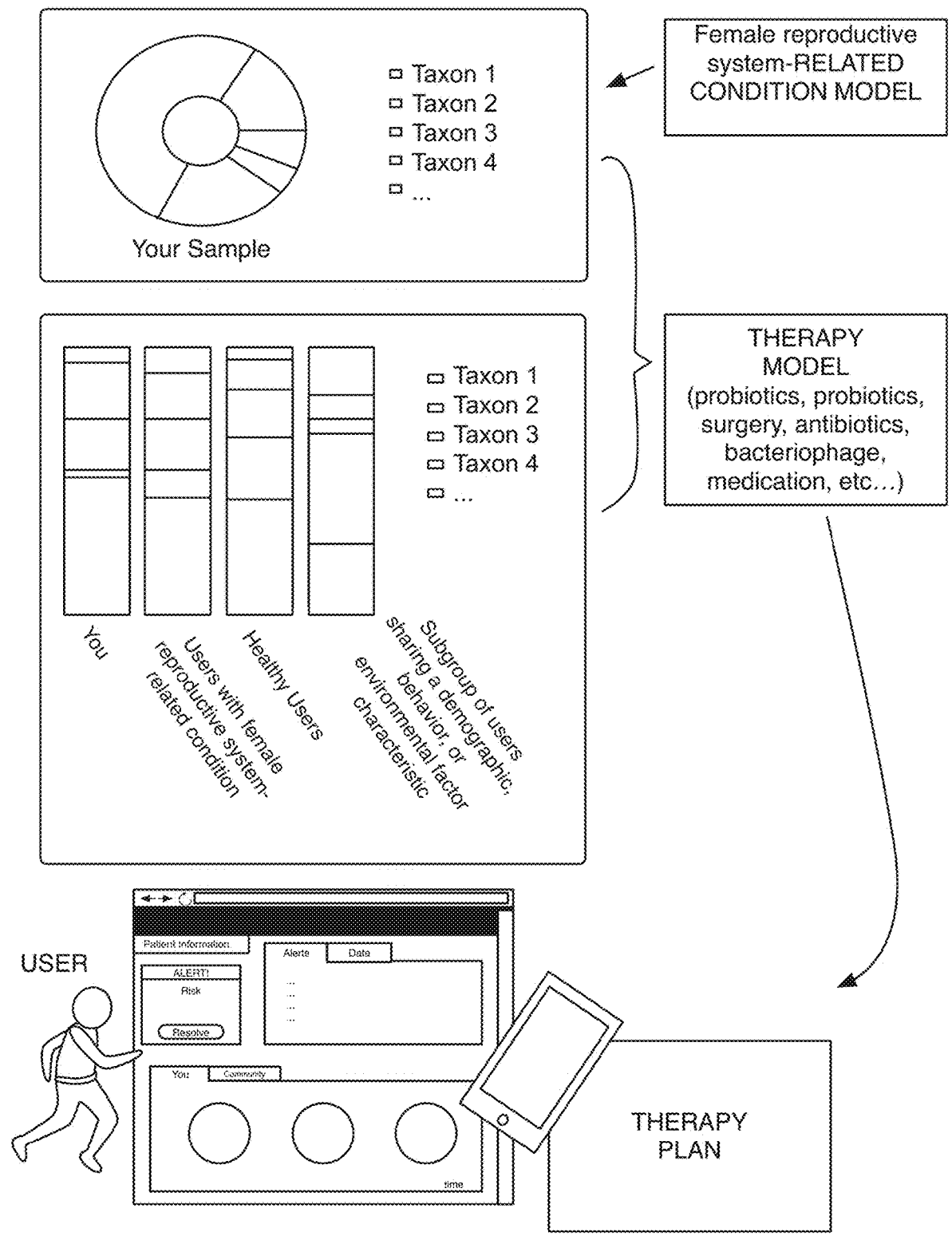
FIG. 22 includes examples of notification provision.

In variations, as shown in FIG. 22, Block S160 can include presenting female reproductive system-related characterizations (e.g., information extracted from the characterizations; as part of facilitating therapeutic intervention; etc.), such as at a web interface, a mobile application, and/or any other suitable interface, but presentation of information can be performed in any suitable manner. However, the microorganism dataset of the user can additionally or alternatively be used in any other suitable manner to enhance the models of the method 100, and Block S160 can be performed in any suitable manner.

3.6 Facilitating Therapeutic Intervention.

Figure 25:
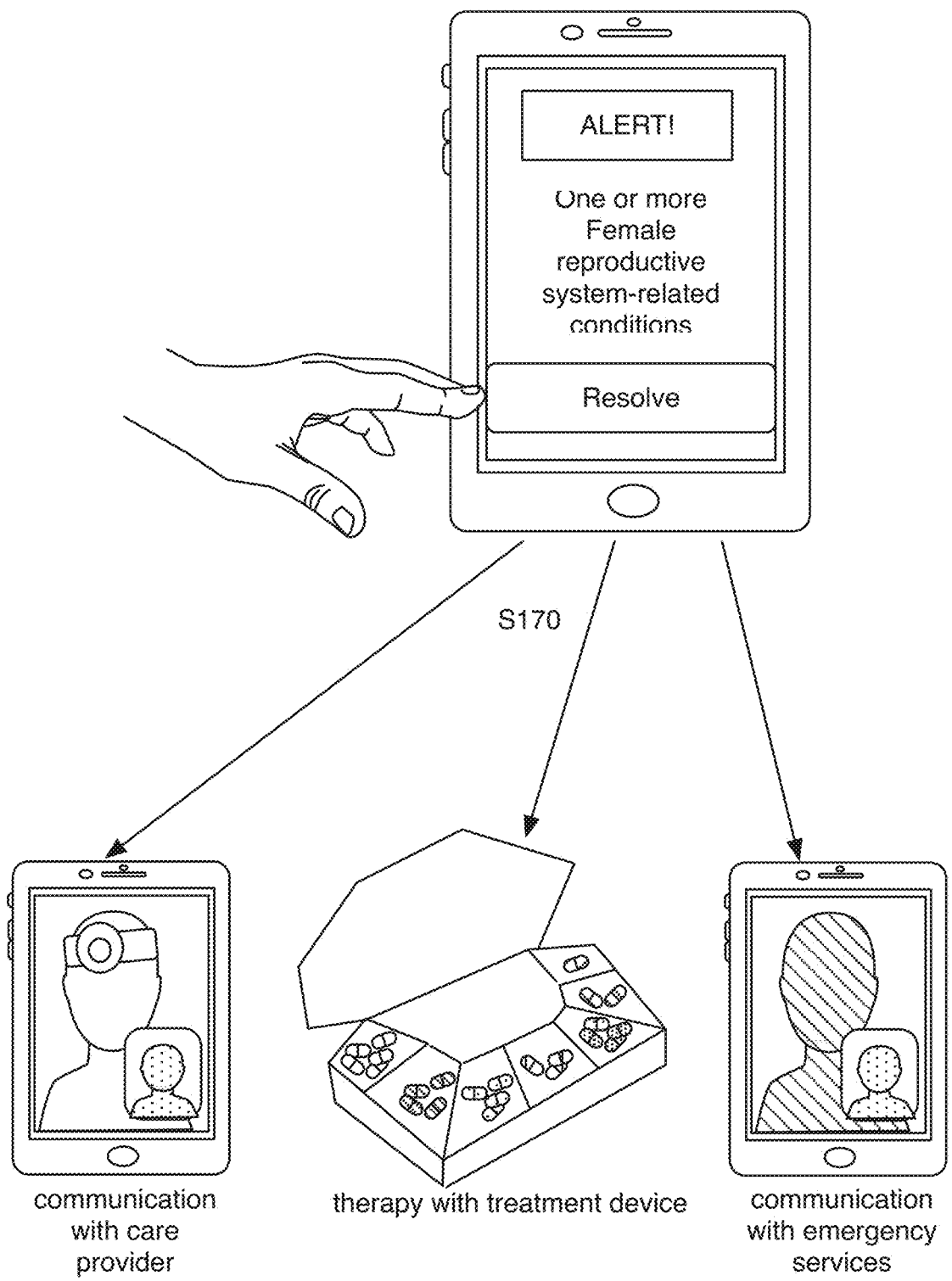
FIG. 25 includes promoting a therapy in an embodiment of a method.

As shown in FIG. 25, embodiments of the method 100 can additionally or alternatively include Block S170, which can include facilitating therapeutic intervention (e.g., promoting therapies, providing therapies, facilitating provision of therapies, etc.) for one or more female reproductive system-related conditions for one or more users (e.g., based upon a female reproductive system-related characterization and/or a therapy model). Block S170 can function to recommend, promote, provide, and/or otherwise facilitate therapeutic intervention in relation to one or more therapies for a user, such as to shift the microbiome composition and/or functional diversity of a user toward a desired equilibrium state (and/or otherwise improving a state of the female reproductive system-related condition, etc.) in relation to one or more female reproductive system-related conditions. Block S170 can include provision of a customized therapy to the user according to their microbiome composition and functional features, where the customized therapy can include a formulation of microorganisms configured to correct dysbiosis characteristic of users having the identified characterization. As such, outputs of Block S140 can be used to directly promote a customized therapy formulation and regimen (e.g., dosage, usage instructions) to the user based upon a trained therapy model. Additionally or alternatively, therapy provision can include recommendation of available therapeutic measures configured to shift microbiome composition and/or functional features toward a desired state. In variations, therapies can include any one or more of: consumables, topical therapies (e.g., lotions, ointments, antiseptics, etc.), medication (e.g., medications associated with any suitable medication type and/or dosage, etc.), bacteriophages, environmental treatments, behavioral modification (e.g., diet modification therapies, stress-reduction therapies, physical activity-related therapies, etc.), diagnostic procedures, other medical-related procedures, and/or any other suitable therapies associated with female reproductive system-related conditions. Consumables can include any one or more of: food and/or beverage items (e.g., probiotic and/or prebiotic food and/or beverage items, etc.), nutritional supplements (e.g., vitamins, minerals, fiber, fatty acids, amino acids, prebiotics, probiotics, etc.), consumable medications, and/or any other suitable therapeutic measure. In an example, providing one or more therapies and/or otherwise facilitating therapeutic intervention can include providing a recommendation for the one or more therapies to one or more users at one or more computing devices (e.g., at a user interface such as a web application, presented at the computing devices; etc.) associated with the one or more users.

For example, a combination of commercially available probiotic supplements can include a suitable probiotic therapy for the user according to an output of the therapy model. In another example, the method 100 can include determining a female reproductive system-related condition risk for the user for the female reproductive system-related condition based on a female reproductive system-related condition model (e.g., and/or user microbiome features); and promoting a therapy to the user based on the female reproductive system-related condition risk.

In a variation, facilitating therapeutic intervention can include promoting a diagnostic procedure (e.g., for facilitating detection of female reproductive system-related conditions, which can motivate subsequent promotion of other therapies, such as for modulation of a user microbiome for improving a user health state associated with one or more female reproductive system-related conditions; etc.). Diagnostic procedures can include any one or more of: medical history analyses, imaging examinations, cell culture tests, antibody tests, skin prick testing, patch testing, blood testing, challenge testing, performing portions of embodiments of the method 100, and/or any other suitable procedures for facilitating the detecting (e.g., observing, predicting, etc.) of female reproductive system-related conditions. Additionally or alternatively, diagnostic device-related information and/or other suitable diagnostic information can be processed as part of a supplementary dataset (e.g., in relation to Block S120, where such data can be used in determining and/or applying characterization models, therapy models, and/or other suitable models; etc.), and/or collected, used, and/or otherwise processed in relation to any suitable portions of embodiments of the method 100 (e.g., administering diagnostic procedures for users for monitoring therapy efficacy in relation to Block S180; etc.)

In another variation, Block S170 can include promoting a bacteriophage-based therapy. In more detail, one or more populations (e.g., in terms of colony forming units) of bacteriophages specific to a certain bacteria (or other microorganism) represented in the user can be used to downregulate or otherwise eliminate populations of the certain bacteria. As such, bacteriophage-based therapies can be used to reduce the size(s) of the undesired population(s) of bacteria represented in the user. Complementarily, bacteriophage-based therapies can be used to increase the relative abundances of bacterial populations not targeted by the bacteriophage(s) used.

In another variation, facilitating therapeutic intervention (e.g., providing therapies, etc.) can include provision of notifications to a user regarding the recommended therapy, other forms of therapy, female reproductive system-related characterizations, and/or other suitable data. In a specific example, providing a therapy to a user can include providing therapy recommendations (e.g., substantially concurrently with providing information derived from a female reproductive system-related characterization for a user; etc.) and/or other suitable therapy-related information (e.g., therapy efficacy; comparisons to other individual users, subgroups of users, and/or populations of users; therapy comparisons; historic therapies and/or associated therapy-related information; psychological therapy guides such as for cognitive behavioral therapy; etc.), such as through presenting notifications at a web interface (e.g., through a user account associated with and identifying a user; etc.). Notifications can be provided to a user by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a user can provide access, by the user, to a user account of the user, where the user account includes information regarding the user's female reproductive system-related characterization, detailed characterization of aspects of the user's microbiome (e.g., in relation to correlations with female reproductive system-related conditions; etc.), and/or notifications regarding suggested therapeutic measures (e.g., generated in Blocks S140 and/or S170, etc.). In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S170. Notifications and/or probiotic therapies can additionally or alternatively be provided directly through an entity associated with a user (e.g., a caretaker, a spouse, a significant other, a healthcare professional, etc.). In some further variations, notifications can additionally or alternatively be provided to an entity (e.g., healthcare professional) associated with a user, such as where the entity is able to facilitate provision of the therapy (e.g., by way of prescription, by way of conducting a therapeutic session, through a digital telemedicine session using optical and/or audio sensors of a computing device, etc.). Providing notifications and/or otherwise facilitating therapeutic, however, be performed in any suitable manner.

3.7 Monitoring Therapy Effectiveness.

Figure 23:
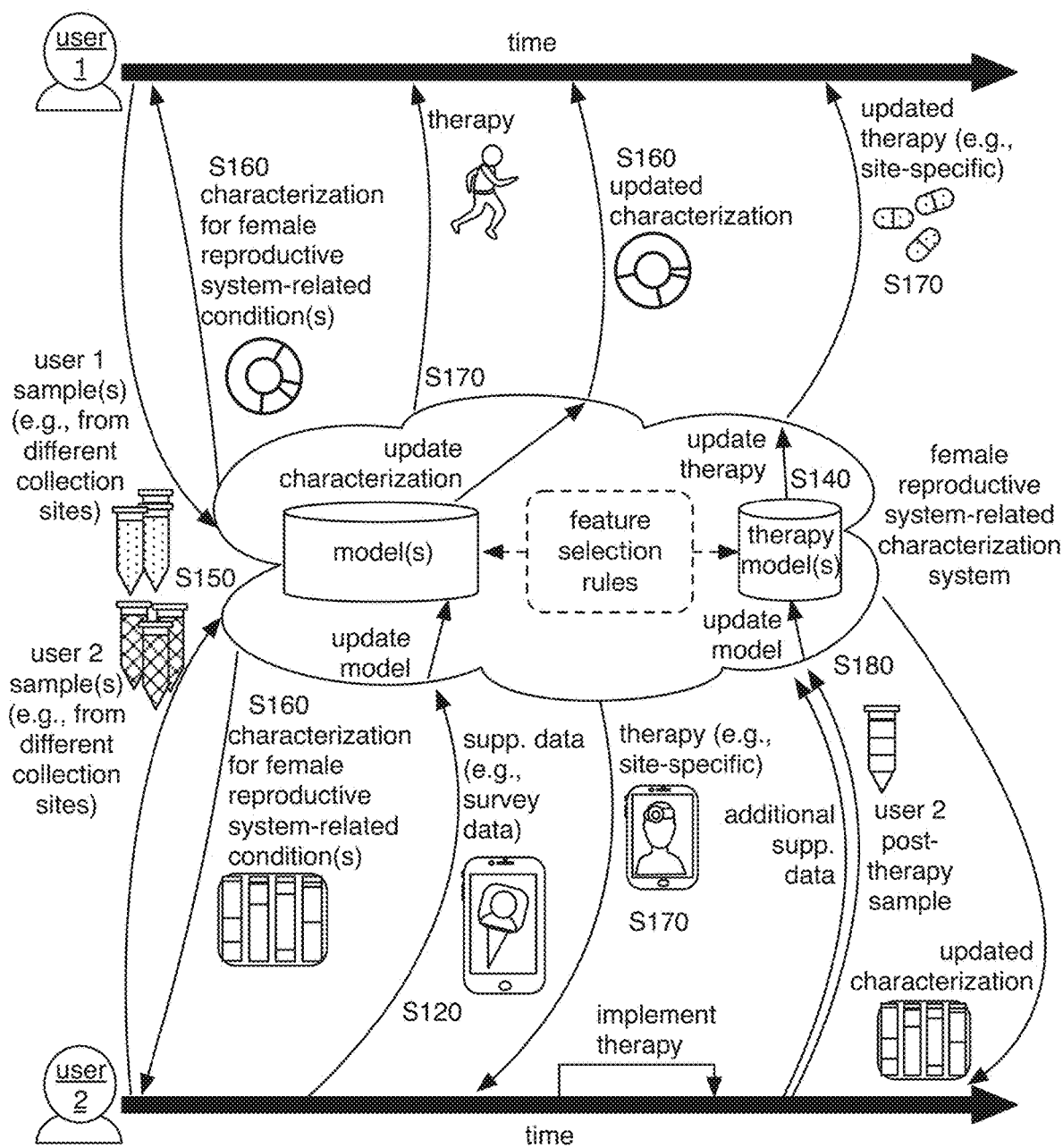
FIG. 23 includes a schematic representation of variations of an embodiment of the method.

As shown in FIG. 23, the method 100 can additionally or alternatively include Block S180, which can include: monitoring effectiveness of one or more therapies and/or monitoring other suitable components (e.g., microbiome characteristics, etc.) for the user (e.g., based upon processing a series of biological samples from the user), over time. Block S180 can function to gather additional data regarding positive effects, negative effects, and/or lack of effectiveness of one or more therapies (e.g., suggested by the therapy model for users of a given characterization, etc.) and/or monitoring microbiome characteristics (e.g., to assess microbiome composition and/or functional features for the user at a set of time points, etc.).

Monitoring of a user during the course of a therapy promoted by the therapy model (e.g., by receiving and analyzing biological samples from the user throughout therapy, by receiving survey-derived data from the user throughout therapy) can thus be used to generate a therapy-effectiveness model for each characterization provided by the characterization process of Block S130, and each recommended therapy measure provided in Blocks S140 and S170.

In Block S180, the user can be prompted to provide additional biological samples, supplementary data, and/or other suitable data at one or more key time points of a therapy regimen that incorporates the therapy, and the additional biological sample(s) can be processed and analyzed (e.g., in a manner similar to that described in relation to Block S120) to generate metrics characterizing modulation of the user's microbiome composition and/or functional features. For instance, metrics related to one or more of: a change in relative abundance of one or more taxonomic groups represented in the user's microbiome at an earlier time point, a change in representation of a specific taxonomic group of the user's microbiome, a ratio between abundance of a first taxonomic group of bacteria and abundance of a second taxonomic group of bacteria of the user's microbiome, a change in relative abundance of one or more functional families in a user's microbiome, and any other suitable metrics can be used to assess therapy effectiveness from changes in microbiome composition and/or functional features. Additionally or alternatively, survey-derived data from the user, pertaining to experiences of the user while on the therapy (e.g., experienced side effects, personal assessment of improvement, behavioral modifications, symptom improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy) and/or other suitable user characteristics (e.g., behaviors, conditions, etc.); generating a post-therapy female reproductive system-related characterization of the first user in relation to the female reproductive system-related condition based on the female reproductive system-related characterization model and the post-therapy biological sample; and promoting an updated therapy to the user for the female reproductive system-related condition based on the post-therapy female reproductive system-related characterization (e.g., based on a comparison between the post-therapy female reproductive system-related characterization and a pre-therapy female reproductive system-related characterization; etc.) and/or the user adherence to the therapy (e.g., modifying the therapy based on positive or negative results for the user microbiome in relation to the female reproductive system-related condition; etc.). Additionally or alternatively, other suitable data (e.g., supplementary data describing user behavior associated with one or more female reproductive system-related conditions; supplementary data describing a female reproductive system-related condition such as observed symptoms; etc.) can be used in determining a post-therapy characterization (e.g., degree of change from pre- to post-therapy in relation to the female reproductive system-related condition; etc.), updated therapies (e.g., determining an updated therapy based on effectiveness and/or adherence to the promoted therapy, etc.).

In an example, the method 100 can include collecting supplementary data (e.g., survey-derived data; informing statuses of female reproductive system-related conditions, such as in relation to symptom severity; etc.); determining the female reproductive system-related characterization for the user based on the user microbiome features and the supplementary data; facilitating therapeutic intervention in relation to a therapy for the female reproductive system-related condition (e.g., promoting the therapy to the user; etc.), based on the female reproductive system-related characterization; collecting a post-therapy biological sample from the user (e.g., after facilitating the therapeutic intervention; etc.); collecting subsequent supplementary data (e.g., including at least one of second survey-derived data and device data; etc.); and determining a post-therapy female reproductive system-related characterization for the user for the female reproductive system-related condition based on the subsequent supplementary data and post-therapy user microbiome features associated with the post-therapy biological sample. In the example, the method 100 can include facilitating therapeutic intervention in relation to an updated therapy (e.g., a modification of the therapy; a different therapy; etc.) for the user for improving the female reproductive system-related condition, based on the post-therapy female reproductive system-related characterization, such as where the updated therapy can include at least one of a consumable, a device-related therapy, a surgical operation, a psychological-associated therapy, a behavior modification therapy, and an environmental factor modification therapy. In the example determining the post-therapy female reproductive system-related characterization can include determining a comparison between microbiome characteristics of the user and reference microbiome characteristics corresponding to a user subgroup sharing at least one of a behavior and an environmental factor (and/or other suitable characteristic) associated with the female reproductive system-related condition, based on the post-therapy microbiome features, and where facilitating therapeutic intervention in relation to the updated therapy can include presenting the comparison to the user for facilitating at least one of the behavior modification therapy and the environmental factor modification therapy and/or other suitable therapies. However, Block S180 can be performed in relation to additional biological samples, additional supplementary data, and/or other suitable additional data in any suitable manner.

Therapy effectiveness, processing of additional biological samples (e.g., to determine additional female reproductive system-related characterizations, therapies, etc.), and/or other suitable aspects associated with continued biological sample collection, processing, and analysis in relation to female reproductive system-related conditions can be performed at any suitable time and frequency for generating, updating, and/or otherwise processing models (e.g., characterization models, therapy models, etc.), and/or for any other suitable purpose (e.g., as inputs associated with other portions of embodiments of the method 100). However, Block S180 can be performed in any suitable manner.

3.8 Processing a Microorganism Database

The method 100 can additionally or alternatively include Block S185, which can include processing (e.g., generating, applying, storing data in, etc.) one or more microorganism databases. Block S185 can function to perform processing in relation to a database including marker information, microbiome features, associations with one or more conditions, and/or other suitable data (e.g., for facilitating characterization processes, such as for comparison to user microorganism features in generating one or more characterizations; etc.). For example, the taxonomic database can store microorganism genetic sequences in association with a corresponding plurality taxa, which can be stored in association with one or more corresponding conditions.

Markers can include any one or more of: genetic sequences, peptide sequences, biomarkers, targets, features (e.g., microbiome composition features, microbiome phylogenetic diversity features, microbiome functional diversity features, etc.), and/or any other suitable markers indicative of microorganisms (e.g., taxa) and/or associated conditions. Genetic sequences stored by the taxonomic database preferably include one or more gene sequences for rRNA (e.g., a variable region of an rRNA gene sequence), which can include any one or more of: 16S, 18S, 30S, 40S, 50S, 60S, 5S, 23S, 5.8S, 28S, 70S, 80S, intergenic regions between each region and/or any other suitable rRNA gene. Genetic sequences preferably include one or more gene sequences associated with HPV, and/or sequences associated with any suitable female reproductive system-related conditions. Additionally or alternatively, genetic sequences can be associated with other RNA genes, protein genes, and/or any other suitable types of genes. One or more markers stored by the taxonomic database preferably share a marker characteristic, which can include one or more of: conserved genetic sequences across the plurality of taxa (e.g., semi-conserved genetic sequences including a variable region), conserved peptide sequences, shared biomarkers, and/or any other suitable marker-associated information.

Markers are preferably associated with a plurality of taxa (e.g., any suitable taxa described herein), in order to enable mapping of user microorganism sequences to particular taxa based on a comparison with stored markers.

Processing a microorganism database can include determining a set of reference markers for the database (e.g., based on predicted reads derived from primers selected based on a shared marker characteristic across a plurality of taxa; etc.); determining a target list of taxa (e.g., associated with vaginal-related conditions); filtering the target list of taxa based on a comparison (e.g., sequence comparison) against the reference markers (e.g., while using optimization parameters); and storing, at the database, the filtered taxa in association with corresponding reference markers.

In examples, determining a set of reference markers is preferably based on one or more primers (e.g., primers to be used in amplification of genetic material from biological samples, as in Block S110, etc.). For example, the method 100 can include: predicting amplicons for 16S rRNA genes based on primers (e.g., V4 primers GTGCCAGCMGCCGCGGTAA (SEQ ID NO: 85) for forward, and GGACTACHVGGGTWTCTAAT (SEQ ID NO: 86) for reverse, etc.) allowing annealing satisfying a threshold condition (e.g., up to 2 mismatches over the entire sequence) for comparison to sequences from a reference database (e.g., SILVA database); filtering the amplicons based on degeneracy (e.g., filtering out degenerate amplicons that expand to more than 20 possible non-degenerate sequences); modifying the filtered amplicons to represent a forward read (e.g., including the forward primer and 125 bp to the 3' end of the forward primer, etc.) and a reverse read (e.g., including the reverse primer and 124 bp to the 3' end of the reverse primer, etc.); processing the modified amplicons (e.g., removing the primers); and storing the processed amplicons (e.g., the 125 bp after the forward read plus the 124 bp after the reverse read; in concatenated form; etc.) as reference markers. Additionally or alternatively, amplicon prediction, processing, and/or associated operations can be based on any suitable primers, and/or can be configured in any suitable manner for determining reference markers.

In variations, the method 100 can include determining a target list of taxa (e.g., a set of genera and a set of species associated with a set of conditions, etc.), which preferably includes processing condition-related information sources (e.g., third-party information sources such as scientific literature, clinical trials, etc.; sources including information regarding conditions, associated microorganisms, and/or associated markers, etc.). In a variation, Block S110 can include manually processing condition-related information sources (e.g., with human curation of markers and/or associated information, etc.) to generate the target list of taxa. Determining target taxa can include automatically processing condition-related information sources. For example, Block S110 can include: generating a list of online information sources; obtaining the online information sources based on the list; processing the online information sources to extract a set of taxa, associated conditions, and/or other associated data (e.g., through applying natural language processing techniques, etc.) for generating the target list of taxa. Determining the target list of taxa preferably includes filtering the target list of taxa based on a comparison with the set of reference markers, such as analogous to that described in PCT App. No. PCT/US2016/051,156 filed 9 Sep. 2016, which is herein incorporated in its entirety by this reference, and/or can function in any suitable manner.

In examples, the method 100 can include associating reference markers from the set of reference markers to taxa from the target list of taxa, such as based on a performing a sequence similarity search using 100% identity over 100% of the length of a genetic sequence associated with one or more taxa from the plurality of taxa (e.g., a 16S rRNA gene V4 region for a taxa), against the set of reference markers. However, any suitable identity parameter, length parameter, and/or other suitable parameters can be applied to a sequence similarity search, and associating reference markers with taxa can be performed in any suitable manner. Reference markers for different taxa of a preliminary target list are preferably filtered according to optimization parameters (e.g., optimizing for sensitivity, specificity, precision, negative predicting value, and/or other metrics, such as through using confusion matrices, etc.). In an example, as shown in Tables 4-5, taxa from the preliminary target list can be filtered based on an optimization parameter threshold (e.g., requiring each of the optimization parameters to exceed 90%; requiring precision of over 95%; etc.). In another example, Block S120 can include: generating a plurality of sub-databases associating a given taxa to different numbers of reference markers (e.g., sequences), resulting in different optimization parameter profiles. In a specific example, Block S110 can include: accepting a first subset of reference markers unambiguously corresponding to a taxa; ranking reference markers from a second subset of reference markers based on a quotient of dt/ti, where "ti" represents an annotation of the sequence to a taxa of interest, and "dt" represents an annotation of the sequence to a different taxa; generating a set of sub-databases for a taxa based on different quotient conditions (e.g., a sub-database optimized for specificity based on a quotient condition of 0; a sub-database optimized for sensitivity based on a quotient condition of 100); determining sets of optimization parameters for the set of sub-databases; filtering the preliminary target list of taxa based on sub-databases for the taxa corresponding to optimization parameters satisfying the optimization parameter thresholds; and storing the filtered taxa (e.g., as shown in Tables 4-5) in association with the corresponding reference markers at the taxonomic database. Additionally or alternatively, determining the target list of taxa can be performed in any suitable manner.

In examples, the method 100 can include predicting amplicons for L1 genes from HPV genomes based on primers (e.g., CGTCCCAAAGGAAACTGATC (SEQ ID NO: 64), CGACCTAAAGGAAACTGATC (SEQ ID NO: 65), CGTCCAAAAGGAAACTGATC (SEQ ID NO: 66), GCCAAGGGGAAACTGATC (SEQ ID NO: 67), CGTCC-CAAAGGATACTGATC (SEQ ID NO: 68), CGTC-CAAGGGGATACTGATC (SEQ ID NO: 69), CGACCTAAAGGGAATTGATC (SEQ ID NO: 70), CGTCCTAATGGGAATTGGTC (SEQ ID NO: 71), CGACCTAGTGGAAATTGATC (SEQ ID NO: 72), CGACCAAGGGGATATTGATC (SEQ ID NO: 73), GCC-CAACGGAAACTGATC (SEQ ID NO: 74), CGACC-CAAGGGAAACTGGTC (SEQ ID NO: 75), CGTCCTAAAGGAAACTGGTC (SEQ ID NO: 76), GCGACCCAATGCAAATTGGT (SEQ ID NO: 77), CGTCCTAAAGGGAATTGATC (SEQ ID NO: 78) for forward primers and GCACAGGGACATAACAATGG (SEQ ID NO: 58), GCGCAGGGCCACAATAATGG (SEQ ID NO: 59), GCACAGGGACATAATAATGG (SEQ ID NO: 60), GCCCAGGGCCACAACAATGG (SEQ ID NO: 61), GCTCAGGGTTTAAACAATGG (SEQ ID NO: 62), GCACAAGGCCATAATAATGG (SEQ ID NO: 63) for reverse primers) allowing a maximum of 2 mismatches, using as template genome sequences from HPV reference database (e.g. PaVE database). In a specific example, the generated amplicons can be modified to obtain a final short concatenated amplicon, where the amplicon can include a forward primer (20 bp) followed by 125 bp of amplicon from 5' to 3'. The same procedure can be applied to reverse sequence of the amplicon, including the reverse primer followed by 125 bp of target sequence; where both modified reads can be concatenated to create a final short amplicon of 250 bp; where the final amplicons can be clustered (e.g., using CD-HIT, etc.) to reduce sequence redundancy; and where the database can also include the complete amplicon plus 75 pb extensions in both directions.

Additionally or alternatively, processing a microorganism database can include identifying reference markers and associated taxa based on processing biological samples received from a population of users in relation to supplementary datasets received from the population of users (e.g., determining correlations with self-reported conditions for the users based on microbiome composition features, microbiome phylogenetic diversity features and/or microbiome functional diversity features derived from biological samples collected from the users), but determining reference markers corresponding to target taxa can be performed in any suitable manner. However, processing a taxonomic database can be performed in any suitable manner.

3.9 Validating.

The method 100 can additionally or alternatively include Block S190, which recites: validating. Block S190 can function to validate any suitable portions of embodiments of the method 100 and/or any suitable components of embodiments of the system 200. For example, validating can include validating the process used in generating one or more female reproductive system-related characterizations for a user based on microbiome datasets, microbiome features, and/or a microbiome database, such as in order to facilitate accurate determination of user microbiome parameters and/or reference microbiome parameter ranges (e.g., for relative abundances of a target taxa). Validating preferably includes performing one or more portions of embodiments of the method 100 and/or applying one or more components of embodiments of the system 200 for one or more reference components (e.g., reference samples with known microbiome composition, microbiome phylogenetic diversity, and/or microbiome functional diversity, such as in relation to the target list of taxa; reference experimental techniques; etc.).

Figure 15:
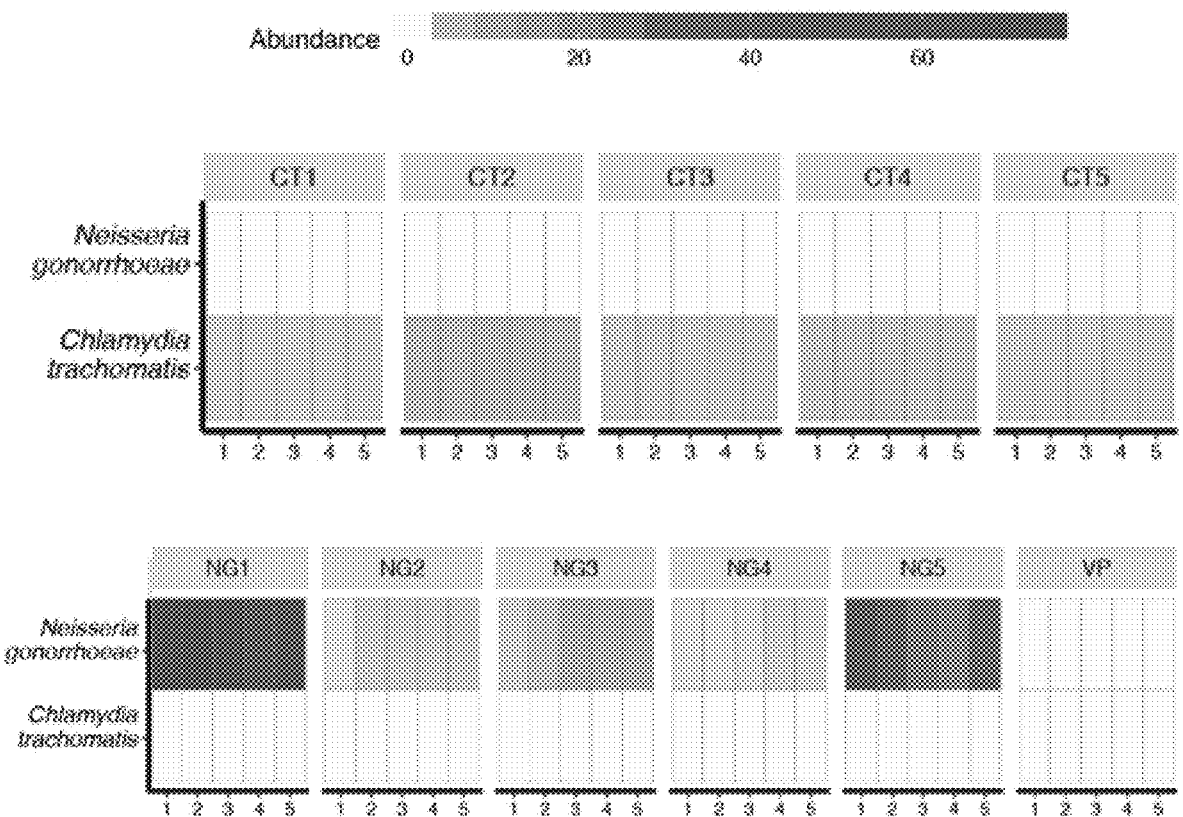
FIG. 15 includes a specific example of experimental validation.

In a variation, validating can include generating reference samples based on diluting genetic material (e.g., to any suitable ratio) associated with target taxa (e.g., synthetic genetic material such as synthetic double-stranded DNA representative of the V4 region of the 16S rRNA gene for different target taxa, etc.); and processing the reference samples by performing one or more of portions of the embodiment of the method 100 (e.g., Blocks S110-S130, etc.) to verify detection of target taxa associated with the reference samples. In a variation, validating can include processing reference samples derived from real and/or synthetic biological samples (e.g., vaginal samples with live or recombinant material of known composition, etc.) to verify detection of target taxa associated with the reference samples. In an example, detection of bacterial targets for a women's health assay can be validated. In a specific example, control samples (e.g., negative for the bacterial targets), first reference samples positive for *C. trachomatis*, and second reference samples positive for *N. gonorrhoeae* can be used as inputs for a women's health assay to evaluate detection capabilities (e.g., as shown in FIG. 15, including ten de-identified clinical verification specimens (iSpecimen) containing either *C. trachomatis* (n=5) or *N. gonorrhoeae* (n=5), as well as a vaginal pool (VP) constructed by combining 96 vaginal samples from 11 individuals, tested for the presence of either pathogen using 16S rRNA gene amplification and sequencing, where five replicates of each specimen were tested, and where relative abundance of the two pathogens in each replicate experiment is shown, on a scale from light (absent) to dark (100% relative abundance), etc.), where four STI-associated targets (i.e., *C. trachomatis, M. genitalium, N. gonorrhoeae,* and *T. pallidum*) were not present in any of the samples from the healthy subject set, nor in a set of vaginal samples used to validate the performance of the digene test on extracted DNA, and where in a set of samples used to compare the HPV genotyping part of the assay to the digene test, *C. trachomatis* and *M. genitalium* was found in certain specimens.

Additionally or alternatively, validating can include modifying (e.g., updating; etc.) one or more parameters, features, and/or other suitable data associated with one or more portions of embodiments of the method 100 based on the results of validating the characterization process (e.g., to improve accuracy, precision, and/or other suitable metrics associated with parameters, features, and/or other suitable data; etc.) and/or other suitable portions of embodiments of the method 100.

Validating can additionally or alternatively include determining a comparison to a reference assay and/or other suitable experimental technique. In variations, validating can include determining comparisons to a reference assay (e.g., digene High-Risk HPV HC2 DNA test)

In an example, sampling performance can be compared with a reference HPV assay (e.g., digene HPV detection test). In a specific example, first samples can be collected using a women's health assay associated with embodiments of the method 100 and/or system 200, and second samples can be collected using a reference HPV assay, such as for performing validation experiments, such as for use in performing spiking and intra-run technical repeatability experiments (e.g., described herein) by using homogenized vaginal pools (e.g., by combining vaginal samples derived individuals who sampled themselves multiple times, etc.).

In an example, amplification and sequence-based HPV type identification (e.g., associated with embodiments of the method 100 and/or system 200) can be compared with a reference HPV assay (e.g., digene HPV detection test; a hrHPV probe and/or lrHPV probe of the digene HPV detection test; etc.).

In an example, HPV sequencing associated with a women's health assay (e.g., associated with portions of embodiments of the method 100) can be evaluated against a reference HPV assay (e.g., digene HPV detection test). In a specific example, for hrHPV genotyping, agreement was 95.3% with a kappa of 0.804; after removal of samples in which the digene hrHPV probe showed cross-reactivity with lrHPV types, the sensitivity and specificity of the hrHPV genotyping assay were 94.5% and 96.6%, respectively, with a kappa of 0.841; for lrHPV genotyping, agreement was 93.9% with a kappa of 0.788, while sensitivity and specificity were 100% and 92.9%, respectively.

In a specific example, performance of the reference HPV assay can be compared by evaluating performance on self-sampled, paired vaginal samples, using controls and calibrators, such as where results from the reference HPV assay can be used as a standard for comparison, where results from a women's health assay (e.g., associated with embodiments of the method 100 and/or system 200) can be considered to be positive for a HPV type if the number of reads assigned to that HPV type divided by the normalized number of reads assigned to a spiked-in control is greater than a threshold (e.g., 0.1, etc.), and where agreement between the women's health assay and the reference HPV assay can be evaluated Cohen's kappa (e.g., where the level of agreement can be defined by the range: 0-0.2, poor; 0.21-0.40, fair; 0.41-0.6, moderate; 0.61-0.8, good; 0.81-1.00, very good; etc.).

Figure 16:
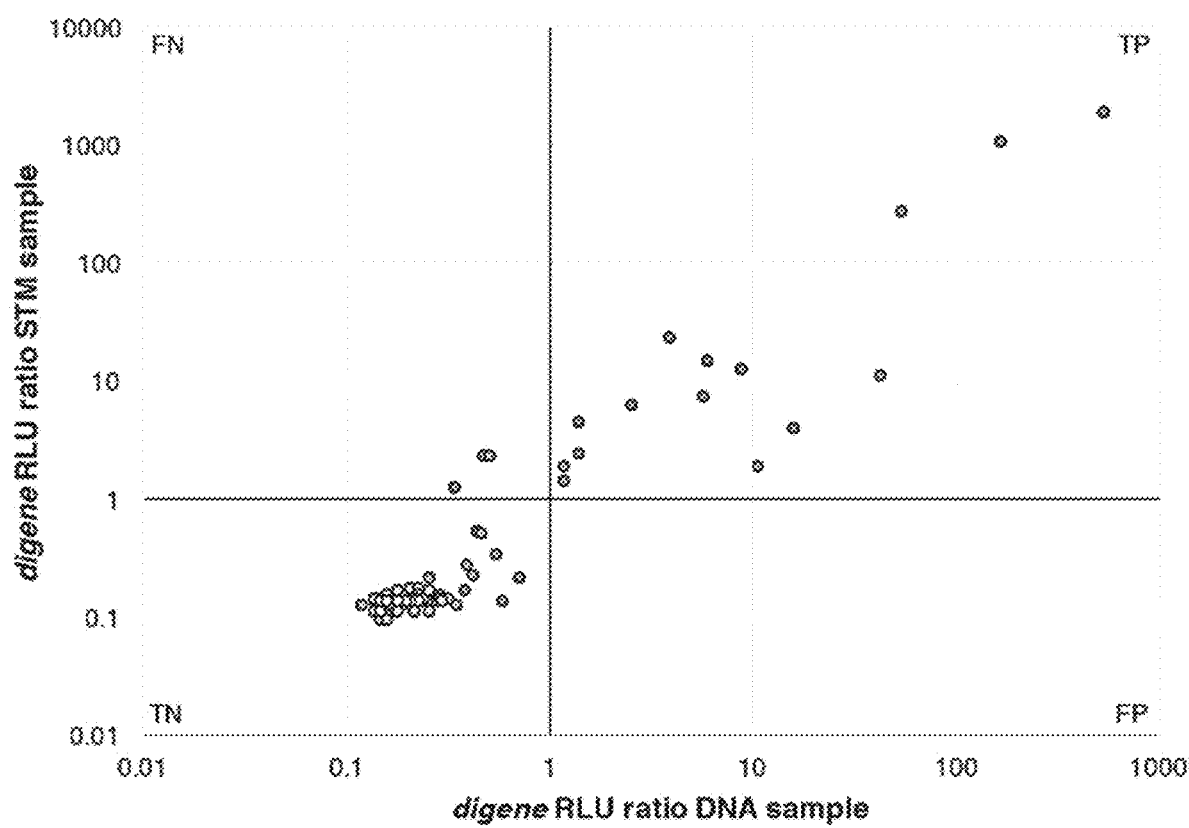
FIG. 16 includes a specific example of experimental validation.

In examples, performance on extracted DNA (e.g., extracted vaginal DNA) and/or other suitable samples can be evaluated for a reference assay to assess the performance of the reference assay (e.g., digene HPV detection test, etc.), such as shown in FIG. 16 (e.g., including digene HC2 High-Risk HPV assay performance on a set of 87 paired, self-collected cervicovaginal samples, where samples were tested directly from STM tubes or from a paired sample after DNA extraction, where lines show the cutoff of the digene assay (RLU ratio=1), where TN, true negative; TP, true positive; FN, false negative; FP, false positive; etc.) and Table 12 (e.g., including performance for digene HC2 High-Risk HPV assay performance on a set of 87 paired, self-collected vaginal samples, where one set of samples was collected using a digene brush resuspended in digene Specimen Transport medium ("digene STM"), and the second set was extracted DNA from swabs suspended in tubes with lysis/stabilization buffer ("digene DNA"), etc.).

Figure 17A:
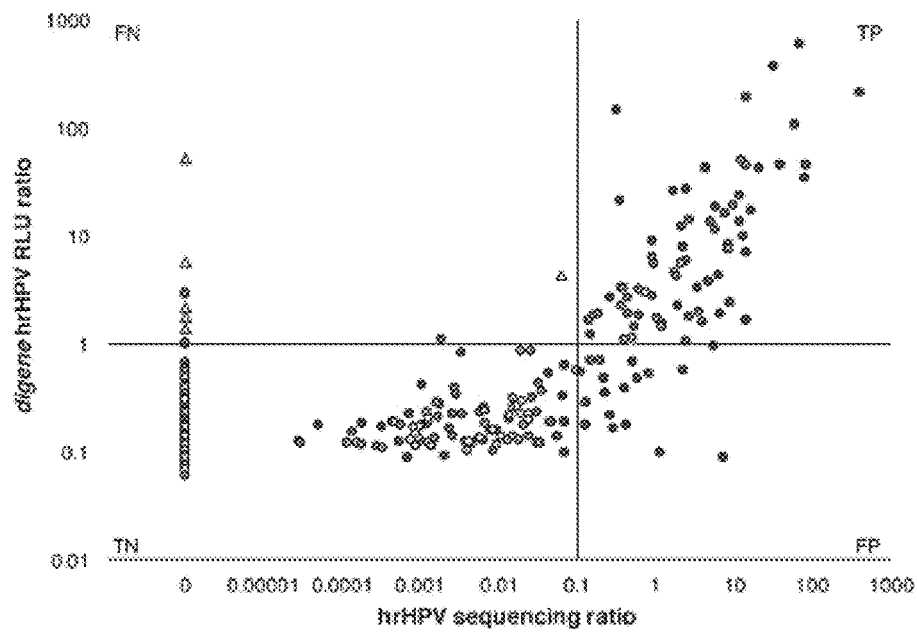
FIG. 17A-B includes a specific example of experimental validation.

In examples, performance on clinical samples (e.g., clinical vaginal samples) and/or other suitable samples can be evaluated through comparison between a women's health assay and a reference assay (e.g., digene HPV detection test, etc.), such as for performance of hrHPV sequencing, such as shown in FIG. 17A (e.g., including results from DNA from 718 vaginal samples extracted and tested by PCR amplification and sequencing using HPV primers, and additionally used directly in the digene assay using the HC2 hrHPV (FIG. 17A) or lrHPV (FIG. 17B) probe mix, where for each sample, the x-axis shows the normalized ratio of reads assigned to validated HPV types over reads assigned to a spiked-in internal control, while the Y-axis shows the digene HPV probe RLU values normalized over the assay's cut-off RLU, where the lines show the cutoff for each of the assays, where FIG. 17A includes a comparison of hrHPV test results in a subset of 601 samples, and where six samples that were positive in the digene hrHPV assay and negative in the hrHPV genotyping assay, but in which lrHPV sequences were detected by genotyping, are shown as triangles, etc.) and Table 13 (e.g., including results for comparison of the women's health assay and a digene HC2 hrHPV assay to detect hrHPV; where of the 601 samples, 504 were negative in both tests, while 69 were positive in both tests; where the genotyping assay was considered positive if the normalized number of reads assigned to any of the validated hrHPV types (16, 18, 31, 33, 35, 39, 45, 51, 52, 56, 58, 59, 66, and 68) divided by the number of reads assigned to a spike in control was greater than 0.1; where the digene test was considered positive if the measured RLU was equal to or greater than the assay's cutoff (RLU ratio of 1 or higher); and where positive correlation was found between the number of normalized hrHPV sequencing reads and the digene HC2 hrHPV RLU ratios, etc.).

Figure 17B:
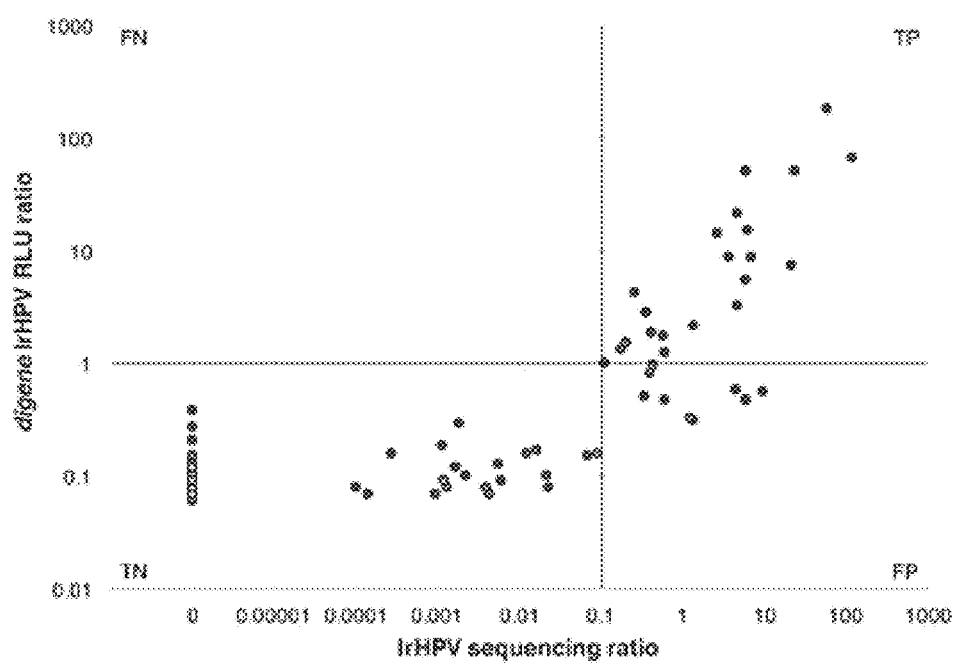

In examples, performance on clinical samples (e.g., clinical vaginal samples) and/or other suitable samples can be evaluated through comparison between a women's health assay and a reference assay (e.g., digene HPV detection test, etc.), such as for performance of lrHPV sequencing, such as shown in FIG. 17B (e.g., where FIG. 17B includes a comparison of lrHPV test results in a subset of 148 samples, and, etc.) and Table 14 (e.g., where of the 148 samples, 118 were negative in both tests, while 21 were positive in both tests; where the genotyping assay was considered positive if the normalized number of reads assigned to any of the validated lrHPV types (6, 11, 42, 43, 44) divided by the number of reads assigned to a spike in control was greater than 0.1; where the digene test was considered positive if the measured RLU was equal to or greater than the assay's cutoff (RLU ratio of 1 or higher); and where the number of normalized lrHPV sequencing reads was positively correlated to the digene HC2 lrHPV RLU ratios, etc.).

Figure 18A:
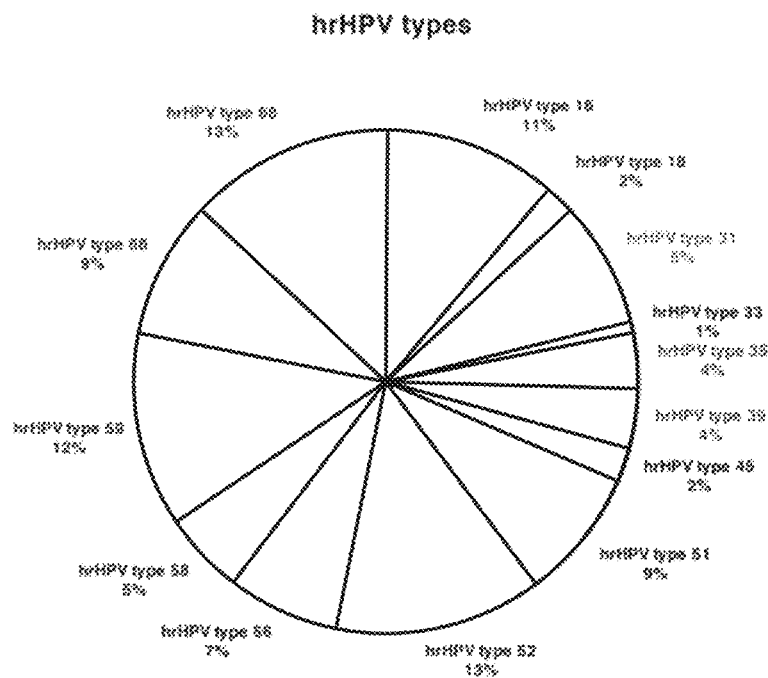
FIG. 18A-B includes a specific example of experimental validation.
Figure 18B:
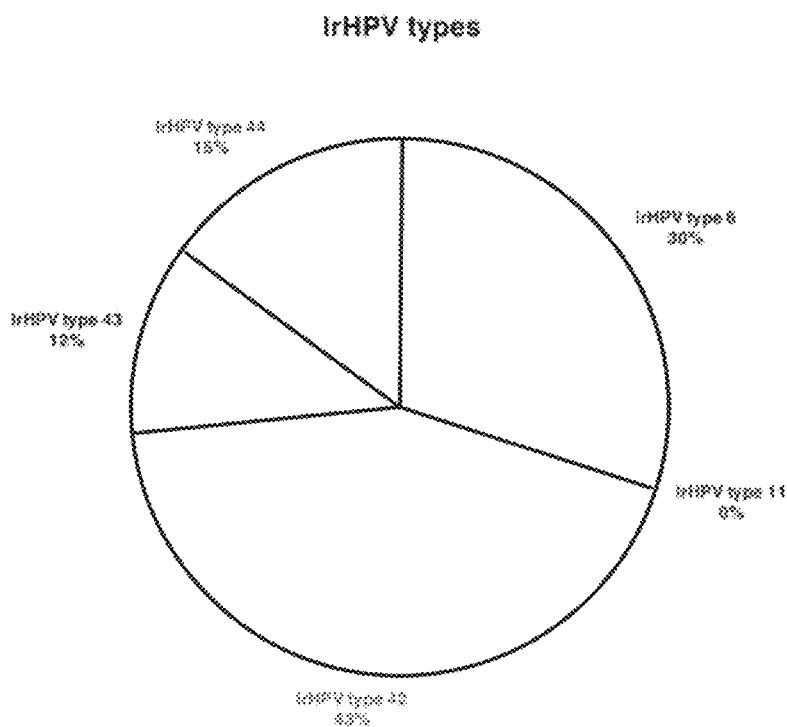

In examples prevalence of hrHPV and lrHPV types in clinical samples can be compared between a women's health assay and a reference assay (e.g., digene HPV detection test, etc.), such as shown in FIGS. 18A and 18B (e.g., including results for combined 718 samples).

Validating can additionally or alternatively include in vitro validation (e.g., of any suitable taxa and/or targets, such as taxa and/or targets associated with a women's health assay; etc.). In a variation, validating can include in vitro validation of bacterial targets (e.g., 32 bacterial targets described in Table 1, etc.). In a specific example, in vitro validation can include using synthetic DNAs, such as synthetic DNAs including the V4 region of the 16S rRNA gene including primer regions (e.g., based on a SILVA representative sequence; where the SILVA representative sequence per taxa can be chosen by performing an all-against-all sequence comparison of all sequences in a taxa, and identifying as representative the sequence that shared the highest similarity with the largest number of sequences in the set; etc.) plus 75 additional bases to both the 5' and 3' side, with one sDNA per target (e.g., as shown in Table 7). In a specific example, to validate that each target could be detected in a vaginal swab specimen, each sDNA (e.g., 3 ng) can be spiked into aliquots (e.g., 500 µl) of a vaginal pool, created by combining vaginal specimens of women included in this study, and DNA was extracted from each spiked vaginal pool; where each spike-in experiment was performed in triplicate; and where bacterial targets were detected by amplification using PCR targeting the 16S rRNA gene, sequencing, and a bioinformatics pipeline, such as portions of embodiments of the method 100; where each target was detected above limit of detection (LOD) in each of the triplicate spiked-in amplification reactions performed on the extracted DNA from the vaginal pool. Additionally or alternatively, LOD of targets (e.g., bacterial targets) can be determined. In a specific example, limit of blank (LOB) can be calculated using wells of a PCR plate (e.g., blank wells of a 96-well PCR plate where wells of the first row and first column of the plate each contained 200 pg/µl of synthetic 16S rRNA gene DNA from different targets; etc.); where the LOB was set as the average number of reads in these blank wells plus 1.65 standard deviations; where pools of bacterial sDNAs were mixed in different ratios (e.g., each bacterial sDNA was randomly assigned to one of two pools, A and B, that each contained sDNAs in equimolar amount); where each pool was serially diluted in PCR grade water (e.g., Pool A dilutions were mixed 1:1 with undiluted Pool B and vice versa); where pool A/B combinations were used in triplicate for DNA extraction, amplification, and sequencing as described below; where for each target, the LOD was defined as the lowest concentration of sDNA where at least two of the three replicates contained at least 2 reads for that target in a sample with 10,000 reads or more; where using the LOD, a lower threshold for detection for each taxa at its LOD as the LOB (48.27) plus the standard deviation of the taxa at LOD*1.65 can be calculated; and where the threshold is used to correctly assign a taxa as identified in a sample at or above its LOD. In a specific example, for targets that had both a species and a genus level sDNA present in the mixed pools A and B, a bioinformatic correction can be applied: the total reads for a genus-level target for which a species within that genus was also present in the mixed pools, was defined as the total measured reads for the genus and subtracting all those reads corresponding to species-level targets belonging to that genus in the same pool mix (e.g., only reads that match to a genus and not to a species level can be assigned to the genus).

In a variation, validating can include in vitro validation of HPV targets (e.g., HPV targets described in Table 1, etc.). In a specific example, fragments of the L1 gene of approximately 600 bp long can be used. In a specific example, synthetic DNA sequences representing 5 lrHPV and 19 hrHPV types (e.g., included in a women's health assay) can be described in Table 8. In a specific example, to validate that each target can be detected in a vaginal swab specimen, each HPV sDNA (e.g., 3 ng) can be spiked into aliquots (e.g., 500 µl) of a vaginal pool created by combining vaginal specimens of women included in this study, and DNA was extracted from each spiked vaginal pool; where the spiked HPV targets were detected by amplification using the PCR targeting the L1 gene and bioinformatics pipeline (e.g., portions of embodiments of the method 100); where each spike-in experiment was performed in triplicate; where each HPV target was detected above the LOD in each of the triplicate spiked-in amplification reactions performed on the extracted DNA from the vaginal pool; where each target had a ratio >0.1 for the number of HPV-assigned reads divided by the total number of normalized reads assigned to an internal spike-in control. In a specific example, to determine the LOD of HPV targets, 10-fold serial dilutions of the sDNAs representing HPV targets were made in nuclease-free water, ranging from $10^5$ to $10^2$ molecules per µl; where dilutions of one target were inversely combined with dilutions of another target, forming different pairs of HPV sDNAs. Each dilution pair was used directly as template for PCR in triplicate as described below.

However, validating can be performed in any suitable manner.

4. System

Figure 2:
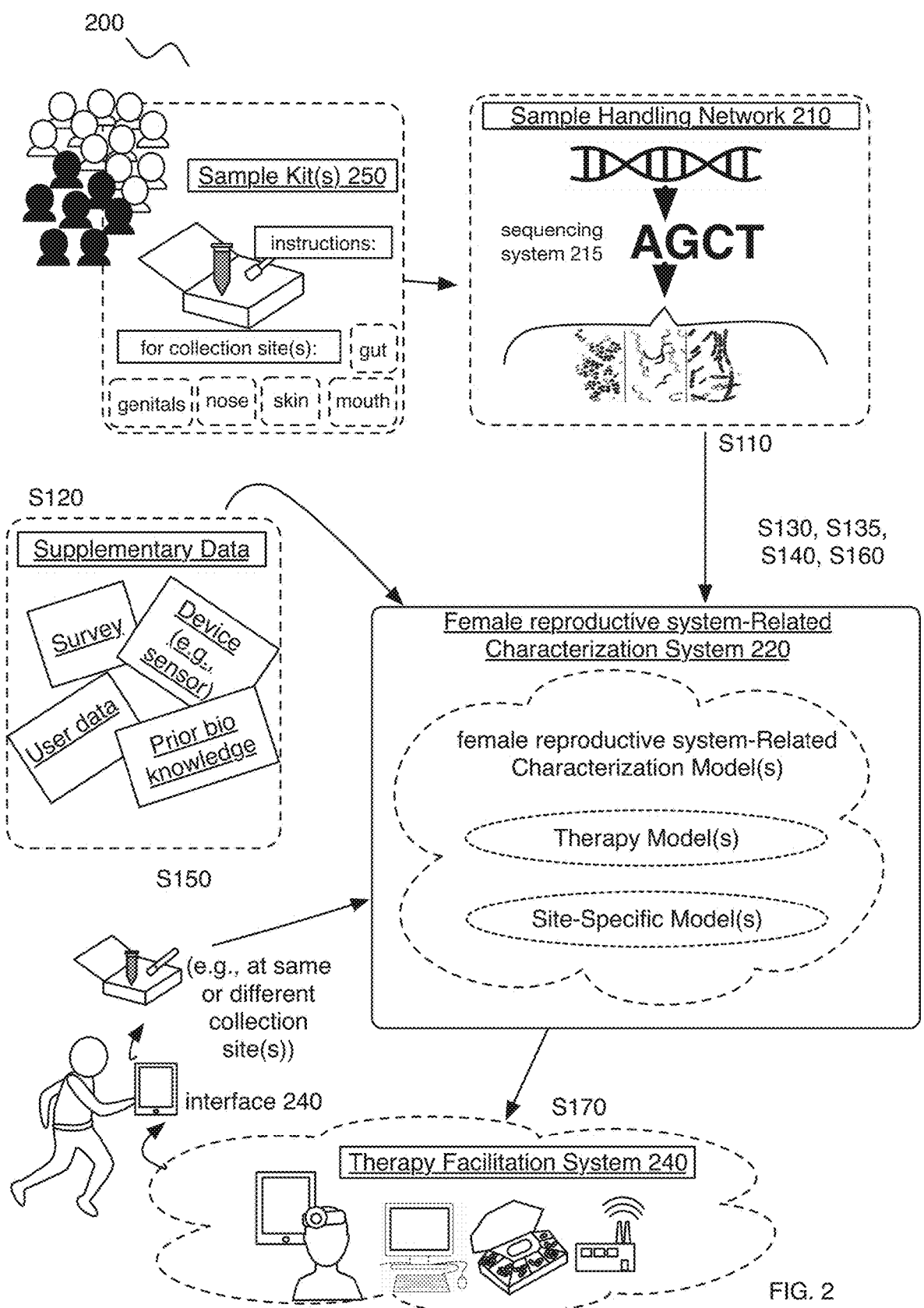
FIG. 2 includes embodiments of a method and system.

As shown in FIG. 2, embodiments of the system 200 (e.g., for characterizing a female reproductive system-related condition) can include any one or more of: a handling system (e.g., a sample handling system, etc.) 210 operable to collect and/or process biological samples (e.g., collected by users and included in containers including pre-processing reagents; etc.) from one or more users (e.g., a human subject, patient, animal subject, environmental ecosystem, care provider, etc.) for facilitating determination of a microorganism dataset (e.g., microorganism genetic sequences; microorganism sequence dataset; etc.); a female reproductive system-related characterization system 220 operable to determine microbiome features (e.g., microbiome composition features; microbiome functional features; diversity features; relative abundance ranges; such as based on a microorganism dataset and/or other suitable data; etc.), determine female reproductive system-related characterizations (e.g., female reproductive system-related condition characterizations, therapy-related characterizations, characterizations for users, etc.); and/or a therapy facilitation system 230 operable to facilitate therapeutic intervention (e.g., promote a therapy, etc.) for one or more female reproductive system-related conditions (e.g., based on one or more female reproductive system-related conditions; for improving one or more female reproductive system-related conditions; etc.).

Embodiments of the system 200 can include one or more handling systems 210, which can function to receive and/or process (e.g., fragment, amplify, sequence, generate associated datasets, etc.) biological samples to transform microorganism nucleic acids and/or other components of the biological samples into data (e.g., genetic sequences that can be subsequently aligned and analyzed; microorganism datasets; etc.) for facilitating generation of female reproductive system-related characterizations and/or therapeutic intervention. The handling system 210 can additionally or alternatively function to provide sample kits 250 (e.g., including sample containers, instructions for collecting samples from one or more collection sites, etc.) to a plurality of users (e.g., in response to a purchase order for a sample kit 250), such as through a mail delivery system. The handling system 210 can include one or more sequencing systems 215 (e.g., next-generation sequencing systems, sequencing systems for targeted amplicon sequencing, sequencing-by-synthesis techniques, capillary sequencing technique, Sanger sequencing, pyrosequencing techniques, nanopore sequencing techniques, etc.) for sequencing one or more biological samples (e.g., sequencing microorganism nucleic acids from the biological samples, etc.), such as in generating microorganism data (e.g., microorganism sequence data, other data for microorganism datasets, etc.). Next-generation sequencing systems (e.g., next-generation sequencing platforms, etc.) can include any suitable sequencing systems (e.g., sequencing platforms, etc.) for one or more of high-throughput sequencing (e.g., facilitated through high-throughput sequencing technologies; massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, etc.), any generation number of sequencing technologies (e.g., second-generation sequencing technologies, third-generation sequencing technologies, fourth-generation sequencing technologies, etc.), amplicon-associated sequencing (e.g., targeted amplicon sequencing), sequencing-by-synthesis, tunnelling currents sequencing, sequencing by hybridization, mass spectrometry sequencing, microscopy-based techniques, and/or any suitable next-generation sequencing technologies. Additionally or alternatively, sequencing systems 215 can implement any one or more of capillary sequencing, Sanger sequencing (e.g., microfluidic Sanger sequencing, etc.), pyrosequencing, nanopore sequencing (Oxford nanopore sequencing, etc.), and/or any other suitable types of sequencing facilitated by any suitable sequencing technologies.

The handling system 210 can additionally or alternatively include a library preparation system operable to automatically prepare biological samples (e.g., fragment and amplify using primers compatible with genetic targets associated with the female reproductive system-related condition) in a multiplex manner to be sequenced by a sequencing system; and/or any suitable components. The handling system 210 can perform any suitable sample processing techniques described herein. However, the handling system 210 and associated components can be configured in any suitable manner.

Embodiments of the system 200 can include one or more female reproductive system-related characterization systems 220, which can function to determine, analyze, characterize, and/or otherwise process microorganism datasets (e.g., based on processed biological samples leading to microorganism genetic sequences; alignments to reference sequences; etc.), microbiome features (e.g., individual variables; groups of variables; features relevant for phenotypic prediction, for statistical description; variables associated with a sample obtained from an individual; variables associated with female reproductive system-related conditions; variables describing fully or partially, in relative or absolute quantities the sample's microbiome composition and/or functionality; etc.), models, and/or other suitable data for facilitating female reproductive system-related characterization and/or therapeutic intervention. In examples, the female reproductive system-related characterization system 220 can identify data associated with the information of the features that statistically describe the differences between samples associated with one or more female reproductive system-related conditions (e.g., samples associated with presence, absence, risk of, propensity for, and/or other aspects related to female reproductive system-related conditions etc.), such as where the differing analyses can provide complementing views into the features differentiating the different samples (e.g., differentiating the subgroups associated with presence or absence of a condition, etc.). In a specific example, individual predictors, a specific biological process, and/or statistically inferred latent variables can provide complementary information at different levels of data complexity to facilitate varied downstream opportunities in relation to characterization, diagnosis, and/or treatment. In another specific example, the female reproductive system-related characterization system 220 process supplementary data for performing one or more characterization processes.

The female reproductive system-related characterization system 220 can include, generate, apply, and/or otherwise process female reproductive system-related characterization models, which can include any one or more of female reproductive system-related condition models for characterizing one or more female reproductive system-related conditions (e.g., determining propensity of one or more female reproductive system-related conditions for one or more users, etc.), therapy models for determining therapies, and/or any other suitable models for any suitable purposes associated with the embodiments of the system 200 and/or method 100. In a specific example, the female reproductive system-related characterization system 220 can generate and/or apply a therapy model (e.g., based on cross-condition analyses, etc.) for identifying and/or characterizing a therapy used to treat one or more female reproductive system-related conditions. Different female reproductive system-related characterization models (e.g., different combinations of female reproductive system-related characterization models; different models applying different analytical techniques; different inputs and/or output types; applied in different manners such as in relation to time and/or frequency; etc.) can be applied (e.g., executed, selected, retrieves, stored, etc.) based on one or more of: female reproductive system-related conditions (e.g., using different female reproductive system-related characterization models depending on the female reproductive system-related condition or conditions being characterized, such as where different female reproductive system-related characterization models possess differing levels of suitability for processing data in relation to different female reproductive system-related conditions and/or combinations of conditions, etc.), users (e.g., different female reproductive system-related characterization models based on different user data and/or characteristics, demographic characteristics, genetics, environmental factors, etc.), female reproductive system-related characterizations (e.g., different female reproductive system-related characterization models for different types of characterizations, such as a therapy-related characterization versus a diagnosis-related characterization, such as for identifying relevant microbiome composition versus determining a propensity score for a female reproductive system-related condition; etc.), therapies (e.g., different female reproductive system-related characterization models for monitoring efficacy of different therapies, etc.), body sites (e.g., different female reproductive system-related characterization models for processing microorganism datasets corresponding to biological samples from different sample collection sites; etc.), supplementary data, and/or any other suitable components. However, female reproductive system-related characterization models can be tailored and/or used in any suitable manner for facilitating female reproductive system-related characterization and/or therapeutic intervention.

The female reproductive system-related characterization system 220 can preferably determine site-specific female reproductive system-related characterizations (e.g., site-specific analyses). In examples, the female reproductive system-related characterization system 220 can generating and/or apply different site-specific female reproductive system-related characterization models. In specific examples, different site-specific female reproductive system-related characterization models can be generated and/or can be applied based on different microbiome features, such as site-specific features associated with the one or more body sites that the site-specific female reproductive system-related characterization model is associated with (e.g., using gut site-specific features derived from samples collected at gut collection sites of subjects, and correlated with one or more female reproductive system-related conditions, such as for generating a gut site-specific female reproductive system-related characterization model that can be applied for determining characterizations based on user samples collected at user gut collection sites; etc.). Site-specific female reproductive system-related characterization models, site-specific features, samples, site-specific therapies, and/or other suitable entities (e.g., able to be associated with a body site, etc.) are preferably associated with at least one body site (e.g., corresponding to a sample collection site; etc.) including one or more of a gut site (e.g., characterizable based on stool samples, etc.), skin site, nose site, genital site (e.g., associated with genitals, genitalia; vaginal site; etc.), mouth site, and/or any suitable body region. In examples, different female reproductive system-related characterization models can be tailored to different types of inputs, outputs, female reproductive system-related characterizations, female reproductive system-related conditions (e.g., different phenotypic measures that need to be characterized), and/or any other suitable entities. However, site-specific female reproductive system-related characterizations can be configured in any manner and determined in any manner by a female reproductive system-related characterization system 220 and/or other suitable components.

Female reproductive system-related characterization models, other models, other components of embodiments of the system 200, and/or suitable portions of embodiments of the method 100 (e.g., characterization processes, determining microbiome features, determining female reproductive system-related characterizations, etc.) can employ analytical techniques including any one or more of: univariate statistical tests, multivariate statistical tests, dimensionality reduction techniques, artificial intelligence approaches (e.g., machine learning approaches, etc.), performing pattern recognition on data (e.g., identifying correlations between female reproductive system-related conditions and microbiome features; etc.), fusing data from multiple sources (e.g., generating characterization models based on microbiome data and/or supplementary data from a plurality of users associated with one or more female reproductive system-related conditions, such as based on microbiome features extracted from the data; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. Artificial intelligence approaches can include any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.) reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), an ensemble method (e.g., boosting, boostrapped aggregation, AdaBoost, stacked generalization, gradient boosting machine method, random forest method, etc.), and/or any suitable artificial intelligence approach. However, data processing can be employed in any suitable manner.

The female reproductive system-related characterization system 220 can perform cross-condition analyses for a plurality of female reproductive system-related conditions (e.g., generating multi-condition characterizations based on outputs of different female reproductive system-related characterization models, such as multi-condition microbiome features; etc.). For example, the female reproductive system-related characterization system can characterize relationships between female reproductive system-related conditions based on microorganism data, microbiome features, and/or other suitable microbiome characteristics of users associated with (e.g., diagnosed with, characterized by, etc.) a plurality of female reproductive system-related conditions. In a specific example, cross-condition analyses can be performed based on characterizations for individual female reproductive system-related conditions (e.g., outputs from female reproductive system-related characterization models for individual female reproductive system-related conditions, etc.). Cross-condition analyses can include identification of condition-specific features (e.g., associated exclusively with a single female reproductive system-related condition, etc.), multi-condition features (e.g., associated with two or more female reproductive system-related conditions, etc.), and/or any other suitable types of features. Cross-condition analyses can include determination of parameters informing correlation, concordance, and/or other similar parameters describing relationships between two or more female reproductive system-related conditions, such as by evaluating different pairs of female reproductive system-related conditions. However, the female reproductive system-related characterization system and/or other suitable components can be configured in any suitable manner to facilitate cross-condition analyses (e.g., applying analytical techniques for cross-condition analysis purposes; generating cross-condition characterizations, etc.).

The female reproductive system-related characterization system 220 preferably includes a remote computing system (e.g., for applying female reproductive system-related characterization models, etc.), but can additionally or alternatively include any suitable computing systems (e.g., local computing systems, user devices, handling system components, etc.). However, the female reproductive system-related characterization system 220 can be configured in any suitable manner.

Embodiments of the system 200 can include one or more therapy facilitation systems 230, which can function to facilitate therapeutic intervention (e.g., promote one or more therapies, etc.) for one or more female reproductive system-related conditions (e.g., facilitating modulation of a user microbiome composition and functional diversity for improving a state of the user in relation to one or more female reproductive system-related conditions, etc.). The therapy facilitation system 230 can facilitate therapeutic intervention for any number of female reproductive system-related conditions associated with any number of body sites (e.g., corresponding to any suitable number of collection sites of samples; etc.), such as based on site-specific characterizations (e.g., multi-site characterizations associated with a plurality of body sites; etc.), multi-condition characterizations, other characterizations, and/or any other suitable data. The therapy facilitation system 230 can include any one or more of: a communications system (e.g., to communicate therapy recommendations, selections, discouragements, and/or other suitable therapy-related information to a computing device (e.g., user device and/or care provider device; mobile device; smart phone; desktop computer; at a website, web application, and/or mobile application accessed by the computing device; etc.); to enable telemedicine between a care provider and a subject in relation to a female reproductive system-related condition; etc.), an application executable on a user device (e.g., indicating microbiome composition and/or functionality for a user; etc.), a medical device (e.g., a biological sampling device, such as for collecting samples from different collection sites; medication provision devices; surgical systems; etc.), a user device (e.g., biometric sensors), and/or any other suitable component. One or more therapy facilitation systems 230 can be controllable, communicable with, and/or otherwise associated with the female reproductive system-related characterization system 220. For example, the female reproductive system-related characterization system 220 can generate characterizations of one or more female reproductive system-related conditions for the therapy facilitation system 230 to present (e.g., transmit, communicate, etc.) to a corresponding user (e.g., at an interface 240, etc.). In another example, the therapy facilitation system 230 can update and/or otherwise modify an application and/or other software of a device (e.g., user smartphone) to promote a therapy (e.g., promoting, at a to-do list application, lifestyle changes for improving a user state associated with one or more female reproductive system-related conditions, etc.). However, the therapy facilitation system 230 can be configured in any other manner.

As shown in FIG. 25, embodiments of the system 200 can additionally or alternatively include an interface 240, which can function to improve presentation of microbiome characteristics, female reproductive system-related condition information (e.g., propensity metrics; therapy recommendations; comparisons to other users; other characterizations; etc.), and/or specific information (e.g., any suitable data described herein) associated with (e.g., included in, related to, derivable from, etc.) one or more female reproductive system-related characterizations. In examples, the interface 240 can present female reproductive system-related condition information including a microbiome composition (e.g., taxonomic groups; relative abundances; etc.), functional diversity (e.g., relative abundance of genes associated with particular functions, and propensity metrics for one or more female reproductive system-related conditions, such as relative to user groups sharing a demographic characteristic (e.g., smokers, exercisers, users on different dietary regimens, consumers of probiotics, antibiotic users, groups undergoing particular therapies, etc.). However, the interface 240 can be configured in any suitable manner.

While the components of embodiments of the system 200 are generally described as distinct components, they can be physically and/or logically integrated in any manner. For example, a computing system (e.g., a remote computing system, a user device, etc.) can implement portions and/or all of the female reproductive system-related characterization system 220 (e.g., apply a microbiome-related condition model to generate a characterization of female reproductive system-related conditions for a user, etc.) and the therapy facilitation system 230 (e.g., facilitate therapeutic intervention through presenting insights associated with microbiome composition and/or function; presenting therapy recommendations and/or information; scheduling daily events at a calendar application of the smartphone to notify the user in relation to therapies for improving female reproductive system-related, etc.). In an example, embodiments of the system 200 can omit a therapy facilitation system 230. In an example, the system 200 can include a women's health assay (e.g., described herein, etc.) that can complement conventional and/or current approaches for in-clinic cervical cancer screening, other suitable women's health screening, other suitable in-clinic approaches associated with women's health, and/or any suitable approaches. However, the functionality of embodiments of the system 200 can be distributed in any suitable manner amongst any suitable system components. However, the components of embodiments of the system 200 can be configured in any suitable manner

5. Other

Embodiments of the method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

TABLE 1

| Target | Taxonomic rank | Association | Health condition |
|---|---|---|---|
| Aerococcus | genus | Associated | Bacterial Vaginosis |
| Aerococcus christensenii | species | Associated | Bacterial Vaginosis |
| Atopobium | genus | Associated | Bacterial Vaginosis |
| Atopobium vaginae | species | Associated | Bacterial Vaginosis |
| Chlamydia trachomatis | species | Associated | Sexually Transmitted Infection |
| | species | Associated | Cervicitis |
| | species | Associated | Pelvic Inflammatory Disease |
| | species | Associated | Idiopathic Infertility |
| Dialister micraerophilus | species | Associated | Bacterial Vaginosis |
| Fusobacterium | genus | Associated | Bacterial Vaginosis |
| Fusobacterium nucleatum | species | Inversely associated | Human papillomavirus Infection |
| Gardnerella | genus | Associated | Bacterial Vaginosis |
| | genus | Associated | Human papillomavirus Infection |
| Gardnerella vaginalis | species | Associated | Bacterial Vaginosis |
| | species | Associated | Aerobic Vaginitis |
| | species | Associated | Human papillomavirus Infection |
| Gemella | genus | Associated | Bacterial Vaginosis |
| Lactobacillus | genus | Inversely associated | Cervicitis |
| | genus | Inversely associated | Bacterial Vaginosis |
| Lactobacillus iners | species | Inversely associated | Bacterial Vaginosis |
| | species | Inversely associated | Human papillomavirus Infection |
| Lactobacillus jensenii | species | Inversely associated | Bacterial Vaginosis |

TABLE 1-continued

| Target | Taxonomic rank | Association | Health condition |
|---|---|---|---|
| Megasphaera | genus | Associated | Bacterial Vaginosis |
| Mobiluncus | genus | Associated | Bacterial Vaginosis |
| Mobiluncus curtisii | species | Associated | Bacterial Vaginosis |
| Mobiluncus mulieris | species | Associated | Bacterial Vaginosis |
| Mycoplasma genitalium | species | Associated | Sexually Transmitted Infection |
| | species | Associated | Cervicitis |
| | species | Associated | Infertility |
| Neisseria gonorrhoeae | species | Associated | Sexually Transmitted Infection |
| | species | Associated | Pelvic Inflammatory Disease |
| | species | Associated | Infertility |
| Papillibacter | genus | Associated | Bacterial Vaginosis |
| Parvimonas | genus | Associated | Bacterial Vaginosis |
| Pep toniphilus | genus | Associated | Bacterial Vaginosis |
| Peptostreptococcus | genus | Associated | Bacterial Vaginosis |
| Porphyromonas | genus | Associated | Bacterial Vaginosis |
| Prevotella | genus | Associated | Bacterial Vaginosis |
| Prevotella amnii | species | Associated | Bacterial Vaginosis |
| Prevotella timonensis | species | Associated | Bacterial Vaginosis |
| Sneathia | genus | Associated | Bacterial Vaginosis |
| | genus | Associated | Human papillomavirus Infection |
| Staphylococcus aureus | species | Associated | Aerobic Vaginitis |
| Streptococcus agalactiae | species | Associated | Aerobic Vaginitis |
| Treponema pallidum | species | Associated | Sexually Transmitted Infection |
| HPV (any described types) | — | Associated | Human papillomavirus Infection |
| lrHPV (types 6, 11, 42, 43, and 44) | — | Associated | Genital warts |
| hrHPV (types 16, 18, 31, 33, 35, 39,45, 51, 52, 56, 58, 59, 66, and 68) | — | Associated | Cervical Cancer |
| | — | Associated | SIL (High & Low) |
| | — | Associated | Cervicitis |

TABLE 2

| Condition | Site | Organism | Association |
|---|---|---|---|
| Chlamydia | Gut | Bacteroides sp. AR20 | Associated |
| Chlamydia | Gut | Bacteroides sp. AR29 | Inversely Associated |
| Chlamydia | Gut | Bacteroides sp. D22 | Associated |
| Chlamydia | Gut | Alistipes sp. EBA6-25cl2 | Associated |
| Endometriosis | Gut | Actinobacteria | Inversely Associated |
| Endometriosis | Gut | Alistipes sp. EBA6-25cl2 | Associated |
| Endometriosis | Gut | Bacteroidales | Associated |
| Endometriosis | Gut | Bacteroides | Associated |
| Endometriosis | Gut | Bacteroides sp. AR20 | Associated |
| Endometriosis | Gut | Bacteroides sp. AR29 | Associated |
| Endometriosis | Gut | Bacteroides sp. D22 | Associated |
| Endometriosis | Gut | Bacteroidetes | Associated |
| Endometriosis | Gut | Bacteroidia | Associated |
| Endometriosis | Gut | Barnesiella | Associated |
| Endometriosis | Gut | Barnesiella intestinihominis | Associated |
| Endometriosis | Gut | Betaproteobacteria | Inversely Associated |
| Endometriosis | Gut | Blautia luti | Associated |
| Endometriosis | Gut | Blautia sp. Ser8 | Associated |
| Endometriosis | Gut | Burkholderiales | Inversely Associated |
| Endometriosis | Gut | Clostridia | Inversely Associated |
| Endometriosis | Gut | Clostridiales | Inversely Associated |
| Endometriosis | Gut | Collinsella | Inversely Associated |
| Endometriosis | Gut | Coriobacteriales | Inversely Associated |
| Endometriosis | Gut | Dorea | Inversely Associated |
| Endometriosis | Gut | Dorea longicatena | Inversely Associated |
| Endometriosis | Gut | Eggerthella | Associated |
| Endometriosis | Gut | Eisenbergiella tayi | Associated |
| Endometriosis | Gut | Faecalibacterium prausnitzii | Inversely Associated |
| Endometriosis | Gut | Flavobacteriales | Associated |
| Endometriosis | Gut | Flavobacteriia | Associated |
| Endometriosis | Gut | Fusicatenibacter saccharivorans | Inversely Associated |
| Endometriosis | Gut | Lachnospira pectinoschiza | Inversely Associated |
| Endometriosis | Gut | Lactobacillaceae | Associated |
| Endometriosis | Gut | Megasphaera | Inversely Associated |
| Endometriosis | Gut | Odoribacter | Associated |
| Endometriosis | Gut | Oscillospiraceae | Associated |
| Endometriosis | Gut | Roseburia | Inversely Associated |
| Endometriosis | Gut | Roseburia sp. 11SE39 | Inversely Associated |
| Endometriosis | Gut | Ruminococcaceae | Inversely Associated |
| Endometriosis | Gut | Sarcina | Inversely Associated |
| Endometriosis | Gut | Subdoligranulum variabile | Inversely Associated |
| Endometriosis | Gut | Sutterellaceae | Associated |
| Endometriosis | Gut | Terrisporobacter | Inversely Associated |
| Genital Herpes | Gut | Bifidobacterium | Inversely Associated |
| Genital Herpes | Gut | Actinobacteria | Inversely Associated |
| Genital Herpes | Gut | Alistipes sp. EBA6-25cl2 | Inversely Associated |
| Genital Herpes | Gut | Alistipes sp. HGB5 | Associated |
| Genital Herpes | Gut | Anaerostipes sp. 5_1_63FAA | Inversely Associated |
| Genital Herpes | Gut | Bacteroides acidifaciens | Inversely Associated |
| Genital Herpes | Gut | Bacteroides sp. AR20 | Associated |
| Genital Herpes | Gut | Bacteroides sp. AR29 | Associated |
| Genital Herpes | Gut | Bacteroides sp. D22 | Associated |
| Genital Herpes | Gut | Bacteroides thetaiotaomicron | Associated |
| Genital Herpes | Gut | Bifidobacteriaceae | Inversely Associated |
| Genital Herpes | Gut | Bifidobacteriales | Inversely Associated |
| Genital Herpes | Gut | Bifidobacterium | Inversely Associated |
| Genital Herpes | Gut | Blautia luti | Associated |
| Genital Herpes | Gut | Faecalibacterium prausnitzii | Inversely Associated |
| Genital Herpes | Gut | Flavonifractor plautii | Associated |
| Genital Herpes | Gut | Fusicatenibacter | Inversely Associated |
| Genital Herpes | Gut | Fusicatenibacter saccharivorans | Associated |
| Genital Herpes | Gut | Hespellia | Associated |
| Genital Herpes | Gut | Lachnospira pectinoschiza | Associated |
| Genital Herpes | Gut | Moryella | Associated |
| Genital Herpes | Gut | Oscillospiraceae | Associated |
| Genital Herpes | Gut | Roseburia sp. 11SE39 | Inversely Associated |
| Genital Herpes | Gut | Subdoligranulum variabile | Inversely Associated |
| Genital Warts | Gut | Bifidobacteriaceae | Inversely Associated |

TABLE 2-continued

| Condition | Site | Organism | Association |
|---|---|---|---|
| Genital Warts | Gut | Bifidobacteriales | Inversely Associated |
| Genital Warts | Gut | Bifidobacterium | Inversely Associated |
| Genital Warts | Gut | Clostridia | Inversely Associated |
| Genital Warts | Gut | Clostridiales | Inversely Associated |
| Genital Warts | Gut | Negativicutes | Inversely Associated |
| Genital Warts | Gut | Selenomonadales | Inversely Associated |
| Genital Warts | Gut | Veillonellaceae | Inversely Associated |
| Gonorrhea | Gut | Alistipes sp. RMA 9912 | Associated |
| Gonorrhea | Gut | Bacteroides caccae | Inversely Associated |
| Gonorrhea | Gut | Bacteroides sp. AR29 | Inversely Associated |
| Gonorrhea | Gut | Bacteroides sp. D22 | Inversely Associated |
| Gonorrhea | Gut | Bacteroides vulgatus | Inversely Associated |
| Gonorrhea | Gut | Bilophila sp. 4_1_30 | Inversely Associated |
| Gonorrhea | Gut | Intestinimonas | Associated |
| Gonorrhea | Gut | Prevotellaceae | Associated |
| Painful Periods | Gut | Actinobacteria | Inversely Associated |
| Painful Periods | Genital | Actinobacteria | Inversely Associated |
| Painful Periods | Gut | Alistipes putredinis | Associated |
| Painful Periods | Gut | Alistipes sp. EBA6-25cl2 | Associated |
| Painful Periods | Gut | Alistipes sp. NML05A004 | Associated |
| Painful Periods | Gut | Alphaproteobacteria | Associated |
| Painful Periods | Gut | Anaerostipes sp. 5_1_63FAA | Associated |
| Painful Periods | mouth | Bacilli | Associated |
| Painful Periods | Genital | Bacilli | Associated |
| Painful Periods | Gut | Bacteroidaceae | Associated |
| Painful Periods | Gut | Bacteroidales | Associated |
| Painful Periods | Gut | Bacteroides | Associated |
| Painful Periods | Gut | Bacteroides caccae | Associated |
| Painful Periods | Gut | Bacteroides sp. AR20 | Associated |
| Painful Periods | Gut | Bacteroides sp. AR29 | Associated |
| Painful Periods | Gut | Bacteroides sp. D22 | Associated |
| Painful Periods | Gut | Bacteroides sp. SLC1-38 | Associated |
| Painful Periods | Gut | Bacteroides thetaiotaomicron | Associated |
| Painful Periods | Gut | Bacteroidetes | Associated |
| Painful Periods | Gut | Bacteroidia | Associated |
| Painful Periods | Gut | Barnesiella intestinihominis | Associated |
| Painful Periods | Gut | Blautia luti | Associated |
| Painful Periods | Gut | Blautia sp. Ser8 | Inversely Associated |
| Painful Periods | Gut | Blautia sp. YHC-4 | Associated |
| Painful Periods | Gut | Blautia stercoris | Inversely Associated |
| Painful Periods | Gut | Blautia wexlerae | Inversely Associated |
| Painful Periods | Gut | Butyricimonas | Inversely Associated |
| Painful Periods | Gut | Clostridia | Inversely Associated |
| Painful Periods | Gut | Clostridiaceae | Inversely Associated |
| Painful Periods | Gut | Clostridiales | Inversely Associated |
| Painful Periods | Gut | Clostridium | Inversely Associated |
| Painful Periods | Gut | Collinsella | Inversely Associated |
| Painful Periods | Gut | Collinsella aerofaciens | Inversely Associated |
| Painful Periods | Gut | Collinsella aerofaciens | Associated |
| Painful Periods | Gut | Coriobacteriaceae | Inversely Associated |
| Painful Periods | Gut | Coriobacteriales | Inversely Associated |
| Painful Periods | Gut | Coriobacteriia | Inversely Associated |
| Painful Periods | Gut | Dielma | Inversely Associated |
| Painful Periods | Gut | Dielma | Associated |
| Painful Periods | Gut | Dorea formicigenerans | Inversely Associated |
| Painful Periods | Gut | Dorea longicatena | Inversely Associated |
| Painful Periods | Gut | Eggerthella | Associated |
| Painful Periods | Gut | Eggerthella sp. HGA1 | Associated |
| Painful Periods | Gut | Eisenbergiella | Associated |
| Painful Periods | Gut | Eisenbergiella tayi | Associated |
| Painful Periods | Gut | Faecalibacterium | Inversely Associated |
| Painful Periods | Gut | Faecalibacterium prausnitzii | Inversely Associated |
| Painful Periods | mouth | Firmicutes | Associated |
| Painful Periods | Gut | Flavobacteriaceae | Associated |
| Painful Periods | Gut | Flavobacteriales | Associated |
| Painful Periods | Gut | Flavobacteriia | Associated |
| Painful Periods | Gut | Flavonifractor plautii | Associated |
| Painful Periods | Gut | Fusicatenibacter | Inversely Associated |
| Painful Periods | Gut | Fusicatenibacter saccharivorans | Inversely Associated |
| Painful Periods | Gut | Hespellia | Associated |
| Painful Periods | Gut | Lachnospira pectinoschiza | Associated |
| Painful Periods | Gut | Lactobacillaceae | Associated |
| Painful Periods | Genital | Lactobacillaceae | Associated |
| Painful Periods | Genital | Lactobacillales | Associated |
| Painful Periods | Gut | Lactobacillus | Associated |
| Painful Periods | Genital | Lactobacillus | Associated |
| Painful Periods | Gut | Marvinbryantia | Inversely Associated |
| Painful Periods | Gut | Megasphaera | Inversely Associated |
| Painful Periods | Gut | Moryella | Associated |
| Painful Periods | Gut | Odoribacter | Inversely Associated |
| Painful Periods | Gut | Odoribacter splanchnicus | Inversely Associated |
| Painful Periods | Gut | Oscillospiraceae | Associated |
| Painful Periods | Gut | Parabacteroides | Associated |
| Painful Periods | mouth | Porphyromonadaceae | Inversely Associated |
| Painful Periods | Gut | Rhodospirillales | Associated |
| Painful Periods | Gut | Roseburia inulinivorans | Inversely Associated |
| Painful Periods | Gut | Roseburia sp. 11SE39 | Inversely Associated |
| Painful Periods | Gut | Ruminococcaceae | Inversely Associated |
| Painful Periods | Gut | Sarcina | Inversely Associated |
| Painful Periods | Gut | Selenomonadales | Inversely Associated |
| Painful Periods | Gut | Subdoligranulum | Inversely Associated |
| Painful Periods | Gut | Subdoligranulum variabile | Inversely Associated |
| Painful Periods | Gut | Terrisporobacter | Inversely Associated |
| Painful Periods | Gut | Terrisporobacter | Associated |
| Polycystic Ovarian Syndrome | Gut | Bacteroidaceae | Associated |
| Polycystic Ovarian Syndrome | Gut | Bacteroides | Associated |
| Polycystic Ovarian Syndrome | Gut | Barnesiella intestinihominis | Associated |
| Polycystic Ovarian Syndrome | Gut | Clostridiaceae | Inversely Associated |

TABLE 2-continued

| Condition | Site | Organism | Association |
|---|---|---|---|
| Polycystic Ovarian Syndrome | Gut | Coriobacteriaceae | Inversely Associated |
| Polycystic Ovarian Syndrome | Gut | Coriobacteriales | Inversely Associated |
| Polycystic Ovarian Syndrome | Gut | Coriobacteriia | Inversely Associated |
| Polycystic Ovarian Syndrome | Gut | Eggerthella | Associated |
| Polycystic Ovarian Syndrome | Gut | Eggerthella sp. HGA1 | Associated |
| Polycystic Ovarian Syndrome | Gut | Eisenbergiella | Associated |
| Polycystic Ovarian Syndrome | Gut | Flavonifractor plautii | Associated |
| Polycystic Ovarian Syndrome | Gut | Lachnospira pectinoschiza | Associated |
| Polycystic Ovarian Syndrome | Gut | Lactobacillaceae | Associated |
| Polycystic Ovarian Syndrome | Gut | Lactobacillus | Associated |
| Polycystic Ovarian Syndrome | Gut | Moryella | Associated |
| Polycystic Ovarian Syndrome | Gut | Roseburia sp. 11SE39 | Associated |
| Polycystic Ovarian Syndrome | Gut | Sarcina | Inversely Associated |
| Polycystic Ovarian Syndrome | Gut | Terrisporobacter | Inversely Associated |
| Urinary Tract Infection | skin | Bacteroidales | Inversely Associated |
| Urinary Tract Infection | skin | Bacteroidia | Inversely Associated |
| Yeast Infection | Gut | Acidaminococcaceae | Inversely Associated |
| Yeast Infection | Gut | Actinobacteria | Inversely Associated |
| Yeast Infection | Genital | Actinobacteria | Inversely Associated |
| Yeast Infection | Gut | Actinobacteria | Inversely Associated |
| Yeast Infection | Genital | Actinomycetales | Inversely Associated |
| Yeast Infection | Gut | Alistipes sp. EBA6-25cl2 | Associated |
| Yeast Infection | nose | Anaerococcus | Inversely Associated |
| Yeast Infection | Gut | Anaerostipes sp. 5_1_63FAA | Inversely Associated |
| Yeast Infection | mouth | Bacilli | Associated |
| Yeast Infection | Genital | Bacilli | Associated |
| Yeast Infection | Gut | Bacteroidaceae | Associated |
| Yeast Infection | Gut | Bacteroidales | Associated |
| Yeast Infection | Gut | Bacteroides | Associated |
| Yeast Infection | Gut | Bacteroides sp. AR20 | Associated |
| Yeast Infection | Gut | Bacteroides sp. AR29 | Associated |
| Yeast Infection | Gut | Bacteroides sp. D22 | Associated |
| Yeast Infection | Gut | Bacteroides sp. EBA5-17 | Associated |
| Yeast Infection | Gut | Bacteroides sp. SLC1-38 | Associated |
| Yeast Infection | Gut | Bacteroides thetaiotaomicron | Associated |
| Yeast Infection | Gut | Bacteroidetes | Associated |
| Yeast Infection | Gut | Bacteroidia | Associated |
| Yeast Infection | Gut | Barnesiella | Associated |
| Yeast Infection | Gut | Barnesiella intestinihominis | Associated |
| Yeast Infection | Gut | Betaproteobacteria | Inversely Associated |
| Yeast Infection | Gut | Bifidobacteriaceae | Inversely Associated |
| Yeast Infection | Gut | Bifidobacteriales | Inversely Associated |
| Yeast Infection | Gut | Bifidobacterium | Inversely Associated |
| Yeast Infection | Gut | Blautia luti | Inversely Associated |
| Yeast Infection | Gut | Blautia sp. YHC-4 | Associated |
| Yeast Infection | Gut | Burkholderiales | Inversely Associated |
| Yeast Infection | Gut | Butyricimonas | Inversely Associated |
| Yeast Infection | Gut | Butyricimonas | Associated |
| Yeast Infection | Gut | Clostridia | Inversely Associated |
| Yeast Infection | Gut | Clostridiaceae | Inversely Associated |
| Yeast Infection | Gut | Clostridiales | Inversely Associated |
| Yeast Infection | Gut | Collinsella | Inversely Associated |
| Yeast Infection | Gut | Collinsella aerofaciens | Inversely Associated |
| Yeast Infection | Gut | Coriobacteriaceae | Inversely Associated |
| Yeast Infection | Gut | Coriobacteriales | Inversely Associated |
| Yeast Infection | Gut | Coriobacteriia | Inversely Associated |
| Yeast Infection | Gut | Corynebacteriaceae | Inversely Associated |
| Yeast Infection | Genital | Corynebacteriaceae | Inversely Associated |
| Yeast Infection | Gut | Corynebacteriales | Inversely Associated |
| Yeast Infection | Genital | Corynebacteriales | Inversely Associated |
| Yeast Infection | Gut | Corynebacterium | Inversely Associated |
| Yeast Infection | Genital | Corynebacterium | Inversely Associated |
| Yeast Infection | Gut | Dorea | Inversely Associated |
| Yeast Infection | Gut | Dorea formicigenerans | Inversely Associated |
| Yeast Infection | Gut | Dorea longicatena | Inversely Associated |
| Yeast Infection | Gut | Eisenbergiella | Associated |
| Yeast Infection | Gut | Eisenbergiella tayi | Associated |
| Yeast Infection | Gut | Enterorhabdus | Inversely Associated |
| Yeast Infection | Gut | Erysipelatoclostridium | Inversely Associated |
| Yeast Infection | Gut | Erysipelotrichaceae | Inversely Associated |
| Yeast Infection | Gut | Erysipelotrichales | Inversely Associated |
| Yeast Infection | Gut | Erysipelotrichia | Inversely Associated |
| Yeast Infection | Gut | Faecalibacterium prausnitzii | Inversely Associated |
| Yeast Infection | Genital | Firmicutes | Associated |
| Yeast Infection | Gut | Firmicutes | Inversely Associated |
| Yeast Infection | Gut | Flavonifractor plautii | Associated |
| Yeast Infection | Gut | Fusicatenibacter | Inversely Associated |
| Yeast Infection | Gut | Fusicatenibacter saccharivorans | Inversely Associated |
| Yeast Infection | Gut | Hespellia | Associated |
| Yeast Infection | Gut | Lachnospira pectinoschiza | Associated |
| Yeast Infection | nose | Lactobacillaceae | Associated |
| Yeast Infection | Gut | Lactobacillaceae | Associated |
| Yeast Infection | Genital | Lactobacillaceae | Associated |
| Yeast Infection | Genital | Lactobacillales | Associated |
| Yeast Infection | nose | Lactobacillus | Associated |
| Yeast Infection | Gut | Lactobacillus | Associated |
| Yeast Infection | Genital | Lactobacillus | Associated |
| Yeast Infection | Gut | Marvinbryantia | Inversely Associated |
| Yeast Infection | Gut | Moryella | Associated |
| Yeast Infection | Gut | Negativicutes | Inversely Associated |
| Yeast Infection | Gut | Odoribacter splanchnicus | Inversely Associated |
| Yeast Infection | Gut | Oscillospira | Associated |
| Yeast Infection | Gut | Oscillospiraceae | Associated |
| Yeast Infection | Gut | Parabacteroides | Associated |

TABLE 2-continued

| Condition | Site | Organism | Association |
|---|---|---|---|
| Yeast Infection | Gut | *Phascolarctobacterium* | Inversely Associated |
| Yeast Infection | Gut | *Prevotellaceae* | Inversely Associated |
| Yeast Infection | Gut | *Proteobacteria* | Inversely Associated |
| Yeast Infection | Gut | *Roseburia inulinivorans* | Inversely Associated |
| Yeast Infection | Gut | *Roseburia* sp. 11SE39 | Inversely Associated |
| Yeast Infection | Gut | *Sarcina* | Inversely Associated |
| Yeast Infection | Gut | *Selenomonadales* | Inversely Associated |
| Yeast Infection | Gut | *Subdoligranulum* | Inversely Associated |
| Yeast Infection | Gut | *Subdoligranulum variabile* | Associated |
| Yeast Infection | Gut | *Sutterella wadsworthensis* | Inversely Associated |
| Yeast Infection | Gut | *Sutterella wadsworthensis* | Associated |
| Yeast Infection | Gut | *Sutterellaceae* | Inversely Associated |
| Yeast Infection | Gut | *Terrisporobacter* | Associated |
| Yeast Infection | Gut | *Veillonellaceae* | Inversely Associated |
| Yeast Infection | Gut | *Verrucomicrobiae* | Associated |
| Yeast Infection | Gut | *Verrucomicrobiales* | Associated |

TABLE 3

| Condition | Organism | Association |
|---|---|---|
| Human Papillomavirus Infection | HR-HPV | Associated |
| Human Papillomavirus Infection | *Gardnerella* | Associated |
| Human Papillomavirus Infection | *Gardnerella vaginalis* | Associated |
| Human Papillomavirus Infection | *Sneathia* | Associated |
| Human Papillomavirus Infection | *Fusobacterium nucleatum* | Inversely associated |
| Human Papillomavirus Infection | *Lactobacillus iners* | Inversely associated |
| Cervical Cancer | HR-HPV | Associated |
| Squamous Intraepithelial Lesions (High- and Low-grade) | HR-HPV | Associated |
| Sexually Transmitted Infection | *Chlamydia trachomatis* | Associated |
| Sexually Transmitted Infection | *Mycoplasma genitalium* | Associated |
| Sexually Transmitted Infection | *Neisseria gonorrhoeae* | Associated |
| Sexually Transmitted Infection | *Treponema pallidum* | Associated |
| Cervicitis | HR-HPV | Associated |
| Cervicitis | *Chlamydia trachomatis* | Associated |
| Cervicitis | *Mycoplasma genitalium* | Associated |
| Cervicitis | *Lactobacillus* | Inversely associated |
| Pelvic Inflammatory Disease | *Chlamydia trachomatis* | Associated |
| Pelvic Inflammatory Disease | *Neisseria gonorrhoeae* | Associated |
| Bacterial Vaginosis | *Aerococcus* | Associated |
| Bacterial Vaginosis | *Aerococcus christensenii* | Associated |
| Bacterial Vaginosis | *Atopobium* | Associated |
| Bacterial Vaginosis | *Atopobium vaginae* | Associated |
| Bacterial Vaginosis | *Dialister micraerophilus* | Associated |
| Bacterial Vaginosis | *Fusobacterium* | Associated |
| Bacterial Vaginosis | *Gardnerella* | Associated |
| Bacterial Vaginosis | *Gardnerella vaginalis* | Associated |
| Bacterial Vaginosis | *Gemella* | Associated |

TABLE 3-continued

| Condition | Organism | Association |
|---|---|---|
| Bacterial Vaginosis | *Megasphaera* | Associated |
| Bacterial Vaginosis | *Mobiluncus* | Associated |
| Bacterial Vaginosis | *Mobiluncus curtisii* | Associated |
| Bacterial Vaginosis | *Mobiluncus mulieris* | Associated |
| Bacterial Vaginosis | *Papillibacter* | Associated |
| Bacterial Vaginosis | *Parvimonas* | Associated |
| Bacterial Vaginosis | *Peptoniphilus* | Associated |
| Bacterial Vaginosis | *Peptostreptococcus* | Associated |
| Bacterial Vaginosis | *Porphyromonas* | Associated |
| Bacterial Vaginosis | *Prevotella* | Associated |
| Bacterial Vaginosis | *Prevotella amnii* | Associated |
| Bacterial Vaginosis | *Prevotella timonensis* | Associated |
| Bacterial Vaginosis | *Sneathia* | Associated |
| Bacterial Vaginosis | *Lactobacillus* | Inversely associated |
| Bacterial Vaginosis | *Lactobacillus iners* | Inversely associated |
| Bacterial Vaginosis | *Lactobacillus jensenii* | Inversely associated |
| Aerobic Vaginitis | *Gardnerella vaginalis* | Associated |
| Aerobic Vaginitis | *Staphylococcus aureus* | Associated |
| Aerobic Vaginitis | *Streptococcus agalactiae* | Associated |
| Idiopathic Infertility | *Chlamydia trachomatis* | Associated |
| Idiopathic Infertility | *Mycoplasma genitalium* | Associated |
| Idiopathic Infertility | *Neisseria gonorrhoeae* | Associated |

TABLE 4

| Genus | Sensitivity | Specificity | Precision | NPV |
|---|---|---|---|---|
| *Aerococcus* | 99.41 | 100.00 | 100.00 | 99.99 |
| *Anaerotruncus* | 98.16 | 99.99 | 99.21 | 99.99 |
| *Atopobium* | 97.11 | 100.00 | 100.00 | 99.99 |
| *Eggerthella* | 100.00 | 99.99 | 99.01 | 100.00 |
| *Enterococcus* | 98.39 | 99.99 | 99.33 | 99.99 |
| *Fusobacterium* | 97.97 | 99.99 | 99.64 | 99.99 |
| *Gardnerella* | 97.91 | 100.00 | 100.00 | 99.99 |
| *Gemella* | 99.10 | 99.99 | 99.88 | 99.99 |
| *Lactobacillus* | 90.27 | 100.00 | 100.00 | 99.87 |
| *Leptotrichia* | 98.69 | 100.00 | 100.00 | 99.99 |
| *Megasphaera* | 97.96 | 99.99 | 99.84 | 99.99 |
| *Mobiluncus* | 100.00 | 100.00 | 100.00 | 100.00 |
| *Mycoplasma* | 98.29 | 100.00 | 100.00 | 99.99 |
| *Papillibacter* | 100.00 | 100.00 | 100.00 | 100.00 |
| *Parvimonas* | 98.35 | 99.99 | 99.81 | 99.99 |
| *Peptoniphilus* | 92.8 | 100.00 | 100.00 | 99.98 |
| *Peptostreptococcus* | 96.86 | 99.99 | 99.54 | 99.99 |
| *Porphyromonas* | 98.88 | 100.00 | 100.00 | 99.99 |
| *Prevotella*[1] | 92.38 | 100.00 | 100.00 | 99.91 |
| *Sneathia* | 98.68 | 100.00 | 100.00 | 99.99 |
| *Staphylococcus* | 99.21 | 99.99 | 99.99 | 99.93 |
| *Streptococcus* | 98.89 | 99.99 | 99.95 | 99.96 |
| *Ureaplasma* | 99.41 | 100.00 | 100.00 | 99.99 |
| *Veillonella* | 94.27 | 100.00 | 100.00 | 99.97 |

TABLE 5

| Species | Sensitivity | Specificity | PPV | NPV |
|---|---|---|---|---|
| *Aerococcus christensenii* | 100.00 | 100.00 | 100.00 | 100.00 |
| *Atopobium vaginae* | 100.00 | 100.00 | 100.00 | 100.00 |
| *Bulleidia extructa* | 100.00 | 100.00 | 100.00 | 100.00 |
| *Campylobacter ureolyticus* | 100.00 | 100.00 | 100.00 | 100.00 |
| *Chlamydia trachomatis* | 98.23 | 100.00 | 100.00 | 100.00 |
| *Dialister micraerophilus* | 100.00 | 100.00 | 93.75 | 100.00 |

TABLE 5-continued

| Species | Sensitivity | Specificity | PPV | NPV |
|---|---|---|---|---|
| Eggerthia catenaformis | 90.00 | 100.00 | 100.00 | 100.00 |
| Fusobacterium nucleatum | 97.06 | 100.00 | 92.03 | 100.00 |
| Gardnerella vaginalis | 100.00 | 100.00 | 100.00 | 100.00 |
| Lactobacillus brevis | 95.69 | 100.00 | 99.01 | 100.00 |
| Lactobacillus delbrueckii | 98.95 | 100.00 | 98.95 | 100.00 |
| Lactobacillus fermentum | 97.16 | 100.00 | 98.56 | 100.00 |
| Lactobacillus iners | 95.00 | 100.00 | 100.00 | 100.00 |
| Lactobacillus jensenii | 100.00 | 100.00 | 94.74 | 100.00 |
| Lactobacillus kefiranofaciens | 100.00 | 100.00 | 98.04 | 100.00 |
| Lactobacillus rhamnosus | 93.27 | 100.00 | 96.3 | 100.00 |
| Lactobacillus salivarius | 97.53 | 100.00 | 96.34 | 100.00 |
| Megasphaera micronuciformis | 100.00 | 100.00 | 100.00 | 100.00 |
| Microbacterium halophilum | 100.00 | 100.00 | 100.00 | 100.00 |
| Mobiluncus curtisii | 100.00 | 100.00 | 100.00 | 100.00 |
| Mobiluncus mulieris | 100.00 | 100.00 | 100.00 | 100.00 |
| Mycoplasma genitalium | 100.00 | 100.00 | 100.00 | 100.00 |
| Mycoplasma hominis | 100.00 | 100.00 | 100.00 | 100.00 |
| Neisseria gonorrhoeae | 100.00 | 100.00 | 97.92 | 100.00 |
| Peptostreptococcus anaerobius | 100.00 | 100.00 | 100.00 | 100.00 |
| Porphyromonas gingivalis | 94.34 | 100.00 | 100.00 | 100.00 |
| Prevotella amnii | 100.00 | 100.00 | 100.00 | 100.00 |
| Prevotella bivia | 100.00 | 100.00 | 97.87 | 100.00 |
| Prevotella disiens | 100.00 | 100.00 | 95.00 | 100.00 |
| Prevotella timonensis | 100.00 | 100.00 | 100.00 | 100.00 |
| Staphylococcus aureus | 99.80 | 99.94 | 93.60 | 100.00 |
| Streptococcus agalactiae | 99.74 | 100.00 | 98.95 | 100.00 |
| Thermosipho atlanticus | 100.00 | 100.00 | 100.00 | 100.00 |
| Thermovirga lienii | 100.00 | 100.00 | 100.00 | 100.00 |
| Trueperella bernardiae | 100.00 | 100.00 | 100.00 | 100.00 |
| Veillonella montpellierensis | 100.00 | 100.00 | 100.00 | 100.00 |

TABLE 6

| Type | # Clusters | TP | FN | FP | TN | Sensitivity | Specificity | Precision | NPV | Status |
|---|---|---|---|---|---|---|---|---|---|---|
| HPV type 16 | 3 | 19795 | 0 | 0 | 15929 | 100 | 100 | 100 | 100 | PASS |
| HPV type 18 | 1 | 800 | 0 | 0 | 34924 | 100 | 100 | 100 | 100 | PASS |
| HPV type 26 | 1 | 18 | 0 | 0 | 35706 | 100 | 100 | 100 | 100 | PASS |
| HPV type 31 | 1 | 136 | 0 | 0 | 35588 | 100 | 100 | 100 | 100 | PASS |
| HPV type 33 | 3 | 641 | 0 | 0 | 35083 | 100 | 100 | 100 | 100 | PASS |
| HPV type 35 | 1 | 108 | 0 | 0 | 35616 | 100 | 100 | 100 | 100 | PASS |
| HPV type 39 | 1 | 140 | 0 | 0 | 35584 | 100 | 100 | 100 | 100 | PASS |
| HPV type 45 | 1 | 244 | 0 | 0 | 35480 | 100 | 100 | 100 | 100 | PASS |
| HPV type 51 | 1 | 65 | 0 | 0 | 35659 | 100 | 100 | 100 | 100 | PASS |
| HPV type 52 | 2 | 744 | 0 | 0 | 34980 | 100 | 100 | 100 | 100 | PASS |
| HPV type 53 | 1 | 84 | 0 | 0 | 35640 | 100 | 100 | 100 | 100 | PASS |
| HPV type 56 | 1 | 29 | 0 | 0 | 35695 | 100 | 100 | 100 | 100 | PASS |
| HPV type 58 | 1 | 7412 | 0 | 0 | 28312 | 100 | 100 | 100 | 100 | PASS |
| HPV type 59 | 1 | 78 | 0 | 0 | 35646 | 100 | 100 | 100 | 100 | PASS |
| HPV type 66 | 1 | 165 | 0 | 0 | 35559 | 100 | 100 | 100 | 100 | PASS |
| HPV type 68 | 2 | 242 | 0 | 0 | 35482 | 100 | 100 | 100 | 100 | PASS |
| HPV type 70 | 1 | 165 | 0 | 0 | 35559 | 100 | 100 | 100 | 100 | PASS |
| HPV type 73 | 1 | 12 | 0 | 0 | 35712 | 100 | 100 | 100 | 100 | PASS |
| HPV type 82 | 2 | 44 | 0 | 0 | 35680 | 100 | 100 | 100 | 100 | PASS |
| HPV type 6 | 2 | 2695 | 0 | 0 | 33029 | 100 | 100 | 100 | 100 | PASS |
| HPV type 11 | 2 | 908 | 0 | 0 | 34816 | 100 | 100 | 100 | 100 | PASS |
| HPV type 40 | 1 | 102 | 0 | 0 | 35622 | 100 | 100 | 100 | 100 | PASS |
| HPV type 42 | 1 | 210 | 0 | 0 | 35514 | 100 | 100 | 100 | 100 | PASS |
| HPV type 54 | 2 | 11 | 0 | 0 | 35713 | 100 | 100 | 100 | 100 | PASS |

TABLE 7

| Microorganism | Sequence |
| --- | --- |
| *Aerococcus* | TATAAGAGAAGAACAAATTGTAGAGTAACTGCTACAGTCTTGACGGTATCTTATCAGAAAGCCA<br>CGGCTAACTACGTGCCAGCAGCCGCGGTAATACGTAGGTGGCAAGCGTTGTCCGGATTTATTGG<br>GCGTAAAGGGAGCGCAGGTGGTTTCTTAAGTCTGATGTGAAAGCCCACGGCTTAACCGTGGAGG<br>GTCATTGGAAACTGGGAAACTTGAGTACAGAAGAGGAATGTGGAACTCCATGTGTAGCGGTGGA<br>ATGCGTAGATATATGGAAGAACACCAGTGGCGAAGGCGACATTCTGGTCTGTTACTGACACTGA<br>GGCTCGAAAGCGTGGGGAGCAAACAGGATTAGATACCCTGGTAGTCCACGCCGTAAACGATGAG<br>TGCTAGGTGTTGGAGGGTTTCCGCCCTTCAGTGCCGCAGTTAACGCATTAAGCACTCC (SEQ ID NO: 1) |
| *Aerococcus christensenii* | TGTAAGAGAAGAACAAATTGTAGAGTAACTGCTACAGTCTTGACGGTATCTTACCAGAAAGCCA<br>CGGCTAACTACGTGCCAGCAGCCGCGGTAATACGTAGGTGGCAAGCGTTGTCCGGATTTATTGG<br>GCGTAAAGGGGGCGCAGGCTGCTTCTTAAGTCTGATGTGAAAGCCCACGGCTTAACCGTGGAAG<br>TGCATTGGAAACTGGGAAGCTTGAGTACAGAAGAGGAAAGTGGAACTCCATGTGTAGCGGTGGA<br>ATGCGTAGATATATGGAAGAACACCAGTGGCGAAAGCGACTTTCTGGTCTGTCACTGACGCTGA<br>GGCCCGAAAGCGTGGGTAGCAAACAGGATTAGATACCCTGGTAGTCCACGCCGTAAACGATGAG<br>CGCTAGGTGTTGGAGGGTTTCCACCCTTCAGTGCCGCAGCTAACGCATTAAGCGCTCC (SEQ ID NO: 2) |
| *Atopobium* | TTCGGGTTGTAAACCGCTTTCAGCAGGGACGAGGCGAAAGTGACGGTACCTGCAGAAGAAGCCC<br>CGGCTAACTACGTGCCAGCAGCCGCGGTAATACGTAGGGGGCAAGCGTTATCCGGATTCATTGG<br>GCGTAAAGCGCTCGTAGGCGGTCTGTTAGGTCGGGAGTTAAATCCGGGGGCTCAACCCCCGCTC<br>GCTCCCGATACCGGCAGACTTGAGTTTGGTAGGGGAAGGTGGAATTCCTAGTGTAGCGGTGGAA<br>TGCGCAGATATTAGGAAGAACACCAGTGGCGAAGGCGGCCTTCTGGGCCATAACTGACGCTGA<br>GAGCGAAAGCTAGGGGAGCAAACAGGATTAGATACCCTGGTAGTCCTAGCCGTAAACGATGGAC<br>ACTAGGTGTGGGGGAATATTTCTTCCGTGCCGCAGCTAACGCATTAAGTGTCCCGCC (SEQ ID NO: 3) |
| *Atopobium vaginae* | CGGGTTGTAAACCGCTTTCAGCAGGGACCAGGCCGCAAGGTGACGGTACCTGCACAAGAAGCCC<br>CGGCTAACTACGTGCCAGCAGCCGCGGTAATACGTAGGGGGCAAGCGTTATCCGGATTCATTGG<br>GCGTAAAGCGCGCGTAGGCGGTCTGTTAGGTCAGGAGTTAAATCTGGGGGCTCAACCCCTATCC<br>GCTCCTGATACCGGCAGGCTTGAGTCTGGTAGGGGAAGATGGAATTCCAAGTGTAGCGGTGAAA<br>TGCGCAGATATTTGGAAGAACACCGGTGGCGAAGGCGGTCTTCTGGGCCATGACTGACGCTGAG<br>GCGCGAAAGCTAGGGGAGCGAACAGGATTAGATACCCTGGTAGTCCTACCTGTAAACGATGGAC<br>ACTAGGTGTGGGGAGATTATACTTTCCGTGCCGCAGCTAACGCATTAAGTGTCCCGC (SEQ ID NO: 4) |
| *Chlamydia trachomatis* | CGCTTGGGAATAAGAGAAGGCGGTTAATACCCGCTGGATTTGAGCGTACCAGGTAAAGAAGCAC<br>CGGCTAACTCCGTGCCAGCAGCTGCGGTAATACGGAGGGTGCTAGCGTTAATCGGATTTATTGG<br>GCGTAAAGGGCGTGTAGGCGGAAAGGTAAGTTAGTTGTCAAAGATCGGGGCTCAACCCCGAGTC<br>GGCATCTAATACTATTTTTCTAGAGGGTAGATGGAGAAAAAGGGAATTTCACGTGTAGCGGTGA<br>ATGCGTAGATATGTGGAAGAACACCAGTGGCGAAGGCGCTTTTCTAATTTATACCTGACGCTAA<br>GGCGCGAAAGCAAGGGGAGCAAACAGGATTAGATACCCTGGTAGTCCTTGCCGTAAACGATGCA<br>TACTTGATGTGGATGGTCTCAACCCCATCCGTGTCGGAGCTAACGCGTTAAGTATGCC (SEQ ID NO: 5) |
| *Dialister micraerophilus* | GATTCGGGACGAAAGGCCATATGTGAATAATATATGGAAATGACGGTACCGAAAAAGCAAGCCA<br>CGGCTAACTACGTGCCAGCAGCCGCGGTAATACGTAGGTGGCAAGCGTTGTCCGGAATTATTGG<br>GCGTAAAGCGCGCGCAGGCGGTCACTTAAGTCCATCTTAGAAGTGCGGGGCTTAACCCCGTGAT<br>GGGATGGAAACTGGGAGACTGGAGTATCGGAGAGGAAAGTGGAATTCCTAGTGTAGCGGTGAAA<br>TGCGTAGATATTAGGAAGAACACCGGTGGCGAAGGCGACTTTCTGGACGAAAACTGACGCTGAG<br>GCGCGAAAGCGTGGGGAGCAAACAGGATTAGATACCCTGGTAGTCCACGCCGTAAACGATGGAT<br>ACTAGGTGTAGGAGGTATCGACCCCTTCTGTGCCGGAGTTAACGCAATAAGTATCCC (SEQ ID NO: 6) |
| *Fusobacterium* | TTTTCGGAATGTAAAGTGCTTTCAGTTGGGAAGAAAGAAATGACGGTACCAACAGAAGAAGTGA<br>CGGCTAAATACGTGCCAGCAGCCGCGGTAATACGTATGTCACGAGCGTTATCCGGATTTATTGG<br>GCGTAAAGCGCGTCTAGGTGGTTATGTAAGTCTGATGTGAAAATGCAGGGCTCAACTCTGTATT<br>GCGTTGGAAACTGTATAACTAGAGTACTGGAGAGGTAAGCGGAACTACAAGTGTAGAGGTGAAA<br>TTCGTAGATATTTGTAGGAATGCCGATGGGGAAGCCAGCTTACTGGACAGATACTGACGCTAAA<br>GCGCGAAAGCGTGGGTAGCAAACAGGATTAGATACCCTGGTAGTCCACGCTGTAAACGATGATT<br>ACTAGGTGTTGGGGGTCGAACCTCAGCGCCCAAGCAAACGCGATAAGTAATCCGCCT (SEQ ID NO: 7) |
| *Fusobacterium nucleatum* | TTTTCGGAATGTAAAGTGCTTTCAGTTGGGAAGAAAAAAATGACGGTACCAACAGAAGAAGTGA<br>CGGCTAAATACGTGCCAGCAGCCGCGGTAATACGTATGTCACGAGCGTTATCCGGATTTATTGG<br>GCGTAAAGCGCGTCTAGGTGGTTATATAAGTCTGATGTGAAAATGCAGGGCTCAACTCTGTATT<br>GCGTTGGAAACTGTATAACTAGAGTACTGGAGAGGTAAGCGGAACTACAAGTGTAGAGGTGAAA<br>TTCGTAGATATTTGTAGGAATGCCGATGGGGAAGCCAGCTTACTGGACAGATACTGACGCTGAA<br>GCGCGAAAGCGTGGGTAGCAAACAGGATTAGATACCCTGGTAGTCCACGCCGTAAACGATGATT<br>ACTAGGTGTTGGGGGTCGAACCTCAGCGCCCAAGCAAACGCGATAAGTAATCCGCCT (SEQ ID NO: 8) |
| *Gardnerella* | GGGTTGTAAACCGCTTTTGATTGGGAGCAAGCCTTTTGGGTGAGTGTACCTTTCGAATAAGCGC<br>CGGCTAACTACGTGCCAGCAGCCGCGGTAATACGTAGGGCGCAAGCGTTATCCGGAATTATTGG<br>GCGTAAAGAGCTTGTAGGCGGTTCGTCGCGTCTGGTGTGAAAGCCCATCGCTTAACGGTGGGTT<br>TGCGCCGGGTACGGGCGGGCTAGAGTGCAGTAGGGGAGACTGAAATTCTCGGTGTAACGGTGGA |

TABLE 7-continued

| Microorganism | Sequence |
|---|---|
| | ATGTGTAGATATCGGGAAGAACACCAATGGCGAAGGCAGGTCTCTGGGCTGTTACTGACGCTGA<br>GAAGCGAAAGCGTGGGGAGCGAACAGGATTAGATACCCTGGTAGTCCACGCCGTAAACGGTGGA<br>CGCTGGATGTGGGGCCCATTCCACGGGTTCTGTGTCGGAGCTAACGCGTTAAGCGTCC (SEQ ID NO: 9) |
| Gardnerella vaginalis | CGGGTTGTAAACCGCTTTTGATTGGGAGCAAGCTTTCGGGTGAGTGTACCTTTCGAATAAGCGC<br>CGGCTAACTACGTGCCAGCAGCCGCGGTAATACGTAGGGCGCAAGCGTTATCCGGAATTATTGG<br>GCGTAAAGAGCTTGTAGGCGGTTCGTCGCGTCTGGTGTGAAAGCCCATCGCTTAACGGTGGGTT<br>TGCGCCGGGTACGGGCGGGCTAGAGTGCAGTAGGGGAGACTGGAATTCCCGGTGTAACGGTGGA<br>ATGTGTAGATATCGGGAAGAACACCAATGGCGAAGGCAGGTCTCTGGGCTGTTACTGACGCTGA<br>GAAGCGAAAGCGTGGGGAGCGAACAGGATTAGATACCCTGGTAGTCCACGCCGTAAACGGTGGA<br>CGCTGGATGTGGGGCCCATTCCACGGGTTCCGTGTCGGAGCTAACGCGTTAAGCGTCC (SEQ ID NO: 10) |
| Gemella | TGTTAGGGAAGAATGATTGTGTAGTAACTATACACAGTAGAGACGGTACCTAACCAGAAAGCCA<br>CGGCTAACTACGTGCCAGCAGCCGCGGTAATACGTAGGTGGCAAGCGTTGTCCGGAATTATTGG<br>GCGTAAAGCGCGCGCAGGTGGTTTAATAAGTCTGATGTGAAAGCCCACGGCTCAACCGTGGAGG<br>GTCATTGGAAACTGTTAAACTTGAGTGCAGGAGAGAAAAGTGGAATTCCTAGTGTAGCGGTGAA<br>ATGCGTAGAGATTAGGAGGAACACCAGTGGCGAAGGCGGCTTTTTGGCCTGTAACTGACACTGA<br>GGCGCGAAAGCGTGGGGAGCAAACAGGATTAGATACCCTGGTAGTCCACGCCGTAAACGATGAG<br>TGCTAAGTGTTGGTCTCATAAGAGATCAGTGCTGCAGCTAACGCATTAAGCACTCCGC (SEQ ID NO: 11) |
| Lactobacillus | TGGTAGTGAAGAAAGATAGAGGTAGTAACTGGCCTTTATTTGACGGTAATTACTTAGAAAGTCA<br>CGGCTAACTACGTGCCAGCAGCCGCGGTAATACGTAGGTGGCAAGCGTTGTCCGGATTTATTGG<br>GCGTAAAGCGAGTGCAGGCGGTTCAATAAGTCTGATGTGAAAGCCTTCGGCTCAACCGGAGAAT<br>TGCATCAGAAACTGTTGAACTTGAGTGCAGAAGAGGAGAGTGGAACTCCATGTGTAGCGGTGAA<br>ATGCGTAGATATATGGAAGAACACCAGTGGCGAAGGCGGCTCTCTGGTCTGCAACTGACGCTGA<br>GGCTCGAAAGCATGGGTAGCGAACAGGATTAGATACCCTGGTAGTCCATGCCGTAAACGATGAG<br>TGCTAAGTGTTGGGAGGTTTCCGCCTCTCAGTGCTGCAGCTAACGCATTAAGCACTCC (SEQ ID NO: 12) |
| Lactobacillus iners | TGTTGGTGAAGAAGGACAGGGGTAGTAACTGACCTTTGTTTGACGGTAATCAATTAGAAAGTCA<br>CGGCTAACTACGTGCCAGCAGCCGCGGTAATACGTAGGTGGCAAGCGTTGTCCGGATTTATTGG<br>GCGTAAAGCGAGTGCAGGCGGCTCGATAAGTCTGATGTGAAAGCCTTCGGCTCAACCGGAGAAT<br>TGCATCAGAAACTGTCGAGCTTGAGTACAGAAGAGGAGAGTGGAACTCCATGTGTAGCGGTGAA<br>ATGCGTAGATATATGGAAGAACACCGGTGGCGAAGGCGGCTCTCTGGTCTGTTACTGACGCTGA<br>GGCTCGAAAGCATGGGTAGCGAACAGGATTAGATACCCTGGTAGTCCATGCCGTAAACGATGAG<br>TGCTAAGTGTTGGGAGGTTTCCGCCTCTCAGTGCTGCAGCTAACGCATTAAGCACTCC (SEQ ID NO: 13) |
| Lactobacillus jensenii | TGTTGGTGAAGAAGGATAGAGGTAGTAACTGGCCTTTATTTGACGGTAATCAACCAGAAAGTCA<br>CGGCTAACTACGTGCCAGCAGCCGCGGTAATACGTAGGTGGCAAGCGTTGTCCGGATTTATTGG<br>GCGTAAAGCGAGCGCAGGCGGATTGATAAGTCTGATGTGAAAGCCTTCGGCTCAACCGAAGAAC<br>TGCATCAGAAACTGTCAATCTTGAGTGCAGAAGAGGAGAGTGGAACTCCATGTGTAGCGGTGAA<br>ATGCGTAGATATATGGAAGAACACCAGTGGCGAAGGCGGCTCTCTGGTCTGTAACTGACGCTGA<br>GGCTCGAAAGCATGGGTAGCGAACAGGATTAGATACCCTGGTAGTCCATGCCGTAAACGATGAG<br>TGCTAAGTGTTGGGAGGTTTCCGCCTCTCAGTGCTGCAGCTAACGCATTAAGCACTCC (SEQ ID NO: 14) |
| Megasphaera | ATATGGGACGAACAGGACATCGGTTAATACCCGGTGTCTTTGACGGTACCGTAAGAGAAAGCCA<br>CGGCTAACTACGTGCCAGCAGCCGCGGTAATACGTAGGTGGCAAGCGTTGTCCGGAATTATTGG<br>GCGTAAAGGGCGCGCAGGCGGCATCGCAAGTCGGTCTTAAAAGTGCGGGGCTTAACCCCGTGAG<br>GGGACCGAAACTGTGAAGCTCGAGTGTCGGAGAGGAAAGCGGAATTCCTAGTGTAGCGGTGAAA<br>TGCGTAGATATTAGGAGGAACACCAGTGGCGAAAGCGGCTTTCTGGACGACAACTGACGCTGAG<br>GCGCGAAAGCCAGGGGAGCAAACGGGATTAGATACCCCGGTAGTCCTGGCCGTAAACGATGGAT<br>ACTAGGTGTAGGAGGTATCGACTCCTTCTGTGCCGGAGTTAACGCAATAAGTATCCC (SEQ ID NO: 15) |
| Mobiluncus | ACTCCTTTTTCTCGCGAAAAAGGCACAGCTTTGGCTGTGTTGATGGTAGTGGGGGAAGAAGCGC<br>CGGCTAACTACGTGCCAGCAGCCGCGGTAATACGTAGGGCGCGAGCGTTGTCCGGATTTATTGG<br>GCGTAAAGAGCTCGTAGGTGGTTCGTCGCGTCTGTCGTGAAAGCCAGCAGCTTAACTGTTGGTC<br>TGCGGTGGGTACGGGCGGGCTTGAGTGCGGTATGGGTGACTGGAATTCCTGGTGTAGCGGTGGA<br>ATGCGCAGATATCAGGAGGAACACCGATGGCGAAGGCAGGTCACTGGGCCGTTACTGACACTGA<br>GGAGCGAAAGCGTGGGGAGCGAACAGGATTAGATACCCTGGTAGTCCACGCTGTAAACGTTGGG<br>AACTAGGTGTGGGGATGCTATCCTGTGTTTCTGCGCCGTAGCTAACGCATTAAGTTCC (SEQ ID NO: 16) |
| Mobiluncus curtisii | ACTCCTTTTTCTCGCGAAAAAGGCACAGTTTTGGCTGTGTTGATGGTAGTGGGGGAAGAAGCGC<br>CGGCTAACTACGTGCCAGCAGCCGCGGTAATACGTAGGGCGCGAGCGTTGTCCGGATTTATTGG<br>GCGTAAAGAGCTCGTAGGTGGTTCGTCGCGTCTGTCGTGAAAGCCAGCAGCTTAACTGTTGGTC<br>TGCGGTGGGTACGGGCGGGCTTGAGTGCGGTAGGGGTGACTGGAATTCCTGGTGTAGCGGTGGA<br>ATGCGCAGATATCAGGAGGAACACCGATGGCGAAGGCAGGTCACTGGGCCGTTACTGACACTGA<br>GGAGCGAAAGCGTGGGGAGCGAACAGGATTAGATACCCTGGTAGTCCACGCTGTAAACGTTGGG<br>AACTAGGTGTGGGGATGCTATCCTGTGTCTCTGCGCCGTAGCTAACGCATTAAGTTCC (SEQ ID NO: 17) |

TABLE 7-continued

| Microorganism | Sequence |
|---|---|
| Mobiluncus mulieris | ACTCCTTTTTCTCGTGAAAAAGGCATGCTTTTGGGTGTGTTGATGGTAGCGGGGGAAGAAGCGC<br>CGGCTAACTACGTGCCAGCAGCCGCGGTAATACGTAGGGCGCGAGCGTTGTCCGGATTTATTGG<br>GCGTAAAGAGCTCGTAGGTGGTTCGTCGCGTCTGTCGTGAAAGCCAGCAGCTTAACTGTTGGTC<br>TGCGGTGGGTACGGGCGGGCTTGAGTGCGGTAGGGGTGACTGGAATTCCTGGTGTAGCGGTGGA<br>ATGCGCAGATATCAGGAGGAACACCGATGGCGAAGGCAGGTCACTGGGCCGTTACTGACGCTGA<br>GGAGCGAAAGCGTGGGGAGCGAACAGGATTAGATACCCTGGTAGTCCACGCTGTAAACGTTGGG<br>AACTAGGTGTGGGGATGCTATCCTGTGTTTCTGCGCCGTAGCTAACGCATTAAGTTCC (SEQ<br>ID NO: 18) |
| Mycoplasma genitalium | ATTTGGGAAGAATGACTCTAGCAGGCAATGGCTGGAGTTTGACTGTACCACTTTGAATAAGTGA<br>CGACTAACTATGTGCCAGCAGTCGCGGTAATACATAGGTCGCAAGCGTTATCCGGATTTATTGG<br>GCGTAAAGCAAGCGCAGGCGGATTGAAAAGTCTGGTGTTAAAGGCAGCTGCTTAACAGTTGTAT<br>GCATTGGAAACTATCAGTCTAGAGTGTGGTAGGGAGTTTTGGAATTTCATGTGGAGCGGTGAAA<br>TGCGTAGATATATGAAGGAACACCAGTGGCGAAGGCGAAAACTTAGGCCATTACTGACGCTTAG<br>GCTTGAAAGTGTGGGGAGCAAATAGGATTAGATACCCTAGTAGTCCACACCGTAAACGATAGAT<br>ACTAGCTGTCGGAGCGATCCCTTCGGTAGTGAAGTTAACACATTAAGTATCTCGCCT (SEQ<br>ID NO: 19) |
| Neisseria gonorrhoeae | TGTCAGGGAAGAAAAGGCTGTTGCCAATATCGGCGGCCGATGACGGTACCTGAAGAATAAGCAC<br>CGGCTAACTACGTGCCAGCAGCCGCGGTAATACGTAGGGTGCGAGCGTTAATCGGAATTACTGG<br>GCGTAAAGCGGGCGCAGACGGTTACTTAAGCAGGATGTGAAATCCCCGGGCTCAACCCGGGAAC<br>TGCGTTCTGAACTGGGTGACTCGAGTGTGTCAGAGGGAGGTGGAATTCCACGTGTAGCAGTGAA<br>ATGCGTAGAGATGTGGAGGAATACCGATGGCGAAGGCAGCCTCCTGGGATAACACTGACGTTCA<br>TGTCCGAAAGCGTGGGTAGCAAACAGGATTAGATACCCTGGTAGTCCACGCCCTAAACGATGTC<br>AATTAGCTGTTGGGCAACTTGATTGCTTGGTAGCGTAGCTAACGCGTGAAATTGACCG (SEQ<br>ID NO: 20) |
| Papillibacter | AGGCTTTCGGGTTGTAAACTCCTTTGACGAGGGACGATGATGACGGTACCTCGAAAACAAGCCA<br>CGGCTAACTACGTGCCAGCAGCCGCGGTAATACGTAGGTGGCAAGCGTTGTCCGGATTTACTGG<br>GTGTAAAGGGCGCGTAGGCGGGCAGGCAAGTCAGATGTGAAATCTCCGGGCTCAACCCGGAAAT<br>TGCATTTGAAACTGCAGGTCTTGAGTATCGGAGAGGCAAGCGGAATTCCTAGTGTAGCGGTGAA<br>ATGCGTAGATATTAGGAGGAACACCAGTGGCGAAGGCGGCTTGCTGGACGACAACTGACGCTGA<br>GGCGCGAAAGCGTGGGGAGCAAACAGGATTAGATACCCTGGTAGTCCATGCCCTAAACGATGAA<br>TATATGTGTGGGGGGACTGACCCCTTCCGTGCCGGAGTAACACAATAAGTATTCCACC (SEQ<br>ID NO: 21) |
| Parvimonas | AGGTTTTCGAATCGTAAAGCTCTGTCCTATGAGAAGATAATGACGGTATCATAGGAGGAAGCCC<br>CGGCTAAATACGTGCCAGCAGCCGCGGTAATACGTATGGGCGAGCGTTGTCCGGAATTATTGG<br>GCGTAAAGGGTACGTAGGCGGTTTTTTAAGTCAGGTGTGAAAGCGTGAGGCTTAACCTCATTAA<br>GCACTTGAAACTGGAAGACTTGAGTGAAGGAGAGGAAAGTGGAATTCCTAGTGTAGCGGTGAAA<br>TGCGTAGATATTAGGAGGAATACCGGTGGCGAAGGCGACTTTCTGGACTTTTACTGACGCTCAG<br>GTACGAAAGCGTGGGGAGCAAACAGGATTAGATACCCTGGTAGTCCACGCCGTAAACGATGAAT<br>GCTAGGTGTTGGGAGTCAAATCTCGGTGCCGAAGTTAACACATTAAGCATTCCGCCT (SEQ<br>ID NO: 22) |
| Peptoniphilus | AGGCTTTCGAGTCGTAAAGTTCTTTTATATGGGAAGATAATGACGGTACCATAAGAAAAAGCCC<br>CGGCTAACTACGTGCCAGCAGCCGCGGTAATACGTAGGGGGCTAGCGTTGTCCGGAATCACTGG<br>GCGTAAAGGGTTCGCAGGCGGAAATGCAAGTCAGATGTAAAAGGCAGTAGCTTAACTACTGTAA<br>GCATTTGAAACTGCATATCTTGAGAAGAGTAGAGGTAAGTGGAATTTTTAGTGTAGCGGTGAAA<br>TGCGTAGATATTAAAAAGAATACCGGTGGCGAAGGCGACTTACTGGGCTCATTCTGACGCTGAG<br>GAACGAAAGCGTGGGTAGCAAACAGGATTAGATACCCTGGTAGTCCACGCTGTAAACGATGAGT<br>GCTAGGTATCGGAATAATTCGGTGCCGCAGTTAACACATTAAGCACTCCGCCTGGGG (SEQ<br>ID NO: 23) |
| Pepto-streptococcus | AGGTCTTCGGATCGTAAAGTTCTGTTGCAGGGGAAGATAATGACGGTACCCTGTGAGGAAGCCC<br>CGGCTAACTACGTGCCAGCAGCCGCGGTAATACGTAGGGGGCTAGCGTTATCCGGATTTACTGG<br>GCGTAAAGGGTGCGTAGGTGGTCCTTCAAGTCGGTGGTTAAAGGCTACGGCTCAACCGTAGTAA<br>GCCGCCGAAACTGGAGGACTTGAGTGCAGGAGAGGAAAGTGGAATTCCCAGTGTAGCGGTGAAA<br>TGCGTAGATATTGGGAGGAACACCAGTAGCGAAGGCGGCTTTCTGGACTGCAACTGACACTGAG<br>GCACGAAAGCGTGGGTAGCAAACAGGATTAGATACCCTGGTAGTCCACGCTGTAAACGATGAGT<br>ACTAGGTGTCGGGGGTTACCCCCCTCGGTGCCGCAGCTAACGCATTAAGTACTCCGC (SEQ<br>ID NO: 24) |
| Porphyromonas | TTCTTTTGTAGGGGAATAACGGACGGCACGTGTGCCGTAGTGAATGTACCCTACGAATAAGCAT<br>CGGCTAACTCCGTGCCAGCAGCCGCGGTAATACGGAGGATGCGAGCGTTATCCGGATTTATTGG<br>GTTTAAAGGGTGCGTAGGCGGCCTGTTAAGTCAGCGGTGAAATCTAGGAGCTTAACTCCTAAAT<br>TGCCATTGATACTGGCGGGCTTGAGTGTAGATGAGGTAGGCGGAATGCGTGGTGTAGCGGTGGA<br>ATGCATAGATATCACGCAGAACTCCAATTGCGAAGGCAGCTTACTAAGGTACAACTGACGCTGA<br>AGCACGAAAGCGTGGGTATCAAACAGGATTAGATACCCTGGTAGTCCACGCAGTAAACGATGAT<br>AACTGGGCGTATGCGATATACAGTATGCTCCTAAGCGAAAGCGTTAAGTTATCCACCT (SEQ<br>ID NO: 25) |
| Prevotella | TGCTTTTATAAGGGAATAAAGTGAGTCTCGTGAGACTTTTTGCATGTACCTTATGAATAAGGAC<br>CGGCTAATTCCGTGCCAGCAGCCGCGGTAATACGGAGGTCCGGGCGTTATCCGGATTTATTGG<br>GTTTAAAGGGAGCGTAGGCCGGAGATTAAGCGTGTTGTGAAATGTAGAAGCTCAACGTCTGCAC<br>TGCAGCGCGAACTGGTTTCCTTGAGTACGTACAAAGTGGGCGGAATTCGTGGTGTAGCGGTGAA<br>ATGCTTAGATATCACGAAGAACTCCGATTGCGAAGGCAGCTCACTGGAGCGCAACTGACGCTGA |

TABLE 7-continued

| Microorganism | Sequence |
|---|---|
| | AGCTCGAAAGTGCGGGTATCGAACAGGATTAGATACCCTGGTAGTCCGCACGGTAAACGATGGA<br>TGCCCGCTGTTGGTCTGAATAGGTCAGCGGCCAAGCGAAAGCATTAAGCATCCCACCT (SEQ<br>ID NO: 26) |
| Prevotella amnii | TGCTTTTATATGGGAATAAAGTGAGGGACGTGTCCCTTATTGCATGTACCATATGAATAAGGAC<br>CGGCTAATTCCGTGCCAGCAGCCGCGGTAATACGGAAGGTCCAGGCGTTATCCGGATTTATTG<br>GTTTAAAGGGAGCGTAGGCTGTTTGTTAAGCGTGTTGTGAAATGTAGGAGCTCAACTTTTAGAT<br>TGCAGCGCGAACTGGCAGACTTGAGTGCGCACAACGTAGGCGGAATTCATGGTGTAGCGGTGAA<br>ATGCTTAGATATCATGACGAACTCCGATTGCGAAGGCAGCTTACGGGAGCGCAACTGACGCTAA<br>AGCTCGAAGGTGCGGGTATCGAACAGGATTAGATACCCTGGTAGTCCGCACAGTAAACGATGGA<br>TGCCCGCTGTTAGCACCCTAGTGTTAGCGGCTAAGCGAAAGCATTAAGCATCCCACCTG (SEQ<br>ID NO: 27) |
| Prevotella timonensis | TGCTTTTATGTGGGGATAAAGTGCGTGACGTGTCATGCATTGCAGGTACCACATGAATAAGGAC<br>CGGCTAATTCCGTGCCAGCAGCCGCGGTAATACGGAAGGTCCGGGCGTTATCCGGATTTATTG<br>GTTTAAAGGGAGCGTAGGCTGTCTATTAAGCGTGTTGTGAAATTTACCGGCTCAACCGGTGGCT<br>TGCAGCGCGAACTGGTCGACTTGAGTATGCAGGAAGTAGGCGGAATTCATGGTGTAGCGGTGAA<br>ATGCTTAGATATCATGACGAACTCCGATTGCGCAGGCAGCTTACTGTAGCATAACTGACGCTGA<br>TGCTCGAAAGTGCGGGTATCAAACAGGATTAGATACCCTGGTAGTCCGCACGGTAAACGATGGA<br>TGCTCGCTATTCGTCCTTTTTGGATGAGTGGCCAAGTGAAAACATTAAGCATCCCACC (SEQ<br>ID NO: 28) |
| Sneathia | GTTTTAGGACTGTAAAACACTTTTAGTAGGGAAGAAAAAATGACGGTACCTACAGAAGAAGCGA<br>CGGCTAAATACGTGCCAGCAGCCGCGGTAATACGTATGTCGCGAGCGTTATCCGGAATTATTGG<br>GCTTAAAGGGCATCTAGGCGGTTAAACAAGTTGAAGGTGAAAACCTGTGGCTCAACCATAGGCT<br>TGCCTACAAAACTGTATAACTAGAGTACTGGAAAGGTGGGTGGAACTACACGAGTAGAGGTGAA<br>ATTCGTAGATATGTGTAGGAATGCCGATGATGAAGATAACTCACTGGACAGCAACTGACGCTGA<br>AGTGCGAAAGCTAGGGGAGCAAACAGGATTAGATACCCTGGTAGTCCTAGCTGTAAACGATGAT<br>CACTGGGTGTGGGGATTCGAAGTCTCTGTGCCGAAGCAAAAGCGATAAGTGATCCGCC (SEQ<br>ID NO: 29) |
| Staphylococcus aureus | TATTAGGGAAGAACATATGTGTAAGTAACTGTGCACATCTTGACGGTACCTAATCAGAAAGCCA<br>CGGCTAACTACGTGCCAGCAGCCGCGGTAATACGTAGGTGGCAAGCGTTATCCGGAATTATTGG<br>GCGTAAAGCGCGCGTAGGCGGTTTTTTAAGTCTGATGTGAAAGCCCACGGCTCAACCGTGGAGG<br>GTCATTGGAAACTGGAAAACTTGAGTGCAGAAGAGGAAAGTGGAATTCCATGTGTAGCGGTGAA<br>ATGCGCAGAGATATGGAGGAACACCAGTGGCGAAGGCGACTTTCTGGTCTGTAACTGACGCTGA<br>TGTGCGAAAGCGTGGGGATCAAACAGGATTAGATACCCTGGTAGTCCACGCCGTAAACGATGAG<br>TGCTAAGTGTTAGGGGGTTTCCGCCCCTTAGTGCTGCAGCTAACGCATTAAGCACTCC (SEQ<br>ID NO: 30) |
| Streptococcus agalactiae | GTTAGAGAAGAACGTTGGTAGGAGTGGAAAATCTACCAAGTGACGGTAACTAACCAGAAAGGGA<br>CGGCTAACTACGTGCCAGCAGCCGCGGTAATACGTAGGTCCCGAGCGTTGTCCGGATTTATTGG<br>GCGTAAAGCGAGCGCAGGCGGTTCTTTAAGTCTGAAGTTAAAGGCAGTGGCTTAACCATTGTAC<br>GCTTTGGAAACTGGAGGACTTGAGTGCAGAAGGGGAGAGTGGAATTCCATGTGTAGCGGTGAAA<br>TGCGTAGATATATGGAGGAACACCGGTGGCGAAAGCGGCTCTCTGGTCTGTAACTGACGCTGAG<br>GCTCGAAAGCGTGGGGAGCAAACAGGATTAGATACCCTGGTAGTCCACGCCGTAAACGATGAGT<br>GCTAGGTGTTAGGCCCTTTCCGGGGCTTAGTGCCGCAGCTAACGCATTAAGCACTCC (SEQ<br>ID NO: 31) |
| Treponema pallidum | GCCGACGAAGAATGAGGACGGGAGGGAATGCCCGTTTGATGACGGTAGTCGTGCGAATAAGCCC<br>CGGCTAATTACGTGCCAGCAGCCGCGGTAACACGTAAGGGGCGAGCGTTGTTCGGAATTATTGG<br>GCGTAAAGGGCATGCAGGCGGACTGGTAAGCCTGGTGTGAAATCCCCGAGCTCAACTTGGGAAC<br>TGCACTGGGTACTGCTGGTCTAGAATCACGGAGGGGAAACCGGAATTCCAAGTGTAGGGGTGGA<br>ATCTGTAGATATTTGGAAGAACACCGGTGGCGAAGGCGGGTTTCTGGCCGATGATTGACGCTGA<br>GGTGCGAAGGTGTGGGGAGCAACAGGATTAGATACCCTGGTAGTCCACACAGTAAACGATGTA<br>CACTAGGTGTTGGGGCATGAGTCTCGGCGCCGACGCGAACGCATTAAGTGTACCGCCT (SEQ<br>ID NO: 32) |

TABLE 8

| HPV type | Risk type | Sequence |
|---|---|---|
| HPV6 | Low-risk | TATGTTAACACCCCGAGCGGCTCTTTGGTGTCCTCTGAGGCACAATTGTTTAATAAGCCATA<br>TTGGCTACAAAAAGCCCAGGGACATAACAATGGTATTTGTTGGGGTAATCAACTGTTTGTTA<br>CTGTGGTAGATACCACACGCAGTACCAACATGACATTATGTGCATCCGTAACTACATCTTCC<br>ACATACACCAATTCTGATTATAAAGAGTACATGCGTCATGTGGAAGAGTATGATTTACAATT<br>TATTTTTCAATTATGTAGCATTACATTGTCTGCTGAAGTAATGGCCTATATTCACACAATGA<br>ATCCCTCTGTTTTGGAAGACTGGAACTTTGGGTTATCGCCTCCCCCAAATGGTACATTAGAA<br>GATACCTATAGGTATGTGCAGTCACAGGCCATTACCTGTCAAAAGCCCACTCCTGAAAAGGA<br>AAAGCCAGATCCCTATAAGAACCTTAGTTTTTGGGAGGTTAATTTAAAAGAAAAGTTTTCTA<br>GTGAATTGGATCAGTATCCTTTGGGACGCAAGTTTTTGTTACAAAGTGGATATAGGGGAC<br>GG TCCTCTATTCGTACAGGTGTTAAGCGCCCTGCTGTTTCCAA (SEQ ID NO: 33) |

TABLE 8-continued

| HPV type | Risk type | Sequence |
|---|---|---|
| HPV$_{11}$ | Low-risk | CATCTACATACACCTAGTGGCTCATTGGTGTCTTCAGAGGCTCAAGCATCTAGTCAACCAGA<br>TTGGCTTCAAAAGGCTCAGGGACATAACAATGGTATTTGCTGGGGAAACCACTTGTTTGTTA<br>CTGTGGTAGATACCACACGCAGTACAAATATGACACTATGTGCATCTGTGTCTAAATCTGCT<br>ACATACACTAATTCAGATTATAAGGAATACATGCGCCATGTGGAGGAGTTTGATTTACAGTT<br>TATTTTTCAATTGTGTAGCATTACATTATCTGCAGAAGTCATGGCCTATATACACACAATGA<br>ATCCTTCTGTTTTGGAGGACTGGAACTTTGGTTTATCGCCTCCACCAAATGGTACACTGGAG<br>GATACTTATAGATATGTACAGTCACAGGCCATTACCTGTCAGAAACCCACACCTGAAAAAGA<br>AAAACAGGATCCCTATAAGGATATGAGTTTTTTGGGAGGTTAACTTAAAAGAAAAGTTTTCAA<br>GTGAATTAGATCAGTTTCCCCTTGGACGTAAGTTTTTATTGCAAAGTGGATATCGAGGAC<br>GG ACGTCTGCTCGTACAGGTATAAAGCGCCCAGCTCTCTGTAA (SEQ ID NO: 34) |
| HPV$_{16}$ | High-risk | TATTTTCCTACACCTAGTGGTTCTATGGTTACCTCTGATGCCCAAATATTCAATAAACCTTA<br>TTGGTTACAACGAGCACAGGGCCACAATAATGGCATTTGTTGGGTAACCAACTATTTGTTA<br>CTGTTGTTGATACTACACGCAGTACAAATATGTCATTATGTGCTGCCATATCTACTTCAGAA<br>ACTACATATAAAAATACTAACTTTAAGGAGTACCTACGACATGGGGAGGAATATGATTTACA<br>GTTTATTTTTCAACTGTGCAAAATAACCTTAACTGCAGACGTTATGACATACATACATTCTA<br>TGAATTCCACTATTTTGGAGGACTGGAATTTTGGTCTACAACCTCCCCCAGGAGGCACACTA<br>GAAGATACTTATAGGTTTGTAACCCAGGCAATTGCTTGTCAAAAACATACACCTCCAGCACC<br>TAAAGAAGATGATCCCCTTAAAAAATACACTTTTTGGGAAGTAAATTTAAAGGAAAGTTTT<br>CTGCAGACCTAGATCAGTTTCCTTTAGGACGCAAATTTTTACTACAAGCAGGATTGAAGG<br>CC AAACCAAAATTTACATTAGGAAAACGAAAAGCTACACCCACCAC (SEQ ID NO: 35) |
| HPV$_{18}$ | High-risk | TATTCTCCCTCTCCAAGTGGCTCTATTGTTACCTCTGACTCCCAGTTGTTTAATAAACCATA<br>TTGGTTACATAAGGCACAGGGTCATAACAATGGTGTTTGCTGGCATAATCAATTATTTGTTA<br>CTGTGGTAGATACCACTCCCAGTACCAATTTAACAATATGTGCTTCTACACAGTCTTGTATA<br>CCTGGGCAATATGATGCTACCAAATTTAAGCAGTATAGCAGACATGTTGAGGAATATGATTT<br>GCAGTTTATTTTTCAGTTGTGTACTATTACTTTAACTGCAGATGTTATGTCCTATATTCATA<br>GTATGAATAGCAGTATTTTAGAGGATTGGAACTTTGGTGTTCCCCCCCCCCCAACTACTAGT<br>TTGGTGGATACATATCGTTTTGTACAATCTGTTGCTATTACCTGTCAAAAGGATGCTGCACC<br>GGCTGAAAATAAGGATCCCTATGATAAGTTAAAGTTTTGGAATGTGGATTTAAAGGAAAAGT<br>TTTCTTTAGACTTAGATCAATATCCCCTTGGACGTAAATTTTTGGTTCAGGCTGGATTGC<br>GT CGCAAGCCCACCATAGGCCCTCGCAAACGTTCTGCTCCATCTGCCAC (SEQ ID NO: 36) |
| HPV$_{26}$ | High-risk | TATTCTGCTACACCTAGTGGCTCTATGGTTACTTCGGATGCACAACTATTTAATAAGCCATA<br>CTGGTTACAACGTGCACAGGGTCATAATAATGGTATCTGTTGGGGCAATCAATTGTTTGTTA<br>CCTGTGTTGATACCACCCGCAGTACTAACCTTACCATTAGTACATTATCTGCAGCATCTGCA<br>TCCACTCCATTTAAACCATCTGATTATAAACAATTTATAAGACATGGCGAAGAATATGAATT<br>ACAATTTATATTTCAGTTGTGTAAAATAACACTTACAACAGATGTTATGGCTTACATACATT<br>TAATGAATGCCTCCATATTGGAGGATTGGAATTTTGGACTAACCTTACCTCCCACTGCTAGT<br>TTGGAAGATGCCTATAGGTTTATTAAAAACTCTGCTACTACCTGTCAGCGTAACGCCCCTCC<br>TGTGCCAAAGGAAGATCCTTTTCAAAAATTTAAATTTTGGGATGTAGATTTAAAAGAAAAAT<br>TTTCTATTGATTTGGATCAATTTCCACTAGGGCGTAAGTTTATGTTACAGGCCGGCATAC<br>AA CGGCGGCCGAAACTAGGCACCAAACGTCCCTTATCTTCTACCTCTTC (SEQ ID NO: 37) |
| HPV$_{31}$ | High-risk | TACTTTCCTACACCTAGCGGCTCCATGGTTACTTCAGATGCACAAATTTTTAATAAACCATA<br>TTGGATGCAACGTGCTCAGGGACACAATAATGGTATTTGTTGGGGCAATCAGTTATTTGTTA<br>CTGTGGTAGATACCACACGTAGTACCAATATGTCTGTTTGTGCTGCAATTGCAAACAGTGAT<br>ACTACATTTAAAAGTAGTAATTTTAAAGAGTATTTAAGACATGGTGAGGAATTTGATTTACA<br>ATTTATATTTCAGTTATGCAAAATAACATTATCTGCAGACATAATGACATATATTCACAGTA<br>TGAATCCTGCTATTTTGGAAGATTGGAATTTTGGATTGACCACACCTCCCTCAGGTTCTTTG<br>GAGGATACCTATAGGTTTGTCACCTCACAGGCCATTACATGTCAAAAAACTGCCCCCCAAAA<br>GCCCAAGGAAGATCCATTTAAAGATTATGTATTTTGGGAGGTTAATTTAAAAGAAAAGTTTT<br>CTGCAGATTTAGATCAGTTTCCACTGGGTCGCAAATTTTTATTACAGGCAGGATATAGGG<br>CA CGTCCTAAATTTAAAGCAGGTAAACGTAGTGCACCCCTCAGCATC (SEQ ID NO: 38) |
| HPV$_{33}$ | High-risk | TTTTTTCCCACTCCTAGTGGATCAATGGTTACTTCCGAATCTCAGTTATTTAATAAGCCATA<br>TTGGCTACAACGTGCACAAGGTCATAATAATGGTATTTGTTGGGGCAATCAGGTATTGTTA<br>CTGTGGTAGATACCACTCGCAGTACTAATATGACTTTATGCACACAAGTAACTAGTGACAGT<br>ACATATAAAAATGAAAATTTTAAAGAATATATAAGACATGTTGAAGAATATGATCTACAGTT<br>TGTTTTTCAACTATGCAAAGTTACCTTAACTGCAGAAGTTATGACATATATTCATGCTATGA<br>ATCCAGATATTTTAGAAGATTGGCAATTTGGTTTAACACCTCCTCCATCTGCTAGTTTACAG<br>GATACCTATAGGTTTGTTACCTCTCAGGCTATTACGTGTCAAAAAACAGTACCTCCAAAGGA<br>AAAGGAAGACCCCTTAGGTAAATATACATTTTGGGAAGTGGATTTAAAGGAAAATTTTCAG<br>CAGATTTAGATCAGTTTCCTTTGGGACGCAAGTTTTTATTACAGGCAGGTCTTAAAGCAA<br>AA CCTAAACTTAAACGTGCAGCCCCCACATCCACCCGCACATC (SEQ ID NO: 39) |
| HPV$_{35}$ | High-risk | TATTTTCCTACTCCTAGTGGCTCTATGGTAACCTCCGATGCACAAATATTTAATAAACCATA<br>TTGGTTGCAACGTGCACAAGGCCATAATAATGGTATTTGTTGGGAGTAACCAATTGTTTGTTA<br>CTGTAGTTGATACAACCCGTAGTACAAATATGTCTGTGTTCTGCTGTGTCTTCTAGTGAC<br>AGTACATATAAAAATGACAATTTTAAGGAATATTTAAGGCATGGTGAAGAATATGATTTACA<br>GTTTATTTTTCAGTTATGTAAAATAACACTAACAGCAGATGTTATGACATATATTCATAGTA<br>TGAACCCGTCCATTTTAGAGGATTGGAATTTTGGCCTTACACCACCGCCTTCTGGTACCTTA<br>GAGGACACATATCGCTATGTAACATCACAGGCTGTAACTTGTCAAAAACCCAGTGCACCAAA |

TABLE 8-continued

| HPV type | Risk type | Sequence |
|---|---|---|
| | | ACCTAAAGATGATCCATTAAAAAATTATACTTTTTGGGAGGTTGATTTAAAGGAAAAGTTTT CTGCAGACTTAGATCAATTTCCGTTGGGCCGTAAATTTTTGTTACAAGCAGGACTAAAGG CC AGGCCTAATTTTAGATTAGGCAAGCGTGCAGCTCCAGCATCT (SEQ ID NO: 40) |
| HPV<sub>39</sub> | High-risk | TACTGCCCCTCTCCCAGCGGTTCCATGGTAACCTCTGATTCCCAGTTATTTAATAAGCCTTA TTGGCTACATAAGGCCCAGGGCCACAACAATGGTATATGTTGGCATAATCAATTATTTCTTA CTGTTGTGGACACTACCCGTAGTACCAACTTTACATTATCTACCTCTATAGAGTCTTCCA TACCTTCTACATATGATCCTTCTAAGTTTAAGGAATATACCAGGCACGTGGAGGAGTATGATTT ACAATTTATATTTCAACTGTGTACTGTCACATTAACAACTGATGTTATGTCTTATATTCACA TATGAATTCCTCTATATTGGACAATTGGAATTTTGCTGTAGCTCCTCCACCATCTGCCAGT TTGGTAGACACTTACAGATACCTACAGTCTGCAGCCATTACATGTCAAAAGGATGCTCCA ACCTGAAAAGAAAGATCCATATGACGGTCTAAAGTTTTGGAATGTTGACTTAAGGGAAAGT TTAGTTTGGAACTTGATCAATTCCCTTTGGGACGTAAATTTTTGTTGCAGGCCAGGGTCC GC AGGCGCCCTACTATAGGTCCCCGAAAGCGGCCTGCTGCATCCACTTC (SEQ ID NO: 41) |
| HPV<sub>40</sub> | Low-risk | TATTACTCCACACCAAGTGGATCCTTGGTTACCTCTGATTCTCAGATATTTAACAAGCCATT GTGGATACAAAAGGCCCAGGGCCATAACAATGGCATATGTTTTGGCAATCAGTTATTTGTTA AGTTGTAGACACCACTCGTAGCACTAATTTAACCTTATGTGCTGCCACACAGTCCCCCACA CAACCCCATATAATAACAGTAATTTCAAGGAATATTTGCGTCATGGGGAGGAGTTTGATTT GCAGTTTATTTTTCAGTTATGTGTAATTACCTTAAATGCAGAGGTTATGACATATATTCATG AATGGATCCTACGTTGTTGGAGGATTGGAACTTTAAAATTGCTCCTCCAGCCTCTGCATCC TTAGAGGATACATATAGGTTCCTTACCAACAAGGCTATTGCCTGTCAGCGCGATGCGCCCCC AAGGTACGGGAGGATCCATATAAAAAATATAAATTTTGGGATGTCAATTTAACAGAAAGAT TTTCTTCCCAATTAGATCAATTTCCATTAGGACGTAAGTTCCTTATGCAGGCTGGTGTAC GT GCAGGGCCTAGGTTTAAATCCAGGAAGCGCCCTGCCCCTTCCTCGTC (SEQ ID NO: 42) |
| HPV<sub>42</sub> | Low-risk | TATTATCCTACCCCTAGTGGTTCTATGGTAACATCTGATGCACAACTATTTAATAAACCATA TTGGTTACAACAAGCACAAGGACACAATAATGGTATATGTTGGGGAAATCAGCTATTTTAA TGTGGTTGATACTACCCGTAGTACTAACATGACTTTGTGTGCCACTGCAACATCTGGTGAT ACATATACAGCTGCTAATTTTAAGGAATATTTAAGACATGCTGAAGAATATGATGTGCAATT TATATTTCAATTGTGTAAATAACATTAACTGTTGAAGTTATGTCATATATACACAATATGA ATCCTAACATATTAGAGGAGTGGAATGTTGGTGTTGCACCACCACCTTCAGGAACTTTAGAA GATAGTTATAGGTATGTACAATCAGAAGCTATTCGCTGTCAGGCTAAGGTAACAACGCCAGA AAAAAGGATCCTTATTCAGACTTTTGGTTTTGGGAGGTAAATTTATCTGAAAAGTTTTCTA TGATTTAGATCAATTTCCTTTAGGTAGAAAGTTTTTACTGCAGGCCGGGTTGCGTGCAA GG CCTAAACTGTCTGTAGGTAAACGAAAGGCGTCTACAGCTAA (SEQ ID NO: 43) |
| HPV<sub>45</sub> | High-risk | TATTCCCCTTCTCCCAGTGGCTCTATTATTACTTCTGATTCTCAATTATTTAATAAGCCATA TTGGTTACATAAGGCCCAGGGCCATAACAATGGTATTTGTTGGCATAATCAGTTGTTTGTTA TGTAGTGGACACTACCCGCAGTACTAATTTAACCATTATGTGCCTCTACACAAAATCCTGTG CAAGTACATATGACCCTACTAAGTTTAAGCAGTATAGTAGACATGTGGAGGAATATGATTT ACAGTTTATTTTTCAGTTGTGCACTATTACTTTAACTGCAGAGGGTTATGTCATATATCCATA GTATGAATAGTAGTATATTAGAAAATTGGAATTTTGGTGTCCCTCCACCACCTACTACAAGT TTGGTGGATACATATCGTTTTGTGCAATCAGTTGCTGTTACCTGTCAAAAGGATACTACACC TCCAGAAAAGCAGGATCCATATGATAAATTAAAGTTTTGGACTGTTGACCTAAAGGAAAAAT TTTCCTCCGATTTGGATCAATATCCCCTTGGTCGAAAGTTTTTAGTTCAGGCTGGGTTAC GT CGTAGGCCTACCATAGGACCTCGTAAGCGTCCTGCTGCTTCCACGTC (SEQ ID NO: 44) |
| HPV<sub>51</sub> | High-risk | TACTCTGCTACTCCCAGTGGGTCTATGATAACATCTGATTCTCAAATTTTTAATAAGCCTTA TTGGCTCCACCGTGCGCAGGGTCACAATAATGGCATTTGCTGGAACAATCAGCTTTTTATTA CCTGTGTTGATACTACCAGAAGTACAAATTTAACTATTAGCACTGCCACTGCTGCGGTTTCC CCAACATTTACTCCAAGTAACTTTAAGCAATATATTAGGCATGGGGAAGAGTATGAATTGCA ATTTATTTTTCAATTATGTAAAATTACTTTAACTACAGAGGTAATGGCTTATTTACACACAA TGGATCCTACCATTCTTGAACAGTGGAATTTTGGATTAACATTACCTCCGTCTGCTAGTTTG GAGGATGCATATAGGTTTGTTAGAAATGCAGCTACTGCTGTCAAAAGGACACCCCTCCACA GGCTAAGCCAGATCCTTTGCCAAATATAAATTTTGGGATGTTGATTTAAAGGAACGATTTT CTTTAGATTTAGACCAATTTGCATTGGGTCGCAAGTTTTTGTTGCAGGTTGGCGTACAAC GC AAGCCCAGACCAGGCCTTAAACGCCCGGCCTCATCGGCATCCTCT (SEQ ID NO: 45) |
| HPV<sub>52</sub> | High-risk | TTTTTTCCTACTCCTAGTGGTTCTATGGTAACCTCAGAATCCCAATTATTTAATAAACCGTA CTGGTTACAACGTGCGCAGGGCCACAATAATGGCATATGTTGGGGCAATCAGTTGTTTGTCA CAGTTGTGGATACCACTCGTAGCACTAACATGACTTTATGTGCTGAGGTTAAAAAGGAAAGC ACATATAAAAATGAAAATTTAAGGAATACCTTCGTCATGGCGAGGAATTTGATTTACAATT TATTTTTCAATTGTGCAAAATTACATTAACAGCTGATGTTATGACATACATTCATAAGATGG ATGCCACTATTTAGAGGACTGGCAATTTGGCCTTACCCCACCACCGTCTGCATCTTTGGAG GACACACATACAGATTTGTCACTTCTACTGCTATAACTTGTCAAAAAACACACCACCTAAAGG AAAGGAAGATCCTTTAAAGGACTATATGTTTTGGGAGGTGGATTTAAAAGAAAAGTTTTCTG CAGATTTAGATCAGTTTCCTTTAGGTAGGAAGTTTTTGTTACAGGCAGGGCTACAGGCTA GG CCCAAACTAAAACGCCCTGCATCATCGGCCCCACGTACCCTC (SEQ ID NO: 46) |
| HPV<sub>53</sub> | High-risk | TATGTTGCTACACCCTAGTGGGTCTATGATAACTTCAGAGGCTCAATTGTTTAATAAGCCATA TTGGCTGCAACGTGCCCAGGGACATAATAATGGCATCTGTTGGAACAATCAGTTATTTGTAA |

TABLE 8-continued

| HPV type | Risk type | Sequence |
|---|---|---|
| | | CTGTTGTGGATACCACCAGGAATACAAACATGACTCTTTCCGCAACCACACAGTCTATGTCT ACATATAATTCAAAGCAAATTAAACAGTATGTTAGACATGCAGAGGAATATGAATTACAATT TGTGTTTCAACTATGTAAAATATCCCTGTCTGCTGAGGTTATGGCCTATTTACATACTATGA ATTCTACCTTACTGGAAGACTGGAATATAGGTTTGTCGCCTCCTGTTGCCACTAGCTTAGAG GACAAATACAGATATGTGAAAAGTGCAGCTATAACCTGTCAAAAGGATCAGCCCCCTCCTGA AAAGCAGGACCCACTATCTAAATATAAATTTTGGGAGGTCAATTTGCAAAACAGTTTTTCTG CTGATTTGGATCAGTTTCCTCTTGGCAGGAAGTTTTTAATGCAGGTTGGGGTCCGTACTA AA CCGCCTGTATCCTCTAAAAAACGCTCTGCTTCTACTACA (SEQ ID NO: 47) |
| HPV$_{54}$ | Low-risk | TATGCTGCAACTCCTAGTGGCTCTATGGTAACATCTGAATACCAAATATTTAATAAGCCATA CTGGTTACAACGGGCCCAGGGTCAAAACAATGGTATTTGTTGGGGCAATCAGGTGTTTTTAA CAGTTGTAGATACCACCCGTAGTACTAACCTAACATTGTGTGCTACAGCATCCACGCAGGAT AGCTTTAATAATTCTGACTTTAGGGAGTATATTAGACATGTGGAGGAATATGATTTACAGTT TATATTTCAGTTATGTACCATAACCCTTACAGCAGATGTTATGGCTATATTCATGGAATGA ATCCCACTATTCTAGAGGACTGGAACTTTGGTATAACCCCCCCAGCTACAAGTAGTTTGGAG GACACATATAGGTTTGTACAGTCACAGGCCATTGCATGTCAAAAGAATAATGCCCCTGCAAA GGAAAAGGAGGATCCTTACAGTAAATTTAATTTTTGGACTGTTGACCTTAAGGAACGATTTT CATCTGACCTTGACCAGTTTCCCTTGGGTCGCAAGTTTTTACTACAGGCTGGCCTACGTG CA CGTCCGCGCCTTCGGCCTGTAAAGCGTGCAGCCCCTTCCTCCTC (SEQ ID NO: 48) |
| HPV$_{56}$ | High-risk | ATGTTGCTACGCCTAGTGGGTCTATGATTACGTCTGAGGCACAGTTATTTAATAAACCTTAT TGGTTGCAACGTGCCCAAGGCCATAATAATGGCATTTGCTGGGGTAATCAATTATTTGTTAC TGTAGTAGATACTACTAGAAGTACTAACATGACTATTAGTACTGCTACAGAACAGTTAAGTA AATATGATGCACGAAAAATTAATCAGTACCTTAGACATGTGGAGGAATATGAATTACAATTT GTTTTTCAATTATGCAAAATTACTTTGTCTGCAGAGGTTATGGCATATTTACATAATATGAA TGCTAACCTACTGGAGGACTGGAATATTGGGTTATCCCCGCCAGTGGCCACCAGCCTAGAAG ATAAATATAGATATGTTAGAAGCACAGCTATAACATGTCAACGGGAACAGCCACCAACAGAA AAACAGGACCCATTAGCTAAATATAAATTTTGGGATGTTAACTTACAGGACAGTTTTTCTAC AGACCTGGATCAATTTCCACTGGGTAGAAAATTTTTAATGCAACTGGGCACTAGGTCAAA GC CTGCTGTAGCTACCTCTAAAAAGCGATCTGCTCCTACCTC (SEQ ID NO: 49) |
| HPV$_{58}$ | High-risk | TTTTTTCCAACTCCTAGTGGCTCTATAGTTACCTCAGAATCACAATTATTTAATAAGCCTTA TTGGCTACAGCGTGCACAAGGTCATAACAATGGCATTTGCTGGGGCAATCAGTTATTTGTTA CCGTGGTTGATACCACTCGTAGCACTAATATGACATTATGCACTGAAGTAACTAAGGAAGGT ACATATAAAAATGATAATTTTAAGGAATATGTACGTCATGTTGAAGAATATGACTTACAG TTTGTTTTTCAGCTTTGCAAATTACACTAACTGCAGAGATAATGACATATATACATACTATGG ATTCCAATATTTTGGAGGACTGGCAATTTGGTTTAACACCTCCTCCGTCTGCCAGTTTACAG GACACATATAGATTTGTTACCTCCCAGGCTATTACTTGCCAAAAAACAGCACCCCCTAAAGA AAAGGAAGATCCATTAAATAAATATACTTTTTGGGAGGTTAACTTAAAGGAAAAGTTTTCTG CAGATCTAGATCAGTTTCCTTTGGGACGAAAGTTTTTATTACAATCAGGCCTTAAAGCAA AG CCCAGACTAAAACGTTCGGCCCCTACTACCCGTGCACCATC (SEQ ID NO: 50) |
| HPV$_{59}$ | High-risk | TATTCCCCTTCCCCAAGTGGGTCTGTGGTTACTTCTGATTCACAATTATTTAATAAACCATA TTGGCTGCACAAGGCTCAGGGTTTAAACAATGGTATATGTTGGCACAATCAATTGTTTTTAA CAGTTGTAGATACTACTCGCAGCACCAATCTTTCTGTGTGCTTCTACTACTTCTTCTATT CCTAATGTATACACACCTACCAGTTTTAAAGAATATGCCAACATGTGGAGGAATTTGATTT GCAGTTTATATTTCAACTGTGTAAAATAACATTAACTACAGAGGTAATGTCATACATTCATA ATATGAATACCACTATTTTGGAGGATTGGAATTTTGGTGTTACACCACCTCCTACTGCTAGT TTAGTTGACACATACCGTTTTGTTCAATCTGCTGCTGTAACTTGTCAAAAGGACACCGCACC GCCAGTTAAACAGGACCCTTATGCACAAACTAAAGTTTTGGCCTGTAGATCTTAAGGAAGGT TTTCTGCAGATCTTGATCAGTTTCCTTTGGGACGTAAATTTTTATTGCAATTAGGAGCA GA CCTAAGCCCACTATAGGCCCACGCAAACGTGCAGCGCCTGCCCCTAC (SEQ ID NO: 51) |
| HPV66 | High-risk | TATGTTGCTACTCCTAGTGGGTCCATGATTACCTCTGAGGCCCAATTATTTAATAAACCTTA TTGGTTGCAACGTGCACAGGGCCATAATAATGGCATATGCTGGGGTAATCAGGTATTTGTTA CTGTTGTGGATACTACCAGAAGCACCAACATGACTATTAATGCAGCTAAAAGCACATTAACT AAATATGATGCCCGTGAAATCAATCAATACCTTCGCCATGTGGAGGAATATGAACTACAGTT TGTGTTTCAACTTTGTAAAATAACCTTAACTGCAGAAGTTATGCATATTTGCATAATATGA ATAATACTTTATTAGACGATTGGAATATTGGCTTATCCCCACCAGTTGCAACTAGCTTAGAG GATAAATATAGGTATATTAAAGCACAGCTATTACATGTCAGAGGGAACAGCCCCTGCAGA AAAGCAGGATCCCCTGGCTAAATATAAGTTTTGGAAGTTAATTTACAGGACAGCTTTTCTG CAGACCTGGATCAGTTTCCTTTGGGTAGAAAATTTTTAATGCAACTAGGCCCTAGACCCC (SEQ ID NO: 52) |
| HPV68a | High-risk | TATGCCCCCTCGCCTAGCGGGTCTATGGTGTCCTCTGACTCCCAGTTATTTAACAAGCCCTA TTGGCTGCACAAGGCACAGGGACCACAATGTGTATTTGTTGGCATAATCAATTATTTCTTA CCGTTGTGGATACAACGCGCAGTACTAATTTTACATTGTCCACTACTACAGACTCTACTGTA CCAGCTGTGTATGATTCTAATAAATTTAAGGAATATGTTAGGCATGTTGAGGAATATGATTT GCAGTTTATATTTCAGTTGTGTACTATAACATTATCCACTGATGTAATGTCATATATACATA CTATGAATCCTGCTATTTTGGATGATTGGAATTTTGGTGTTGCCCCTCCACCATCTGCTAGT CTTGTAGATACATACCGCTACCTACAATCAGCAGCAATTACATGTCAAAAGGACGCCCCTGC ACCTGTTAAAAAGATCCCTATGATGGTCTTAACTTTTGGAATGTGGATTTAAAGGAAAGT TTAGTTCTGAACTGGACCAATTCCCATTAGGACGCAAATTTCTGTTACAGGCAGGTGTTC GC AGACGGCCCACCATAGGCCCTCGTAAACGCACTGCCACTGCAGCTAC (SEQ ID NO: 53) |

TABLE 8-continued

| HPV type | Risk type | Sequence |
|---|---|---|
| HPV68b | High-risk | TATGCCCCCTCGCCTAGTGGGTCTATGGTATCCTCAGACTCCCAGTTATTTAACAAGCCCTA<br>TTGGCTGCACAAGGCACAGGGACACAACAATGGTATTTGTTGGCATAATCAATTATTTCTTA<br>CTGTTGTGGATACCACTCGCAGTACCAATTTTACTTTGTCTACTACTACTGAATCAGCTGTA<br>CCAAATATTTATGATCCTAATAAATTTAAGGAATATATTGGCATGTTGAGGAATATGATTT<br>GCAATTTATATTTCAGTTGTGTACTATAACATTGTCCACTGATGTAATGTCCTATATACATA<br>CTATGAATCCTGCTATTTTGGATGATTGGAATTTTGGTGTTGCCCCTCCACCATCTGCTAGT<br>CTTGTAGATACATACCGCTATCTGCAATCAGCAGCAATTACATGTCAAAAAGACGCCCCTGC<br>ACCCTACTAAAAGGATCCATATGATGGCTTAAACTTTTGGAATGTAAATTTAAAGGAAAAGT<br>TTAGTTCTGAACTGGACCAGTTTCCTTTAGGACGCAAATTTCTTTTACAGGCAGGCGTCC<br>GC CGACGACCCACTATAGGCCCCCGTAAACGCCCCGCCACAGCAACTAC (SEQ ID<br>NO: 54) |
| lHPV70 | High-risk | TATTCCCCTTCCCCAAGTGGCTCTATGGTCTCTTCTGATTCCCAGTTGTTTAATAAGCCCTA<br>TTGGTTGCATAAGGCCCAGGGACACAATAATGGCATTTGTTGGCATAACCAGTTGTTTATTA<br>CTGTGGTGGACACTACACGTAGTACTAATTTTACATTGTCTGCCTGCACCGAAACGGCCATA<br>CCTGCTGTATATAGCCCTACAAAGTTTAAGGAATATACTAGGCATGTGGAGGAATATGATTT<br>ACAATTTATATTTCAATTGTGTACTATCACATTAACTGCTGACGTTATGGCCTACATCCATA<br>CTATGAATCCTGCAATTTTGGACAATTGGAATATAGGAGTTACCCCTCCACCATCTGCAAGC<br>TTGGTGGACACGTATAGGTATTTACAATCAGCAGCTATAGCATGTCAAAAGGATGCTCCTAC<br>ACCTGAAAAAAGGATCCCTATGACGATTTAAAATTTTGGAATGTTGATTTAAAGGAAAAGT<br>TTAGTACAGAACTAGATCAGTTTCCTTTGGGGCGCAAATTTTTACTACAGGTAGGGGCTC<br>GC AGACGTCCTACTATAGGCCCTCGCAAACGCCCTGCGTCAGCTAAATC (SEQ ID<br>NO: 55) |
| HPV73 | High-risk | TTTTATCCTACACCTAGTGGTTCCATGGTTTCTTCAGATGCACAGTTGTTTAATAAACCTTA<br>TTGGTTGCAAAAGGCACAGGGACAAAATAATGGTATTTGTTGGCATAATCAATTATTTTTAA<br>CTGTTGTAGATACTACTAGAAGCACTAATTTTTCTGTATGTGTAGGTACACAGGCTAGTAGC<br>TCTACTACAACGTATGCCAACTCTAATTTTAAGGAATATTTAAGACATGCAGAAGAGTTTGA<br>TTTACAGTTTGTTTTTCAGTTATGTAAAATTAGTTTAACTACTGAGGTAATGACATATATAC<br>ATTCTATGAATTCTACTATATTGGAAGAGTGGAATTTTGGTCTTACCCCACCACCGTCAGGT<br>ACTTTAGAGGAAACATATAGATATGTAACATCACAGGCTATTAGTTGCCAACGTCCTCAACC<br>TCCTAAAGAAACAGAGGACCCATATGCCAAGCTATCCTTTTGGGATGTAGATCTTAAGGAAA<br>AGTTTTCTGCAGAATTAGACCAGTTTCCTTTGGGAAGAAAATTTTTATTACAACTTGGTA<br>TG CGTGCACGTCCTAAGTTACAAGCTTCTAAACGTTCTGCATCTGCTACCAC (SEQ<br>ID NO: 56) |
| HPV82 | High-risk | TATTCAGCTACTCCCAGTGGTTCTATGATAACCTCTGATTCTCAGATTTTTAATAAGCCTTA<br>TTGGTTGCATCGCGCCCAGGGCCACAATAATGGCATTTGCTGGAATAATCAGCTTTTATTA<br>CTTGTGTTGACACTACTAAAAGTACCAATTTAACCATTAGCACTGCTGTTACTCCATCTGTT<br>GCACAAACATTTACTCCAGCAAACTTTAAGCAGTACATTAGGCATGGGAAGAATATGAATT<br>GCAATTTATATTTCAATTGTGTAAAATCACTTTAACTACTGAAATTATGGCTTACCTGCACA<br>CCATGGATTCTACAATTTTAGAACAGTGGAATTTTGGATTAACATTGCCCCCTCCGCTAGT<br>TTGGAGGATGCCTATCGATTTGTAAAAAATGCAGCAACATCCTGTCACAAGGACAGTCCTCC<br>ACAGGCTAAAGAAGACCCTTTGGCAAAATATAATTTTGGAATGTAGACCTTAAGGAACGCT<br>TTTCTTTGGATTTGGATCAGTTTGCATTGGGTCGCAAGTTTTTATTACAAATCGGTGCCC<br>AA CGCAAACCCAGACCAGGCCTTAAAAGGCCTGCCCCATCCTCTTCCGCT (SEQ ID<br>NO: 57) |

TABLE 9

| Name | Sequence (5'→3') |
|---|---|
| HPV_PGMY11-A_Reverse | GCACAGGGACATAACAATGG (SEQ ID NO: 58) |
| HPV_PGMY11-B_Reverse | GCGCAGGGCCACAATAATGG (SEQ ID NO: 59) |
| HPV_PGMY11-C_Reverse | GCACAGGGACATAATAATGG (SEQ ID NO: 60) |
| HPV_PGMY11-D_Reverse | GCCCAGGGCCACAACAATGG (SEQ ID NO: 61) |
| HPV_PGMY11-E_Reverse | GCTCAGGGTTTAAACAATGG (SEQ ID NO: 62) |
| HPV_PGMY11-CvJJ_Reverse | GCACAAGGCCATAATAATGG (SEQ ID NO: 63) |
| HPV_PGMY09-F_Forward | CGTCCCAAAGGAAACTGATC (SEQ ID NO: 64) |

TABLE 9-continued

| Name | Sequence (5'→3') |
|---|---|
| HPV_PGMY09-G_Forward | CGACCTAAAGGAAACTGATC (SEQ ID NO: 65) |
| HPV_PGMY09-H_Forward | CGTCCAAAAGGAAACTGATC (SEQ ID NO: 66) |
| HPV_PGMY09-I_Forward | GCCAAGGGGAAACTGATC (SEQ ID NO: 67) |
| HPV_PGMY09-J_Forward | CGTCCCAAAGGATACTGATC (SEQ ID NO: 68) |
| HPV_PGMY09-K_Forward | CGTCCAAGGGGATACTGATC (SEQ ID NO: 69) |
| HPV_PGMY09-L_Forward | CGACCTAAAGGGAATTGATC (SEQ ID NO: 70) |
| HPV_RSMY09-L_Forward | CGTCCTAATGGGAATTGGTC (SEQ ID NO: 71) |

TABLE 9-continued

| Name | Sequence (5'→3') |
|---|---|
| HPV_PGMY09-M_Forward | CGACCTAGTGGAAATTGATC (SEQ ID NO: 72) |
| HPV_PGMY09-N_Forward | CGACCAAGGGGATAITGATC (SEQ ID NO: 73) |
| HPV_PGMY09-P_Forward | GCCCAACGGAAACTGATC (SEQ ID NO: 74) |
| HPV_PGMY09-Q_Forward | CGACCCAAGGGAAACTGGTC (SEQ ID NO: 75) |
| HPV_PGMY09-R_Forward | CGTCCTAAAGGAAACTGGTC (SEQ ID NO: 76) |
| HPV_HMB01_Forward | GCGACCCAATGCAAATTGGT (SEQ ID NO: 77) |
| HPV_RSMY09-LvJJ_Forward | CGTCCTAAAGGGAATTGATC (SEQ ID NO: 78) |

TABLE 10

| Dilution | Taxa | LOD |
|---|---|---|
| 1:100 | Mycoplasma genitalium | 52.6 |
| 1:100 | Porphyromonas | 59.1 |
| 1:250 | Dialister micraerophilus | 49.0 |
| 1:250 | Atopobium vaginae | 49.0 |
| 1:250 | Chlamydia trachomatis | 49.8 |
| 1:250 | Fusobacterium | 50.6 |
| 1:250 | Peptoniphilus | 51.8 |
| 1:250 | Gemella | 51.8 |
| 1:250 | Gardnerella vaginalis | 54.3 |
| 1:250 | Neisseria gonorrhoeae | 55.7 |
| 1:250 | Lactobacillus iners | 55.9 |
| 1:500 | Lactobacillus jensenii | 49.0 |
| 1:500 | Aerococcus | 50.3 |
| 1:500 | Streptococcus agalactiae | 50.6 |
| 1:500 | Sneathia | 51.0 |
| 1:500 | Atopobium | 51.0 |
| 1:500 | Parvimonas | 51.1 |
| 1:500 | Gardnerella | 51.7 |
| 1:500 | Papillibacter | 52.2 |
| 1:500 | Staphylococcus aureus | 52.3 |
| 1:500 | Aerococcus christensenii | 52.3 |
| 1:500 | Megasphaera | 53.0 |
| 1:500 | Prevotella amnii | 54.3 |
| 1:1000 | Prevotella | 50.6 |
| 1:1000 | Mobiluncus curtisii | 51.0 |
| 1:1000 | Peptostreptococcus | 51.0 |
| 1:1000 | Prevotella timonensis | 52.6 |
| 1:1000 | Fusobacterium nucleatum | 65.2 |
| 1:1000 | Lactobacillus | 1346.9 |

TABLE 11

| HPV type | Dilution | Threshold |
|---|---|---|
| 6 | 1:100 | 87.7 |
| 11 | 1:100 | 76.1 |
| 16 | 1:100 | 46.4 |
| 18 | 1:100000 | 47.7 |
| 31 | 1:1 | 224.8 |
| 33 | 1:100 | 52.5 |
| 39 | 1:100000 | 56.2 |
| 42 | 1:100 | 58.3 |
| 45 | 1:100 | 66.5 |
| 51 | 1:100000 | 41.6 |
| 52 | 1:100 | 114.9 |
| 53 | 1:100 | 46.8 |
| 56 | 1:100 | 40.8 |
| 58 | 1:100 | 50.2 |
| 59 | 1:100 | 55.6 |
| 66 | 1:100000 | 41.6 |
| 68a | 1:1 | 149.3 |
| 68b | 1:1 | 73.6 |

TABLE 12

| | digene STM hrHPV+ | digene STM hrHPV− | Sum |
|---|---|---|---|
| digene DNA hrHPV+ | 15 | 0 | 15 |
| digene DNA hrHPV− | 3 | 69 | 72 |
| Sum | 18 | 69 | 87 |

TABLE 13

| | digene hrHPV+ | digene hrHPV− | Sum |
|---|---|---|---|
| Genotyping hrHPV+ | 69 | 18 | 87 |
| Genotyping hrHPV− | 10 | 504 | 514 |
| Sum | 79 | 522 | 601 |

TABLE 14

| | digene lrHPV+ | digene lrHPV− | Sum |
|---|---|---|---|
| Genotyping lrHPV+ | 21 | 9 | 30 |
| Genotyping lrHPV− | 0 | 118 | 118 |
| Sum | 21 | 127 | 148 |

We claim:

1. A method for characterizing at least one female reproductive system-related condition associated with microorganisms, the method comprising:
   determining a microorganism sequence dataset associated with a set of subjects based on microorganism nucleic acids from samples associated with the set of subjects, wherein the microorganism sequence dataset is usable for identifying microbiome features and the samples comprise at least one sample associated with the at least one female reproductive system-related condition;
   collecting, for the set of subjects, supplementary data associated with the at least one female reproductive system-related condition;
   determining a set of microbiome composition features based on the microorganism sequence dataset, wherein the set of microbiome composition features comprises a first subset of microbiome composition features associated with a set of bacterial targets;
   generating a female reproductive system-related characterization model based on the supplementary data and the set of microbiome composition features, wherein the female reproductive system-related characterization model is associated with the at least one female reproductive system-related condition;
   determining a female reproductive system-related characterization for a user for the at least one female reproductive system-related condition based on the female reproductive system-related characterization model; and
   providing, based on the female reproductive system-related characterization, a therapy to the user for facilitating improvement of the at least one female reproductive system-related condition, the therapy being determined based on a therapy model and the user microbiome features,
   wherein the at least one female reproductive system-related condition comprises at least one of bacterial vaginosis, cervicitis, pelvic inflammatory disease, idiopathic infertility, aerobic vaginitis, and infertility,
   wherein the therapy comprises at least one of a consumable, a device-related therapy, a surgical operation, a psychological-associated therapy, and a behavior modification therapy.

2. The method of claim 1,
   wherein the at least one female reproductive system-related condition further comprises an HPV infection,
   wherein the set of microbiome composition features further comprises a second subset of microbiome features associated with a set of HPV targets;
   wherein the set of bacterial targets comprises at least one of *Aerococcus* (genus), *Aerococcus christensenii* (species), *Atopobium* (genus), *Atopobium vaginae* (species), *Chlamydia trachomatis* (species), *Dialister micraerophilus* (species), *Fusobacterium* (genus), *Fusobacterium nucleatum* (species), *Gardnerella* (genus), *Gardnerella vaginalis* (species), *Gemella* (genus), *Lactobacillus* (genus), *Lactobacillus iners* (species), *Lactobacillus jensenii* (species), *Megasphaera* (genus), *Mobiluncus* (genus), *Mobiluncus curtisii* (species), *Mobiluncus mulieris* (species), *Mycoplasma genitalium* (species), *Neisseria gonorrhoeae* (species), *Papillibacter* (genus), *Parvimonas* (genus), *Peptoniphilus* (genus), *Peptostreptococcus* (genus), *Porphyromonas* (genus), *Prevotella* (genus), *Prevotella amnii* (species), *Prevotella timonensis* (species), *Sneathia* (genus), *Staphylococcus aureus* (species), *Streptococcus agalactiae* (species), and *Treponema pallidum* (species); and
   wherein the set of HPV targets comprises at least one of HPV types 6, 11, 42, 43, 44, 16, 18, 31, 33, 35, 39, 45, 51, 52, 56, 58, 59, 66, and 68.

3. The method of claim 1,
   wherein the supplementary data indicates a lack of the at least one female reproductive system-related condition for a subset of subjects from the set of subjects,
   wherein determining the set of microbiome features comprises determining healthy reference microbiome parameters ranges associated with the subset of subjects based on the microorganism sequence dataset, and
   wherein generating the female reproductive system-related characterization model comprises generating the female reproductive system-related characterization model based on the supplementary data and the healthy reference microbiome parameters ranges.

4. The method of claim 1,
   wherein the at least one female reproductive system-related condition comprises at least one of chlamydia, endometriosis, genital herpes, genital warts, gonorrhea, painful periods, polycystic ovarian syndrome, urinary tract infection, and yeast infection, and
   wherein the set of microbiome composition features is associated with at least one of: *Bacteroides* sp. AR20, *Bacteroides* sp. AR29, *Bacteroides* sp. D22, *Alistipes* sp. EBA6-25cl2, *Actinobacteria, Bacteroidales, Bacteroides, Bacteroidetes, Bacteroidia, Barnesiella, Barnesiella intestinihominis, Betaproteobacteria, Blautia luti, Blautia* sp. Ser8, *Burkholderiales, Clostridia, Clostridiales, Collinsella, Coriobacteriales, Dorea, Dorea longicatena, Eggerthella, Eisenbergiella tayi, Faecalibacterium prausnitzii, Flavobacteriales, Flavobacteriia, Fusicatenibacter saccharivorans, Lachnospira pectinoschiza,* Lactobacillaceae, *Megasphaera, Odoribacter,* Oscillospiraceae, *Roseburia, Roseburia* sp. 11SE39, Ruminococcaceae, *Sarcina, Subdoligranulum variabile,* Sutterellaceae, *Terrisporobacter, Bifidobacterium, Alistipes* sp. HGB5, *Anaerostipes* sp. 5_1_63FAA, *Bacteroides acidifaciens, Bacteroides thetaiotaomicron,* Bifidobacteriaceae, *Bifidobacteriales, Flavonifractor plautii, Fusicatenibacter, Hes-*

*pellia, Moryella, Negativicutes, Selenomonadales,* Veillonellaceae, *Alistipes* sp. RMA 9912, *Bacteroides caccae, Bacteroides vulgatus, Bilophila* sp. 4_1_30, *Intestinimonas,* Prevotellaceae, *Alistipes putredinis, Alistipes* sp. NML05A004, *Alphaproteobacteria, Bacilli,* Bacteroidaceae, *Bacteroides* sp. SLC1-38, *Blautia* sp. YHC-4, *Blautia stercoris, Blautia wexlerae, Butyricimonas,* Clostridiaceae, *Clostridium, Collinsella aerofaciens,* Coriobacteriaceae, *Coriobacteriia, Dielma, Dorea formicigenerans, Eggerthella* sp. HGA1, *Eisenbergiella, Faecalibacterium, Firmicutes,* Flavobacteriaceae, Lactobacillales, *Lactobacillus, Marvinbryantia, Odoribacter splanchnicus, Parabacteroides,* Porphyromonadaceae, *Rhodospirillales, Roseburia inulinivorans, Subdoligranulum,* Acidaminococcaceae, Actinomycetales, *Anaerococcus, Bacteroides* sp. EBA5-17, Corynebacteriaceae, *Corynebacteriales, Corynebacterium, Enterorhabdus, Erysipelatoclostridium,* Erysipelotrichaceae, *Erysipelotrichales, Erysipelotrichia, Oscillospira, Phascolarctobacterium, Proteobacteria, Sutterella wadsworthensis, Verrucomicrobiae,* and *Verrucomicrobiales.*

5. The method of claim 1, wherein providing the therapy comprises providing a recommendation for the therapy to the user at a computing device associated with the user.

6. A method for characterizing at least one female reproductive system-related condition associated with microorganisms, the method comprising:
   collecting a sample from a user, wherein the sample comprises microorganism nucleic acids corresponding to the microorganisms associated with the at least one female reproductive system-related condition;
   determining a microorganism dataset associated with the user based on the microorganism nucleic acids of the sample, the microorganism dataset including a microorganism sequence dataset usable for identifying microbiome features;
   determining user microbiome composition features based on the microorganism dataset, wherein the user microbiome composition features are associated with the at least one female reproductive system-related condition, the user microbiome composition features comprising a first subset of microbiome composition features associated with a set of bacterial targets;
   determining a female reproductive system-related characterization for the user for the at least one female reproductive system-related condition based on the user microbiome features; and
   facilitating, based on the female reproductive system-related characterization, therapeutic intervention in relation to a therapy for the user for facilitating improvement of the at least one female reproductive system-related condition, the being determined based on a therapy model and the user microbiome features,
   wherein the at least one female reproductive system-related condition comprises at least one of bacterial vaginosis, cervicitis, pelvic inflammatory disease, idiopathic infertility, aerobic vaginitis, and infertility,
   wherein the therapy comprises at least one of a consumable, a device-related therapy, a surgical operation, a psychological-associated therapy, and a behavior modification therapy.

7. The method of claim 6,
   wherein the at least one female reproductive system-related condition comprises an HPV infection;
   wherein the user microbiome composition features further comprises a second subset of user microbiome composition features associated with a set of HPV targets;
   wherein the set of bacterial targets comprises at least one of *Aerococcus* (genus), *Aerococcus christensenii* (species), *Atopobium* (genus), *Atopobium vaginae* (species), *Chlamydia trachomatis* (species), *Dialister micraerophilus* (species), *Fusobacterium* (genus), *Fusobacterium nucleatum* (species), *Gardnerella* (genus), *Gardnerella vaginalis* (species), *Gemella* (genus), *Lactobacillus* (genus), *Lactobacillus iners* (species), *Lactobacillus jensenii* (species), *Megasphaera* (genus), *Mobiluncus* (genus), *Mobiluncus curtisii* (species), *Mobiluncus mulieris* (species), *Mycoplasma genitalium* (species), *Neisseria gonorrhoeae* (species), *Papillibacter* (genus), *Parvimonas* (genus), *Peptoniphilus* (genus), *Peptostreptococcus* (genus), *Porphyromonas* (genus), *Prevotella* (genus), *Prevotella amnii* (species), *Prevotella timonensis* (species), *Sneathia* (genus), *Staphylococcus aureus* (species), *Streptococcus agalactiae* (species), and *Treponema pallidum* (species); and
   wherein the set of HPV targets comprises at least one of HPV types 6, 11, 42, 43, 44, 16, 18, 31, 33, 35, 39, 45, 51, 52, 56, 58, 59, 66, and 68.

8. The method of claim 6,
   wherein the at least one female reproductive system-related condition comprises at least one of chlamydia, endometriosis, genital herpes, genital warts, gonorrhea, painful periods, polycystic ovarian syndrome, urinary tract infection, and yeast infection, and
   wherein the user microbiome composition features are associated with at least one of: *Bacteroides* sp. AR20, *Bacteroides* sp. AR29, *Bacteroides* sp. D22, *Alistipes* sp. EBA6-25cl2, *Actinobacteria,* Bacteroidales, *Bacteroides, Bacteroidetes, Bacteroidia, Barnesiella, Barnesiella intestinihominis, Betaproteobacteria, Blautia luti, Blautia* sp. Ser8, Burkholderiales, *Clostridia,* Clostridiales, *Collinsella,* Coriobacteriales, *Dorea, Dorea longicatena, Eggerthella, Eisenbergiella tayi, Faecalibacterium prausnitzii,* Flavobacteriales, *Flavobacteriia, Fusicatenibacter saccharivorans, Lachnospira pectinoschiza,* Lactobacillaceae, *Megasphaera, Odoribacter,* Oscillospiraceae, *Roseburia, Roseburia* sp. 11SE39, Ruminococcaceae, *Sarcina, Subdoligranulum variabile,* Sutterellaceae, *Terrisporobacter, Bifidobacterium, Alistipes* sp. HGB5, *Anaerostipes* sp. 5_1_63FAA, *Bacteroides acidifaciens, Bacteroides thetaiotaomicron,* Bifidobacteriaceae, Bifidobacteriales, *Flavonifractor plautii, Fusicatenibacter, Hespellia, Moryella, Negativicutes, Selenomonadales,* Veillonellaceae, *Alistipes* sp. RMA 9912, *Bacteroides caccae, Bacteroides vulgatus, Bilophila* sp. 4_1_30, *Intestinimonas,* Prevotellaceae, *Alistipes putredinis, Alistipes* sp. NML05A004, *Alphaproteobacteria, Bacilli,* Bacteroidaceae, *Bacteroides* sp. SLC1-38, *Blautia* sp. YHC-4, *Blautia stercoris, Blautia wexlerae, Butyricimonas,* Clostridiaceae, *Clostridium, Collinsella aerofaciens,* Coriobacteriaceae, *Coriobacteriia, Dielma, Dorea formicigenerans, Eggerthella* sp. HGA1, *Eisenbergiella, Faecalibacterium, Firmicutes,* Flavobacteriaceae, Lactobacillales, *Lactobacillus, Marvinbryantia, Odoribacter splanchnicus, Parabacteroides,* Porphyromonadaceae, *Rhodospirillales, Roseburia inulinivorans, Subdoligranulum,* Acidaminococcaceae, Actinomycetales, *Anaerococcus, Bacteroides* sp. EBA5-17, Corynebacteriaceae, *Corynebac-*

*teriales, Corynebacterium, Enterorhabdus, Erysipelatoclostridium*, Erysipelotrichaceae, *Erysipelotrichales*, Erysipelotrichia, *Oscillospira, Phascolarctobacterium*, Proteobacteria, *Sutterella wadsworthensis*, Verrucomicrobiae, Verrucomicrobiales.

9. The method of claim 8,
wherein the at least one female reproductive system-related condition comprises at least one of endometriosis, urinary tract infection, and yeast infection, and
wherein the user microbiome composition features is associated with at least one of: *Actinobacteria, Alistipes* sp. EBA6-25cl2, *Bacteroidales, Bacteroides, Bacteroides* sp. AR20, *Bacteroides* sp. AR29, *Bacteroides* sp. D22, *Bacteroidetes, Bacteroidia, Barnesiella, Barnesiella intestinihominis, Betaproteobacteria, Blautia luti, Blautia* sp. Ser8, *Burkholderiales, Clostridia, Clostridiales, Collinsella, Coriobacteriales, Dorea, Dorea longicatena, Eggerthella, Eisenbergiella tayi, Faecalibacterium prausnitzii, Flavobacteriales, Flavobacteriia, Fusicatenibacter saccharivorans, Lachnospira pectinoschiza*, Lactobacillaceae, *Megasphaera, Odoribacter*, Oscillospiraceae, *Roseburia, Roseburia* sp. 11SE39, Ruminococcaceae, *Sarcina, Subdoligranulum variabile*, Sutterellaceae, *Terrisporobacter*, Acidaminococcaceae, *Actinomycetales, Anaerococcus, Anaerostipes* sp. 5_1_63FAA, *Bacilli*, Bacteroidaceae, *Bacteroides* sp. EBA5-17, *Bacteroides* sp. SLC1-38, *Bacteroides thetaiotaomicron*, Bifidobacteriaceae, *Bifidobacteriales, Bifidobacterium, Blautia* sp. YHC-4, *Butyricimonas*, Clostridiaceae, *Collinsella aerofaciens*, Coriobacteriaceae, *Coriobacteriia*, Corynebacteriaceae, *Corynebacteriales, Corynebacterium, Dorea formicigenerans, Eisenbergiella, Enterorhabdus, Erysipelatoclostridium*, Erysipelotrichaceae, *Erysipelotrichales, Erysipelotrichia, Firmicutes, Flavonifractor plautii, Fusicatenibacter, Hespellia*, Lactobacillales, *Lactobacillus, Marvinbryantia, Moryella, Negativicutes, Odoribacter splanchnicus, Oscillospira, Parabacteroides, Phascolarctobacterium*, Prevotellaceae, *Proteobacteria, Roseburia inulinivorans, Selenomonadales, Subdoligranulum, Sutterella wadsworthensis*, Veillonellaceae, *Verrucomicrobiae*, and *Verrucomicrobiales*.

10. The method of claim 8,
wherein the at least one female reproductive system-related condition comprises at least one of painful periods and polycystic ovarian syndrome, and
wherein the user microbiome composition features are associated with at least one of: *Actinobacteria, Alistipes putredinis, Alistipes* sp. EBA6-25cl2, *Alistipes* sp. NML05A004, *Alphaproteobacteria, Anaerostipes* sp. 5_1_63FAA, *Bacilli*, Bacteroidaceae, *Bacteroidales, Bacteroides, Bacteroides caccae, Bacteroides* sp. AR20, *Bacteroides* sp. AR29, *Bacteroides* sp. D22, *Bacteroides* sp. SLC1-38, *Bacteroides thetaiotaomicron, Bacteroidetes, Bacteroidia, Barnesiella intestinihominis, Blautia luti, Blautia* sp. Ser8, *Blautia* sp. YHC-4, *Blautia stercoris, Blautia wexlerae, Butyricimonas, Clostridia*, Clostridiaceae, *Clostridiales, Clostridium, Collinsella, Collinsella aerofaciens*, Coriobacteriaceae, *Coriobacteriales, Coriobacteriia, Dielma, Dorea formicigenerans, Dorea longicatena, Eggerthella, Eggerthella* sp. HGA1, *Eisenbergiella, Eisenbergiella tayi, Faecalibacterium, Faecalibacterium prausnitzii, Firmicutes*, Flavobacteriaceae, *Flavobacteriales, Flavobacteriia, Flavonifractor plautii, Fusicatenibacter, Fusicatenibacter saccharivorans, Hespellia, Lachnospira pectinoschiza*, Lactobacillaceae, Lactobacillales, *Lactobacillus, Marvinbryantia, Megasphaera, Moryella, Odoribacter, Odoribacter splanchnicus*, Oscillospiraceae, *Parabacteroides*, Porphyromonadaceae, *Rhodospirillales, Roseburia inulinivorans, Roseburia* sp. 11SE39, Ruminococcaceae, *Sarcina, Selenomonadales, Subdoligranulum, Subdoligranulum variabile*, and *Terrisporobacter*.

11. The method of claim 8,
wherein the at least one female reproductive system-related condition comprises at least one of chlamydia, genital herpes, genital warts, and gonorrhea, and
wherein the user microbiome composition features are associated with at least one of: *Bifidobacterium, Actinobacteria, Alistipes* sp. HGB5, *Anaerostipes* sp. 5_1_63FAA, *Bacteroides acidifaciens, Bacteroides thetaiotaomicron*, Bifidobacteriaceae, *Bifidobacteriales, Blautia luti, Faecalibacterium prausnitzii, Flavonifractor plautii, Fusicatenibacter, Fusicatenibacter saccharivorans, Hespellia, Lachnospira pectinoschiza, Moryella*, Oscillospiraceae, *Roseburia* sp. 11SE39, *Subdoligranulum variabile, Clostridia, Clostridiales, Negativicutes, Selenomonadales*, Veillonellaceae, *Alistipes* sp. RMA 9912, *Bacteroides caccae, Bacteroides vulgatus, Bilophila* sp. 4_1_30, *Intestinimonas*, and Prevotellaceae.

12. The method of claim 6, wherein the therapy comprises at least one of a consumable, a device-related therapy, a surgical operation, a psychological-associated therapy, and a behavior modification therapy, and wherein facilitating therapeutic intervention comprises providing a recommendation for the therapy to the user at a computing device associated with the user.

13. A method for characterizing at least one female reproductive system-related condition associated with microorganisms, the method comprising:
collecting a sample from a user, wherein the sample comprises microorganism nucleic acids corresponding to the microorganisms associated with the at least one female reproductive system-related condition;
determining a microorganism dataset associated with the user based on the microorganism nucleic acids of the sample, the microorganism dataset including a microorganism sequence dataset usable for identifying microbiome features;
determining user microbiome features based on the microorganism dataset, wherein the user microbiome features are associated with the at least one female reproductive system-related condition, the user microbiome composition features comprising a first subset of microbiome composition features associated with a set of bacterial targets; and
determining a female reproductive system-related characterization for the user for the at least one female reproductive system-related condition based on the user microbiome features; and
facilitating a therapy for the user for the at least one female reproductive system-related condition, the therapy being determined based on a therapy model and the user microbiome features,
wherein the at least one female reproductive system-related condition comprises at least one of bacterial vaginosis, cervicitis, pelvic inflammatory disease, idiopathic infertility, aerobic vaginitis, and infertility, wherein the therapy comprises at least one of a consumable, a device-related therapy, a surgical operation, a psychological-associated therapy, and a behavior modification therapy.

14. The method of claim 13, wherein determining the microorganism dataset comprises:
performing first primer-based amplification for bacterial targets associated with the at least one female reproductive system-related condition; and
performing second primer-based amplification for HPV targets associated with the at least one female reproductive system-related condition.

15. The method of claim 14, wherein the HPV targets comprise at least one of HPV types 42, 39, 56, 35, 66, 33, and 42, and wherein performing the second primer-based amplification for the HPV targets comprises performing the second primer-based amplification with at least one of a first HPV-associated primer and a second HPV-associated primer, wherein the first HPV-associated primer comprises a first primer sequence comprising CGTCCTAAAGGGAATTGATC (SEQ ID NO: 78), and wherein the second HPV-associated primer comprises a second primer sequence comprising GCACAAGGCCATAATAATGG (SEQ ID NO: 63).

16. The method of claim 14,
wherein performing the second primer-based amplification for the HPV targets comprises performing the second primer-based amplification with a set of components comprising:
a set of primers associated with the L1 protein of the HPV targets, and
a set of synthetic dsDNA spike molecules of known concentration and comprising known scrambled nucleotide sequences with similar ATGC composition to at least one sequence region of the HPV targets;
wherein the user microbiome features comprise at least one ratio of sequencing reads between the HPV targets and the set of synthetic dsDNA spike molecules; and
wherein determining the female reproductive system-related characterization comprises determining the female reproductive system-related characterization for the user for the at least one female reproductive system-related condition based on the at least one ratio of sequencing reads between the HPV targets and the set of synthetic dsDNA spike molecules.

17. The method of claim 13, wherein the at least one female reproductive system-related condition is associated with bacterial targets and HPV targets, and wherein determining the microorganism dataset comprises:
determining a first set of processed sequence reads associated with the bacterial targets based on filtering of a first set of sequence reads derived from the microorganism nucleic acids; and
determining a second set of processed sequence reads associated with the HPV targets based on filtering of a second set of sequence reads derived from the microorganism nucleic acids,
wherein determining the user microbiome features comprises determining the user microbiome features based on the first and the second set of processed sequence reads.

18. The method of claim 17, wherein determining the user microbiome features comprises:
determining first alignment data based on alignment of the first set of processed sequence reads to 16S rRNA gene sequences associated with the bacterial targets;
determining second alignment data based on alignment of the second set of processed sequence reads to HPV sequences associated with the HPV targets; and
determining the user microbiome features based on the first and the second alignment data.

19. The method of claim 13,
wherein the at least one female reproductive system-related condition comprises an HPV infection and at least one of bacterial vaginosis, cervicitis, pelvic inflammatory disease, idiopathic infertility, aerobic vaginitis, and infertility,
wherein the user microbiome features comprises a first subset of user microbiome features associated with a set of bacterial targets, and a second subset of user microbiome features associated with a set of HPV targets,
wherein the set of bacterial targets comprises at least one of *Aerococcus* (genus), *Aerococcus christensenii* (species), *Atopobium* (genus), *Atopobium vaginae* (species), *Chlamydia trachomatis* (species), *Dialister micraerophilus* (species), *Fusobacterium* (genus), *Fusobacterium nucleatum* (species), *Gardnerella* (genus), *Gardnerella vaginalis* (species), *Gemella* (genus), *Lactobacillus* (genus), *Lactobacillus iners* (species), *Lactobacillus jensenii* (species), *Megasphaera* (genus), *Mobiluncus* (genus), *Mobiluncus curtisii* (species), *Mobiluncus mulieris* (species), *Mycoplasma genitalium* (species), *Neisseria gonorrhoeae* (species), *Papillibacter* (genus), *Parvimonas* (genus), *Peptoniphilus* (genus), *Peptostreptococcus* (genus), *Porphyromonas* (genus), *Prevotella* (genus), *Prevotella amnii* (species), *Prevotella timonensis* (species), *Sneathia* (genus), *Staphylococcus aureus* (species), *Streptococcus agalactiae* (species), and *Treponema pallidum* (species), and
wherein the set of HPV targets comprises at least one of HPV types 6, 11, 42, 43, 44, 16, 18, 31, 33, 35, 39, 45, 51, 52, 56, 58, 59, 66, and 68.

20. The method of claim 19, wherein the set of bacterial targets comprises at least one of *Actinomyces* (genus), *Alloiococcus* (genus), *Anaerococcus* (genus), *Anaeroglobus* (genus), *Anaerostipes* (genus), *Anaerotruncus* (genus), *Arcanobacterium* (genus), *Arthrospira* (genus), *Bacteroides* (genus), *Bulleidia* (genus), *Campylobacter* (genus), *Catenibacterium* (genus), Coriobacteriaceae (family), *Corynebacterium* (genus), *Dialister* (genus), *Eggerthella* (genus), *Enterococcus* (genus), *Escherichia* (genus), *Finegoldia* (genus), Lactobacillaceae (family), Lactobacillales (order), *Leptotrichia* (genus), *Moryella* (genus), *Mycoplasma* (genus), *Peptococcus* (genus), Porphyromonadaceae (family), Prevotellaceae (family), *Pseudomonas* (genus), *Ruminococcus* (genus), *Segniliparus* (genus), *Shigella* (genus), *Staphylococcus* (genus), *Streptococcus* (genus), *Treponema* (genus), *Ureaplasma* (genus), *Veillonella* (genus), Veillonellaceae (family), *Aerococcus* spp. (genus), *Algoriphagus aquatilis* (species), *Anaerococcus* spp. (genus), *Anaerococcus tetradius* (species), *Anaerococcus vaginalis* (species), *Anoxybacillus pushchinoensis* (species), *Atopobium* spp. (genus), *Bacteroides fragilis* (species), *Bacteroides* spp. (genus), *Bifidobacterium animalis* subsp. *lactis* (species), *Bifidobacterium dentium* (species), *Bifidobacterium lactis* (species), *Bifidobacterium longum* subsp. *suis* (species), *Bulleidia extructa* (species), *Burkholderia fungorum* (species), *Burkholderia phenoliruptrix* (species), *Caldicellulosiruptor saccharolyticus* (species), *Campylobacter* spp. (genus), *Campylobacter ureolyticus* (species), *Candida albicans* (species), *Candida glabrata* (species), *Candida* krusei (species), Candida lusitaniae (species), Candidatus Mycoplasma girerdii (species), Catenibacterium spp. (genus), Chondromyces robustus (species), Clostridiales BVAB2 (species), Clostridiales BVAB3 (species), Clostridium cavendishii (species), Clostridium viride (species), Cryobacterium psychrophilum (species), Dickeya chrysanthemi (species), Eggerthia catenaformis (species), Erwinia chrysanthemi (species), Escherichia coli (species), Escherichia fergusonii (species), Exiguobacterium acetylicum (species), Fusobacterium spp. (genus), Gardnerella spp. (genus), Gemella sp. (genus), Haemophilus ducreyi (species), Klebsiella granulomatis (species), Lachnospiraceae BVAB1 (species), Lactobacillus acidophilus (species), Lactobacillus brevis (species), Lactobacillus casei (species), Lactobacillus casei Shirota (species), Lactobacillus crispatus (species), Lactobacillus delbrueckii (species), Lactobacillus fermentum (species), Lactobacillus gasseri (species), Lactobacillus johnsonii (species), Lactobacillus kefiranofaciens (species), Lactobacillus paracasei FJ861111.1 (species), Lactobacillus pentosus strain S-PT84 (species), Lactobacillus plantarum (species), Lactobacillus reuteri (species), Lactobacillus reuteri RC-14 (species), Lactobacillus rhamnosus (species), Lactobacillus rhamnosus (strain BMX 54) (species), Lactobacillus rhamnosus BMX 54 (species), Lactobacillus rhamnosus GR-1 (species), Lactobacillus salivarius (species), Lactobacillus vaginalis (species), Leptotrichia spp. (genus), Maribacter orientalis (species), Megasphaera genomosp (species), Megasphaera micronuciformis (species), Megasphaera spp. (genus), Microbacterium halophilum (species), Moorella glycerini (species), Mycoplasma hominis (species), Mycoplasma muris (species), Paeniclostridium sordellii (species), Papillibacter spp. (genus), Parastreptomyces abscessus (species), Parvimonas micra (species), Parvimonas spp. (genus), Pasteurella multocida (species), Pediococcus ethanolidurans (species), Peptoniphilus harei (species), Peptoniphilus indolicus (species), Peptoniphilus spp. (genus), Peptostreptococcus anaerobius (species), Peptostreptococcus massiliae (species), Peptostreptococcus spp. (genus), Porphyromonas gingivalis (species), Porphyromonas levii (species), Porphyromonas sp. (genus), Porphyromonas uenonis (species), Prevotella bivia (species), Prevotella disiens (species), Prevotella intermedia (species), Prevotella oralis (species), Prevotella oris (species), Pseudomonas spp. (genus), Ralstonia pickettii (species), Ruminococcus spp. (genus), Sanguibacter keddieii (species), Sneathia amnii (species), Sneathia sanguinegens (species), Sneathia spp. (genus), Staphylococcus mulans (species), Staphylococcus pasteuri (species), Staphylococcus simiae (species), Staphylococcus simulans (species), Staphylococcus spp. (genus), Staphylococcus warneri (species), Streptococcus anginosus (species), Streptococcus intermedius (species), Streptococcus pyogenes (species), Streptococcus viridans (species), Thermosipho atlanticus (species), Thermovirga lienii (species), Trichomonas vaginalis (species), Trueperella bernardiae (species), Ureaplasma parvum (species), Ureaplasma urealyticum (species), Veillonella montpellierensis (species), Veillonella parvula (species), Virgibacillus proomii (species), and Zobellia laminariae (species).

21. The method of claim 13,
wherein the at least one female reproductive system-related condition comprises at least one of chlamydia, endometriosis, genital herpes, genital warts, gonorrhea, painful periods, polycystic ovarian syndrome, urinary tract infection, and yeast infection, and
wherein the user microbiome features are associated with at least one of: *Bacteroides* sp. AR20, *Bacteroides* sp. AR29, *Bacteroides* sp. D22, *Alistipes* sp. EBA6-25cl2, *Actinobacteria*, *Bacteroidales*, *Bacteroides*, *Bacteroidetes*, *Bacteroidia*, *Barnesiella*, *Barnesiella intestinihominis*, *Betaproteobacteria*, *Blautia luti*, *Blautia* sp. Ser8, *Burkholderiales*, *Clostridia*, *Clostridiales*, *Collinsella*, *Coriobacteriales*, *Dorea*, *Dorea longicatena*, *Eggerthella*, *Eisenbergiella tayi*, *Faecalibacterium prausnitzii*, *Flavobacteriales*, *Flavobacteriia*, *Fusicatenibacter saccharivorans*, *Lachnospira pectinoschiza*, Lactobacillaceae, *Megasphaera*, *Odoribacter*, Oscillospiraceae, *Roseburia*, *Roseburia* sp. 11SE39, Ruminococcaceae, *Sarcina*, *Subdoligranulum variabile*, Sutterellaceae, *Terrisporobacter*, *Bifidobacterium*, *Alistipes* sp. HGB5, *Anaerostipes* sp. 5_1_63FAA, *Bacteroides acidifaciens*, *Bacteroides thetaiotaomicron*, Bifidobacteriaceae, *Bifidobacteriales*, *Flavonifractor plautii*, *Fusicatenibacter*, *Hespellia*, *Moryella*, *Negativicutes*, *Selenomonadales*, Veillonellaceae, *Alistipes* sp. RMA 9912, *Bacteroides caccae*, *Bacteroides vulgatus*, *Bilophila* sp. 4_1_30, *Intestinimonas*, Prevotellaceae, *Alistipes putredinis*, *Alistipes* sp. NML05A004, *Alphaproteobacteria*, *Bacilli*, Bacteroidaceae, *Bacteroides* sp. SLC1-38, *Blautia* sp. YHC-4, *Blautia stercoris*, *Blautia wexlerae*, *Butyricimonas*, Clostridiaceae, *Clostridium*, *Collinsella aerofaciens*, Coriobacteriaceae, *Coriobacteriia*, *Dielma*, *Dorea formicigenerans*, *Eggerthella* sp. HGA1, *Eisenbergiella*, *Faecalibacterium*, *Firmicutes*, Flavobacteriaceae, Lactobacillales, *Lactobacillus*, *Marvinbryantia*, *Odoribacter splanchnicus*, *Parabacteroides*, Porphyromonadaceae, *Rhodospirillales*, *Roseburia inulinivorans*, *Subdoligranulum*, Acidaminococcaceae, *Actinomycetales*, *Anaerococcus*, *Bacteroides* sp. EBA5-17, Corynebacteriaceae, *Corynebacteriales*, *Corynebacterium*, *Enterorhabdus*, *Erysipelatoclostridium*, Erysipelotrichaceae, *Erysipelotrichales*, *Erysipelotrichia*, *Oscillospira*, *Phascolarctobacterium*, *Proteobacteria*, *Sutterella wadsworthensis*, *Verrucomicrobiae*, *Verrucomicrobiales*.

22. The method of claim 21, wherein the sample is associated with a gut site, wherein the user microbiome features comprise site-specific composition features associated with the gut site, and wherein the site-specific composition features are associated with at least one of: *Bacteroides* sp. AR20, *Bacteroides* sp. AR29, *Bacteroides* sp. D22, *Alistipes* sp. EBA6-25cl2, *Actinobacteria*, *Bacteroidales*, *Bacteroides*, *Bacteroidetes*, *Bacteroidia*, *Barnesiella*, *Barnesiella intestinihominis*, *Betaproteobacteria*, *Blautia luti*, *Blautia* sp. Ser8, *Burkholderiales*, *Clostridia*, *Clostridiales*, *Collinsella*, *Coriobacteriales*, *Dorea*, *Dorea longicatena*, *Eggerthella*, *Eisenbergiella tayi*, *Faecalibacterium prausnitzii*, *Flavobacteriales*, *Flavobacteriia*, *Fusicatenibacter saccharivorans*, *Lachnospira pectinoschiza*, Lactobacillaceae, *Megasphaera*, *Odoribacter*, Oscillospiraceae, *Roseburia*, *Roseburia* sp. 11SE39, Ruminococcaceae, *Sarcina*, *Subdoligranulum variabile*, Sutterellaceae, *Terrisporobacter*, *Bifidobacterium*, *Alistipes* sp. HGB5, *Anaerostipes* sp. 5_1_63FAA, *Bacteroides acidifaciens*, *Bacteroides thetaiotaomicron*, Bifidobacteriaceae, *Bifidobacteriales*, *Flavonifractor plautii*, *Fusicatenibacter*, *Hespellia*, *Moryella*, *Negativicutes*, *Selenomonadales*, Veillonellaceae, *Alistipes* sp. RMA 9912, *Bacteroides caccae*, *Bacteroides vulgatus*, *Bilophila* sp. 4_1_30, *Intestinimonas*, Prevotellaceae, *Alistipes putredinis*, *Alistipes* sp. NML05A004, *Alphaproteobacteria*, Bacteroidaceae, *Bacteroides* sp. SLC1-38, *Blautia* sp. YHC-4, *Blautia stercoris*, *Blautia wexlerae*, *Butyricimonas*, Clostridiaceae,

*Clostridium, Collinsella aerofaciens,* Coriobacteriaceae, *Coriobacteriia, Dielma, Dorea formicigenerans, Eggerthella* sp. HGA1, *Eisenbergiella, Faecalibacterium, Flavobacteriaceae, Lactobacillus, Marvinbryantia, Odoribacter splanchnicus, Parabacteroides, Rhodospirillales, Roseburia inulinivorans, Subdoligranulum,* Acidaminococcaceae, *Bacteroides* sp. EBA5-17, Corynebacteriaceae, *Corynebacteriales, Corynebacterium, Enterorhabdus, Erysipelatoclostridium,* Erysipelotrichaceae, *Erysipelotrichales, Erysipelotrichia, Firmicutes, Oscillospira, Phascolarctobacterium, Proteobacteria, Sutterella wadsworthensis, Verrucomicrobiae,* and *Verrucomicrobiales.*

23. The method of claim 21, wherein the sample is associated with a body site comprising at least one of a skin site, a genital site, a mouth site, and a nose site, wherein the user microbiome features comprise site-specific composition features associated with the body site, and wherein the site-specific composition features are associated with at least one of: *Actinobacteria, Bacilli, Firmicutes,* Lactobacillaceae, Lactobacillales, *Lactobacillus,* Porphyromonadaceae, *Bacteroidales, Bacteroidia, Actinomycetales, Anaerococcus,* Corynebacteriaceae, *Corynebacteriales,* and *Corynebacterium.*

\* \* \* \* \*

SEQUENCE LISTING

<160> NUMBER OF SEQ ID NOS: 86

<210> SEQ ID NO 1
<211> LENGTH: 442
<212> TYPE: DNA
<213> ORGANISM: Artificial Sequence
<220> FEATURE:
<223> OTHER INFORMATION: Synthetic construct

<400> SEQUENCE: 1
tataagagaa gaacaaattg tagagtaact gctacagtct tgacggtatc ttatcagaaa     60

```
gccacggcta actacgtgcc agcagccgcg gtaatacgta ggtggcaagc gttgtccgga      120
tttattgggc gtaaagggag cgcaggtggt ttcttaagtc tgatgtgaaa gcccacggct      180
taaccgtgga gggtcattgg aaactgggaa acttgagtac agaagaggaa tgtggaactc      240
catgtgtagc ggtggaatgc gtagatatat ggaagaacac cagtggcgaa ggcgacattc      300
tggtctgtta ctgacactga ggctcgaaag cgtggggagc aaacaggatt agataccctg      360
gtagtccacg ccgtaaacga tgagtgctag gtgttggagg gtttccgccc ttcagtgccg      420
cagttaacgc attaagcact cc                                              442
```

```
<210> SEQ ID NO 2
<211> LENGTH: 442
<212> TYPE: DNA
<213> ORGANISM: Artificial Sequence
<220> FEATURE:
<223> OTHER INFORMATION: Synthetic construct

<400> SEQUENCE: 2
tgtaagagaa gaacaaattg tagagtaact gctacagtct tgacggtatc ttaccagaaa       60
gccacggcta actacgtgcc agcagccgcg gtaatacgta ggtggcaagc gttgtccgga      120
tttattgggc gtaaaggggg cgcaggctgc ttcttaagtc tgatgtgaaa gcccacggct      180
taaccgtgga agtgcattgg aaactgggaa gcttgagtac agaagaggaa agtggaactc      240
catgtgtagc ggtggaatgc gtagatatat ggaagaacac cagtggcgaa agcgactttc      300
tggtctgtca ctgacgctga ggcccgaaag cgtgggtagc aaacaggatt agataccctg      360
gtagtccacg ccgtaaacga tgagcgctag gtgttggagg gtttccaccc ttcagtgccg      420
cagctaacgc attaagcgct cc                                              442
```

```
<210> SEQ ID NO 3
<211> LENGTH: 441
<212> TYPE: DNA
<213> ORGANISM: Artificial Sequence
<220> FEATURE:
<223> OTHER INFORMATION: Synthetic construct

<400> SEQUENCE: 3
ttcgggttgt aaaccgcttt cagcagggac gaggcgaaag tgacggtacc tgcagaagaa       60
gccccggcta actacgtgcc agcagccgcg gtaatacgta gggggcaagc gttatccgga      120
ttcattgggc gtaaagcgct cgtaggcggt ctgttaggtc gggagttaaa tccggggct       180 caaccccgc tcgctcccga taccggcaga cttgagtttg gtaggggaag gtggaattcc       240
tagtgtagcg gtgaatgcg cagatattag gaagaacacc agtggcgaag gcggccttct       300
gggccataac tgacgctgag gagcgaaagc taggggagca aacaggatta gataccctgg      360
tagtcctagc cgtaaacgat ggacactagg tgtgggggaa tatttcttcc gtgccgcagc      420
taacgcatta agtgtcccgc c                                              441
```

```
<210> SEQ ID NO 4
<211> LENGTH: 441
<212> TYPE: DNA
<213> ORGANISM: Artificial Sequence
<220> FEATURE:
<223> OTHER INFORMATION: Synthetic construct

<400> SEQUENCE: 4
cgggttgtaa accgctttca gcagggacca ggccgcaagg tgacggtacc tgcacaagaa       60
```

```
gccccggcta actacgtgcc agcagccgcg gtaatacgta gggggcaagc gttatccgga    120
ttcattgggc gtaaagcgcg cgtaggcggt ctgttaggtc aggagttaaa tctgggggct    180 caaccccta ccgctcctga taccggcagg cttgagtctg gtaggggaag atggaattcc     240
aagtgtagcg gtgaaatgcg cagatatttg gaagaacacc ggtggcgaag gcggtcttct    300
gggccatgac tgacgctgag gcgcgaaagc taggggagcg aacaggatta gatacctgg    360 tagtcctacc tgtaaacgat ggacactagg tgtggggaga ttatactttc cgtgccgcag    420
ctaacgcatt aagtgtcccg c                                              441
```

```
<210> SEQ ID NO 5
<211> LENGTH: 442
<212> TYPE: DNA
<213> ORGANISM: Artificial Sequence
<220> FEATURE:
<223> OTHER INFORMATION: Synthetic construct

<400> SEQUENCE: 5
cgcttgggaa taagagaagg cggttaatac ccgctggatt tgagcgtacc aggtaaagaa    60
gcaccggcta actccgtgcc agcagctgcg gtaatacgga gggtgctagc gttaatcgga    120
tttattgggc gtaaagggcg tgtaggcgga aaggtaagtt agttgtcaaa gatcggggct    180
caaccccgag tcggcatcta atactatttt tctagagggt agatggagaa aagggaattt    240
cacgtgtagc ggtgaaatgc gtagatatgt ggaagaacac cagtggcgaa ggcgcttttc    300
taatttatac ctgacgctaa ggcgcgaaag caagggagc aaacaggatt agatacctg     360 gtagtccttg ccgtaaacga tgcatacttg atgtggatgg tctcaacccc atccgtgtcg    420
gagctaacgc gttaagtatg cc                                             442
```

```
<210> SEQ ID NO 6
<211> LENGTH: 441
<212> TYPE: DNA
<213> ORGANISM: Artificial Sequence
<220> FEATURE:
<223> OTHER INFORMATION: Synthetic construct

<400> SEQUENCE: 6
gattcgggac gaaaggccat atgtgaataa tatatggaaa tgacggtacc gaaaaagcaa    60
gccacggcta actacgtgcc agcagccgcg gtaatacgta ggtggcaagc gttgtccgga    120
attattgggc gtaaagcgcg cgcaggcggt cacttaagtc catcttagaa gtgcgggct    180 taaccccgtg atgggatgga aactgggaga ctggagtatc ggagaggaaa gtggaattcc    240
tagtgtagcg gtgaaatgcg tagatattag gaagaacacc ggtggcgaag gcgactttct    300
ggacgaaaac tgacgctgag gcgcgaaagc gtggggagca acaggatta gatacctgg     360 tagtccacgc cgtaaacgat ggatactagg tgtaggaggt atcgacccct tctgtgccgg    420
agttaacgca ataagtatcc c                                              441
```

```
<210> SEQ ID NO 7
<211> LENGTH: 441
<212> TYPE: DNA
<213> ORGANISM: Artificial Sequence
<220> FEATURE:
<223> OTHER INFORMATION: Synthetic construct

<400> SEQUENCE: 7
ttttcggaat gtaaagtgct ttcagttggg aagaaagaaa tgacggtacc aacagaagaa    60
gtgacggcta aatacgtgcc agcagccgcg gtaatacgta tgtcacgagc gttatccgga    120
```

| | |
|---|---|
| tttattgggc gtaaagcgcg tctaggtggt tatgtaagtc tgatgtgaaa atgcagggct | 180 |
| caactctgta ttgcgttgga aactgtataa ctagagtact ggagaggtaa gcggaactac | 240 |
| aagtgtagag gtgaaattcg tagatatttg taggaatgcc gatggggaag ccagcttact | 300 |
| ggacagatac tgacgctaaa gcgcgaaagc gtgggtagca aacaggatta gatacctgg | 360 |
| tagtccacgc tgtaaacgat gattactagg tgttgggggt cgaacctcag cgcccaagca | 420 |
| aacgcgataa gtaatccgcc t | 441 |

<210> SEQ ID NO 8
<211> LENGTH: 441
<212> TYPE: DNA
<213> ORGANISM: Artificial Sequence
<220> FEATURE:
<223> OTHER INFORMATION: Synthetic construct

<400> SEQUENCE: 8

| | |
|---|---|
| ttttcggaat gtaaagtgct ttcagttggg aagaaaaaaa tgacggtacc aacagaagaa | 60 |
| gtgacggcta aatacgtgcc agcagccgcg gtaatacgta tgtcacgagc gttatccgga | 120 |
| tttattgggc gtaaagcgcg tctaggtggt tatataagtc tgatgtgaaa atgcagggct | 180 |
| caactctgta ttgcgttgga aactgtataa ctagagtact ggagaggtaa gcggaactac | 240 |
| aagtgtagag gtgaaattcg tagatatttg taggaatgcc gatggggaag ccagcttact | 300 |
| ggacagatac tgacgctgaa gcgcgaaagc gtgggtagca aacaggatta gatacctgg | 360 |
| tagtccacgc cgtaaacgat gattactagg tgttgggggt cgaacctcag cgcccaagca | 420 |
| aacgcgataa gtaatccgcc t | 441 |

<210> SEQ ID NO 9
<211> LENGTH: 442
<212> TYPE: DNA
<213> ORGANISM: Artificial Sequence
<220> FEATURE:
<223> OTHER INFORMATION: Synthetic construct

<400> SEQUENCE: 9

| | |
|---|---|
| gggttgtaaa ccgcttttga ttgggagcaa gccttttggg tgagtgtacc tttcgaataa | 60 |
| gcgccggcta actacgtgcc agcagccgcg gtaatacgta gggcgcaagc gttatccgga | 120 |
| attattgggc gtaaagagct tgtaggcggt tcgtcgcgtc tggtgtgaaa gcccatcgct | 180 |
| taacggtggg tttgcgccgg gtacgggcgg gctagagtgc agtaggggag actgaaattc | 240 |
| tcggtgtaac ggtggaatgt gtagatatcg gaagaacacc aatggcgaa ggcaggtctc | 300 |
| tgggctgtta ctgacgctga gaagcgaaag cgtgggagc gaacaggatt agataccctg | 360 |
| gtagtccacg ccgtaaacgg tggacgctgg atgtggggcc cattccacgg gttctgtgtc | 420 |
| ggagctaacg cgttaagcgt cc | 442 |

<210> SEQ ID NO 10
<211> LENGTH: 442
<212> TYPE: DNA
<213> ORGANISM: Artificial Sequence
<220> FEATURE:
<223> OTHER INFORMATION: Synthetic construct

<400> SEQUENCE: 10

| | |
|---|---|
| cgggttgtaa accgcttttg attgggagca agctttcggg tgagtgtacc tttcgaataa | 60 |
| gcgccggcta actacgtgcc agcagccgcg gtaatacgta gggcgcaagc gttatccgga | 120 |

```
attattgggc gtaaagagct tgtaggcggt tcgtcgcgtc tggtgtgaaa gcccatcgct    180
taacggtggg tttgcgccgg gtacgggcgg gctagagtgc agtaggggag actggaattc    240
ccggtgtaac ggtggaatgt gtagatatcg ggaagaacac caatggcgaa ggcaggtctc    300
tgggctgtta ctgacgctga gaagcgaaag cgtggggagc gaacaggatt agataccctg    360
gtagtccacg ccgtaaacgg tggacgctgg atgtggggcc cattccacgg gttccgtgtc    420
ggagctaacg cgttaagcgt cc                                              442
```

```
<210> SEQ ID NO 11
<211> LENGTH: 442
<212> TYPE: DNA
<213> ORGANISM: Artificial Sequence
<220> FEATURE:
<223> OTHER INFORMATION: Synthetic construct

<400> SEQUENCE: 11
tgttagggaa gaatgattgt gtagtaacta tacacagtag agacggtacc taaccagaaa    60
gccacggcta actacgtgcc agcagccgcg gtaatacgta ggtggcaagc gttgtccgga   120
attattgggc gtaaagcgcg cgcaggtggt ttaataagtc tgatgtgaaa gcccacggct   180
caaccgtgga gggtcattgg aaactgttaa acttgagtgc aggagagaaa agtggaattc   240
ctagtgtagc ggtgaaatgc gtagagatta ggaggaacac cagtggcgaa ggcggctttt   300
tggcctgtaa ctgacactga ggcgcgaaag cgtgggagc aaacaggatt agataccctg   360
gtagtccacg ccgtaaacga tgagtgctaa gtgttggtct cataagagat cagtgctgca   420
gctaacgcat taagcactcc gc                                              442
```

```
<210> SEQ ID NO 12
<211> LENGTH: 442
<212> TYPE: DNA
<213> ORGANISM: Artificial Sequence
<220> FEATURE:
<223> OTHER INFORMATION: Synthetic construct

<400> SEQUENCE: 12
tggtagtgaa gaaagataga ggtagtaact ggcctttatt tgacggtaat tacttagaaa    60
gtcacggcta actacgtgcc agcagccgcg gtaatacgta ggtggcaagc gttgtccgga   120
tttattgggc gtaaagcgag tgcaggcggt tcaataagtc tgatgtgaaa gccttcggct   180
caaccggaga attgcatcag aaactgttga acttgagtgc agaagaggag agtggaactc   240
catgtgtagc ggtggaatgc gtagatatat ggaagaacac cagtggcgaa ggcggctctc   300
tggtctgcaa ctgacgctga ggctcgaaag catgggtagc gaacaggatt agataccctg   360
gtagtccatg ccgtaaacga tgagtgctaa gtgttgggag gtttccgcct ctcagtgctg   420
cagctaacgc attaagcact cc                                              442
```

```
<210> SEQ ID NO 13
<211> LENGTH: 442
<212> TYPE: DNA
<213> ORGANISM: Artificial Sequence
<220> FEATURE:
<223> OTHER INFORMATION: Synthetic construct

<400> SEQUENCE: 13
tgttggtgaa gaaggacagg ggtagtaact gacctttgtt tgacggtaat caattagaaa    60
gtcacggcta actacgtgcc agcagccgcg gtaatacgta ggtggcaagc gttgtccgga   120
tttattgggc gtaaagcgag tgcaggcggc tcgataagtc tgatgtgaaa gccttcggct   180
```

```
caaccggaga attgcatcag aaactgtcga gcttgagtac agaagaggag agtggaactc    240
catgtgtagc ggtgaaatgc gtagatatat ggaagaacac cggtggcgaa ggcggctctc    300
tggtctgtta ctgacgctga ggctcgaaag catgggtagc gaacaggatt agataccctg    360
gtagtccatg ccgtaaacga tgagtgctaa gtgttgggag gtttccgcct ctcagtgctg    420
cagctaacgc attaagcact cc                                             442

<210> SEQ ID NO 14
<211> LENGTH: 442
<212> TYPE: DNA
<213> ORGANISM: Artificial Sequence
<220> FEATURE:
<223> OTHER INFORMATION: Synthetic construct

<400> SEQUENCE: 14
tgttggtgaa gaaggataga ggtagtaact ggcctttatt tgacggtaat caaccagaaa    60
gtcacggcta actacgtgcc agcagccgcg gtaatacgta ggtggcaagc gttgtccgga    120
tttattgggc gtaaagcgag cgcaggcgga ttgataagtc tgatgtgaaa gccttcggct    180
caaccgaaga actgcatcag aaactgtcaa tcttgagtgc agaagaggag agtggaactc    240
catgtgtagc ggtggaatgc gtagatatat ggaagaacac cagtggcgaa ggcggctctc    300
tggtctgtaa ctgacgctga ggctcgaaag catgggtagc gaacaggatt agataccctg    360
gtagtccatg ccgtaaacga tgagtgctaa gtgttgggag gtttccgcct ctcagtgctg    420
cagctaacgc attaagcact cc                                             442

<210> SEQ ID NO 15
<211> LENGTH: 441
<212> TYPE: DNA
<213> ORGANISM: Artificial Sequence
<220> FEATURE:
<223> OTHER INFORMATION: Synthetic construct

<400> SEQUENCE: 15
atatgggacg aacaggacat cggttaatac ccggtgtctt tgacggtacc gtaagagaaa    60
gccacggcta actacgtgcc agcagccgcg gtaatacgta ggtggcaagc gttgtccgga    120
attattgggc gtaaagggcg cgcaggcggc atcgcaagtc ggtcttaaaa gtgcgggct    180 taaccccgtg aggggaccga aactgtgaag ctcgagtgtc ggagaggaaa gcggaattcc    240
tagtgtagcg gtgaaatgcg tagatattag gaggaacacc agtggcgaaa gcggctttct    300
ggacgacaac tgacgctgag gcgcgaaagc caggggagca acgggattaa gatacccgg    360 tagtcctggc cgtaaacgat ggatactagg tgtaggaggt atcgactcct tctgtgccgg    420
agttaacgca ataagtatcc c                                              441

<210> SEQ ID NO 16
<211> LENGTH: 442
<212> TYPE: DNA
<213> ORGANISM: Artificial Sequence
<220> FEATURE:
<223> OTHER INFORMATION: Synthetic construct

<400> SEQUENCE: 16
actccttttt ctcgcgaaaa aggcacagct ttggctgtgt tgatggtagt gggggaagaa    60
gcgccggcta actacgtgcc agcagccgcg gtaatacgta gggcgcgagc gttgtccgga    120
tttattgggc gtaaagagct cgtaggtggt tcgtcgcgtc tgtcgtgaaa gccagcagct    180
```

```
taactgttgg tctgcggtgg gtacgggcgg gcttgagtgc ggtatgggtg actggaattc    240
ctggtgtagc ggtggaatgc gcagatatca ggaggaacac cgatggcgaa ggcaggtcac    300
tgggccgtta ctgacactga ggagcgaaag cgtggggagc aacaggatt agataccctg     360 gtagtccacg ctgtaaacgt tgggaactag gtgtggggat gctatcctgt gtttctgcgc    420
cgtagctaac gcattaagtt cc                                             442

<210> SEQ ID NO 17
<211> LENGTH: 442
<212> TYPE: DNA
<213> ORGANISM: Artificial Sequence
<220> FEATURE:
<223> OTHER INFORMATION: Synthetic construct

<400> SEQUENCE: 17 actcctttt  ctcgcgaaaa aggcacagtt ttggctgtgt tgatggtagt gggggaagaa     60
gcgccggcta actacgtgcc agcagccgcg gtaatacgta gggcgcgagc gttgtccgga   120
tttattgggc gtaaagagct cgtaggtggt tcgtcgcgtc tgtcgtgaaa gccagcagct   180
taactgttgg tctgcggtgg gtacgggcgg gcttgagtgc ggtaggggtg actggaattc   240
ctggtgtagc ggtggaatgc gcagatatca ggaggaacac cgatggcgaa ggcaggtcac   300
tgggccgtta ctgacactga ggagcgaaag cgtggggagc aacaggatt agataccctg    360 gtagtccacg ctgtaaacgt tgggaactag gtgtggggat gctatcctgt gtctctgcgc   420
cgtagctaac gcattaagtt cc                                            442

<210> SEQ ID NO 18
<211> LENGTH: 442
<212> TYPE: DNA
<213> ORGANISM: Artificial Sequence
<220> FEATURE:
<223> OTHER INFORMATION: Synthetic construct

<400> SEQUENCE: 18 actcctttt  ctcgtgaaaa aggcatgctt ttgggtgtgt tgatggtagc gggggaagaa     60
gcgccggcta actacgtgcc agcagccgcg gtaatacgta gggcgcgagc gttgtccgga   120
tttattgggc gtaaagagct cgtaggtggt tcgtcgcgtc tgtcgtgaaa gccagcagct   180
taactgttgg tctgcggtgg gtacgggcgg gcttgagtgc ggtaggggtg actggaattc   240
ctggtgtagc ggtggaatgc gcagatatca ggaggaacac cgatggcgaa ggcaggtcac   300
tgggccgtta ctgacgctga ggagcgaaag cgtggggagc aacaggatt agataccctg    360 gtagtccacg ctgtaaacgt tgggaactag gtgtggggat gctatcctgt gtttctgcgc   420
cgtagctaac gcattaagtt cc                                            442

<210> SEQ ID NO 19
<211> LENGTH: 441
<212> TYPE: DNA
<213> ORGANISM: Artificial Sequence
<220> FEATURE:
<223> OTHER INFORMATION: Synthetic construct

<400> SEQUENCE: 19
atttgggaag aatgactcta gcaggcaatg gctggagttt gactgtacca ctttgaataa     60
gtgacgacta actatgtgcc agcagtcgcg gtaatacata ggtcgcaagc gttatccga    120 tttattgggc gtaaagcaag cgcaggcgga ttgaaaagtc tggtgttaaa ggcagctgct   180
taacagttgt atgcattgga aactatcagt ctagagtgtg gtagggagtt ttggaatttc   240
```

```
atgtggagcg gtgaaatgcg tagatatatg aaggaacacc agtggcgaag gcgaaaactt    300
aggccattac tgacgcttag gcttgaaagt gtggggagca ataggatta gatacccctag    360 tagtccacac cgtaaacgat agatactagc tgtcggagcg atcccttcgg tagtgaagtt    420
aacacattaa gtatctcgcc t                                              441

<210> SEQ ID NO 20
<211> LENGTH: 442
<212> TYPE: DNA
<213> ORGANISM: Artificial Sequence
<220> FEATURE:
<223> OTHER INFORMATION: Synthetic construct

<400> SEQUENCE: 20
tgtcagggaa gaaaaggctg ttgccaatat cggcggccga tgacggtacc tgaagaataa     60
gcaccggcta actacgtgcc agcagccgcg gtaatacgta gggtgcgagc gttaatcgga    120
attactgggc gtaaagcggg cgcagacggt tacttaagca ggatgtgaaa tccccgggct    180
caacccggga actgcgttct gaactgggtg actcgagtgt gtcagaggga ggtggaattc    240
cacgtgtagc agtgaaatgc gtagagatgt ggaggaatac cgatggcgaa ggcagcctcc    300
tgggataaca ctgacgttca tgtccgaaag cgtgggtagc aaacaggatt agatacccctg    360 gtagtccacg ccctaaacga tgtcaattag ctgttgggca acttgattgc ttggtagcgt    420
agctaacgcg tgaaattgac cg                                             442

<210> SEQ ID NO 21
<211> LENGTH: 442
<212> TYPE: DNA
<213> ORGANISM: Artificial Sequence
<220> FEATURE:
<223> OTHER INFORMATION: Synthetic construct

<400> SEQUENCE: 21
aggctttcgg gttgtaaact cctttgacga gggacgatga tgacggtacc tcgaaaacaa     60
gccacggcta actacgtgcc agcagccgcg gtaatacgta ggtggcaagc gttgtccgga    120
tttactgggt gtaaagggcg cgtaggcggg caggcaagtc agatgtgaaa tctccgggct    180
caacccggaa attgcatttg aaactgcagg tcttgagtat cggagaggca agcggaattc    240
ctagtgtagc ggtgaaatgc gtagatatta ggaggaacac cagtggcgaa ggcggcttgc    300
tggacgacaa ctgacgctga ggcgcgaaag cgtgggagc aaacaggatt agatacccctg    360 gtagtccatg ccctaaacga tgaatatatg tgtgggggga ctgaccccctt ccgtgccgga    420 gtaacacaat aagtattcca cc                                             442

<210> SEQ ID NO 22
<211> LENGTH: 441
<212> TYPE: DNA
<213> ORGANISM: Artificial Sequence
<220> FEATURE:
<223> OTHER INFORMATION: Synthetic construct

<400> SEQUENCE: 22
aggttttcga atcgtaaagc tctgtcctat gagaagataa tgacggtatc ataggaggaa     60
gccccggcta aatacgtgcc agcagccgcg gtaatacgta tggggcgagc gttgtccgga    120
attattgggc gtaaagggta cgtaggcggt ttttttaagtc aggtgtgaaa gcgtgaggct    180
taacctcatt aagcacttga aactggaaga cttgagtgaa ggagaggaaa gtggaattcc    240
```

```
tagtgtagcg gtgaaatgcg tagatattag gaggaatacc ggtggcgaag gcgactttct    300
ggacttttac tgacgctcag gtacgaaagc gtggggagca acaggatta gatacccctgg    360 tagtccacgc cgtaaacgat gaatgctagg tgttgggagt caaatctcgg tgccgaagtt    420
aacacattaa gcattccgcc t                                              441

<210> SEQ ID NO 23
<211> LENGTH: 441
<212> TYPE: DNA
<213> ORGANISM: Artificial Sequence
<220> FEATURE:
<223> OTHER INFORMATION: Synthetic construct

<400> SEQUENCE: 23
aggctttcga gtcgtaaagt tcttttatat gggaagataa tgacggtacc ataagaaaaa     60
gccccggcta actacgtgcc agcagccgcg gtaatacgta gggggctagc gttgtccgga    120
atcactgggc gtaaagggtt cgcaggcgga atgcaagtc agatgtaaaa ggcagtagct    180
taactactgt aagcatttga aactgcatat cttgagaaga gtagaggtaa gtggaatttt    240
tagtgtagcg gtgaaatgcg tagatattaa aaagaatacc ggtggcgaag gcgacttact    300
gggctcattc tgacgctgag gaacgaaagc gtgggtagca acaggatta gatacccctgg    360 tagtccacgc tgtaaacgat gagtgctagg tatcggaata attcggtgcc gcagttaaca    420
cattaagcac tccgcctggg g                                              441

<210> SEQ ID NO 24
<211> LENGTH: 441
<212> TYPE: DNA
<213> ORGANISM: Artificial Sequence
<220> FEATURE:
<223> OTHER INFORMATION: Synthetic construct

<400> SEQUENCE: 24
aggtcttcgg atcgtaaagt tctgttgcag gggaagataa tgacggtacc ctgtgaggaa     60
gccccggcta actacgtgcc agcagccgcg gtaatacgta gggggctagc gttatccgga    120
tttactgggc gtaaagggtg cgtaggtggt ccttcaagtc ggtggttaaa ggctacggct    180
caaccgtagt aagccgccga aactggagga cttgagtgca ggagaggaaa gtggaattcc    240
cagtgtagcg gtgaaatgcg tagatattgg gaggaacacc agtagcgaag gcggctttct    300
ggactgcaac tgacactgag gcacgaaagc gtgggtagca acaggatta gatacccctgg    360 tagtccacgc tgtaaacgat gagtactagg tgtcgggggt taccccctc ggtgccgcag    420 ctaacgcatt aagtactccg c                                              441

<210> SEQ ID NO 25
<211> LENGTH: 442
<212> TYPE: DNA
<213> ORGANISM: Artificial Sequence
<220> FEATURE:
<223> OTHER INFORMATION: Synthetic construct

<400> SEQUENCE: 25
ttcttttgta ggggaataac ggacggcacg tgtgccgtag tgaatgtacc ctacgaataa     60
gcatcggcta actccgtgcc agcagccgcg gtaatacgga ggatgcgagc gttatccgga    120
tttattgggt ttaaagggtg cgtaggcggc ctgttaagtc agcggtgaaa tctaggagct    180
taactcctaa attgcattg atactggcgg gcttgagtgt agatgaggta ggcggaatgc    240
gtggtgtagc ggtggaatgc atagatatca cgcagaactc caattgcgaa ggcagcttac    300
```

```
taaggtacaa ctgacgctga agcacgaaag cgtgggtatc aaacaggatt agataccctg    360
gtagtccacg cagtaaacga tgataactgg gcgtatgcga tatacagtat gctcctaagc    420
gaaagcgtta agttatccac ct                                             442
```

```
<210> SEQ ID NO 26
<211> LENGTH: 442
<212> TYPE: DNA
<213> ORGANISM: Artificial Sequence
<220> FEATURE:
<223> OTHER INFORMATION: Synthetic construct

<400> SEQUENCE: 26
tgcttttata agggaataaa gtgagtctcg tgagactttt tgcatgtacc ttatgaataa     60
ggaccggcta attccgtgcc agcagccgcg gtaatacgga aggtccgggc gttatccgga    120
tttattgggt ttaaagggag cgtaggccgg agattaagcg tgttgtgaaa tgtagaagct    180
caacgtctgc actgcagcgc gaactggttt ccttgagtac gtacaaagtg gcggaattc     240 gtggtgtagc ggtgaaatgc ttagatatca cgaagaactc cgattgcgaa ggcagctcac    300
tggagcgcaa ctgacgctga agctcgaaag tgcgggtatc gaacaggatt agataccctg    360
gtagtccgca cggtaaacga tggatgcccg ctgttggtct gaataggtca gcggccaagc    420
gaaagcatta agcatcccac ct                                             442
```

```
<210> SEQ ID NO 27
<211> LENGTH: 442
<212> TYPE: DNA
<213> ORGANISM: Artificial Sequence
<220> FEATURE:
<223> OTHER INFORMATION: Synthetic construct

<400> SEQUENCE: 27
tgcttttata tgggaataaa gtgagggacg tgtcccttat tgcatgtacc atatgaataa     60
ggaccggcta attccgtgcc agcagccgcg gtaatacgga aggtccaggc gttatccgga    120
tttattgggt ttaaagggag cgtaggctgt tgttaagcg tgttgtgaaa tgtaggagct    180
caacttttag attgcagcgc gaactggcag acttgagtgc gcacaacgta ggcggaattc     240
atggtgtagc ggtgaaatgc ttagatatca tgacgaactc cgattgcgaa ggcagcttac    300
gggagcgcaa ctgacgctaa agctcgaagg tgcgggtatc gaacaggatt agataccctg    360
gtagtccgca cagtaaacga tggatgcccg ctgttagcac ctagtgttag cggctaagcg    420
aaagcattaa gcatcccacc tg                                             442
```

```
<210> SEQ ID NO 28
<211> LENGTH: 442
<212> TYPE: DNA
<213> ORGANISM: Artificial Sequence
<220> FEATURE:
<223> OTHER INFORMATION: Synthetic construct

<400> SEQUENCE: 28
tgcttttatg tggggataaa gtgcgtgacg tgtcatgcat tgcaggtacc acatgaataa     60
ggaccggcta attccgtgcc agcagccgcg gtaatacgga aggtccgggc gttatccgga    120
tttattgggt ttaaagggag cgtaggctgt ctattaagcg tgttgtgaaa tttaccggct    180
caaccggtgg cttgcagcgc gaactggtcg acttgagtat gcaggaagta ggcggaattc     240
atggtgtagc ggtgaaatgc ttagatatca tgacgaactc cgattgcgca ggcagcttac    300
```

| | |
|---|---|
| tgtagcataa ctgacgctga tgctcgaaag tgcgggtatc aaacaggatt agatacccctg | 360 |
| gtagtccgca cggtaaacga tggatgctcg ctattcgtcc ttttttggatg agtggccaag | 420 |
| tgaaaacatt aagcatccca cc | 442 |

<210> SEQ ID NO 29
<211> LENGTH: 442
<212> TYPE: DNA
<213> ORGANISM: Artificial Sequence
<220> FEATURE:
<223> OTHER INFORMATION: Synthetic construct

<400> SEQUENCE: 29

| | |
|---|---|
| gttttaggac tgtaaaacac ttttagtagg gaagaaaaaa tgacggtacc tacagaagaa | 60 |
| gcgacggcta aatacgtgcc agcagccgcg gtaatacgta tgtcgcgagc gttatccgga | 120 |
| attattgggc ttaaagggca tctaggcggt taaacaagtt gaaggtgaaa acctgtggct | 180 |
| caaccatagg cttgcctaca aaactgtata actagagtac tggaaaggtg ggtggaacta | 240 |
| cacgagtaga ggtgaaattc gtagatatgt gtaggaatgc cgatgatgaa gataactcac | 300 |
| tggacagcaa ctgacgctga agtgcgaaag ctaggggagc aaacaggatt agatacccctg | 360 |
| gtagtcctag ctgtaaacga tgatcactgg gtgtggggat tcgaagtctc tgtgccgaag | 420 |
| caaaagcgat aagtgatccg cc | 442 |

<210> SEQ ID NO 30
<211> LENGTH: 442
<212> TYPE: DNA
<213> ORGANISM: Artificial Sequence
<220> FEATURE:
<223> OTHER INFORMATION: Synthetic construct

<400> SEQUENCE: 30

| | |
|---|---|
| tattagggaa gaacatatgt gtaagtaact gtgcacatct tgacggtacc taatcagaaa | 60 |
| gccacggcta actacgtgcc agcagccgcg gtaatacgta ggtggcaagc gttatccgga | 120 |
| attattgggc gtaaagcgcg cgtaggcggt ttttaagtc tgatgtgaaa gcccacggct | 180 |
| caaccgtgga gggtcattgg aaactggaaa acttgagtgc agaagaggaa agtggaattc | 240 |
| catgtgtagc ggtgaaatgc gcagagatat ggaggaacac cagtggcgaa ggcgactttc | 300 |
| tggtctgtaa ctgacgctga tgtgcgaaag cgtggggatc aaacaggatt agatacccctg | 360 |
| gtagtccacg ccgtaaacga tgagtgctaa gtgttagggg gtttccgccc cttagtgctg | 420 |
| cagctaacgc attaagcact cc | 442 |

<210> SEQ ID NO 31
<211> LENGTH: 441
<212> TYPE: DNA
<213> ORGANISM: Artificial Sequence
<220> FEATURE:
<223> OTHER INFORMATION: Synthetic construct

<400> SEQUENCE: 31

| | |
|---|---|
| gttagagaag aacgttggta ggagtggaaa atctaccaag tgacggtaac taaccagaaa | 60 |
| gggacggcta actacgtgcc agcagccgcg gtaatacgta ggtcccgagc gttgtccgga | 120 |
| tttattgggc gtaaagcgag cgcaggcggt tctttaagtc tgaagttaaa ggcagtggct | 180 |
| taaccattgt acgctttgga aactggagga cttgagtgca aaggggaga gtggaattcc | 240 |
| atgtgtagcg gtgaaatgcg tagatatatg gaggaacacc ggtggcgaaa gcggctctct | 300 |
| ggtctgtaac tgacgctgag gctcgaaagc gtggggagca aacaggatta gatacccctgg | 360 |

```
tagtccacgc cgtaaacgat gagtgctagg tgttaggccc tttccggggc ttagtgccgc    420
agctaacgca ttaagcactc c                                              441
```

<210> SEQ ID NO 32
<211> LENGTH: 442
<212> TYPE: DNA
<213> ORGANISM: Artificial Sequence
<220> FEATURE:
<223> OTHER INFORMATION: Synthetic construct

<400> SEQUENCE: 32

```
gccgacgaag aatgaggacg ggagggaatg cccgtttgat gacggtagtc gtgcgaataa     60
gccccggcta attacgtgcc agcagccgcg gtaacacgta aggggcgagc gttgttcgga    120
attattgggc gtaaagggca tgcaggcgga ctggtaagcc tggtgtgaaa tccccgagct    180
caacttggga actgcactgg gtactgctgg tctagaatca cggaggggaa accggaattc    240
caagtgtagg ggtggaatct gtagatattt ggaagaacac cggtggcgaa ggcgggtttc    300
tggccgatga ttgacgctga ggtgcgaagg tgtggggagc gaacaggatt agataccctg    360
gtagtccaca cagtaaacga tgtacactag gtgttggggc atgagtctcg gcgccgacgc    420
gaacgcatta agtgtaccgc ct                                              442
```

<210> SEQ ID NO 33
<211> LENGTH: 599
<212> TYPE: DNA
<213> ORGANISM: Artificial Sequence
<220> FEATURE:
<223> OTHER INFORMATION: Synthetic construct

<400> SEQUENCE: 33

```
tatgttaaca ccccgagcgg ctctttggtg tcctctgagg cacaattgtt taataagcca     60
tattggctac aaaaagccca gggacataac aatggtattt gttggggtaa tcaactgttt    120
gttactgtgg tagataccac acgcagtacc aacatgacat tatgtgcatc cgtaactaca    180
tcttccacat acaccaattc tgattataaa gagtacatgc gtcatgtgga agagtatgat    240
ttacaattta tttttcaatt atgtagcatt acattgtctg ctgaagtaat ggcctatatt    300
cacacaatga atccctctgt tttggaagac tggaactttg ggttatcgcc tcccccaaat    360
ggtacattag aagatcccta taggtatgtg cagtcacagg ccattacctg tcaaaagccc    420
actcctgaaa aggaaaagcc agatccctat aagaaccttg ttttttggga ggttaattta    480
aaagaaaagt tttctagtga attggatcag tatcctttgg gacgcaagtt tttgttacaa    540
agtggatata ggggacggtc ctctattcgt acaggtgtta agcgccctgc gtttccaa      599
```

<210> SEQ ID NO 34
<211> LENGTH: 599
<212> TYPE: DNA
<213> ORGANISM: Artificial Sequence
<220> FEATURE:
<223> OTHER INFORMATION: Synthetic construct

<400> SEQUENCE: 34

```
catctacata cacctagtgg ctcattggtg tcttcagagg ctcaagcatc tagtcaacca     60
gattggcttc aaaaggctca gggacataac aatggtattt gctggggaaa ccacttgttt    120
gttactgtgg tagataccac acgcagtaca aatatgacac tatgtgcatc tgtgtctaaa    180
tctgctacat acactaattc agattataag gaatacatgc gccatgtgga ggagtttgat    240
```

```
ttacagttta tttttcaatt gtgtagcatt acattatctg cagaagtcat ggcctatata    300
cacacaatga atccttctgt tttggaggac tggaactttg gtttatcgcc tccaccaaat    360
ggtacactgg aggatactta tagatatgta cagtcacagg ccattacctg tcagaaaccc    420
acacctgaaa aagaaaaaca ggatccctat aaggatatga gttttgggga ggttaactta    480
aaagaaaagt tttcaagtga attagatcag tttccccttg gacgtaagtt tttattgcaa    540
agtggatatc gaggacggac gtctgctcgt acaggtataa agcgcccagc tctctgtaa    599
```

```
<210> SEQ ID NO 35
<211> LENGTH: 602
<212> TYPE: DNA
<213> ORGANISM: Artificial Sequence
<220> FEATURE:
<223> OTHER INFORMATION: Synthetic construct

<400> SEQUENCE: 35
tattttccta cacctagtgg ttctatggtt acctctgatg cccaaatatt caataaacct     60
tattggttac aacgagcaca gggccacaat aatggcattt gttggggtaa ccaactattt    120
gttactgttg ttgatactac acgcagtaca aatatgtcat tatgtgctgc catatctact    180
tcagaaacta catataaaaa tactaacttt aaggagtacc tacgacatgg ggaggaatat    240
gatttacagt ttatttttca actgtgcaaa ataaccttaa ctgcagacgt tatgacatac    300
atacattcta tgaattccac tattttggag gactggaatt ttggtctaca acctccccca    360
ggaggcacac tagaagatac ttataggttt gtaacccagg caattgcttg tcaaaaacat    420
acacctccag cacctaaaga agatgatccc cttaaaaaat acttttttg ggaagtaaat    480 ttaaaggaaa agtttctgc agacctagat cagtttcctt taggacgcaa attttacta    540 caagcaggat tgaaggccaa accaaaattt acattaggaa acgaaaagc tacacccacc    600 ac                                                                    602
```

```
<210> SEQ ID NO 36
<211> LENGTH: 605
<212> TYPE: DNA
<213> ORGANISM: Artificial Sequence
<220> FEATURE:
<223> OTHER INFORMATION: Synthetic construct

<400> SEQUENCE: 36
tattctccct ctccaagtgg ctctattgtt acctctgact cccagttgtt aataaaacca     60
tattggttac ataaggcaca gggtcataac aatggtgttt gctggcataa tcaattattt    120
gttactgtgg tagataccac tcccagtacc aatttaacaa tatgtgcttc tacacagtct    180
cctgtacctg gcaatatga tgctaccaaa tttaagcagt atagcagaca tgttgaggaa    240
tatgatttgc agtttatttt tcagttgtgt actattactt taactgcaga tgttatgtcc    300
tatattcata gtatgaatag cagtatttta gaggattgga actttggtgt tcccccccc    360 ccaactacta gtttggtgga tacatatcgt tttgtacaat ctgttgctat tacctgtcaa    420
aaggatgctg caccggctga aaataaggat ccctatgata agttaaagtt ttggaatgtg    480
gatttaaagg aaaagttttc tttagactta gatcaatatc cccttggacg taaatttttg    540
gttcaggctg gattgcgtcg caagcccacc ataggccctc gcaaacgttc tgctccatct    600
gccac                                                                 605
```

```
<210> SEQ ID NO 37
<211> LENGTH: 605
```

```
<212> TYPE: DNA
<213> ORGANISM: Artificial Sequence
<220> FEATURE:
<223> OTHER INFORMATION: Synthetic construct

<400> SEQUENCE: 37
tattctgcta cacctagtgg ctctatggtt acttcggatg cacaactatt taataagcca    60
tactggttac aacgtgcaca gggtcataat aatggtatct gttggggcaa tcaattgttt   120
gttacctgtg ttgataccac ccgcagtact aaccttacca ttagtacatt atctgcagca   180
tctgcatcca ctccatttaa accatctgat tataaacaat ttataagaca tggcgaagaa   240
tatgaattac aatttatatt tcagttgtgt aaaataacac ttacaacaga tgttatggct   300
tacatacatt taatgaatgc ctccatattg gaggattgga attttggact aaccttacct   360
cccactgcta gtttggaaga tgcctatagg tttattaaaa actctgctac tacctgtcag   420
cgtaacgccc ctcctgtgcc aaaggaagat ccttttcaaa aatttaaatt ttgggatgta   480
gatttaaaag aaaaatttc tattgatttg gatcaatttc cactagggcg taagtttatg   540
ttacaggccg gcatacaacg gcggccgaaa ctaggcacca acgtcccctt atcttctacc   600
tcttc                                                               605

<210> SEQ ID NO 38
<211> LENGTH: 602
<212> TYPE: DNA
<213> ORGANISM: Artificial Sequence
<220> FEATURE:
<223> OTHER INFORMATION: Synthetic construct

<400> SEQUENCE: 38
tactttccta cacctagcgg ctccatggtt acttcagatg cacaaatttt taataaacca    60
tattggatgc aacgtgctca gggacacaat aatggtattt gttggggcaa tcagttattt   120
gttactgtgg tagataccac acgtagtacc aatatgtctg tttgtgctgc aattgcaaac   180
agtgatacta catttaaaag tagtaatttt aaagagtatt taagacatgg tgaggaattt   240
gatttacaat ttatatttca gttatgcaaa ataacattat ctgcagacat aatgacatat   300
attcacagta tgaatcctgc tattttggaa gattggaatt ttggattgac cacacctccc   360
tcaggttctt tggaggatac ctataggttt gtcacctcac aggccattac atgtcaaaaa   420 actgccccc aaaagcccaa ggaagatcca tttaaagatt atgtattttg ggaggttaat   480
ttaaaagaaa agttttctgc agatttagat cagtttccac tgggtcgcaa atttttatta   540
caggcaggat atagggcacg tcctaaattt aaagcaggta acgtagtgc accctcagca   600 tc                                                                  602

<210> SEQ ID NO 39
<211> LENGTH: 599
<212> TYPE: DNA
<213> ORGANISM: Artificial Sequence
<220> FEATURE:
<223> OTHER INFORMATION: Synthetic construct

<400> SEQUENCE: 39 tttttccca ctcctagtgg atcaatggtt acttccgaat ctcagttatt taataagcca    60
tattggctac aacgtgcaca aggtcataat aatggtattt gttggggcaa tcaggtattt   120
gttactgtgg tagataccac tcgcagtact aatatgactt tatgcacaca agtaactagt   180
gacagtacat ataaaaatga aaattttaaa gaatatataa gacatgttga agaatatgat   240
```

```
ctacagtttg tttttcaact atgcaaagtt accttaactg cagaagttat gacatatatt    300
catgctatga atccagatat tttagaagat tggcaatttg gtttaacacc tcctccatct    360
gctagtttac aggataccta taggtttgtt acctctcagg ctattacgtg tcaaaaaaca    420
gtacctccaa aggaaaagga agacccctta ggtaaatata cattttggga agtggattta    480
aaggaaaaat tttcagcaga tttagatcag tttcctttgg gacgcaagtt tttattacag    540
gcaggtctta aagcaaaacc taaacttaaa cgtgcagccc ccacatccac ccgcacatc     599

<210> SEQ ID NO 40
<211> LENGTH: 600
<212> TYPE: DNA
<213> ORGANISM: Artificial Sequence
<220> FEATURE:
<223> OTHER INFORMATION: Synthetic construct

<400> SEQUENCE: 40
tattttccta ctcctagtgg ctctatggta acctccgatg cacaaatatt taataaacca     60
tattggttgc aacgtgcaca aggccataat aatggtatat gttggagtaa ccaattgttt    120
gttactgtag ttgatacaac ccgtagtaca aatatgtctg tgtgttctgc tgtgtcttct    180
agtgacagta catataaaaa tgacaatttt aaggaatatt taaggcatgg tgaagaatat    240
gatttacagt ttattttttca gttatgtaaa ataacactaa cagcagatgt tatgacatat    300
attcatagta tgaacccgtc cattttagag gattggaatt ttggccttac accaccgcct    360
tctggtacct tagaggacac atatcgctat gtaacatcac aggctgtaac ttgtcaaaaa    420
cccagtgcac caaaacctaa agatgatcca ttaaaaaatt atactttttg ggaggttgat    480
ttaaaggaaa agttttctgc agacttagat caatttccgt tgggccgtaa attttttgtta   540 caagcaggac taaaggccag gcctaatttt agattaggca agcgtgcagc tccagcatct    600

<210> SEQ ID NO 41
<211> LENGTH: 605
<212> TYPE: DNA
<213> ORGANISM: Artificial Sequence
<220> FEATURE:
<223> OTHER INFORMATION: Synthetic construct

<400> SEQUENCE: 41
tactgcccct ctcccagcgg ttccatggta acctctgatt cccagttatt aataagcct      60 tattggctac ataaggccca gggccacaac aatggtatat gttggcataa tcaattattt    120
cttactgttg tggacactac ccgtagtacc aactttacat tatctaccct tatagagtct    180
tccatacctt ctacatatga tccttctaag tttaaggaat ataccaggca cgtggaggag    240
tatgatttac aatttatatt tcaactgtgt actgtcacat taacaactga tgttatgtct    300
tatattcaca ctatgaattc ctctatattg gacaattgga attttgctgt agctcctcca    360
ccatctgcca gtttggtaga cacttacaga tacctacagt ctgcagccat acatgtcaa     420 aaggatgctc cagcacctga aaagaaagat ccatatgacg gtctaaagtt ttggaatgtt    480
gacttaaggg aaaagtttag tttggaactt gatcaattcc ctttgggacg taaattttttg   540 ttgcaggcca gggtccgcag gcgccctact ataggtcccc gaaagcggcc tgctgcatcc    600
acttc                                                                605

<210> SEQ ID NO 42
<211> LENGTH: 605
<212> TYPE: DNA
<213> ORGANISM: Artificial Sequence
```

<220> FEATURE:
<223> OTHER INFORMATION: Synthetic construct

<400> SEQUENCE: 42

```
tattactcca caccaagtgg atccttggtt acctctgatt ctcagatatt aacaagcca      60
ttgtggatac aaaaggccca gggcataac aatggcatat gttttggcaa tcagttattt     120
gttacagttg tagacaccac tcgtagcact aatttaacct tatgtgctgc cacacagtcc    180
cccacaccaa ccccatataa taacagtaat ttcaaggaat atttgcgtca tggggaggag    240
tttgatttgc agtttatttt tcagttatgt gtaattacct taaatgcaga ggttatgaca    300
tatattcatg caatggatcc tacgttgttg gaggattgga actttaaaat tgctcctcca    360
gcctctgcat ccttagagga tacatatagg ttccttacca acaaggctat tgcctgtcag    420
cgcgatgcgc cccccaaggt acgggaggat ccatataaaa aatataaatt ttgggatgtc    480
aatttaacag aaagattttc ttcccaatta gatcaatttc cattaggacg taagttcctt    540
atgcaggctg gtgtacgtgc agggcctagg tttaaatcca ggaagcgccc tgccccttcc    600
tcgtc                                                                605
```

<210> SEQ ID NO 43
<211> LENGTH: 599
<212> TYPE: DNA
<213> ORGANISM: Artificial Sequence
<220> FEATURE:
<223> OTHER INFORMATION: Synthetic construct

<400> SEQUENCE: 43

```
tattatccta cccctagtgg ttctatggta acatctgatg cacaactatt taataaacca      60
tattggttac aacaagcaca aggacacaat aatggtatat gttggggaaa tcagctattt     120
ttaactgtgg ttgatactac ccgtagtact aacatgactt tgtgtgccac tgcaacatct    180
ggtgatacat atacagctgc taattttaag gaatatttaa gacatgctga agaatatgat    240
gtgcaattta tatttcaatt gtgtaaaata acattaactg ttgaagttat gtcatatata    300
cacaatatga atcctaacat attagaggag tggaatgttg gtgttgcacc accaccttca    360
ggaactttag aagatagtta taggtatgta caatcagaag ctattcgctg tcaggctaag    420
gtaacaacgc cagaaaaaaa ggatccttat tcagacttttt ggttttggga ggtaaattta    480
tctgaaaagt tttctactga tttagatcaa tttcctttag gtagaaagtt tttactgcag    540
gccgggttgc gtgcaaggcc taaactgtct gtaggtaaac gaaaggcgtc tacagctaa     599
```

<210> SEQ ID NO 44
<211> LENGTH: 605
<212> TYPE: DNA
<213> ORGANISM: Artificial Sequence
<220> FEATURE:
<223> OTHER INFORMATION: Synthetic construct

<400> SEQUENCE: 44

```
tattcccctt ctcccagtgg ctctattatt acttctgatt ctcaattatt aataagcca      60
tattggttac ataaggccca gggccataac aatggtattt gttggcataa tcagttgttt    120
gttactgtag tggacactac ccgcagtact aatttaacat tatgtgcctc tacacaaaat    180
cctgtgccaa gtacatatga ccctactaag tttaagcagt atagtagaca tgtggaggaa    240
tatgatttac agtttatttt tcagttgtgc actattactt taactgcaga ggttatgtca    300
tatatccata gtatgaatag tagtatatta gaaaattgga attttggtgt ccctccacca    360
```

| | | |
|---|---|---|
| cctactacaa gtttggtgga tacatatcgt tttgtgcaat cagttgctgt tacctgtcaa | 420 | |
| aaggatacta cacctccaga aaagcaggat ccatatgata aattaaagtt ttggactgtt | 480 | |
| gacctaaagg aaaaattttc ctccgatttg gatcaatatc cccttggtcg aaagttttta | 540 | |
| gttcaggctg ggttacgtcg taggcctacc ataggacctc gtaagcgtcc tgctgcttcc | 600 | |
| acgtc | 605 | |

<210> SEQ ID NO 45
<211> LENGTH: 603
<212> TYPE: DNA
<213> ORGANISM: Artificial Sequence
<220> FEATURE:
<223> OTHER INFORMATION: Synthetic construct

<400> SEQUENCE: 45

| | | |
|---|---|---|
| tactctgcta ctcccagtgg gtctatgata acatctgatt ctcaaatttt taataagcct | 60 | |
| tattggctcc accgtgcgca gggtcacaat aatggcattt gctggaacaa tcagcttttt | 120 | |
| attacctgtg ttgatactac cagaagtaca aatttaacta ttagcactgc cactgctgcg | 180 | |
| gtttccccaa catttactcc aagtaacttt aagcaatata ttaggcatgg ggaagagtat | 240 | |
| gaattgcaat ttattttca attatgtaaa attactttaa ctacagaggt aatggcttat | 300 | |
| ttacacacaa tggatcctac cattcttgaa cagtggaatt tggattaac attacctccg | 360 | |
| tctgctagtt tggaggatgc atataggttt gttagaaatg cagctactag ctgtcaaaag | 420 | |
| gacacccctc cacaggctaa gccagatcct ttggccaaat ataaattttg ggatgttgat | 480 | |
| ttaaaggaac gattttcttt agatttagac caatttgcat tgggtcgcaa gttttgttg | 540 | |
| caggttggcg tacaacgcaa gcccagacca ggccttaaac gcccggcctc atcggcatcc | 600 | |
| tct | 603 | |

<210> SEQ ID NO 46
<211> LENGTH: 599
<212> TYPE: DNA
<213> ORGANISM: Artificial Sequence
<220> FEATURE:
<223> OTHER INFORMATION: Synthetic construct

<400> SEQUENCE: 46

| | | |
|---|---|---|
| tttttttccta ctcctagtgg ttctatggta acctcagaat cccaattatt taataaaccg | 60 | |
| tactggttac aacgtgcgca gggccacaat aatggcatat gttggggcaa tcagttgttt | 120 | |
| gtcacagttg tggataccac tcgtagcact aacatgactt tatgtgctga ggttaaaaag | 180 | |
| gaaagcacat ataaaaatga aaatttttaag gaataccttc gtcatggcga ggaatttgat | 240 | |
| ttacaattta ttttttcaatt gtgcaaaatt acattaacag ctgatgttat gacatacatt | 300 | |
| cataagatgg atgccactat tttagaggac tggcaatttg gccttacccc accaccgtct | 360 | |
| gcatctttgg aggacacata cagatttgtc acttctactg ctataacttg tcaaaaaaac | 420 | |
| acaccaccta aaggaaagga agatcccttta aaggactata tgtttttggga ggtggattta | 480 | |
| aaagaaaagt tttctgcaga tttagatcag tttcctttag gtaggaagtt tttgttacag | 540 | |
| gcagggctac aggctaggcc caaactaaaa cgccctgcat catcggcccc acgtacctc | 599 | |

<210> SEQ ID NO 47
<211> LENGTH: 597
<212> TYPE: DNA
<213> ORGANISM: Artificial Sequence
<220> FEATURE:
<223> OTHER INFORMATION: Synthetic construct

<400> SEQUENCE: 47

| | | | | | |
|---|---|---|---|---|---|
| tatgttgcta | cacctagtgg | gtctatgata | acttcagagg | ctcaattgtt | taataagcca | 60 |
| tattggctgc | aacgtgccca | gggacataat | aatggcatct | gttggaacaa | tcagttattt | 120 |
| gtaactgttg | tggataccac | caggaataca | aacatgactc | tttccgcaac | cacacagtct | 180 |
| atgtctacat | ataattcaaa | gcaaattaaa | cagtatgtta | gacatgcaga | ggaatatgaa | 240 |
| ttacaatttg | tgtttcaact | atgtaaaata | tccctgtctg | ctgaggttat | ggcctattta | 300 |
| catactatga | attctacctt | actggaagac | tggaatatag | gtttgtcgcc | tcctgttgcc | 360 |
| actagcttag | aggacaaata | cagatatgtg | aaaagtgcag | ctataacctg | tcaaaaggat | 420 |
| cagcccctc | ctgaaaagca | ggacccacta | tctaaatata | aattttggga | ggtcaatttg | 480 |
| caaaacagtt | tttctgctga | tttggatcag | tttcctcttg | gcaggaagtt | tttaatgcag | 540 |
| gttggggtcc | gtactaaacc | gcctgtatcc | tctaaaaaac | gctctgcttc | tactaca | 597 |

<210> SEQ ID NO 48
<211> LENGTH: 602
<212> TYPE: DNA
<213> ORGANISM: Artificial Sequence
<220> FEATURE:
<223> OTHER INFORMATION: Synthetic construct

<400> SEQUENCE: 48

| | | | | | |
|---|---|---|---|---|---|
| tatgctgcaa | ctcctagtgg | ctctatggta | acatctgaat | accaaatatt | taataagcca | 60 |
| tactggttac | aacgggccca | gggtcaaaac | aatggtattt | gttggggcaa | tcaggtgttt | 120 |
| ttaacagttg | tagataccac | ccgtagtact | aacctaacat | tgtgtgctac | agcatccacg | 180 |
| caggatagct | ttaataattc | tgactttagg | gagtatatta | gacatgtgga | ggaatatgat | 240 |
| ttacagttta | tatttcagtt | atgtaccata | acccttacag | cagatgttat | ggcctatatt | 300 |
| catggaatga | atcccactat | tctagaggac | tggaactttg | gtataacccc | cccagctaca | 360 |
| agtagtttgg | aggacacata | taggtttgta | cagtcacagg | ccattgcatg | tcaaaagaat | 420 |
| aatgcccctg | caaaggaaaa | ggaggatcct | tacagtaaat | ttaattttg | gactgttgac | 480 |
| cttaaggaac | gatttcatc | tgaccttgac | cagtttccct | gggtcgcaa | gttttacta | 540 |
| caggctggcc | tacgtgcacg | tccgcgcctt | cggcctgtaa | agcgtgcagc | cccttcctcc | 600 |
| tc | | | | | | 602 |

<210> SEQ ID NO 49
<211> LENGTH: 598
<212> TYPE: DNA
<213> ORGANISM: Artificial Sequence
<220> FEATURE:
<223> OTHER INFORMATION: Synthetic construct

<400> SEQUENCE: 49

| | | | | | |
|---|---|---|---|---|---|
| atgttgctac | gcctagtggg | tctatgatta | cgtctgaggc | acagttattt | aataaacctt | 60 |
| attggttgca | acgtgcccaa | ggccataata | atggcatttg | ctggggtaat | caattatttg | 120 |
| ttactgtagt | agatactact | agaagtacta | acatgactat | tagtactgct | acagaacagt | 180 |
| taagtaaata | tgatgcacga | aaattaatc | agtaccttag | acatgtggag | gaatatgaat | 240 |
| tacaatttgt | ttttcaatta | tgcaaaatta | ctttgtctgc | agaggttatg | gcatatttac | 300 |
| ataatatgaa | tgctaaccta | ctggaggact | ggaatattgg | gttatccccg | ccagtggcca | 360 |
| ccagcctaga | agataaatat | agatatgtta | gaagcacagc | tataacatgt | caacgggaac | 420 |

| | |
|---|---|
| agccaccaac agaaaaacag gacccattag ctaaatataa attttgggat gttaacttac | 480 |
| aggacagttt ttctacagac ctggatcaat ttccactggg tagaaaattt ttaatgcaac | 540 |
| tgggcactag gtcaaagcct gctgtagcta cctctaaaaa gcgatctgct cctacctc | 598 |

<210> SEQ ID NO 50
<211> LENGTH: 599
<212> TYPE: DNA
<213> ORGANISM: Artificial Sequence
<220> FEATURE:
<223> OTHER INFORMATION: Synthetic construct

<400> SEQUENCE: 50

| | |
|---|---|
| tttttttccaa ctcctagtgg ctctatagtt acctcagaat cacaattatt taataagcct | 60 |
| tattggctac agcgtgcaca aggtcataac aatggcattt gctggggcaa tcagttattt | 120 |
| gttaccgtgg ttgataccac tcgtagcact aatatgacta tatgcactga agtaactaag | 180 |
| gaaggtacat ataaaaatga taattttaag gaatatgtac gtcatgttga agaatatgac | 240 |
| ttacagtttg tttttcagct ttgcaaaatt acactaactg cagagataat gacatatata | 300 |
| catactatgg attccaatat tttggaggac tggcaatttg gtttaacacc tcctccgtct | 360 |
| gccagtttac aggacacata tagatttgtt acctcccagg ctattacttg ccaaaaaaca | 420 |
| gcacccccta agaaaagga agatccatta aataaatata cttttgggga ggttaactta | 480 |
| aaggaaaagt tttctgcaga tctagatcag tttcctttgg gacgaaagtt tttattacaa | 540 |
| tcaggcctta aagcaaagcc cagactaaaa cgttcggccc ctactacccg tgcaccatc | 599 |

<210> SEQ ID NO 51
<211> LENGTH: 605
<212> TYPE: DNA
<213> ORGANISM: Artificial Sequence
<220> FEATURE:
<223> OTHER INFORMATION: Synthetic construct

<400> SEQUENCE: 51

| | |
|---|---|
| tattccccttt ccccaagtgg gtctgtggtt acttctgatt cacaattatt taataaacca | 60 |
| tattggctgc acaaggctca gggtttaaac aatggtatat gttggcacaa tcaattgttt | 120 |
| ttaacagttg tagatactac tcgcagcacc aatctttctg tgtgtgcttc tactacttct | 180 |
| tctattccta atgtatacac acctaccagt tttaaagaat atgccagaca tgtggaggaa | 240 |
| tttgatttgc agtttatatt tcaactgtgt aaaataacat taactacaga ggtaatgtca | 300 |
| tacattcata atatgaatac cactattttg gaggattgga attttggtgt tacaccacct | 360 |
| cctactgcta gtttagttga cacataccgt tttgttcaat ctgctgctgt aacttgtcaa | 420 |
| aaggacaccg caccgccagt taaacaggac ccttatgaca aactaaagtt ttggcctgta | 480 |
| gatcttaagg aaaggttttc tgcagatctt gatcagtttc ctttgggacg taaattttta | 540 |
| ttgcaattag gagctagacc taagcccact ataggcccac gcaaacgtgc agcgcctgcc | 600 |
| cctac | 605 |

<210> SEQ ID NO 52
<211> LENGTH: 599
<212> TYPE: DNA
<213> ORGANISM: Artificial Sequence
<220> FEATURE:
<223> OTHER INFORMATION: Synthetic construct

<400> SEQUENCE: 52

| | |
|---|---|
| tatgttgcta ctcctagtgg gtccatgatt acctctgagg cccaattatt taataaacct | 60 |

| | |
|---|---|
| tattggttgc aacgtgcaca gggccataat aatggcatat gctggggtaa tcaggtattt | 120 |
| gttactgttg tggatactac cagaagcacc aacatgacta ttaatgcagc taaaagcaca | 180 |
| ttaactaaat atgatgcccg tgaaatcaat caatacct tc gccatgtgga ggaatatgaa | 240 |
| ctacagtttg tgtttcaact ttgtaaaata accttaactg cagaagttat ggcatatttg | 300 |
| cataatatga ataatacttt attagacgat tggaatattg cttatcccc accagttgca | 360 |
| actagcttag aggataaata taggtatatt aaaagcacag ctattacatg tcagagggaa | 420 |
| cagcccctg cagaaaagca ggatccctg gctaaatata gttttggga agttaattta | 480 |
| caggacagct tttctgcaga cctggatcag tttcctttgg gtagaaaatt tttaatgcaa | 540 |
| ctaggcccta gacccctag acccaaggct agtgtatctg cctctaaaag gcgggcggc | 599 |

<210> SEQ ID NO 53
<211> LENGTH: 605
<212> TYPE: DNA
<213> ORGANISM: Artificial Sequence
<220> FEATURE:
<223> OTHER INFORMATION: Synthetic construct

<400> SEQUENCE: 53

| | |
|---|---|
| tatgccccct cgcctagcgg gtctatggtg tcctctgact cccagttatt taacaagccc | 60 |
| tattggctgc acaaggcaca gggacacaac aatggtattt gttggcataa tcaattattt | 120 |
| cttaccgttg tggatacaac gcgcagtact aattttacat tgtccactac tacagactct | 180 |
| actgtaccag ctgtgtatga ttctaataaa tttaaggaat atgttaggca tgttgaggaa | 240 |
| tatgatttgc agtttatatt tcagttgtgt actataacat tatccactga tgtaatgtca | 300 |
| tatatacata ctatgaatcc tgctatttg gatgattgga attttggtgt tgcccctcca | 360 |
| ccatctgcta gtcttgtaga tacataccgc tacctacaat cagcagcaat tacatgtcaa | 420 |
| aaggacgccc ctgcacctgt taaaaaagat ccctatgatg gtcttaactt ttggaatgtg | 480 |
| gatttaaagg aaaagtttag ttctgaactg gaccaattcc cattaggacg caaatttctg | 540 |
| ttacaggcag gtgttcgcag acggcccacc ataggccctc gtaaacgcac tgccactgca | 600 |
| gctac | 605 |

<210> SEQ ID NO 54
<211> LENGTH: 605
<212> TYPE: DNA
<213> ORGANISM: Artificial Sequence
<220> FEATURE:
<223> OTHER INFORMATION: Synthetic construct

<400> SEQUENCE: 54

| | |
|---|---|
| tatgccccct cgcctagtgg gtctatggta tcctcagact cccagttatt taacaagccc | 60 |
| tattggctgc acaaggcaca gggacacaac aatggtattt gttggcataa tcaattattt | 120 |
| cttactgttg tggataccac tcgcagtacc aattttactt tgtctactac tactgaatca | 180 |
| gctgtaccaa atatttatga tcctaataaa tttaaggaat atattaggca tgttgaggaa | 240 |
| tatgatttgc aatttatatt tcagttgtgt actataacat tgtccactga tgtaatgtcc | 300 |
| tatatacata ctatgaatcc tgctatttg gatgattgga attttggtgt tgcccctcca | 360 |
| ccatctgcta gtcttgtaga tacataccgc tatctgcaat cagcagcaat tacatgtcaa | 420 |
| aaagacgccc ctgcacctac taaaaaggat ccatatgatg gcttaaactt ttggaatgta | 480 |
| aatttaaagg aaaagtttag ttctgaactg gaccagtttc ctttaggacg caaatttctt | 540 |

```
ttacaggcag gcgtccgccg acgacccact ataggccccc gtaaacgccc cgccacagca    600
actac                                                                605

<210> SEQ ID NO 55
<211> LENGTH: 605
<212> TYPE: DNA
<213> ORGANISM: Artificial Sequence
<220> FEATURE:
<223> OTHER INFORMATION: Synthetic construct

<400> SEQUENCE: 55
tattcccctt ccccaagtgg ctctatggtc tcttctgatt cccagttgtt taataagccc    60
tattggttgc ataaggccca gggacacaat aatggcattt gttggcataa ccagttgttt    120
attactgtgg tggacactac acgtagtact aattttacat tgtctgcctg caccgaaacg    180
gccatacctg ctgtatatag ccctacaaag tttaaggaat atactaggca tgtggaggaa    240
tatgatttac aatttatatt tcaattgtgt actatcacat taactgctga cgttatggcc    300
tacatccata ctatgaatcc tgcaattttg gacaattgga atataggagt taccccctcca   360 ccatctgcaa gcttggtgga cacgtatagg tatttacaat cagcagctat agcatgtcaa    420
aaggatgctc ctacacctga aaaaaggat ccctatgacg atttaaaatt ttggaatgtt     480
gatttaaagg aaaagtttag tacagaacta gatcagtttc ctttggggcg caaattttta    540
ctacaggtag gggctcgcag acgtcctact ataggccctc gcaaacgccc tgcgtcagct    600
aaatc                                                                605

<210> SEQ ID NO 56
<211> LENGTH: 608
<212> TYPE: DNA
<213> ORGANISM: Artificial Sequence
<220> FEATURE:
<223> OTHER INFORMATION: Synthetic construct

<400> SEQUENCE: 56
ttttatccta cacctagtgg ttccatggtt tcttcagatg cacagttgtt taataaacct    60
tattggttgc aaaaggcaca gggacaaaat aatggtattt gttggcataa tcaattattt    120
ttaactgttg tagatactac tagaagcact aattttctg tatgtgtagg tacacaggct     180
agtagctcta ctacaacgta tgccaactct aattttaagg aatatttaag acatgcagaa    240
gagtttgatt tacagtttgt ttttcagtta tgtaaaatta gtttaactac tgaggtaatg    300
acatatatac attctatgaa ttctactata ttggaagagt ggaattttgg tcttacccca    360
ccaccgtcag gtactttaga ggaaacatat agatatgtaa catcacaggc tattagttgc    420
caacgtcctc aacctcctaa agaaacagag gacccatatg ccaagctatc cttttgggat   480
gtagatctta aggaaaagtt ttctgcagaa ttagaccagt ttcctttggg aagaaaattt    540
ttattacaac ttggtatgcg tgcacgtcct aagttacaag cttctaaacg ttctgcatct    600
gctaccac                                                             608

<210> SEQ ID NO 57
<211> LENGTH: 606
<212> TYPE: DNA
<213> ORGANISM: Artificial Sequence
<220> FEATURE:
<223> OTHER INFORMATION: Synthetic construct

<400> SEQUENCE: 57
tattcagcta ctcccagtgg ttctatgata acctctgatt ctcagatttt taataagcct    60
```

```
tattggttgc atcgcgccca gggccacaat aatggcattt gctggaataa tcagcttttt    120
attacttgtg ttgacactac taaaagtacc aatttaacca ttagcactgc tgttactcca    180
tctgttgcac aaacatttac tccagcaaac tttaagcagt acattaggca tggggaagaa    240
tatgaattgc aatttatatt tcaattgtgt aaaatcactt taactactga aattatggct    300
tacctgcaca ccatggattc tacaatttta gaacagtgga attttggatt aacattgccc    360
ccctccgcta gtttggagga tgcctatcga tttgtaaaaa atgcagcaac atcctgtcac    420
aaggacagtc ctccacaggc taaagaagac cctttggcaa aatataaatt ttggaatgta    480
gaccttaagg aacgcttttc tttggatttg gatcagtttg catgggtcg caagtttta     540 ttacaaatcg gtgcccaacg caaacccaga ccaggcctta aaaggcctgc cccatcctct    600
tccgct                                                              606

<210> SEQ ID NO 58
<211> LENGTH: 20
<212> TYPE: DNA
<213> ORGANISM: Artificial Sequence
<220> FEATURE:
<223> OTHER INFORMATION: Synthetic construct

<400> SEQUENCE: 58
gcacagggac ataacaatgg                                                20

<210> SEQ ID NO 59
<211> LENGTH: 20
<212> TYPE: DNA
<213> ORGANISM: Artificial Sequence
<220> FEATURE:
<223> OTHER INFORMATION: Synthetic construct

<400> SEQUENCE: 59
gcgcagggcc acaataatgg                                                20

<210> SEQ ID NO 60
<211> LENGTH: 20
<212> TYPE: DNA
<213> ORGANISM: Artificial Sequence
<220> FEATURE:
<223> OTHER INFORMATION: Synthetic construct

<400> SEQUENCE: 60
gcacagggac ataataatgg                                                20

<210> SEQ ID NO 61
<211> LENGTH: 20
<212> TYPE: DNA
<213> ORGANISM: Artificial Sequence
<220> FEATURE:
<223> OTHER INFORMATION: Synthetic construct

<400> SEQUENCE: 61
gcccagggcc acaacaatgg                                                20

<210> SEQ ID NO 62
<211> LENGTH: 20
<212> TYPE: DNA
<213> ORGANISM: Artificial Sequence
<220> FEATURE:
<223> OTHER INFORMATION: Synthetic construct

<400> SEQUENCE: 62
```

-continued gctcagggtt taaacaatgg                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic construct

<400> SEQUENCE: 63
gcacaaggcc ataataatgg                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic construct

<400> SEQUENCE: 64
cgtcccaaag gaaactgatc                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic construct

<400> SEQUENCE: 65
cgacctaaag gaaactgatc                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic construct

<400> SEQUENCE: 66
cgtccaaaag gaaactgatc                                              20

<210> SEQ ID NO 67
<211> LENGTH: 18
<212> TYPE: DNA
<213> ORGANISM: Artificial Sequence
<220> FEATURE:
<223> OTHER INFORMATION: Synthetic construct

<400> SEQUENCE: 67
gccaagggga aactgatc                                                18

<210> SEQ ID NO 68
<211> LENGTH: 20
<212> TYPE: DNA
<213> ORGANISM: Artificial Sequence
<220> FEATURE:
<223> OTHER INFORMATION: Synthetic construct

<400> SEQUENCE: 68
cgtcccaaag gatactgatc                                              20

<210> SEQ ID NO 69
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 69
cgtccaaggg gatactgatc                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic construct

<400> SEQUENCE: 70
cgacctaaag ggaattgatc                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic construct

<400> SEQUENCE: 71
cgtcctaatg ggaattggtc                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic construct

<400> SEQUENCE: 72
cgacctagtg gaaattgatc                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic construct

<400> SEQUENCE: 73
cgaccaaggg gatattgatc                                               20

<210> SEQ ID NO 74
<211> LENGTH: 18
<212> TYPE: DNA
<213> ORGANISM: Artificial Sequence
<220> FEATURE:
<223> OTHER INFORMATION: Synthetic construct

<400> SEQUENCE: 74
gcccaacgga aactgatc                                                 18

<210> SEQ ID NO 75
<211> LENGTH: 20
<212> TYPE: DNA
<213> ORGANISM: Artificial Sequence
<220> FEATURE:
<223> OTHER INFORMATION: Synthetic construct

<400> SEQUENCE: 75
cgacccaagg gaaactggtc                                               20
```

```
<210> SEQ ID NO 76
<211> LENGTH: 20
<212> TYPE: DNA
<213> ORGANISM: Artificial Sequence
<220> FEATURE:
<223> OTHER INFORMATION: Synthetic construct

<400> SEQUENCE: 76
cgtcctaaag gaaactggtc                                                    20

<210> SEQ ID NO 77
<211> LENGTH: 20
<212> TYPE: DNA
<213> ORGANISM: Artificial Sequence
<220> FEATURE:
<223> OTHER INFORMATION: Synthetic construct

<400> SEQUENCE: 77
gcgacccaat gcaaattggt                                                    20

<210> SEQ ID NO 78
<211> LENGTH: 20
<212> TYPE: DNA
<213> ORGANISM: Artificial Sequence
<220> FEATURE:
<223> OTHER INFORMATION: Synthetic construct

<400> SEQUENCE: 78
cgtcctaaag ggaattgatc                                                    20

<210> SEQ ID NO 79
<211> LENGTH: 94
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (30)..(36)
<223> OTHER INFORMATION: n is a, c, g, t, or absent
<220> FEATURE:
<221> NAME/KEY: misc_feature
<222> LOCATION: (70)..(73)
<223> OTHER INFORMATION: n is a, c, g, t, or absent

<400> SEQUENCE: 79
aatgatacgg cgaccaccga gatctacacn nnnnnntcgt cggcagcgtc agatgtgtat        60
aagagacagn nnngtgtgcc agcmgccgcg gtaa                                    94

<210> SEQ ID NO 80
<211> LENGTH: 91
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(31)
<223> OTHER INFORMATION: n is a, c, g, t, or absent
<220> FEATURE:
<221> NAME/KEY: misc_feature
<222> LOCATION: (66)..(69)
<223> OTHER INFORMATION: n is a, c, g, t, or absent

<400> SEQUENCE: 80
caagcagaag acggcatacg agatnnnnnn ngtctcgtgg gctcggagat gtgtataaga        60
gacagnnnnc cggactachv gggtwtctaa t                                       91
```

```
<210> SEQ ID NO 81
<211> LENGTH: 51
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (30)..(37)
<223> OTHER INFORMATION: n is a, c, g, t, or absent

<400> SEQUENCE: 81
aatgatacgg cgaccaccga gatctacacn nnnnnnntcg tcggcagcgt c           51

<210> SEQ ID NO 82
<211> LENGTH: 58
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (34)..(37)
<223> OTHER INFORMATION: n is a, c, g, t, or absent

<400> SEQUENCE: 82
tcgtcggcag cgtcagatgt gtataagaga cagnnnngtg tgccagcmgc cgcggtaa    58

<210> SEQ ID NO 83
<211> LENGTH: 47
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(32)
<223> OTHER INFORMATION: n is a, c, g, t, or absent

<400> SEQUENCE: 83
caagcagaag acggcatacg agatnnnnnn nngtctcgtg ggctcgg                47

<210> SEQ ID NO 84
<211> LENGTH: 60
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(38)
<223> OTHER INFORMATION: n is a, c, g, t, or absent

<400> SEQUENCE: 84
gtctcgtggg ctcggagatg tgtataagag acagnnnncc ggactachvg ggtwtctaat  60

<210> SEQ ID NO 85
<211> LENGTH: 19
<212> TYPE: DNA
<213> ORGANISM: Artificial Sequence
<220> FEATURE:
<223> OTHER INFORMATION: Synthetic construct

<400> SEQUENCE: 85
gtgccagcmg ccgcggtaa                                               19

<210> SEQ ID NO 86
```

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 86
ggactachvg ggtwtctaat                                              20
```